(12) United States Patent
Wittinghofer et al.

(10) Patent No.: US 7,521,538 B2
(45) Date of Patent: Apr. 21, 2009

(54) CRYSTAL STRUCTURE OF THE TERNARY COMPLEX OF 14-3-3/FUSICOCCIN/PMA AND METHODS FOR DESIGNING NEW HERBICIDES

(75) Inventors: Alfred Wittinghofer, Herdecke (DE); Martin Würtele, Mainhardt (DE); Claudia Oecking, Tübingen (DE); Christian Jelich-Ottmann, Tübingen (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 253 days.

(21) Appl. No.: 10/547,226

(22) PCT Filed: Feb. 26, 2004

(86) PCT No.: PCT/EP2004/001931

§ 371 (c)(1),
(2), (4) Date: Jun. 19, 2006

(87) PCT Pub. No.: WO2004/075635

PCT Pub. Date: Sep. 10, 2004

(65) Prior Publication Data

US 2007/0287629 A1    Dec. 13, 2007

(30) Foreign Application Priority Data

Feb. 27, 2003    (EP)    ................................. 03004312

(51) Int. Cl.
*A61K 36/00*    (2006.01)
*G01N 31/00*    (2006.01)

(52) U.S. Cl. .......................................... 530/379; 436/4
(58) Field of Classification Search ...................... None
See application file for complete search history.

(56) References Cited

OTHER PUBLICATIONS

McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Ballio et al., "H NMR Conformational Study of Fusicoccin and Related Compounds: Molecular Conformation and Biological Activity." *Phytochemistry*, vol. 30(1), pp. 137-146 (1991).
Fuglsang et al., "Binding of 14-3-3 Protein to the Plasma Membrane $H^+$-ATPase AHA2 Involves the Three C-terminal Residues $Tyr^{946}$-Thr-Val and Requires Phosphorylation of $Thr^{947*}$." *The Journal of Biological Chemistry*, vol. 274(51), pp. 36774-36780 (1999).
Jahn et al., "Large Scale Expression, Purification and 2D Crystallization of Recombinant Plant Plasma Membrane $H^+$-ATPase." *J. Mol. Biol.*, vol. 309, pp. 465-476 (2001).
Jaspert, Nina and Oecking, Claudia, "Regulatory 14-3-3 proteins bind the atypical motif within the C terminus of the plant plasma membrane $H^+$-ATPase via their typical amphipathic groove." *Planta*, vol. 216, pp. 136-139 (2002).
Oecking et al., "Topology and target interaction of the fusicoccin-binding 14-3-3 homologs of *Commelina communis*." *The Plant Journal*, vol. 12(2), pp. 441-453 (1997).
Oecking, Claudia and Hagemann, Klaus, "Association of 14-3-3 proteins with the C-terminal autoinhibitory domain of the plant plasma-membrane $H^+$-ATPase generates a fusicoccin-binding complex." *Planta*, vol. 207, pp. 480-482 (1999).
Rittinger et al., "Structural Analysis of 14-3-3 Phosphopeptide Complexes Identifies a Dual Role for the Nuclear Export Signal of 14-3-3 in Ligand Binding." *Molecular Cell*, vol. 4, pp. 153-166 (1999).
Roberts, Michael R., "Regulatory 14-3-3 protein-protein interactions in plant cells." *Current Opinion in Plant Biology*, vol. 3, pp. 400-405 (2000).

(Continued)

*Primary Examiner*—Suzanne M. Noakes
(74) *Attorney, Agent, or Firm*—DLA Piper LLP (US)

(57) ABSTRACT

The present invention relates to a crystal of a ternary complex composed of the protein 14-3-3, a ligand thereof and a fragment of Plasma Membrane ATPase (PMA) comprising the coordinates of table 4 or coordinates which differ from the coordinates of table 4 by a root mean square deviation of the C-alpha atoms of less than 3 Angstrom, wherein (a) protein 14-3-3 consists of the amino acid sequence of SEQ ID NO: 1 or of the sequence of a species homolog; (b) the ligand is Fusicocdin; (c) PMA is a C-terminal peptide of up to 15 amino acid residues in length; comprising the amino acid sequence of SEQ ID NO: 2 or comprising the sequence of a species homolog. Moreover, the invention also relates to methods for obtaining crystals of 14-3-3 in ternary complex and to methods relating to the determination of said 14-3-3 crystal coordinates. In addition, the present invention relates to computer modeling of crystal coordinates, to methods for developing a ligand binding to the complex of protein 14-3-3 and PMA and to methods for identifying a potential ligand to the complex of 14-3-3 and PMA. Furthermore, the present invention relates to a method for identifying and selecting a protein or protein complex with increased affinity to a ligand, to nucleic acid molecules encoding PMA or 14-3-3 with decreased affinity to a ligand and to methods of generating transgenic plants encoding PMA or 14-3-3 with decreased affinity to said ligand. Finally, the present invention relates to a device for developing a ligand for the complex of PMA and 14-3-3 and to the use of said device.

12 Claims, 5 Drawing Sheets

OTHER PUBLICATIONS

Sehnke et al., "Consummating Signal Transduction: The Role of 14-3-3 Proteins in the Completion of Signal-Induced Transitions in Protein Activity." *The Plant Cell*, Supp. S339-S354 (Sep. 2002).

Svennelid et al., "Phosphorylation of Thr-948 at the C Terminus of the Plasma Membrane $H^+$-ATPase Creates a Binding Site for the Regulatory 14-3-3 Protein." *The Plant Cell*, vol. 11, pp. 2379-2391 (1999).

Würtele et al., "Structural view of a fungal toxin acting on a 14-3-3 regulatory complex." *The EMBO Journal*, vol. 22(5), pp. 987-994 (2003).

* cited by examiner

SEQUENCE LISTING

<160> NUMBER OF SEQ ID NOS: 6

<210> SEQ ID NO 1
<211> LENGTH: 260
<212> TYPE: PRT
<213> ORGANISM: Nicotiana tabacum

<400> SEQUENCE: 1

```
Met Ala Val Ala Pro Thr Ala Arg Glu Glu Asn Val Tyr Met Ala Lys
1               5                   10                  15

Leu Ala Glu Gln Ala Glu Arg Tyr Glu Glu Met Val Glu Phe Met Glu
            20                  25                  30

Lys Val Ser Asn Ser Leu Gly Ser Glu Glu Leu Thr Val Glu Glu Arg
        35                  40                  45

Asn Leu Leu Ser Val Ala Tyr Lys Asn Val Ile Gly Ala Arg Arg Ala
    50                  55                  60

Ser Trp Arg Ile Ile Ser Ser Ile Glu Gln Lys Glu Glu Ser Arg Gly
65                  70                  75                  80

Asn Glu Glu His Val Asn Ser Ile Arg Glu Tyr Arg Ser Lys Ile Glu
                85                  90                  95

Asn Glu Leu Ser Lys Ile Cys Asp Gly Ile Leu Lys Leu Leu Asp Ala
            100                 105                 110

Lys Leu Ile Pro Ser Ala Ala Ser Gly Asp Ser Lys Val Phe Tyr Leu
        115                 120                 125

Lys Met Lys Gly Asp Tyr His Arg Tyr Leu Ala Glu Phe Lys Thr Gly
    130                 135                 140

Ala Glu Arg Lys Glu Ala Ala Glu Ser Thr Leu Thr Ala Tyr Lys Ala
145                 150                 155                 160

Ala Gln Asp Ile Ala Thr Thr Glu Leu Ala Pro Thr His Pro Ile Arg
                165                 170                 175

Leu Gly Leu Ala Leu Asn Phe Ser Val Phe Tyr Tyr Glu Ile Leu Asn
            180                 185                 190

Ser Pro Asp Arg Ala Cys Asn Leu Ala Lys Gln Ala Phe Asp Glu Ala
        195                 200                 205

Ile Ala Glu Leu Asp Thr Leu Gly Glu Glu Ser Tyr Lys Asp Ser Thr
    210                 215                 220

Leu Ile Met Gln Leu Leu Arg Asp Asn Leu Thr Leu Trp Thr Ser Asp
225                 230                 235                 240

Met Gln Asp Asp Gly Ala Asp Glu Ile Lys Glu Asp Pro Lys Pro Asp
                245                 250                 255

Glu Ala Lys Asn
            260
```

<210> SEQ ID NO 2
<211> LENGTH: 956
<212> TYPE: PRT
<213> ORGANISM: Nicotiana plumbaginifolia

<400> SEQUENCE: 2

Met Gly Glu Lys Pro Glu Val Leu Asp Ala Val Leu Lys Thr Val
1               5                   10                  15

Asp Leu Glu Asn Ile Pro Ile Glu Glu Val Phe Glu Asn Leu Arg Cys
            20                  25                  30

Thr Lys Glu Gly Leu Ser Gly Pro Ala Ala Gln Glu Arg Leu Ala Ile
        35                  40                  45

Phe Gly Tyr Asn Lys Leu Glu Glu Lys Glu Ser Lys Phe Leu Lys
    50                  55                  60

Phe Leu Gly Phe Met Trp Asn Pro Leu Ser Trp Val Met Glu Ala Ala
65                  70                  75                  80

Ala Ile Met Ala Ile Ala Leu Ala Asn Gly Gly Lys Pro Pro Asp
                85                  90                  95

Trp Gln Asp Phe Val Gly Ile Ile Thr Leu Leu Val Ile Asn Ser Thr
            100                 105                 110

Ile Ser Phe Ile Glu Glu Asn Asn Ala Gly Asn Ala Ala Ala Ala Leu
            115                 120                 125

Met Ala Arg Leu Ala Pro Lys Ala Lys Val Leu Arg Asp Gly Lys Trp
        130                 135                 140

Asp Glu Gln Asp Ala Ala Ile Leu Val Pro Gly Asp Ile Ile Ser Ile
145                 150                 155                 160

Lys Leu Gly Asp Ile Ile Pro Ala Asp Ala Arg Leu Leu Glu Gly Asp
                165                 170                 175

Pro Leu Lys Ile Asp Gln Ser Ala Leu Thr Gly Glu Ser Leu Pro Val
            180                 185                 190

Thr Lys Gly Pro Gly Asp Gly Val Tyr Ser Gly Ser Thr Cys Lys Gln
        195                 200                 205

Gly Glu Ile Glu Ala Val Val Ile Ala Thr Gly Val His Thr Phe Phe
    210                 215                 220

Gly Lys Ala Ala His Leu Val Asp Ser Thr Asn Gln Val Gly His Phe
225                 230                 235                 240

Gln Lys Val Leu Thr Ala Ile Gly Asn Phe Cys Ile Cys Ser Ile Ala
                245                 250                 255

Val Gly Met Ile Ile Glu Ile Ile Val Met Tyr Pro Ile Gln His Arg
            260                 265                 270

Lys Tyr Arg Pro Gly Ile Asp Asn Leu Leu Val Leu Leu Ile Gly Gly
        275                 280                 285

Ile Pro Ile Ala Met Pro Thr Val Leu Ser Val Thr Met Ala Ile Gly
    290                 295                 300

Ser His Arg Leu Ala Gln Gln Gly Ala Ile Thr Lys Arg Met Thr Ala
305                 310                 315                 320

Ile Glu Glu Met Ala Gly Met Asp Val Leu Cys Ser Asp Lys Thr Gly
                325                 330                 335

Thr Leu Thr Leu Asn Lys Leu Thr Val Asp Lys Asn Leu Val Glu Val
            340                 345                 350

Phe Ala Lys Gly Val Asp Ala Asp Thr Val Val Leu Met Ala Ala Arg
        355                 360                 365

Ala Ser Arg Thr Glu Asn Gln Asp Ala Ile Asp Thr Ala Ile Val Gly

-continued

```
            370                 375                 380
Met Leu Ser Asp Pro Lys Glu Ala Arg Ala Gly Ile Arg Glu Ile His
385                 390                 395                 400

Phe Leu Pro Phe Asn Pro Thr Asp Lys Arg Thr Ala Leu Thr Tyr Leu
                    405                 410                 415

Asp Gly Glu Gly Lys Met His Arg Val Ser Lys Gly Ala Pro Glu Gln
                420                 425                 430

Ile Leu Asn Leu Ala His Asn Lys Ser Asp Ile Glu Arg Arg Val His
            435                 440                 445

Ser Val Ile Asp Lys Phe Ala Glu Arg Gly Leu Arg Ser Leu Gly Val
450                 455                 460

Ala Tyr Gln Glu Val Pro Glu Gly Arg Lys Glu Ser Thr Gly Gly Pro
465                 470                 475                 480

Trp Gln Phe Ile Gly Leu Leu Pro Leu Phe Asp Pro Pro Arg His Asp
                485                 490                 495

Ser Ala Glu Thr Ile Arg Arg Ala Leu Asn Leu Gly Val Asn Val Lys
                500                 505                 510

Met Ile Thr Gly Asp Gln Leu Ala Ile Gly Lys Glu Thr Gly Arg Arg
            515                 520                 525

Leu Gly Met Gly Thr Asn Met Tyr Pro Ser Ser Ala Leu Leu Gly Gln
530                 535                 540

Thr Lys Asp Glu Ser Ile Ala Ser Leu Pro Ile Asp Glu Leu Ile Glu
545                 550                 555                 560

Lys Ala Asp Gly Phe Ala Gly Val Phe Pro Glu His Lys Tyr Glu Ile
                565                 570                 575

Val Lys Arg Leu Gln Ala Arg Lys His Ile Cys Gly Met Thr Gly Asp
                580                 585                 590

Gly Val Asn Asp Ala Pro Ala Leu Lys Lys Ala Asp Ile Gly Ile Ala
            595                 600                 605

Val Asp Asp Ala Thr Asp Ala Ala Arg Ser Ala Ser Asp Ile Val Leu
610                 615                 620

Thr Glu Pro Gly Leu Ser Val Ile Ile Ser Ala Val Leu Thr Ser Arg
625                 630                 635                 640

Ala Ile Phe Gln Arg Met Lys Asn Tyr Thr Ile Tyr Ala Val Ser Ile
                645                 650                 655

Thr Ile Arg Ile Val Leu Gly Phe Met Leu Leu Ala Leu Ile Trp Lys
                660                 665                 670

Phe Asp Phe Pro Pro Phe Met Val Leu Ile Ile Ala Ile Leu Asn Asp
            675                 680                 685

Gly Thr Ile Met Thr Ile Ser Lys Asp Arg Val Lys Pro Ser Pro Leu
690                 695                 700

Pro Asp Ser Trp Lys Leu Ala Glu Ile Phe Thr Thr Gly Val Val Leu
705                 710                 715                 720

Gly Gly Tyr Leu Ala Met Met Thr Val Ile Phe Phe Trp Ala Ala Tyr
                725                 730                 735

Glu Thr Asp Phe Phe Pro Arg Val Phe Gly Val Ser Thr Leu Gln Lys
                740                 745                 750

Thr Ala Thr Asp Asp Phe Arg Lys Leu Ala Ser Ala Ile Tyr Leu Gln
            755                 760                 765

Val Ser Thr Ile Ser Gln Ala Leu Ile Phe Val Thr Arg Ser Arg Ser
770                 775                 780

Trp Ser Phe Val Glu Arg Pro Gly Leu Leu Leu Val Val Ala Phe Leu
785                 790                 795                 800
```

```
Ile Ala Gln Leu Val Ala Thr Leu Ile Ala Val Tyr Ala Asn Trp Ala
                805                 810                 815

Phe Ala Ala Ile Glu Gly Ile Gly Trp Gly Trp Ala Gly Val Ile Trp
            820                 825                 830

Leu Tyr Asn Leu Val Phe Tyr Phe Pro Leu Asp Ile Ile Lys Phe Leu
                835                 840                 845

Ile Arg Tyr Ala Leu Ser Gly Arg Ala Trp Asp Leu Val Leu Glu Gln
            850                 855                 860

Arg Ile Ala Phe Thr Arg Lys Lys Asp Phe Gly Lys Glu Gln Arg Glu
865                 870                 875                 880

Leu Gln Trp Ala His Ala Gln Arg Thr Leu His Gly Leu Gln Val Pro
                885                 890                 895

Asp Thr Lys Leu Phe Ser Glu Ala Thr Asn Phe Asn Glu Leu Asn Gln
            900                 905                 910

Leu Ala Glu Glu Ala Lys Arg Arg Ala Glu Ile Ala Arg Gln Arg Glu
        915                 920                 925

Leu His Thr Leu Lys Gly His Val Glu Ser Val Val Lys Leu Lys Gly
    930                 935                 940

Leu Asp Ile Glu Thr Ile Gln Gln Ser Tyr Thr Val
945                 950                 955

<210> SEQ ID NO 3
<211> LENGTH: 5
<212> TYPE: PRT
<213> ORGANISM: Artificial sequence
<220> FEATURE:
<223> OTHER INFORMATION: Synthetic construct: phosphate moiety
<220> FEATURE:
<221> NAME/KEY: MOD_RES
<222> LOCATION: (4)..(4)
<223> OTHER INFORMATION: IS OPTIONALLY PHOSPHORYLATED

<400> SEQUENCE: 3

Gln Ser Tyr Thr Val
1               5

<210> SEQ ID NO 4
<211> LENGTH: 7
<212> TYPE: PRT
<213> ORGANISM: Artificial sequence
<220> FEATURE:
<223> OTHER INFORMATION: Synthetic construct: consensus binding motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: misc_feature
<222> LOCATION: (6)..(6)
<223> OTHER INFORMATION: Xaa can be any naturally occurring amino acid

<400> SEQUENCE: 4

Arg Ser Xaa Ser Thr Xaa Pro
1               5

<210> SEQ ID NO 5
<211> LENGTH: 8
<212> TYPE: PRT
<213> ORGANISM: Artificial sequence
<220> FEATURE:
```

-continued

```
<223> OTHER INFORMATION: Synthetic construct: consensus binding motif
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: misc_feature
<222> LOCATION: (7)..(7)
<223> OTHER INFORMATION: Xaa can be any naturally occurring amino acid

<400> SEQUENCE: 5

Arg Xaa Xaa Xaa Ser Thr Xaa Pro
1               5

<210> SEQ ID NO 6
<211> LENGTH: 6
<212> TYPE: PRT
<213> ORGANISM: Artificial sequence
<220> FEATURE:
<223> OTHER INFORMATION: Synthetic construct: phosphate moiety
<220> FEATURE:
<221> NAME/KEY: MOD_RES
<222> LOCATION: (4)..(4)
<223> OTHER INFORMATION: PHOSPHORYLATION

<400> SEQUENCE: 6

Gln Ser Tyr Thr Val Pro
1               5
```

CRYSTAL STRUCTURE OF THE TERNARY COMPLEX OF 14-3-3/FUSICOCCIN/PMA AND METHODS FOR DESIGNING NEW HERBICIDES

CROSS REFERENCE TO RELATED APPLICATIONS

This application is a 35 USC §371 National Stage application of PCT Application No. PCT/EP2004/001931 filed Feb. 26, 2004; which claims the benefit under 35 USC §119(a) of European Patent Application No. 03004312.9 filed Feb. 27, 2003. The disclosure of each of the prior applications is considered part of and is incorporated by reference in the disclosure of this application.

BACKGROUND OF THE INVENTION

The leaves of higher plants contain tightly-regulated openings called stomatal pores. The stomatal pores are located in the epidermis of plant leaves and are created by pairs of so-called "guard cells" which surround the actual opening. Guard cells control both the influx of $CO_2$ as a raw material for photosynthesis and water loss from plants through transpiration to the atmosphere. The exact molecular mechanism underlying the regulation of the pore size is complex and not completely understood. However, the plant plasma membrane $H^+$-ATPase (PMA) plays a pivotal role in this process. In particular, it is responsible for creating and maintaining an electrochemical proton gradient across the plasma membrane of guard cells that provides the driving force for nutrient uptake and maintenance of cell turgor. An increase in the proton gradient is known to result in osmotic swelling of the guard cells, consequently leading to an opening of the stomatal pore.

The polypeptide chain of the plasma membrane $H^+$-ATPase has been shown to form ten transmembrane helices, the N-and C-terminal amino acids of which are both located at the cytoplasmic face of the plasma membrane. In addition, PMA appears to contain a C-terminal regulatory domain (Palmgren et al., 1991) which can act as an intrinsic inhibitor of the proton pump. The autoinhibitory activity of this regulatory domain is relieved by phosphorylation of the penultimate threonine residue and subsequent association with 14-3-3 proteins, as shown recently (Svennelid et al., 1999; Fugisang et al., 1999; Maudoux et al., 2000).

This interaction results in an increased proton pump activity, a swelling of guard cells and ultimately in an opening of stomatal pores. Depending on the degree of proton pump activity, the supply of nutrients and other factors such as ambient temperature, the plant will either show an increased growth rate or a massive loss of water. Several naturally occurring compounds are known to stabilize the interaction of 14-3-3 and PMA. One such compound is Fusicoccin (FC), a diterpene glycoside produced by the fungus *Fusicoccum amygdali* (Ballio et al., 1964). Despite the fact that the fungus is host specific, FC exerts its effects in virtually any higher plant (Marre et al., 1979). Recently it has been shown that 14-3-3 proteins associate with the plant plasma membrane $H^+$-ATPase to generate a ligand binding complex for Fusicoccin (Baunsgaard et al., 1998). However, neither the molecular interactions underlying ligand binding nor the nature of the binding pocket for Fusicoccin are known.

A better understanding of the nature of the ligand binding pocket created by the polypeptide chains of PMA and 14-3-3 in the presence of Fusicoccin would allow to identify the molecular interactions that are required to stabilize PMA in its active state. This could lead to the development of ligands and of transgenic plants with modified properties and would ultimately allow to adapt plants to adverse environmental conditions. Moreover, transgenic plants could be developed, encoding. mutant 14-3-3 or mutant PMA, which would be resistant to fusicoccin action. Such plants could be grown in the presence of fusicoccin, since the mutation would guarantee the selective survival of the transgenic plant. This would open the way to the development of a new class of herbicides to be used in conjunction with the transgenic plant. However, the study of ligand binding requirements of PMa14-3-3 or of the interactions of Fusicoccin is hampered by the fact that the spatial structure of the ligand binding pocket is still unknown. This is partly because crystallization of the ternary complex of PMA/14-3-3 and Fusicoccin has been unsuccessful up to now.

Thus, the technical problem underlying the present invention was to provide the crystal structure of the binding site of Fusicoccin bound to PMA and 14-3-3. The solution to this technical problem is achieved by providing the embodiments characterized in the claims.

SUMMARY OF THE INVENTION

The present invention relates to a crystal of a ternary complex composed of the protein 14-3-3, a ligand thereof and a fragment of Plasma Membrane ATPase (PMA) comprising the coordinates of table 4 or coordinates which differ from the coordinates of table 4 by a root mean square deviation of the C-alpha atoms of less than 3 Angstrom, wherein (a) protein 14-3-3 consists of the amino acid sequence of SEQ ID NO: 1 or of the sequence of a species homolog; (b) the ligand is Fusicoccin; (c) PMA is a C-terminal peptide of up to 15 amino acid residues in length, comprising the amino acid sequence of SEQ ID NO: 2 or comprising the sequence of a species homolog. Moreover, the invention also relates to methods for obtaining the crystals of 14-3-3 in ternary complex and to methods relating to the determination of said 14-3-3 crystal coordinates. In addition, the present invention relates to computer modeling of crystal coordinates, to methods for developing a ligand binding to the complex of protein 14-3-3 and PMA and to methods for identifying a potential ligand to the complex of 14-3-3 and PMA. Furthermore, the present invention relates to a method for identifying and selecting a protein or protein complex with increased affinity to a ligand, relates to nucleic acid molecules encoding PMA or 14-3-3 with decreased affinity to a ligand and to methods of generating transgenic plants encoding PMA or 14-3-3 with decreased affinity to said ligand. Finally, the present invention relates to a device for (developing a ligand for the complex of PMA and 14-3-3 and to the use of said device.

Accordingly, in one aspect the present invention relates to a crystal of a ternary complex composed of the protein 14-3-3, a ligand thereof and a fragment of Plasma Membrane ATPase (PMA) comprising the coordinates of table 4 or coordinates which differ from the coordinates of table 4 by a root mean square deviation of the C-alpha atoms of less than 3 Angstrom, wherein (a) protein 14-3-3 consists of the amino acid sequence of SEQ ID NO: 1 or of the sequence of a species homolog; (b) the ligand is Fusicoccin; (c) PMA is a C-terminal peptide of up to 15 amino acid residues in, length, comprising the amino acid sequence of SEQ ID NO: 2 or comprising the sequence of a species homolog.

DETAILED DESCRIPTION OF THE INVENTION

Fusicoccin (FC) a diterpene glycoside, is a wilt-inducing phytotoxin produced by the fungus *Fusicoccum amygdali*

(Ballio et al., 1964). Despite the fact that the fungus is host-specific, FC exerts its effects in virtually any higher plant (Marre et. al., 1979). The plant plasma membrane H$^+$-ATPase (PMA) has been identified as the molecular target of FC action. This P-type ATPase is responsible for building up an electrochemical proton gradient across the plasma membrane that provides the driving force for nutrient uptake and maintenance of cell turgor (Morsomme & Boutry 2000). Changes of the latter are known to affect the osmotic swelling of the guard cells and consequently the opening of the stomatal pore. The proton pump is composed of ten transmembrane helices locating both the N- and C-terminus at the cytoplasmic face of the plasma membrane (Auer et al., 1998). The enzyme's C-terminus acts as an intrasteric inhibitor, the autoinhibitory activity of which is relieved by phosphorylation of the penultimate threonine residue and subsequent association with 14-3-3 proteins (Svennelid et al., 1999; Fugisang et al., 1999; Maudoux et al., 2000). Members of the eukaryotic 14-3-3 family are highly conserved proteins that have been implicated in the regulation of diverse physiological processes by protein-protein interactions. 14-3-3 proteins bind to their target proteins in a sequence-specific and phosphorylation-dependent manner (Yaffe et al., 2002; Tzivion & Avruch 2002; Sehnke et al., 2002). Binding of fusicoccin to the phosphorylated PMA-14-3-3 complex is thought to stabilize this interaction, thus leading to permanent activation of the H$^+$-pump. In order to analyse the molecular mode of fusicoccin action the structure of plant 14-3-3c (Gene bank AAC49892) was determined with and without a phosphorylated PMA-peptide in the presence and the absence of FC.

Several documents are cited throughout the text of this specification. The disclosure content of the documents cited therein (including any manufacture's specifications, instructions, etc.) is herewith incorporated by reference.

The present application discloses the crystal structure of the ternary complex of a plant 14-3-3 Protein, fusicoccin and a phosphopeptide derived from the C-terminus of the H$^+$-ATPase. In particular, the present invention reveals the ligand binding pocket created by 14-3-3 and PMA and the amino acid residues interacting with the ligand fusicoccin. Initial attempts to obtain ternary crystals by co-crystallation of 14-3-3-protein, fusicoccin and PMA failed. Surprisingly, soaking preformed crystals of 14-3-3 protein in solutions of PMA and fusicoccin yielded crystals of sufficient quality to allow structure determination. Comparison with the corresponding binary 14-3-3/PMA complexes indicated no major conformational change induced by fusicoccin. The compound rather closes a gap in the protein-phosphopeptide interface by a combination of hydrogen bonds and van der Waals contacts. Isothermal titration calorimetry indicates that the toxin by itself binds only weakly to 14-3-3 and that peptide and toxin reciprocally increase each others binding affinity by more than 90 fold. The structures of binary and ternary complexes of 14-3-3c with the phosphopeptide Gln-Ser-Tyr-pThr-Val (QSYpTV)(residues 952-956 of SEQ ID NO: 2, with a phosphothreonine at residue 955), conserved in plant H$^+$-ATPases, revealed that the phosphopeptide occupies the central binding groove of 14-3-3c in an extended conformation. The phosphate moiety of the phosphothreonine forms electrostatic interactions with a positively charged patch formed by residues Lys56, Arg63, and Arg 136 and a H-bond to Tyr137. This indicates that high-affinity binding of 14-3-3 to PMA is dependent on phosphorylation. The structure confirms the notion that the C-terminal YTV-motif is highly conserved in plant P-type H$^+$-ATPases.

Moreover, comparison of the peptide conformation in the binary and ternary complexes indicates the C-terminal Val to adopt a different rotameric conformation to accommodate the toxin (FIG. 2b). Whereas the glycosidic part of the phytotoxin is solvent exposed and forms two hydrogen bonds to Asn49 and Asp222 as well as some hydrophobic interactions, the diterpene part is buried and makes extensive hydrophobic contacts to 14-3-3c, with two additional H-bonds to Asp 222 and Lys 129 (FIG. 2c). The, structure reveals that every minor modifications of the carbocyclic framework are prohibitive for biological activity and their ability to compete with FC for binding. In contrast, more extensive changes and even the complete deletion of the glycosidic part results in an albeit reduced biological activity. The peptide and FC contact each other very closely and together fill the central cavity of 14-3-3 (FIG. 2d). The interaction involves the peptide's C-terminal Val of the peptide and the five- and eight-membered carbocycles of FC. These contacts bury an extra exposed solvent accessible surface of ca. 50 Å$^2$ when compared to the corresponding binary complexes.

As used herein, the following terms and expressions have the indicated meanings.

The term "crystal" refers to an ordered state of matter. Proteins, by their nature are difficult to purify to homogeneity. Even highly purified proteins may be chronically heterogeneous due to modifications, the binding of ligands or a host of other effects. In addition, proteins are crystallized from generally complex solutions that may include not only the target molecule but also buffers, salts, precipitating agents, water and any number of small binding proteins. It is important to note that protein crystals are composed not only of protein, but also of a large percentage of solvents molecules, in particular water. These may vary from 30 to even 90%. Protein crystals may accumulate greater quantities and a diverse range of impurities which cannot be listed here or anticipated in detail. Frequently, heterogeneous masses serve as nucleation centers and the crystals simply grow around them. The skilled person knows that some crystals diffract better than others. Crystals vary in size from a barely observable 20 micron to 1 or more millimeters. Crystals useful for X-ray analysis are typically single, 0.05 mm or larger, and free of cracks and defects. However, advances in technology allow increasingly smaller crystals to be analysed.

The term "14-3-3" or "14-3-3 protein" refers to members of the eukaryotic 14-3-3 family which are highly conserved proteins that have been implicated in the regulation of diverse physiological processes by protein-protein interactions (Yaffe, FEBS Letters, 25669 (2002) 1-5). 14-3-3 proteins bind to their target proteins in a sequence-specific and phosphorylation-dependent manner. The present invention particularly relates to those members of the 14-3-3 family which regulate the activity of plasma membrane H$^+$-ATPase (PMA) by binding to its C-terminus. Preferred in accordance with the present invention is 14-3-3 of tobacco as shown in SEQ ID NO: 1. The term "homolog" or "species homolog" refers to proteins with related amino acid sequence or encoded by related nucleic acid sequences. The person skilled in the art knows criteria that allow a meaningful limitation, i.e. a meaningful definition of the term related. As for the present invention, the term related means with a particular homology or identity in respect to the sequences referred to in the present application. Preferably with at least 90% identity and more preferably 95% identity to a second amino acid sequence. As a practical matter, whether any particular molecule is at least 80%, 90% or 95% identical to a second molecule or fragments thereof, can be determined conventionally using computer programs known to the person skilled in the art. In any case, preferred 14-3-3 molecules are listed, amongst others, in tables 1 and 2 and are preferably selected therefrom.

TABLE 1

The table lists Gene bank accession of tobacco 14-3-3 molecules

| | ACCESSION NUMBER | NAME |
|---|---|---|
| 1 | T02051 | 14-3-3 protein homolog B - common tobacco |
| 2 | T02050 | 14-3-3 protein homolog A - common tobacco |
| 3 | T04131 | 14-3-3 protein, isoform f - common tobacco |
| 4 | T04129 | 14-3-3 protein, isoform e - common tobacco |
| 5 | T04128 | 14-3-3 protein, isoform d - common tobacco |
| 6 | T04127 | 14-3-3 protein, isoform b - common tobacco |
| 7 | CAC84142 | 14-3-3 protein (*Nicotiana tabacum*) |
| 8 | BAB68528 | 14-3-3 protein (*Nicotiana tabacum*) |
| 9 | BAB68527 | 14-3-3 protein (*Nicotiana tabacum*) |
| 10 | BAB68526 | 14-3-3 protein (*Nicotiana tabacum*) |
| 11 | AAK97210 | 14-3-3 protein isoform g [*Nicotiana tabacum*] |

Moreover, also preferred according to the present invention are 14-3-3 molecules selected from table 2

TABLE 2

The table lists Gene bank accession of selected 14-3-3 molecules

| | ACCESSION NUMBER | NAME |
|---|---|---|
| 1 | P93214 | 14-3-3 protein 9 |
| 2 | P93213 | 14-3-3 protein 8 |
| 3 | P93212 | 14-3-3 protein 7 |
| 4 | P93207 | 14-3-3 protein 10 |
| 5 | P93211 | 14-3-3 protein 6 |
| 6 | P93208 | 14-3-3 protein 2 |
| 7 | P93206 | 14-3-3 protein 1 |
| 8 | BAC42545 | putative 14-3-3 protein epsilon (*Arabidopsis thaliana*) |
| 9 | P93209 | 14-3-3 protein 3 (PBLT3) |
| 10 | P93210 | 14-3-3 protein 5 |
| 11 | P42652 | 14-3-3 protein 4 (PBLT4) |
| 12 | H86355 | probable 14-3-3 protein T16E15.8 - *Arabidopsis thaliana* |
| 13 | F96811 | probable 14-3-3 protein, 61538-60485 (imported); - *Arabidopsis thaliana* |
| 14 | C86472 | probable 14-3-3 protein (imported) - *Arabidopsis thaliana* |
| 15 | NP_498217 | Abnormal embryonic PARtitioning of cytoplasm 3; three-PDZ containing protein, isoform a; asymmetrically distributed, contributes to cell polarity and spindle alignment (149.3 kD) (par-3) (*Caenorhabditis elegans*) |
| 16 | NP_493208 | PDZ-containing protein, abnormal embryonic PARtitioning of cytoplasm PAR-6 (34.2 kD) (par-6) (*Caenorhabditis elegans*) |
| 17 | T12088 | 14-3-3 protein - fava bean (fragment) |
| 18 | T12572 | 14-3-3 protein - common ice plant |
| 19 | T04131 | 14-3-3 protein, isoform f - common tobacco |
| 20 | T04129 | 14-3-3 protein, isoform e - common tobacco |
| 21 | T04128 | 14-3-3 protein, isoform d - common tobacco |
| 22 | T04127 | 14-3-3 protein, isoform b - common tobacco |
| 23 | T07392 | 14-3-3 protein tft9 - tomato (fragment) |
| 24 | T07390 | 14-3-3 protein tft8 - tomato (fragment) |
| 25 | T07389 | 14-3-3 protein tft6 - tomato |
| 26 | T07388 | 14-3-3 protein tft3 - tomato |
| 27 | T07387 | 14-3-3 protein tft2 - tomato |
| 28 | T07385 | 14-3-3 protein tft10 - tomato (fragment) |
| 29 | T07383 | 14-3-3 protein tft1 - tomato |
| 30 | S20580 | 14-3-3 protein homolog (clone PHP-O) - Hooker's evening primrose |
| 31 | S20581 | 14-3-3 protein homolog (clone PHP-S) - spinach (fragment) |
| 32 | AAM20176 | putative 14-3-3 protein (*Arabidopsis thaliana*) |
| 33 | AAL85081 | putative 14-3-3 protein GF14kappa (*Arabidopsis thaliana*) |
| 34 | AAL38750 | putative 14-3-3 protein GF14nu (grf7) (*Arabidopsis thaliana*) |
| 35 | AAL15221 | putative 14-3-3 protein GF14upsilon (*Arabidopsis thaliana*) |
| 36 | AAK93673 | putative 14-3-3 protein GF14kappa grf8 (*Arabidopsis thaliana*) |
| 37 | AAK59674 | putative 14-3-3 protein GF14upsilon (grf5) (*Arabidopsis thaliana*) |
| 38 | AAG50088 | putative 14-3-3 protein GF14epsilon (*Arabidopsis thaliana*) |
| 39 | CAD43308 | 14-3-3 protein (*Lycopersicon esculentum*) |
| 40 | CAA67374 | 14-3-3 protein (*Lycopersicon esculentum*) |
| 41 | CAA67373 | 14-3-3 protein (*Lycopersicon esculentum*) |
| 42 | CAA67372 | 14-3-3 protein (*Lycopersicon esculentum*) |
| 43 | CAA65149 | 14-3-3 protein (*Lycopersicon esculentum*) |
| 44 | CAA65146 | 14-3-3 protein (*Lycopersicon esculentum*) |
| 45 | CAA65145 | 14-3-3 protein (*Lycopersicon esculentum*) |
| 46 | AAK11271 | 14-3-3 protein GF14iota (*Arabidopsis thaliana*) |
| 47 | AAG47840 | 14-3-3 protein GF14omicron (*Arabidopsis thaliana*) |
| 48 | P19456 | ATPase 2, plasma membrane-type (Proton pump 2) |
| 49 | AAK26638 | GF14 PsiA (*Brassica napus*) |

TABLE 2-continued

The table lists Gene bank accession of selected 14-3-3 molecules

| | ACCESSION NUMBER | NAME |
|---|---|---|
| 50 | AAK26637 | GF14 kappa (*Brassica napus*) |
| 51 | AAK26636 | GF14 lambda (*Brassica napus*) |
| 52 | AAK26635 | GF14 nu (*Brassica napus*) |
| 53 | AAK26634 | GF14 omega (*Brassica napus*) |
| 54 | Q99002 | 14-3-3 PROTEIN HOMOLOG (TH1433) |
| 55 | AAB17101 | 14.3.3. protein (*Trichoderma harzianum*) |
| 56 | AAK97210 | 14-3-3 protein isoform g (*Nicotiana tabacum*) |
| 57 | AAK38492 | putative 14-3-3 protein (*Oryza sativa*) |
| 58 | AAG52105 | putative 14-3-3 protein; 61538-60485 (*Arabidopsis thaliana*) |
| 59 | AAG50610 | 14-3-3 protein, putative (*Arabidopsis thaliana*) |
| 60 | BAB11565 | 14-3-3 protein GF14 (*Arabidopsis thaliana*) |
| 61 | AAF98570 | Strong similarity to GF14 mu from *Arabidopsis thaliana* gb|AB011545 and is amember of the 14-3-3 protein PFI00244 family |
| 62 | AAF87262 | Contains similarity to 14-3-3 protein GF14 epsilon (GRF10) from *Arabidopsis thaliana* gb|AF145302 and contains a 14-3-3 protein PFI00244 domain. This may be a pseudogene |
| 63 | AAF87261 | Identical to 14-3-3 protein GF14 epsilon (GRF10) from *Arabidopsis thaliana*gb|AF145302 and contains a 14-3-3 protein PFI00244 domain. ESTs gb|H37302, gb|T43075, gb|T88323, gb|T41936, gb|R87021, gb|N37965, gb|Al994245, gb|Z46557, gb|T20402, gb|T44175, gb|T88028 come from this gene |
| 64 | P29307 | 14-3-3-LIKE PROTEIN |
| 65 | P29308 | 14-3-3-LIKE PROTEIN |
| 66 | AAD46005 | Similar to gb|X95905 14-3-3 protein (TFT7) from *Lycopersicon esculentum*. (*Arabidopsis thaliana*) |
| 67 | CAA65150 | 14-3-3 protein (*Lycopersicon esoulentum*) |
| 68 | CAA65148 | 14-3-3 protein (*Lycopersicon esculentum*) |
| 69 | CAA65147 | 14-3-3 protein (*Lycopersicon esculentum*) |
| 70 | CAA44642 | 14-3-3 protein kinase C inhibitor homologue (*Oenothera elata* subsp. *hookeri*) |
| 71 | CAA53700 | 14-3-3 protein 32 kDa endonuclease (*Cucurbita pepo*) |
| 72 | CAA74592 | 14-3-3 protein (*Hordeum vulgare*) |
| 73 | CAA44641 | 14-3-3 protein kinase C inhibitor homologue (*Spinacia oleracea*) |
| 74 | CAA44259 | 14-3-3 protein homologue (*Hordeum vulgare* subsp. *vulgare*) |

However, also comprised by the present invention are chimeric molecules which contain portions of amino acid residues derived from more than one 14-3-3 family member. Likewise, the 14-3-3 polypeptide sequence may be derived from one species or be composed of sequences derived from two or more species homologs. The person skilled in the art knows various techniques of generating chimeric or hybrid nucleic acid molecules which encode chimeric or hybrid protein molecules, as for example fusion PCR (Horton, R. M., Hunt, H. D., Ho, S. N., Pullen, J. K. and Pease, L. R.: Engineering hybrid genes without the use of restriction enzymes—gene splicing by overlap extension. Gene 77: 61-68 (1989)). Generally, said 14-3-3 or PMA protein is obtainable from any plant species, in particular any monocotyledonous and dicotyledonous plant. However, preferred 14-3-3 or PMA molecules are derived from a plant which is selected from the group consisting of corn (*Zea mays*), canola (*Brassica napus, Brassica rapa* ssp.), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*), sunflower (*Helianthus annuus*), safflower (*Carthamus tinctorius*), wheat (*Triticum aestivum*), duckweed (*Lemna*) soybean (*Glycine max*), tobacco (*Nicotiana tabacum*), potato (*Solanum tuberosum*), peanut (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nuciferea*), pineapple (*Ananas comosus*), citrus tree (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beet (*Beta vulgaris*), sugarcane (*Saccharum* spp.), oats, barley, vegetables, ornamentals, and conifers. However, the person skilled in the art knows that even sequences from distantly related organisms such as human may be employed for studies on ligand binding. Accordingly, also chimera, for example between plant and human are conceivable and comprised by the present invention.

The term "PMA" or "plasma membrane H$^+$-ATPase" refers to P-type ATPases such as those described by Palmgren et at. (2001), (Annu Rev Plant Physiol Plant Mol Biol. 2001, 52:817-845). Preferred in accordance with the present invention is PMA2 of *Nicotiana plumbaginifolia* as shown in SEQ ID: 2 or a sequence homolog therefrom. Full-length transmembrane proteins such as the plasma membrane H$^+$-ATPase are usually difficult to crystallize, although 2D crystallization in combination with cryo-electron microscopy and image reconstruction might be used as a feasible approach (Unger V. M. Assessment of electron crystallographic data obtained from two-dimensional crystals of biological specimens. Acta Crystallogr D Biol Crystallogr. 2000 October; 56 (Pt 10):

1259-69). Accordingly, the term PMA, as used herein, also refers to deletion mutants wherein only the cytoplasmic portion of the plasma membrane $H^+$-ATPase is retained. Preferred molecules are peptides comprising the 7, 8, 9, 10, 11, 12, 13, 14, 15, 16 or 17 C-terminal amino acid residues. Most preferably said peptides have the sequence comprising the residues Gln-Ser-Tyr-Thr-Val (QSYTV) (residues 952-956 of SEQ ID NO: 2) or residues from a homologous position of a species homolog. It has recently been shown that phosporylation of the distal threonine residue increase the interaction of PMA and 14-3-3. Accordingly, phosphorylated PMA, particularly Gln-Ser-Tyr-pThr-Val (QSYpTV) (residues 952-956 of SEQ ID NO. 2, with a phosophothreonine at residue 955) is a preferred molecule.

The present invention particularly relates to PMA molecules obtainable from plants. However, also comprised by the present invention are chimeric molecules which contain portions of amino acid residues derived from more than one PMA. Likewise, the PMA molecules may be obtained from one species or be composed of sequences derived from two or more species. The person skilled in the art knows various techniques of generating chimeric or hybrid nucleic acid molecules which encode chimeric or hybrid protein molecules, as outlined more detailed above. PMA molecules are obtainable from any higher plant. Preferably, the PMA molecule is selected from PMA of corn (*Zea mays*), canola (*Brassica napus, Brassica rapa* ssp.), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*), sunflower (*Helianthus annuus*), safflower (*Carthamus tinctorius*), wheat (*Triticum aestivum*), duckweed (*Lemna*) soybean (*Glycine max*), tobacco (*Nicotiana tabacum*), potato (*Solanum tuberosum*), peanut (*Arachis hypogaea*), cotton (*Gossypium barbadense, Gossypium hirsutum*), sweet potato, (*Ipomoea batatus*), cassava (*Manihot esculenta*), coffee (*Coffea* spp.), coconut (*Cocos nucifera*), pineapple (*Ananas comosus*), citrus tree (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beet (*Beta vulgaris*), sugarcane (*Saccharum* spp.), oats, barley, vegetables, ornamentals, and conifers. Moreover, the person skilled in the art knows that even sequences from distantly related organisms such as human may be employed for studies on ligand binding. Accordingly, also chimera, for example between plant and human are conceivable and comprised by the present invention.

While the above mentioned molecules largely only comprise sequences that correspond to naturally occurring or chimeric 14-3-3 or PMA proteins, these can be modified in various ways in order to optimize protein production, protein solubility or crystallization efficiency. Typical examples of such modifications are the N- or C-terminal addition of histidine-residues ("his-tag") or of other tags which confer the above-mentioned properties such as for example HA-tag, Strep-tag, Flag-tag or a Myc-tag. Furthermore, the proteins of the present invention may initially be produced as larger fusion proteins which may be cleaved in a subsequent step by protease treatment (see for example U.S. Pat. No. 5,888,732). Resulting from this preparative step and depending on the design of the recombinant molecule, additional amino acid residues may be present at the N- or C-terminus of the proteins or polypeptides of the present invention. These additional residues usually comprise no more than ten amino acids, while optimally and preferably no additional (foreign) residues remain in terminal position of the proteins after their proteolytic treatment. However, provided these additional residues are without adverse effect on the structure of the proteins and, in particular, on their interactions, the proteins of the present invention may contain additional domains in N- or C-terminal location. In fact the person skilled in the art knows of various domains that may be added and confer an improved expression, solubility or overall stability and that may be helpful during purification or even crystallization. Such domains include GST, MBP (Maltose binding protein), CBD (Chitin binding domain), Inteine, TAP (tandem affinity purification, Gavin, A. C. et al., Nature Vol: 415, 141-147). Moreover, other modifications include the addition of cross-linking reagents such as glutaraldehyde, the addition of alcohols such as glycol or ethanol or the addition of sulhydroxide-blocking or modifying reagents such as phosphorylation, acetylation, oxidation, glucosylation, ribosylation of side chain residues, binding of heavy metal atoms.

The term "ligand", as used herein, describes a compound that binds to the 14-3-3 molecule, the PMA molecule or the binary complex of 14-3-3 and PMA and in particular to a compound that binds to the same binding pocket as the one used by fusicoccin. In general, it is conceivable that ligand binding has a stabilizing or destabilizing effect on the interaction of 14-3-3 and PMA. Preferably, stabilizing compounds of ligands are base on Fusicoccines or Cotylenines and thus include Fusicoccin A and Cotylenin A or derivatives thereof. The ligand bound binary complex is also termed "ternary complex". The term "stabilize" or "destabilize" refers to the stability of the binary complex, i.e. to the equilibrium of PMA and 14-3-3 in solution, which can be is expressed by a dissociation constant $K_D$ [μM]. Addition of a destabilizing compound results in a decrease of the observed $K_D$ of PMA and 14-3-3 (increase of binding affinity) while the addition of a destabilizing compound results in an increase of the observed $K_D$ (decrease of binding affinity).

The term "coordinate" as used herein, refers to the information of the three-dimensional organization or the atoms contributing to a (protein-) structure, preferably the structure of the ternary complex of 14-3-3, PMA and fusicoccin. A common format for coordinate files is the so-called "PDP file format" (PDB=Protein Data Bank, www.pdb.org) which is organized according to the instructions and guidelines given by the Research Collaboratory for Structural Bioinformatics (H. M. Berman, J. Wesibrook, Z. Feng. G. Gilliland, T. N. Bhat, H. Weissig, I. N. Shindyalov, P. E. Bourne: Nucleic Acids Rescarch, 28 pp. 235-242 (2000)) and which allows a graphical representation by programs such as O (Jones et al,. Acta Crystallogr. D. 1 99 1, 47:11 0-11), rasmol (Trends Biochem Sci. 1995:20(9):374), moiscript (Kraulis, P. (1991). J. Appl. Cryst. 24, 946-950), bobscript or Pymol (DELANO, W. L. (2002), The PyMOL Molecular Graphics System, DeLano Scientific, San Carlos, Calif., USA). Preferably, the crystal of the present invention has the coordinates as shown in table 4.

The term "root mean square deviation" (rmsd) is used as a mean of comparing two closely related structures and relates to a deviation in the distance between related atoms of the two structures after structurally minimizing this distance in an alignment. Related proteins with closely related structures will be characterized by relatively low RMSD values whereas more changes will result in an increase of the RMSD value.

The term "Fusicoccin" as used herein relates to a wilt-inducing phytotoxin which is a diterpene glycoside produced by the fungus *Fusicoccum amygdali* and preferably which is described in Ballio et al. (1964).

In a preferred embodiment of the present invention, the crystal coordinates differ from the coordinates of table 4 by a root mean square deviation of the C-alpha atoms of less than 1.5 Angstrom.

In another preferred embodiment of the present invention, the proteins contain chemical modifications including the addition of cross-linking reagents such as glutaraldehyde, the addition of alcohols such as glycol or ethanol or the addition of sulhydroxide-blocking or modifying reagents such as phosphorylation, acetylation, oxidabon, glucosylation, ribosylation of side chain residues, binding of heavy metal atoms and/or up to 10 N-terminal or C-terminal additional amino acid residues. Preferably, the latter residues are histidines or more preferably the residues RGS-(His)$_6$. In some cases the proteins can contain entire additional domains which are added in, order to increase solubility, purification efficiency or stability of the protein. Typical examples of small modifications are the N- or C-terminal addition of histidine residues ("his-tag") or of other tags which confer the above mentioned properties such as for example HA-tag, Strep-tag, Flag-tag or a Myc-tag. Larger modifications include the addition of GST tags (GST=glutathione-S transferase), MBP (Maltose binding protein), CBD (Chitin binding domain), Inteine, TAP (tandem affinity purification, Gavin, A. C. et al., Nature Vol. 415, 141-147); the resulting protein is called a chimeric or fusion protein.

It may be desirable to express the polypeptides or proteins of the present invention as fusion proteins. Fusion proteins can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, tobacco etch virus proteins (TEV protease) factor Xa, thrombin, and enteroprotease. Typical fusion expression vectors include pGEX (Smith et al., Gene 67:31-40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., Gene 69:301-315 (1988)) and pET 11d (Studier et al., Gene Expression Technology: Methods in Enzymology 185:60-89 (1990)).

Accordingly, the proteins of the present invention may initially be produced as larger fusion proteins which are cleaved in a subsequent step by protease treatment (see for example U.S. Pat. No. 5,888,732). Resulting from this preparative step and depending on the design of the recombinant molecule, additional amino acid residues may be present at the N- or C-teriminus of the proteins or polypeptides of the present invention. These additional residues usually comprise no more than ten amino acids, while optimally and preferably no additional (foreign) residues remain in terminal position of the proteins after their proteolytic treatment. However, provided these additional residues are without adverse effect on the structure of the proteins and, in particular, on their intermolecular and intramolecular interactions, the proteins of the present invention may contain additional domains in N- or C-terminal location. In fact the person skilled in the art knows of various domains that may be added and confer an improved expression, solubility or overall stability and that may be helpful during purification or even crystallization. Such domains include GST, MBP (Maltose binding protein), CBD (Chitin binding domain), Inteine, TAP (tandem affinity purification, Gavin, A. C. et al.: Nature Vol. 415, 141-147). Other modifications of smaller compounds include the addition of cross-linking reagents such as glutaraldehyde, the addition of alcohols such as glycol or ethanol or the addition of sulhydroxide-blocking or modifying reagents such as the addition of cross-linking reagents such as glutaraldehyde, the addition of alcohols such as glycol or ethanol or the addition of sulhydroxide-blocking or modifying reagents such as phosphorylation, acetylation, oxidation, glucosylation, ribosylation of side chain residues, binding of heavy metal atoms.

In another preferred embodiment of the present invention, the ligand is a fusicoccane or a Cotylenin. Preferably, the fusicoccane is fusicoccin A and the Cotylenin is Cotylenin A. The term fusicoccin, as used herein, preferably refers to the compound as described by Ballio et al., (1964). Nevertheless, fusicoccin may contain additional side chains or substituted side chains as long as these do not influence the spatial configuration of the terpene ring system.

In more preferred embodiment of the present invention, the modification is phosphorylation, in particular phosphorylation by addition of an orthophosphate onto a threonine residue. In another more preferred embodiment of the present invention, the modification includes the addition of cross-linking reagents such as glutaraldehyde, the addition of alcohols such as glycol or ethanol or the addition of sulhydroxide-blocking or modifying reagents such as phosphorylabon, acetylation, oxidation, glucosylation, ribosylation of side chain residues, binding of heavy metal atoms. Phosphate residues can be added to proteins or polypeptides by enzymatic reactions which are known to the person skilled in the art and which often require the presence of specific recognition sequences. Alternatively, in particular when the polypeptide is only a few residues in length, the phosphate residue can be added during or after synthesis or by the addition of phosphorylated amino acid residues.

In another preferred embodiment of the invention, the crystal further comprises at least one compound selected from the group consisting of HEPES, NaCl, PEG 100, PEG 200, PEG 400, PEG 600, PEG 800, PEG 1000, PEG 2000, PEG 3000 PEG, 4000 PEG, 5000 PEG, 6000, PEG 7000, PEG 8000, isopropanol, citrate buffer, tris buffer, cacodylate buffer, MES-Buffer, dithiothreitol, octylglycopyranoside, uranylacetate.

In another preferred embodiment of the invention, (a) 14-3-3 comprises the amino acids of SEQ NO: 1, (b) PMA is a C-terminal fragment of SEQ ID NO:2 comprising the residues QSYpTV (residues 952-956 of SEQ NO: 2, with a phosphothreonine at residue 955), (c) the ligand is fusicoccin and (d) optionally, one or more components are contained, which are selected from the group consisting of PEG 400, sodium citrate, ammonium acetate, $H^2O_1$DTE and Mg—, Ca—, Na—, Cl—, Br—, I—, Rb—, P—, S—, K—, Mn—, Zn—, Cu—, B—, Mo—, Se—, Si—, Co—, V—, Ni—. Preferably, said C-terminal fragment of PMA consists of the residues QSYpTV (residues 952-956 of SEQ ID NO: 2 with a phosphothreonine at residue 955) with out any further N- or C-terminal amino acid residues.

In a more preferred embodiment of the invention, the crystal has a space group of P6$_5$22 and unit cell dimensions of a=109.0 Å±4 Å, b=109.0 Å±4 Å and c=135.8 Å±4 Å and one 14-3-3 in the asymmetric unit, further being characterized by the coordinates of table 4. In another more preferred embodiment of the invention, the crystal has a space group which is linked to the space group P6₅22 by adequate, and compatible symmetry operations.

The present invention also relates to, a method for obtaining a crystal of 14-3-3 in a ternary complex comprising the steps of contacting 14-3-3 or a fragment thereof with PMA or a fragment thereof and a ligand of the complex of PMA and 14-3-3; addition of PEG 400, sodium citrate, ammonium acetate, H₂O and DTE, thereby allowing the formation of crystals. For obtaining suitable crystals of ternary complexes, 14-3-3 may be expressed recombinantly in bacteria, insect cell culture or mammalian cell culture and purified via standard procedures. Fusicoccin may be purchased, for example from Sigma. PMA phosphopeptides can be synthesized by standard methods known to the person skilled in the art. Crystals of 14-3-3 can be grown, for example by the hanging drop or sitting drop method in solutions containing, for example, 21% PEG 400, 0.1 mM citrate buffer pH 4.7, 0.2 mM ammonium acetate (pH 7.0) and 10 mM DTE. Mature crystals, i.e. crystals with sufficient order allowing x-ray diffraction, are soaked with ligands for 20 min, 1 hour, 2 hours, 4 hours, 6 hours or sometimes up to 10 hours in precipitant solution supplemented to 30% PEG 400 and cryoprotectant (precipitant solution supplemented to 35% PEG 400, 8% isopropanol) prior to freezing in liquid N₂. The person skilled in the art knows that additional factors such as temperature may be crucial for crystal formation. These and other conditions of crystallization as well as strategies to optimise conditions of crystallization have been summarized in "Crystallization of Biological Macromolecules" by Alexander McPherson (Cold Spring Harbor Laboratory; 1st edition (Jan. 15, 1999).

In a preferred embodiment of the invention, the conditions for crystallisation are provided by a reservoir solution, further containing at least one compound selected from the group consisting of a buffer, a salt, a detergent, a reducing agent and a precipitant. The buffer is preferably sodium citrate, however, sodium citrate may be replaced by any other citrate buffer such as potassium citrate. Moreover, citrate buffer may be replaced by any other buffer with a similar buffer capacity and $pK_f$. The term "salt" refers to charged molecules composed of cation and anion and which are held together by ionic interactions. Preferably said salt contains molecules selected from the group consisting of Mg, Ca, Na, Cl, Br, I, Rb, P, S, K, Mn, Zn, Cu, B, Mo, Se, Si, Co, J, V, Ni, wherein these molecules are in their charged state and contain other counterions. The detergent is preferably selected from the group consisting of Triton X-100, NP 40 $C_{12}E_9$, $C_{12}E_8$, n-Dodecyl-β-D-maltoside, Sucrose monolaurate, CTAB, Deoxy-BigChap, n-Decyl-β-D-maltoside, Nony-β-D-glucoside, DDAO, n-Octanoylsucrose, MEGA-8, MEGA-9, IPTG, HEGA-8, HEGA-9, CHAPS, CHAPSO, BAM, CYMAL-2, $C_{14}E_8$, TWEEN and Brij59. Preferably said reducing agent is selected from the group consisting of DTE, β-Mercaptoethanole, Cystein, GSH.

In another preferred embodiment of the invention, a ligand and/or a polypeptide derived from PMA is added to the crystal growth medium after crystal growth; and/or the crystal is soaked in a medium containing a further ligand. Crystals with sufficient order allowing x-ray diffraction, are soaked with ligands for 20 min, up to 1 hour, up to 2 hours, up to 4 hours, up to 6 hours or sometimes up to 10 hours in precipitant solution supplemented with PEG and cryoprotectant, the latter of which preferably contains at least one compound selected from the group consisting of glycerol, ethylene glycol, polyethylene glycol, polyvinylpyrrolidone, methyl-2,4-peritanediol, 1,6-hexahediol, propylene glycol, paratone-N, paraffin oil, DMSO, ethanol, methanol, sucrose, erythritol, xylitol, inositol, raffinose, trehalose, glucose, 2,3-butanediol, lithium acetate, lithium chloride, lithium formate, lithium nitrate, lithium sulphate, magnesium acetate, sodium chloride, sodium formate, sodium nitrate. Preferably, PEG is PEG 400 present in a concentration of 30% and the cryoprotectant is supplemented to 35% PEG 400, 8% isopropanol. Preferably, the ligand or PMA polypeptide is present in a concentration of 0.05-10 mM. Soaking of preformed crystals are performed by standard methods which are described, for example, in Alexander McPherson's (Cold Spring Harbor Laboratory; $1_{st}$ edition (Jan. 15, 1999)). Preferably, the crystal of 14-3-3 is soaked in a solution containing only the PMA polypeptide or the ligand. However, the methods of the present invention also encompass soaking a crystal in solutions containing both PMA polypeptide and at least one ligand. Preferably, the crystal is soaked in solutions containing only one ligand. However, the methods of the present invention also comprises soaking the crystal in more than one type of ligand.

The present invention also relates to a crystal obtainable by the methods of the present invention.

Moreover, the present invention also relates to a method for detecting ligand binding to the complex of the protein 14-3-3 and PMA, comprising soaking the crystal of 14-3-3 and PMA in a solution of compounds to be screened and detecting binding of the compound to the ligand binding protein or the ligand binding site. Preferably, detection of binding is performed by isothermal titration calorimetry, filter-binding methods using radiolabelled compounds, ELISAs, Surface Plasmon Resonance or fluorescence spectroscopic methods.

Furthermore, the present invention also relates to a method for structure determination of a ternary complex of 14-3-3 comprising: (a) generating a crystal by performing the steps of the methods of the present invention; (b) generating and recording x-ray diffraction data; (c) optionally, digitising the data; (d) computationally reconstructing the data by x-ray diffraction; (e) determining the three-dimensional structure of the crystal components; and (f) storing the crystal coordinates generated on a data carrier.

X-ray diffraction may be performed on a beamline such as the ID29 beamline of ESRF, Grenoble. Data may be further processed with XDS [W. Kabsch, *J. Appl. Cryst.* 21, 67 (1988)] and refined with CNS [A. T. Brünger et al. *Acta Cryst.* D 54, 905 (1998)]. Structure can finally be solved with, for example, AmoRe [J. Navaza, *Acta Crystallogr.* A 50, 157 (1994)] and analysed with Xfit [D. E. McRee, J. Struct. Biol. 125, 156 (1999)] while structure validatation may be performed with PROCHECK [R. A. Laskowski, M. W. MacArthur, *J. Appl. Crystallogr.* 26, 283 (1993)] and WHATCHECK [R. W. W. Hooft, G. Vriend, C. Sander, E. E. Abola, *Nature* 381, 272 (1996)]. The final map containing the atomic coordinates of the constituents of the crystal may be stored on a data carrier, typically the data is stored in PDB format or in x-plor format, both of which are known to the person skilled in the art. However, crystal coordinates may as well be stored in simple tables or text files.

In a preferred embodiment of the present invention, the method for structure determination comprises additional steps of computer modeling, wherein computer modeling includes the step of (a) using virtual-screening tools for the search of compounds that bind to the 14-3-3 binding site and make molecular contacts to both 14-3-3 and the C-terminal residue of the peptide; (b) using homology-modeling tools that search for compounds similar to fusicoccin and that make molecular contacts to both 14-3-3 and the C-terminal residue of the peptide; (c) using molecular-modeling algorithms that allow an estimation of the binding affinities of compounds to the 14-3-3-PMA-peptide dimer; or (d) using ligand construction tools that build up organic molecules that fit into the ligand binding site.

In a more preferred embodiment of the present invention, the coordinates of at least one compound of the complex of 14-3-3, PMA and fusicoccin, as shown in table 4, is replaced by different coordinates, including a replacement with modified coordinates. Preferably, said coordinates are those of fusicoccin and they are replaced by the coordinates analogs of fusicoccin or of other molecules binding to the ligand binding pocket in 14-3-3/PMA. Alternatively, the coordinates of fusicoccin may be replaced with the coordinates of modified fusioccin.

The design of molecules with particular structural relationships to part of a protein molecule are well established and described in the literature (see for example COCHRAN, A. G. (2000), Chem. Biol. 7, 85-94; GRZYBOWSKI, B. A., ISHCHENKO, A. V., SHIMADA, J., SHAKHNOVICH, E. I. (2002), Acc. Chem. Res, 35, 261-269; VEJASQUEZ-CAMPOY, A., KISO, Y., FREIRE, E. (2001), Arch. Biochem. Biophys. 380, 169-175; D'AQUINO, J. A., FREIRE, E., AMZEL, L. M. (2000), Proteins: Struc. Func. Genet. Suppl. 4, 93-107.). Any of these so-called "molecular modeling" methods for rational drug design can be used to find a ligand to 14-3-3 that behaves analogously or similar to FC. Most of these molecular modeling methods take into consideration the shape, charge distribution and the distribution of hydrophobic groups, ionic groups and hydrogen bonds in the site of interest of the protein molecule. Using this information, that can be derived from the crystal structure of proteins and protein-ligand complexes, these methods either suggest improvements to existing proposed molecules, construct new molecules on their own that are expected to have good binding affinity, screen through virtual compound libraries for such molecules, or otherwise support the interactive design of new drug compounds in silico. Programs such as GOLD (G. Jones, et al., Development and J. Mol. Biol., 267, 727-748 (1997)); FLEXX (B. Kramer et al., Structure, Functions, and Genetics, Vol. 37, pp. 228-241, 1999); FLEXE (M. Rarey et al., JMB, 261,470-489 (1996)) DOCK (Kuntz, I. D. Science 257: 1078-1082, 1992); AUTODOCK (Morris et al., (1998), J. Computational Chemistry, 19: 1639-1662) are virtual screening programs designed to calculate the binding position and conformation as well as the corresponding binding energy of an organic compound to a protein. These programs are specially trimmed to allow a great number of "dockings", that is calculations of the conformation with the highest binding energy of a compound to a binding site, per time unit. Their binding energy is not always a real value, but can be statistically related to a real binding energy through a validation procedure. These methods lead to molecules, termed here "hits" that have to be accessed by experimental biochemical, structural-biological, molecular-biological or physiological methods for their expected biological activity. The positively assayed molecules constitute thus potential lead candidates for the design of bio-active compounds. In the present case, the binding site or binding pocket for a putative ligand or FC-analog is formed by the PMA peptide and FC interacting residues of 14-3-3. A ligand that binds with high affinity to these residues is likely to stabilize the interaction between the peptide and 14-3-3 and therefore activate the PMA.

The storage medium in which the atomic co-ordinates are provided is preferably random-access memory (RAM), but may also be read-only memory (ROM e.g. CDROM), a diskette or a hard drive. The storage medium may be local to the computer, or may be remote (e.g. a networked storage medium, including the internet). The invention also provides a computer-readable medium for a computer, characterized in that the medium contains atomic co-ordinates of the ternary complex of 14-3-3, PMA and a ligand, wherein the ligand is preferably fusicoccin. The atomic co-ordinates are preferably those as shown in table 4. Any suitable computer can be used in the present invention.

The term "molecular modeling" or "molecular modeling techniques" refers to techniques that generate one or more 3D models of a ligand binding site or other structural feature of a macromolecule. Molecular modeling techniques can be performed manually, with the aid of a computer, or with a combination of these. Molecular modeling techniques can be applied to the atomic co-ordinates of the present invention to derive a range of 3D models and to investigate the structure of ligand binding sites. A variety of molecular modeling methods are available to the skilled person for use according to the invention (G. Klebe and H. Gohlke, Angew. Chem. Int. Ed. 2002, 41, 2644-2676; Jun Zeng: Combinatorial Chemistry & High Throughput Screening, 2000, 3, 355-362 355; Andrea G Cochran, Current Opinion in Chemical Biology 2001, 5:654-659). At the simplest level, visual inspection of a computer model of the structure of 14-3-3 can be used, in association with manual docking of models of functional groups into its binding pockets. Software for implementing molecular modeling techniques may also be used. Typical suites of software include CERIUS2 (Available from Molecular Simulations Inc (www.msi.com)), SYBYL (Available from Tripos Inc (www.tripos.com)), AMBER (Available from Oxford Molecular (www.oxmol.co.uk), HYPERCHEM (Available from Hypercube Inc (www.hyper.com), INSIGHT II (Available from Molecular Simulations Inc (www.msi.com)), CATALYT (Available from Molecular Simulations Inc (www.msi.com)), CHEMSITE (Available from Pyramid Learning (www.chemsite.org)), QUANTA (Available from Molecular Simulations Inc (www.msi.com)) . These packages implement many different algorithmsthat may be used according to the invention(e.g. CHARMm molecular mechanics). Their uses in the methods of the invention include, but are not limited to: (a) interactive modeling of the structure with concurrent geometry optimisation (e.g. QUANTA); (b) molecular dynamics simulation of 14-3-3 structures (e.g. CHARMM, AMBER); (c) normal mode dynamics simulation of 14-3-3 structures (e.g. CHARMM). Modeling-may include one or more steps of energy minimisation with standard molecular mechanics force fields, such as those used in CHARMM and AMBER. These molecular modeling techniques allow the construction of structural models that can be used for in silico drug design and modeling.

In some cases, it may be advantageous to develop new ligands de novo, i.e. not on the basis and as a modification of a pre-existing compound. The term "de novo compound design" refers to a process whereby binding pocket of the target macromolecule (e.g., the complex of 14-3-3 and PMA) are determined; and its surfaces is used as a platform or basis for the rational design of compounds that will interact with those surfaces. Preferably, the compound interacts in a similar fashion as fusicoccin. The molecular modeling steps used in the methods of the invention may use the atomic co-ordinates of the present invention and models or structures derived therefrom, to determine binding surfaces. In particular, the present invention also refers to structures, i.e. PDB-files, of the ternary complex of 14-3-3, wherefrom the coordinates of the fusicoccin atoms have been removed. Any such structure will preferably reveal van der Waals contacts, electrostatic interactions, and/or hydrogen bonding opportunities. Said binding surfaces will typically be used by grid-based techniques (e.g. GRID, CERIUS.sup.2, [Goodford (1985) J. Med. Chem. 28: 849-857]) and/or multiple copy simultaneous search (MCSS) techniques to map favorable interaction positions for functional groups. This preferably reveals positions in the ligand binding pocket of 14-3-3/PMA for interactions such as, but not limited to, those with protons, hydroxyl groups, amine groups, hydrophobic groups (e.g. methyl, ethyl, benzyl) and/or divalent cations.

The term "functional group" refers to chemical groups that interact with one or more sites on an interaction surface of a macromolecule. A "small molecule" is a compound having molecular mass of less than 3000 Daltons, preferably less than 2000 or 1500, still more preferably less than 1000, and most preferably less than 500 Daltons. A "small molecule fragment" is a portion of a small molecule that has at least one functional group. A "small organic molecule" is a small molecule that comprises carbon. Once functional groups or small molecule fragments which can interact with specific sites in the binding surface of 14-3-3 and PMA have been identified, they can be linked in a single compound using either bridging fragments with the correct size and geometry or frameworks which can support the functional groups at favorable orientations, thereby providing a compound according to the invention. Whilst linking of functional groups in this way can be done manually, perhaps with the help of software such as QUANTA or SYBYL, the following software may be used for assistance: HOOK, which links multiple functional groups with molecular templates taken from a database, and/or CAVEAT, which designs linking units to constrain acyclic molecules. Other computer-based approaches to de novo compound design that can be used with the atomic co-ordinates of the present invention include LUDI(15 Bohm (1992) J. Comp. X ed Molec. Design 6: 61-78), SPROUT (Available from chem.leeds.ac. uk/ICAMS/SPROUT.html) and LEAP-FROG (available from Tripos Inc (www.tripos.com)). Suitable in silico libraries include the Available Chemical Directory (MDL Inc), the Derwent World Drug Index (WDI), BioByteMasterFile, the National Cancer Institute database (NCI), and the Maybridge catalog. Compounds in these in silico libraries can also be screened for their ability to interact with the binding pocket of 14-3-3 and PMA by using their respective atomic co-ordinates in automated docking algorithms. An automated docking algorithm is one which permits the prediction of interactions of a number of compounds with a molecule having a given atomic structure. Suitable docking algorithms include: DOCK (Kuntz et al. (1982) J. Mol. Biol. 161: 269-288)), AUTODOCK (Goodsell et al. (1990) Proteins: Structure, Function and Genetics 8: 195-202), MOE-DOCK (Available from Chemical Computing Group Inc. (www.chemcomp.com/)) or FLEXX (Available from Tripos Inc (www.tripos.com)). Docking algorithms can also be used to verify interactions. with ligands designed de novo.

A compound identified by using the methods of the invention preferably interacts with one or more residues of 14-3-3, selected from the group consisting of the amino acids 19, 42, 49, 53, 50, 56, 63, 126, 129, 130, 136, 137, 174, 175, 178, 181, 185, 221, 222, 225, 226, 229, 232, 233, 237 and/or the terminal valine residue of PMA. It is believed that the majority of these residues is crucial for creating the ligand binding pocket in the complex of 14-3-3/PMA. In general, the design strategy might begin by searching for ligands with relatively weak affinity to the residues of PMA and 14-3-3. This binding affinity can be increased by orders of magnitude by a series of rational measures known to the person skilled in the art. These include the modification of the ligand with chemical groups so as to reduce their degrees of freedom lost upon binding to the 14-3-3-Peptide-FC-binding site, the introduction of more potent electrostatic or hydrophobic binding groups, or even the covalent linking of two or more different ligands binding to different positions of the 14-3-3-Peptide-FC-binding site. The latter is additionally interesting due to the fact that 14-3-3 monomers group to form dimmers consisting of two paired 14-3-3 molecules.

Moreover, the present invention also relates to a method for developing a ligand binding to the complex of the protein 14-3-3 and PMA, comprising the steps of the method of any one of claims 12 to 16, further comprising the steps of (a) computer modeling of the crystal structure generated from the crystal of any one of claims 1 to 7; (b) replacing the ligand with a different ligand; (c) selecting a compound potentially fitting into the ligand binding site; (d) contacting the potential ligand with the ligand binding site in an in vitro or in vivo assay; and (e) detecting binding of the potential ligand.

In a preferred embodiment, the methods for developing a ligand comprise the further step of modifying said ligand to alter, add or eliminate a portion thereof suspected of interacting with a binding site of the binding cavity, thereby increasing or decreasing the affinity of the ligand to the binding site or binding cavity. One example of biochemical assay that can be employed to screen for potential FC—analogues includes the use of fluorescent labelled derivatives of the PMA-Peptide. The emitted fluorescence of this derivative is due to change depending on the binding of the peptide to 14-3-3. If the peptide is used with concentrations below its Kd, or mutated PMA with weaker affinity to 14-3-3 is used to reach the same objective, addition of FC or any analogue will lead to the binding of the peptide and a change of fluorescence-emission signal. This signal can be either a change in its intensity or its polarisation. A more simple alternative to fluorescence labelling would be the use of a radio-labelled peptide. The read-out of this assay would be radioactivity accumulated on fixed 14-3-3 proteins after washing the probes to reduce unspecific binding. Fluorescent labels are preferable selected from the group consisting fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine(ROX), 6-carboxy-2',4',7',4,7-hexachlorofluorescein (HEX), 5-carboxyfluorescein (5-FAM), 7-amino-4-methylcoumarin-3-acetic acid (AMCA) or N,N,N',N'-tetramethyl-6-carboxyrhodamine (TAMRA).

High throughput screening is nowadays a standard technique used by pharmaceutical companies in their quest for new active compounds. Modem HTS facilities screen thorough 10 if not 100 thousand compounds from chemical compound libraries daily. HTS can be based on several biochemical, molecular-biological or cell-biological assays. An approach, which can be in some circumstances integrated in a HTS, uses 14-3-3 proteins in a pull-down assay to select for the binding of a ligand from a chemical library consisting of a mixture of chemical compounds. 14-3-3 can be immobilised, e.g. on a chromatography column or some resin beads and incubated with the compound mixture. After washing unspecific binders, 14-3-3 can be eluted from the immobilising material and the co-binding assayed using modern biophysical methods like mass-spectrometry or NMR. The use of a fluorescence labelled PMA in a binding screen like the one described above could be adapted to use in a high throughput screen.

The present invention also provides a method for identifying a potential ligand binding to the complex of 14-3-3 and PMA, comprising the steps of: (a) computer modelling of the crystal structure generated from any of the crystals of the present invention; (b) replacing the ligand with a different ligand; (c) selecting a compound potentially fitting into the ligand binding site; (d) optionally synthesizing the compound of step (c); (e) contacting the potential ligand with the ligand binding site in an in vitro or in vivo assay; and (f) detecting binding of the potential ligand. Moreover, the present invention also provides a method for the production of a ligand with increased or decreased affinity to the ligand binding site, comprising the steps of the methods of the present invention and further the steps of (a) selecting a ligand with the desired properties; and (b) synthesizing the ligand in an amount allowing its commercial use in plant breeding. Such an amount would be anything exceeding 100 g, whereas smaller quantities are generally sufficient for analytical purposes only.

Moreover, the present invention also relates to a method of identifying and selecting a protein or protein complex of 14-3-3 with increased or decreased affinity to the ligand, comprising (a) performing structure assisted protein design with the three-dimensional structure, i.e. the coordinates of the crystal of the present invention, or with the three-dimensional structure derived from any of the methods of the present invention, wherein the protein design is performed in conjunction with computer modelling; (b) modifying a nucleic acid molecule encoding said protein or a fragment thereof, wherein said modification results in the modification of at least one residue suspected of interacting with the ligand or suspected of affecting the interaction of protein and ligand; (c) expressing the modified protein in vitro or in vivo; (d) testing binding to a ligand; and (e) selecting a protein with the desired properties.

Modification of nucleic acids, which can be either DNA or RNA is a standard technique known to the person skilled in the art (e.g. Sambrook et al., "Molecular Cloning, A Laboratory Manual"; CSH Press, Cold Spring Harbor, 1989 or Higgins and Hames (eds.). Preferably, amplification of DNA is accomplished by using polymerase chain reaction (PCR) and the modification is used by appropriate choice of primer oligonucleotides, containing e.g. mutations in respect to wild type 14-3-3 or PMA. The PCR consists of many repetitions of a cycle which consists of: (a) a denaturation step, which melts both strands of a DNA molecule; (b) an annealing steep, which is aimed at allowing the primers to anneal specifically to the melted strands of the DNA molecule; and (c) an extension step, which incorporates to the primers complementary to those of the strand of DNA to which the primers are annealed. The concentrations of primers, nucleotidetriphosphates, enzyme and buffers used will be apparent from and include the process parameters described in the Examples that follow. However, generally, PCR can be performed for example in a 50 µl reaction mixture containing 5 µl of 10×PCR buffer with 1.5 mM mM $MgCl_2$, 200 µM of each deoxynucleoside triphosphate, 0.5 µl of each primer (10 µM), 0.5 µl, 30 ng of microbial genomic template DNA and 2.5 Units of Taq Polymerase. The primers for the amplification may be labelled or be unlabelled. DNA amplification can be performed, e.g., with a model 2400 thermal cycler (Applied Biosystems, Foster City, Calif.): 2 min at 94° C. followed by 35 cycles consisting of annealing (30 s at 50° C.), extension (1 min at 72° C.), denaturation (10 s at 94° C.) and a final annealing step at 55° C. for 1 min as well as a final extension step at 72° C. for 5 min. However, the person skilled in the art knows how to optimize these conditions for the amplification of specific nucleic acid molecules. A further method of nucleic acid amplification is the "reverse transcriptase polymerase chain reaction" (RT-PCR). This method is used when the nucleic acid to be amplified consists of RNA. The term "reverse transcriptase" refers to an enzyme that catalyzes the polymerisation of deoxyribonucleoside triphosphates to form primer extension products that are complementary to a ribonucleic acid template. The enzyme initiates synthesis at the 3'-end of the primer and proceeds toward the 5'-end of the template until synthesis terminates. Examples of suitable polymerizing agents that convert the RNA target sequence into a complementary, copy-DNA (cDNA) sequence are avian myeloblastosis virus reverse transcriptase and *Thermus thermophilus* DNA polymerase, a thermostable DNA polymerase with reverse transcriptase activity marketed by Perkin Elmer. Typically, the genomic RNA/cDNA duplex template is heat denatured during the first denaturation step after the initial reverse transcription step leaving the DNA strand available as an amplification template. Suitable polymerases for use with a DNA template include, for example, *E. coli* DNA polymerase I or its Klenow fragment, T.sub.4 DNA polymerase, Tth polymerase, and Taq polymerase, a heat-stable DNA polymerase isolated from *Thermus aquaticus* and developed and manufactured by Hoffmann-La Roche and commercially available from Perkin Elmer. The latter enzyme is widely used in the amplification and sequencing of nucleic acids. The reaction conditions for using Taq polymerase are known in the art and are described, e.g., PCR Technology, Erlich, H. A. 1989. Stockton Press, New York or Innis, M. A., D. H. Gelfand, J. J. Sninsky, and T. J. White. 1990, PCR Protocols: A guide to methods and applications Academic Press, New York.

The invention also relates to a nucleic acid molecule encoding PMA with decreased affinity to the ligand, wherein (a) PMA contains a mutation in at least one position of the amino acid sequence of SEQ ID NO: 2, wherein the mutation is located in the carboxyterminal peptide QSYTV-COOH (residues 925-956 SEQ ID NO: 2); or (b) PMA is a species homolog containing the mutations indicated in (a). Preferably, said mutation is located in said peptide in position of T and/or V. More preferably, the mutation is selected from the group consisting of T955D, T955E, V956L, V956I, V956S, V956T, V956G, V956A (amino acid numbering of SEQ ID NO:2). Also preferred in accordance with the present invention are double-mutations of the carboxyterminal $T_{955}$, $V_{956}$ residues. Also preferred are chemical modifications of the carboxyterminal residues QSYTV, (residues 925-956 SEQ ID NO: 2), including the addition of hydrophobic groups, in particular to the hydroxy group of threonine.

Furthermore, the present invention also relates to a nucleic acid molecule encoding 14-3-3 with decreased affinity to the ligand, wherein (a) 14-3-3 contains a mutation in at least one position of the amino acid sequence of SEQ ID NO: 1, the position being selected from the group consisting of amino acids 19, 42, 49, 53, 50, 56, 63, 126, 129, 130, 136, 137, 174, 175, 178, 181, 185, 221, 222, 225, 226, 229, 232, 233, 237; or (b) 14-3-3 is a species homolog containing the mutations indicated in (a).

In a preferred embodiment of the present invention, said mutation is selected from the group consisting of N49Q, D222E, F126E and I175E (in respect to SEQ ID NO:1).

The present invention also relates to a method of generating a transgenic plant comprising: (a) generating a recombinant cell expressing the protein encoded by the nucleic acid molecules of the present invention, and (b) growing a plant from the cell of step (a). Moreover, the present invention also relates to a transgenic plant expressing a protein encoded by any of the recombinant or mutant nucleic acid molecules of the present invention.

The recombinant DNA molecule of the invention which encodes an altered 14-3-3 or PMA protein, comprises regulatory sequences allowing for the expression the nucleic acid molecules in plants. Preferably, said regulatory elements comprise a promoter active in plant cells. Expression comprises transcription of the nucleic acid molecule preferably into a translatable mRNA. Regulatory elements ensuring expression in plant cells are well known to those skilled in the art. These regulatory elements may, be homologous or preferably heterologous with respect to the nucleic acid molecule to be expressed and/or with respect to the plant species to be transformed. In general, such regulatory elements comprise a promoter active in plant cells. To obtain expression in all tissues of a transgenic plant, preferably constitutive promoters are used, such as the 35S promoter of CaMV (Odell, Nature 313 (1985), 810-812) or promoters of the polyubiquitin genes of maize (Christensen, Plant Mol. Biol. 18 (1982), 675-689). In order to achieve expression in specific tissues of a transgenic plant it is possible to use tissue specific promoters (see, e.g., Stockhaus, EMBO J. 8 (1989), 2245-2251). Known are also promoters which are specifically active in tubers of potatoes or in seeds of different plants species, such as maize, Vicia, wheat, barley etc. Inducible promoters may be used in order to be able to exactly control expression. An example for inducible promoters are the promoters of genes encoding heat shock proteins. Also microspore-specific regulatory elements and their uses have been described (WO96/16182). Furthermore, the chemically inducible Test-system may be employed (Gatz, Mol. Gen. Genet. 227 (1991); 229-237). Further suitable promoters are known to the person skilled in the art and are described, e.g., in Ward (Plant Mol. Biol. 22 (1993), 361-366). The regulatory elements may further comprise transcriptional and/or translational enhancers functional in plants cells. A plant translational enhancer often used is, e.g., the CaMV omega sequences and/or the inclusion of an intron (Intron-1 from the Shrunken gene of maize, for example) that has been shown to increase expression levels by up to 100-fold. (Maiti, Transgenic Research 6 (1997), 143-156; Ni, Plant Journal 7 (1995), 661-676). Furthermore, the regulatory elements may include transcription termination signals, such as a poly-A signal, which lead to the addition of a poly A tail to the transcript which may improve its stability. The termination signals usually employed are from the Nopaline Synthase gene or from the CaMV 35S RNA gene.

The present invention also relates to vectors, particularly plasmids, cosmids, viruses, bacteriophages and other vectors used conventionally in genetic engineering that contain at least one recombinant DNA molecule according to the invention. Methods which are well known to those skilled in the art can be used to construct varibus plasmids and vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the recombinant DNA molecules and vectors of the invention can be reconstituted into liposomes for delivery to target cells.

Advantageously the above-described vectors of the invention comprises a selectable and/or scorable marker. Selectable marker genes useful for the selection of transformed plant cells, callus, plant tissue and plants are well known, to those skilled in the art and comprise, for example, antimetabolite resistance as the basis of selection for dhfr, which confers resistance to methotrexate (Reiss, Plant Physiol. (Life Sci. Adv.) 13 (1994), 143-149); npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Nat. Acad. Sci. USA 85 (1988), 8047); mannose-6-phosphate isomerase which allows cells to utilize mannose (WO 94/20627) and ODC (ornithine decarboxylase) which confers resistance to the rnmithine decarboxylase inhibitor, 2-(difluoromethyl)-DL-omithine, DFMO (McConlogue, 1987, In: Current Communications in Molecular Biology, Cold Spring Harbor Laboratory. ed.) or deaminase from Aspergillus terreus which confers, resistance to Blasticidin S (Tamura, Biosci. Biotechnol. Biochem. 59 (1995), 2336-2338). Useful scorable marker are also known to those skilled in the art and are commercially available. Advantageously, said marker is a gene encoding luciferase (Giacomin, P I. Sci. 116 (1996), 59-72; Scikantha, J. Bact. 178 (1996), 121), green fluorescent protein (Gerdes, FEBS Lett. 389 (1996), 44-47) or β-glucuronidase (Jefferson, EMBO J. 6 (1987), 3901-3907). This embodiment is particularly useful for simple and rapid screening of cells, tissues and organisms containing a vector of the invention. As described above, various selectable markers can be employed in accordance with the present invention. Advantageously, selectable markers may be used that are suitable for direct selection of transformed plants, for example, the phophinothricin-N-acetyltransferase gene the gene product of which detoxifies the herbicide L-phosphinothricin (glufosinate or BASTA); see, e.g., De Block, EMBO J. 6 (1987), 2513-2518 and Dröge, Planta 187 (1992), 142-151.

The present invention, also relates to host cells comprising a recombinant DNA molecule or vector of the invention. Host cells include prokaryotic and eukaryotic cells such as *E. coli* and yeast, respectively.

The recombinant DNA molecules according to the invention are in particular useful for the genetic manipulation of plant cells, plant tissue and plants in order to obtain plants with modified, preferably with improved or useful phenotypes as described above. Thus, the present invention relates to a method for the production of transgenic plants with altered stomata characteristics compared to wild type plants comprising the introduction of a recombinant DNA molecule of the invention into the genome of a plant, plant cell or plant tissue.

Methods for the introduction of foreign DNA into plants as well as the selection and regeneration of transgenic plants from plant cells and plant tissue are also well known in the art. These include, for example, the transformation of plant cells, plant tissue or plants with T-DNA using *Agrobacterium tumefaciens* or *Agrobacterium rhizogenes*, the fusion of protoplasts, direct gene transfer (see, e.g., EP-A 164 575), injection, electroporation, biolistic methods like particle bombardment and other methods known in the art. The vectors used in the method of the invention may contain further functional elements; for example "left border"- and "right border"-sequences of the T-DNA of *Agrobacterium* which allow for stably integration into the plant genome. Furthermore, methods and vectors are known to the person skilled in the art which permit the generation of marker free transgenic plants, i.e. the selectable or scorable marker gene is lost at a certain stage of plant development or plant breeding. This can be achieved by, for example cotransformation (Lyznik, Plant Mol. Biol. 13 (1989), 151-161; Peng, Plant Mol. Biol. 27 (1995), 91-104) and/or by using systems which utilize enzymes capable of promoting homologous recombination in plants (see; e.g., WO97/08331; Bayley, Plant Mol. Biol. 18 (1992), 353-361); Lloyd, Mol. Gen. Genet. 242 (1994), 653-

657; Maeser, Mol. Gen. Genet. 230 (1991), 170-176; Onouchi, Nucl. Acids Res. 19 (1991), 6373-6378). Methods for the preparation of appropriate vectors are described by, e.g., Sambrook (Molecular Cloning; A Laboratory Manual, 2nd Edition (1989); Cold Spring Harbor Laboratory Press, Cold Spring Harbor, N.Y.).

Suitable strains of *Agrobacterium tumefaciens* and vectors as well as transformation of *Agrobacteria* and appropriate growth and selection media are well known to those skilled in the art and are described in the prior art (GV3101 (pMK90RK), Konez, Mol. Gen. Genet. 204 (1986), 383-396; C58C1 (pGV 3850kan), Deblaere, Nucl. Acid Res. 13 (1985), 4777; Bevan, Nucleic. Acid Res. 12(1984), 8711; Konez, Proc. Natl. Acad. Sci. USA 86(1989), 8467-8471; Konez, Plant Mol. Biol. 20 (1992), 963-976; Koncz, Specialized vectors for gene tagging and expression studies. In: Plant Molecular Biology Manual Vol 2, Gelvin and Schilperoort (Eds.), Dordrecht, The Netherlands: Kluwer Academic Publ. (1994), 1-22;EP-A-120 516; Hoekema: The Binary Plant Vector System, Offsetdrukkerij Kanters B.V., Alblasserdam (1985), Chapter V, Fraley, Crit. Rev. Plant. Sci., 4, 1-46; An, EMBO J. 4 (1985), 277-287). Although the use of *Agrobacterium tumefaciens* is preferred in the method of the invention, other *Agrobacterium* strains, such as *Agrobacterium rhizogenes*, may be used, for example if a phenotype conferred by said strain is desired.

Methods for the transformation using biolistic methods are well known to the person skilled in the art; see, e.g., Wan, Plant Physiol. 104 (1994), 37-48; Vasil, Biotechnology 11 (1993), 1553-1558 and Christou (1996) Trends in Plant Science 1, 423-431. Microinjection can be performed as described in Potrykus and Spangenberg (eds.), Gene Transfer To Plants. Springer Verlag, Berlin, N.Y. (1995).

The transformation of most dicotyledonous plants is possible with the methods described above. But also for the transformation of monocotyledonous plants several successful transformation techniques have been developed. These include the transformation using biolistic methods as, e.g., described above as well as protoplast transformation, electroporaton of partially permeabilized cells, introduction of DNA using glass fibers, etc. Transgenic plant tissue and plants can be regenerated by methods well known in the art (Sambrook et al., 1989).

In general, the plants, plant cells and plant tissue which can be modified with a recombinant DNA molecule or vector according to the invention can be derived from any desired plant species. They can be monocotyledonous plants or dicotyledonous plants, preferably they belong to plant species of interest in agriculture. wood culture or horticulture interest, such as crop plants (e.g. maize, rice, barley, wheat, rye, oats etc.), potatoes, oil producing plants (e.g. oilseed rape, sunflower, peanut, soybean, etc.), cotton, sugar beet, sugar cane, leguminous plants (e.g. beans, peas etc.), wood producing plants, preferably trees, etc.

Thus, the present invention relates also to transgenic plant cells which contain a nucleic acid molecule as defined above or a recombinant DNA molecule or vector according to the invention wherein the nucleic acid molecule is foreign to the transgenic plant cell. By "foreign" it is meant that the nucleic acid molecule is either heterologous with respect to the plant cell, this means derived from a cell or organism with a different genomic background, or is homologous with respect to the plant cell but located in a different genomic environment than the naturally occurring counterpart of said nucleic acid molecule. This means that, if the nucleic acid molecule is homologous with respect to the plant cell, it is not located in its natural location in the genome of said plant cell when stably integrated into the genome, in particular it is surrounded by different genes. In this case the nucleic acid molecule may be either under the control of its own promoter or under the control of a heterologous promoter. The nucleic acid molecule, vector or recombinant DNA molecule according to the invention which is present in the plant cell may either be integrated into the genome of the plant cell or it may be maintained in some form extra-chromosomally.

Furthermore, the present invention relates to transgenic plants or plant tissue comprising plant cells of the invention or obtainable by the above described method. Preferably, the transgenic plant of the invention displays an increased or reduced conductance of stomata and/or the water consumption is increased or reduced as compared to wild type plants.

In yet another aspect, the invention also relates to harvestable parts and to propagation material of the transgenic plants according to the invention which contain transgenic plant cells described above, i.e. at least one recombinant DNA molecule or vector according to the invention and/or which are derived from the above described plants. Harvestable parts can be in principle any useful parts of a plant, for example, leaves, stems, flowers, fruit, seeds, roots etc. Propagation material Includes, for example, seeds, fruits, cuttings, seedlings, tubers, rootstocks etc.

Furthermore, the present invention relates to a method of selection of plants, comprising treating the transgenic plant of the present invention with fusicoccin or with another ligand as identified, developed or produced by any of the methods of the present invention. In general, this method comprises growing a recombinant plant which is capable of expressing a mutant PMA or 14-3-3 protein. When treated with a ligand; e.g. fusicocein; the recombinant plant will be insensitive to the ligand, while plants without the specific mutation will display ligand binding and increased proton pump activity of PMA resulting in a dehydration of said plant. Therefore, this method allows to grow the recombinant plant in the presence of seeds of other plants which will dry-up after treatment with fusicoccin.

It is another aspect of the present invention to provide a device for developing a ligand for the complex of PMA and 14-3-3 comprising (a) a computer readable medium comprising the recombinant nucleotide sequence of the present invention, any of the crystal structure of the present invention or the structural coordinates of table 4; and (b) a computer program for the display of the ligand and the protein or a fragment thereof; and optionally (c) software for the evaluation of potential ligands or proteins.

It is yet another aspect of the present invention to provide the use of the device of the present invention for modelling a ligand or a protein of the ternary complex of 14-3-3, PMA and ligand.

Figure 2:
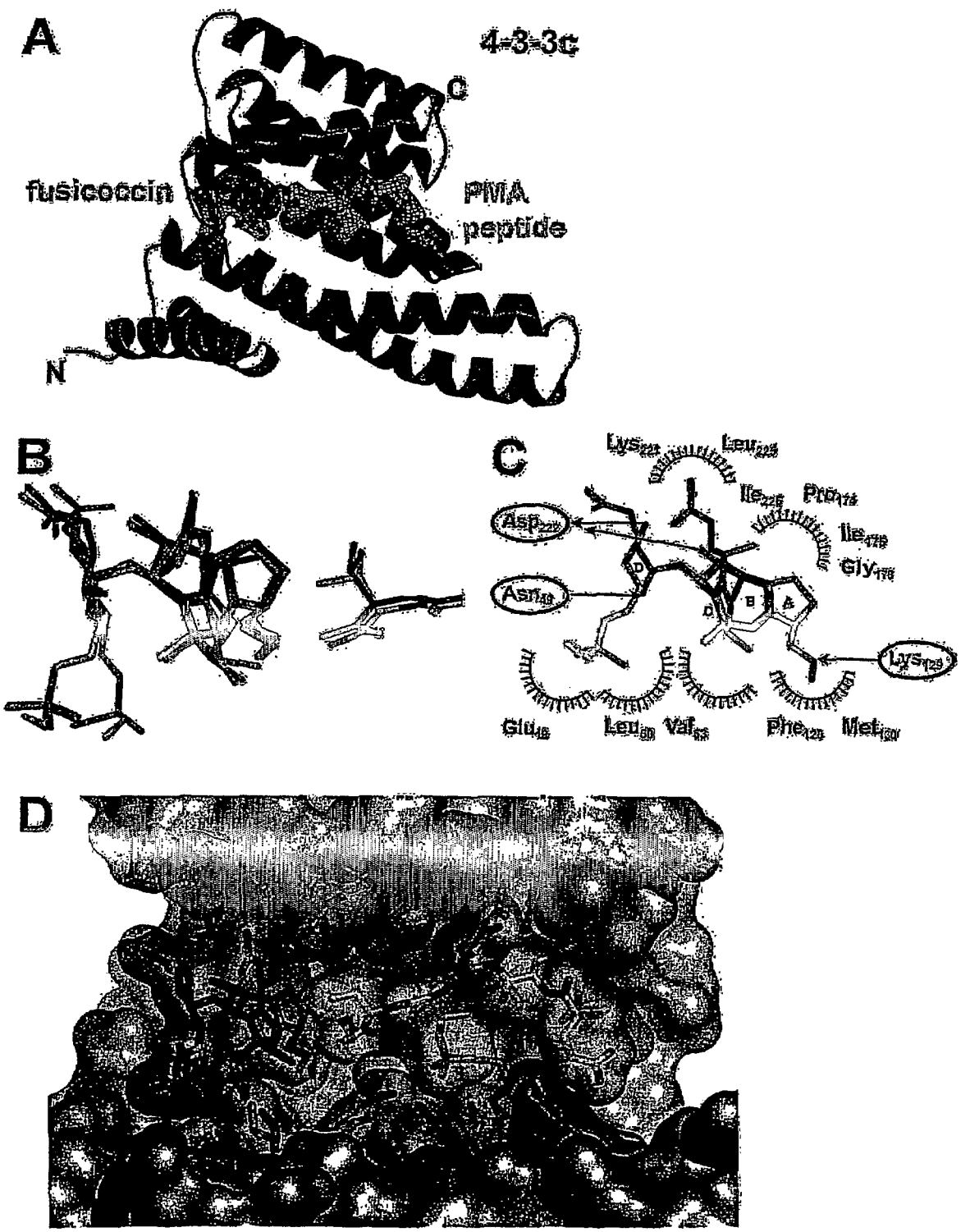

FIG. 2: The ternary 14-3-3-FC-peptide complex. (A) Ribbon diagram of a 14-3-3 monomer with both peptide and FC in the active site; the corresponding $F_o$-$F_c$ OMIT maps were contured at the 2.0σ level. (B) Superimposition of peptide and FC from the binary and ternary complexes, respectively. Also shown is the structure of unbound FC determined by NMR (A. Ballio et al. *Phytochemistry* 30, 137 (1991); A. Ballio et al. *Experimentia,* 24, 631 (1968).). (C) Contacts between the toxin and the 14-3-3, with symbols as in FIG. 2B, carbon and oxygen atoms are shown. (D) Van der Waals surface representation of the active site, showing the close interaction between the two ligands and how they fill the cavity of 14-3-3.

Figure 3:
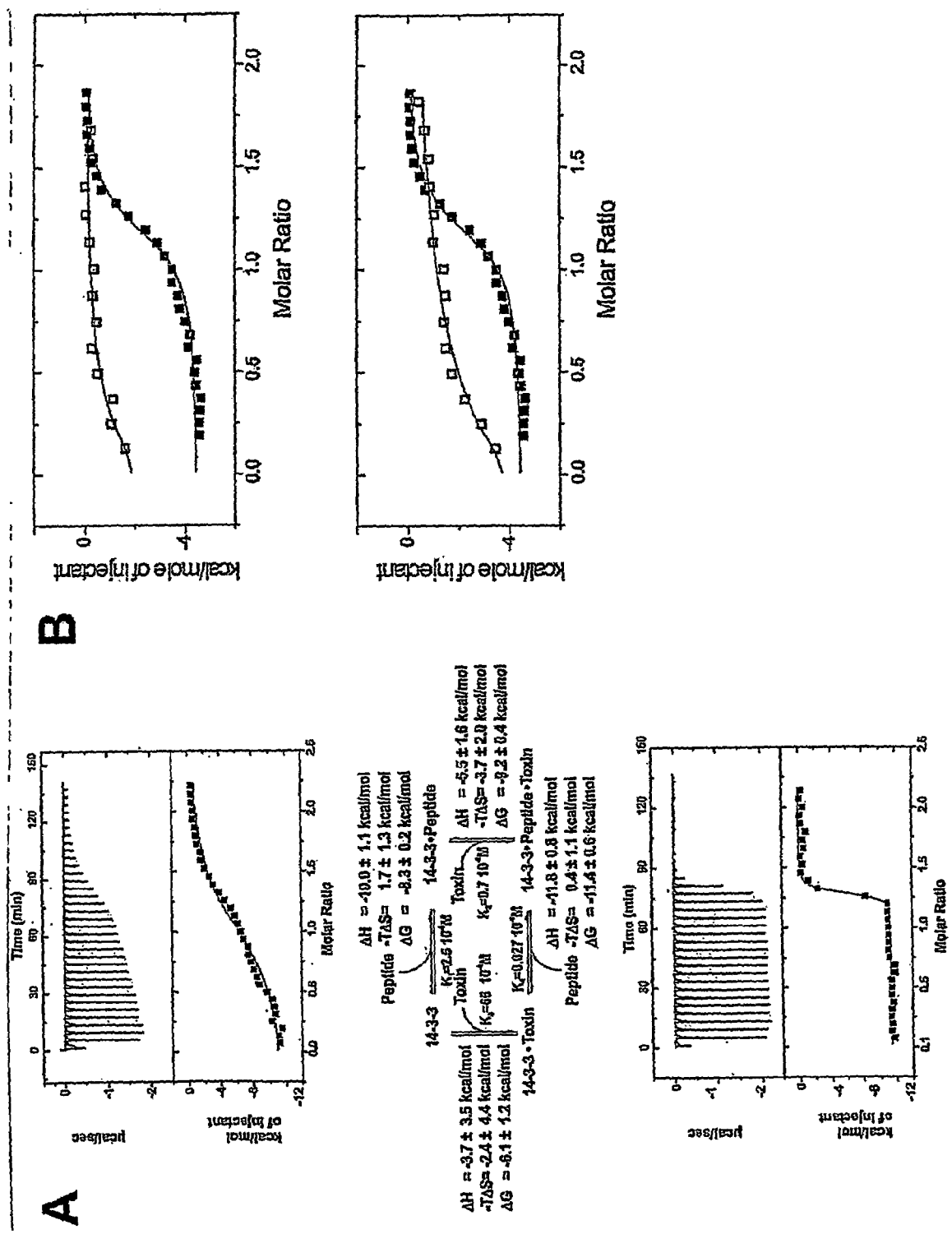

FIG. 3: Thermodynamic measurements and steric requirements of the fusicoccin effect. (A) Thermodynamic cycle of the coupled equilibrium between the three components, and the corresponding experimental values for each equilibrium, center. Two examples for the ITC measurements, which show that the binding between 14-3-3 and the peptide (top panel) is much tighter, as seen by the sharp increase in signal (lower panel) after saturation of the binding site with FC. (B) Compared to the standard peptide QSYpTV (residue 925-956 of SEQ ID NO: 2, with a phosphothreonine at residue 955) (closed symbols), modification (open symbols) by the addition of a C-terminal Pro (top panel) or removal of Val (bottom panel) drastically weakens the binding.

Figure 4:
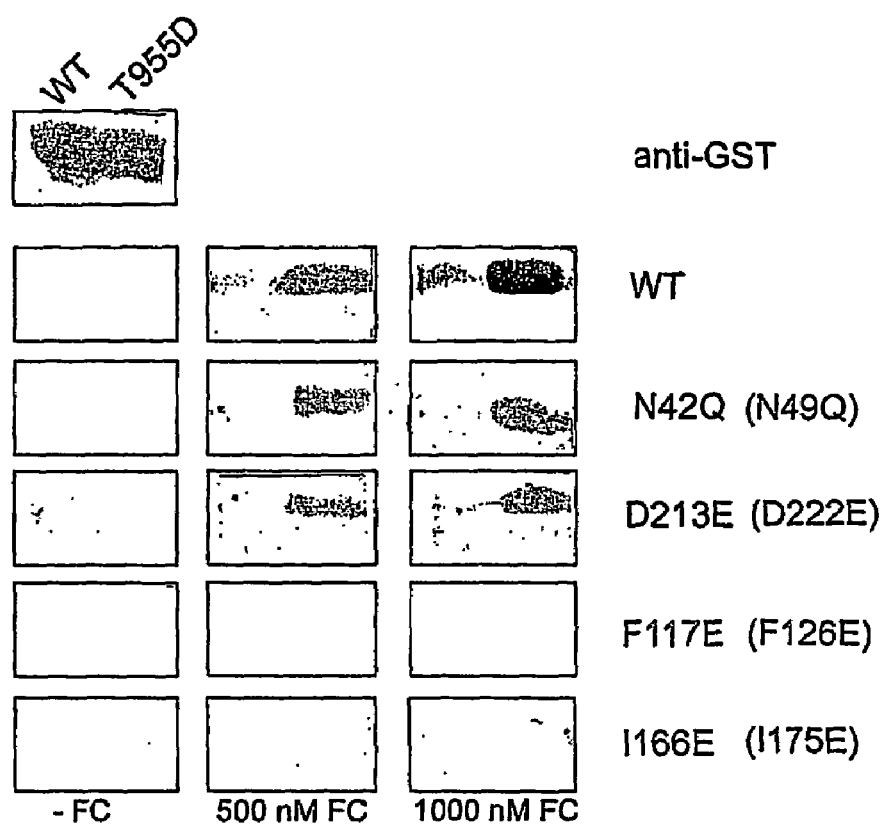

FIG. 4: Far western blot experiment. The figure shows the results of an overlay experiment in the presence of 0, 500 nM and 1000 nM fusicoccin. This assay was performed with the human homolog of tobacco 14-3-3 the corresponding positions of which are shown in brackets.

Figure 5:
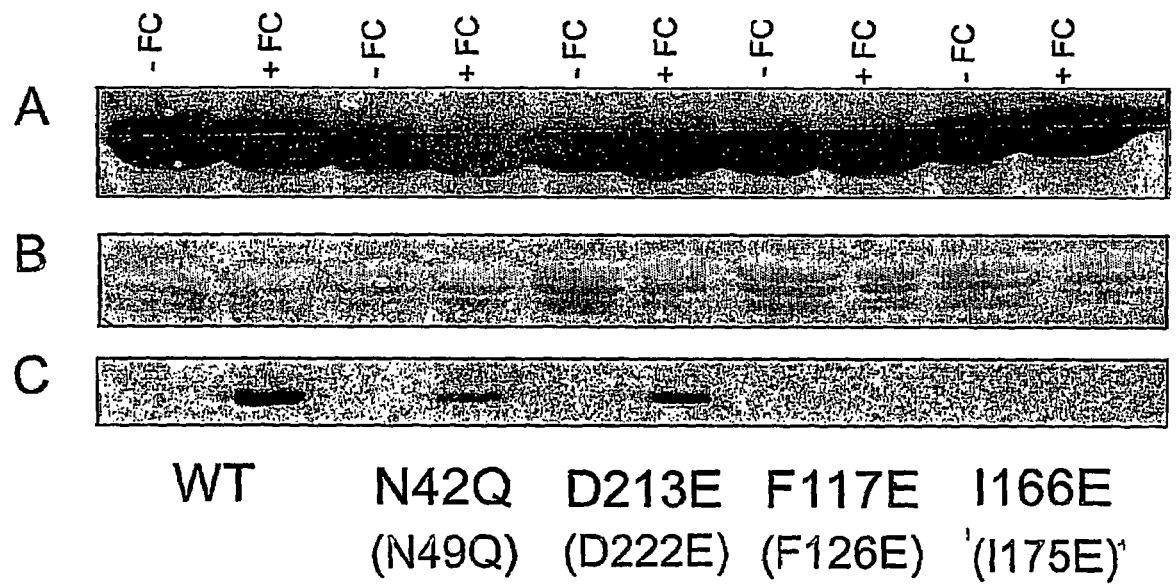

FIG. 5: GST-pulldown experiment. Panel A shows the amount of 14-3-3 protein (input) in an immuno-detection with RGS-His$_6$, panel B shows the amount of GST-PMA2-CT66 (input) and panel C shows the amount of bound 14-3-3 protein after several washing steps. GST-PMA2-CT66 is a GST-tagged construct containing the 66 carboxyterminal residues of PMA2 (SEQ ID NO: 2. This assay was performed with the human homolog of tobacco 14-3-3 the corresponding positions of which are shown in brackets.

The examples illustrate the invention:

EXAMPLE 1

Crystalisation, Data Collection and Refinement Statistics

Tobacco 14-3-3c (Gene bank AAC49892, amino acids 1-260 with an N-terminal His-tag) was expressed recombinantly in *E.coli* and purified via standard procedures. Fusicoccin was purchased from Sigma. Phosphopeptides were synthesized by Biosyntan (Berlin). Crystals were grown by the hanging drop method in solutions containing 21% PEG 400, 0.1 mM citrate buffer pH 4.7, 0.2 mM ammonium acetate (pH 7.0) and 10 mM DTE and belong to the hexagonal spacegroup P6$_5$22 with unit cell dimensions a=109.0 Å, b=109.0 Å, c=135.8 Å and one 14-3-3 monomer in the asymmetric unit. They were soaked with ligands for 4 hours (fusicoccin) or 20 minutes (peptide) in precipitant solution supplemented to 30% PEG 400 and cryoprotectant (precipitant solution supplemented to 35% PEG 400, 8% Isopropanol) prior to freezing in liquid N$_2$. Native 14-3-3c crystals were measured at the X13 beamline at DESY, Hamburg (wavelength 0.8459 Å). Complex crystals were measured at the ID29 beamline of ESRF, Grenoble (0.979 Å). Data was processed with XDS [W. Kabsch, *J. Appl Cryst.* 21, 67 (1988)] and refined with CNS [A. T. Brunger et al. *Acta Cryst. D* 54, 905 (1998)]. Structure was solved with AmoRe [J. Navaza, *Acta Crystallogr.* A 50, 157 (1994)]. Maps where analyzed with Xfit [D. E. McRee, J. Struct. Biol. 125, 156 (1999)] and the structures validated with PROCHECK[R. A. Laskowski, M. W. MacArthur, *J. Appl. Crystallogr.* 26, 283 (1993)] and WHATCHECK [R. W. W. Hooft, G. Vriend, C. Sander, E. E. Abola, *Nature* 381, 272 (1996)]. Models contain residues 5-239 of 14-3-3c. Some amino acids in the loop between helix eight and nine could not be observed in the electron density maps of the structures. 99% of the residues in all structures were located in the most-favourable and favourable (phi, psi) areas of the Rarnachandran diagram. Models have main chain and side chain structural parameters consistently equal or better than those expected from their respective resolution.

Structures of binary and ternary complexes of 14-3-3c with the phosphopeptide Gln-Ser-Tyr-pThr-Val (QSYpTV)(residues 952-956 of SEQ ID NO: 2, with a phosphothreonine at residue 955), conserved in plant H$^+$-ATPases, and with FC were determined using the unliganded 14-3-3c as a starting model. Data for the crystal structure analysis of the different complexes are summarized in Table 3.

TABLE 3

Data Collection and Refinement Statistics. Data for the outermost shell are shown in parenthesis. rmsd, Root mean square deviations from ideal geometry.

|  | NATIVE 14-3-3c | PEPTIDE COMPLEX | TOXIN COMPLEX | TERNARY COMPLEX |
|---|---|---|---|---|
| MEASURED REFLEXIONS | 205883 | 131256 | 74020 | 56531 |
| UNIQUE REFLEXIONS | 15163 | 21328 | 14444 | 13170 |
| RESOLUTION (Å) | 10-2.6(2.7-2.6) | 10-2.3(2.4-2.3) | 10-2.6(2.7-2.6) | 10-2.7(2.8-2.7) |
| COMPLETENESS (%) | 99.1(99.4) | 95.5(98.1) | 96.5(98.3) | 96.8(97.2) |
| I/σ | 33.1(8.2) | 18.1(4.0) | 14.1(5.0) | 14.0(4.2) |
| $R_{SYM}$*(%) | 5.6(35.4) | 5.8(35.1) | 7.3(30.1) | 6.6(30.0) |
| $R_{CRYST}$†(%) | 22.2 | 21.0 | 22.2 | 22.4 |
| $R_{FREE}$‡(%) | 25.7 | 24.4 | 25.8 | 26.3 |
| PROTEIN ATOMS | 1838 | 1875 | 1846 | 1892 |
| SOLVENT MOLECULES | 68 | 176 | 71 | 62 |

TABLE 3-continued

Data Collection and Refinement Statistics. Data for the outermost shell are shown in parenthesis. rmsd, Root mean square deviations from ideal geometry.

|  | NATIVE 14-3-3c | PEPTIDE COMPLEX | TOXIN COMPLEX | TERNARY COMPLEX |
|---|---|---|---|---|
| RMSD OF BOND LENGTHS (Å) | 0.007 | 0.02 | 0.007 | 0.008 |
| RMSD OF BOND ANGLES (°) | 1.2 | 2.0 | 1.2 | 1.2 |

*$R_{sym} = \Sigma |I_{hi} - <I_{hi}>|/\Sigma I_{hi}$, where $I_{hi}$ is the scaled observed intensity of the ith symmetry-related observation of the reflection h and $<I_{hi}>$ the mean value.
†$R_{cryst} = \Sigma_h |F_{oh} - F_{ch}|/\Sigma_h F_{oh}$, where $F_{oh}$ and $F_{ch}$ are the observed and calculated structure factor amplitudes for reflection h.
‡Calculated as $R_{cryst}$ with 5% of the data omitted from structure refinement

EXAMPLE 2

Three-dimensional Organization of 14-3-3 and PMA

Figure 1:
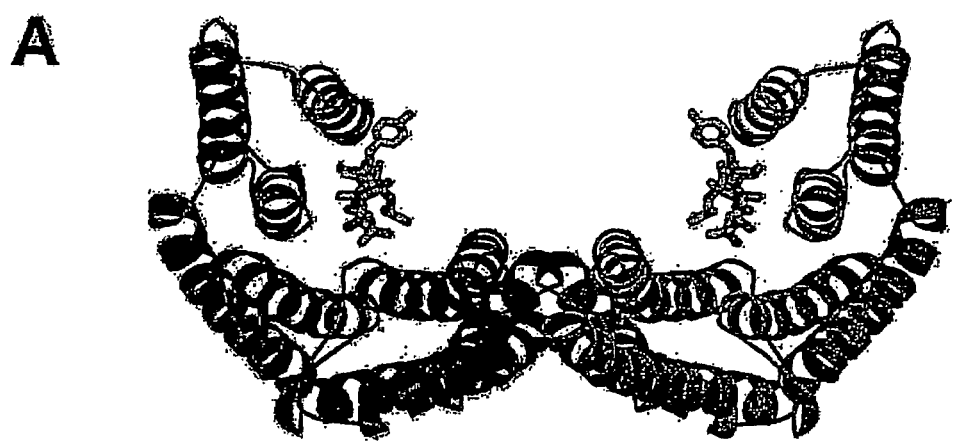
FIG. 1: Phosphopeptide binding to plant 14-3-3. (A) Ribbon plot of the dimeric tobacco 14-3-3c protein bound to the peptide Gln-Ser-Tyr-pThr-Val (residue 925-956 of SEQ ID NO: 2, with a phosphorylated threonine), which constitutes the C-terminal end of PMA2, a H$^+$-ATPase isoform from *N. plumbaginifolia*. (B) scheme of the interaction between peptide and protein where half circles indicate residues forming van der Waals interactions, arrows denote hydrophilic interactions between the indicated residues and the corresponding atoms of the peptide. Nomenclature in human 14-3-3 of some conserved aminoacids is indicated in parenthesis. (C) Superimposition of phosphopeptides from various 14-3-3 complex structures. The present structure is shown with that of 14-3-3ζ with either serotonine N-acetyl transferase (AANAT) (T. Obsil, R. Ghirlando, D. C. Klein, S. Ganguly, F. Dyda, Cell 105, 257 (2001)) or with model peptides (K. Rittinger et al. Mol. Cell, 4, 153 (1999); M. B. Yaffe et al. Cell 91, 961 (1997).).
Figure 1:
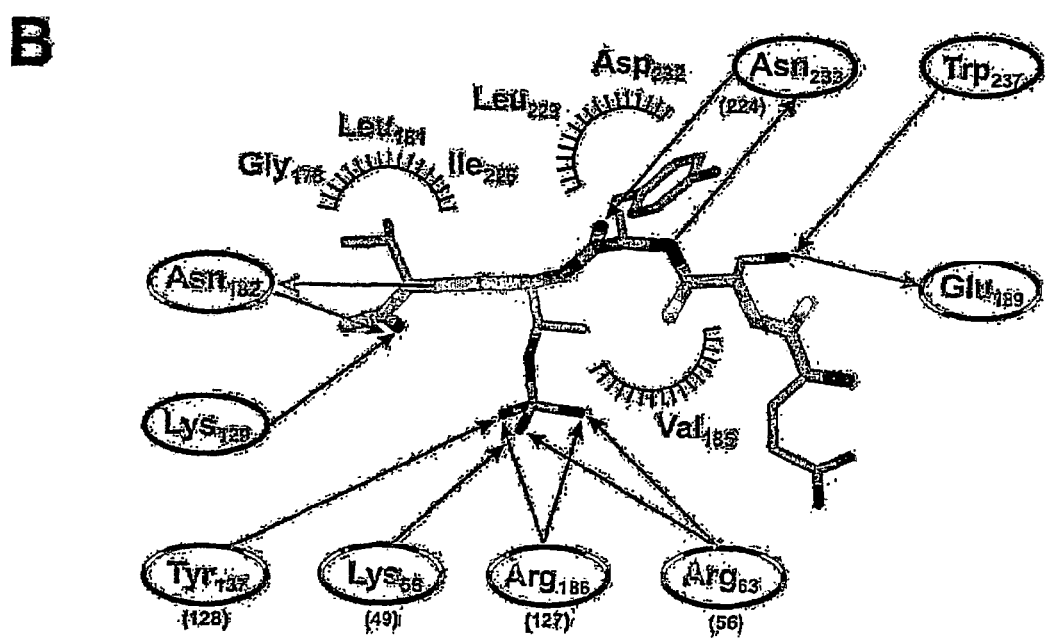
Figure 1:
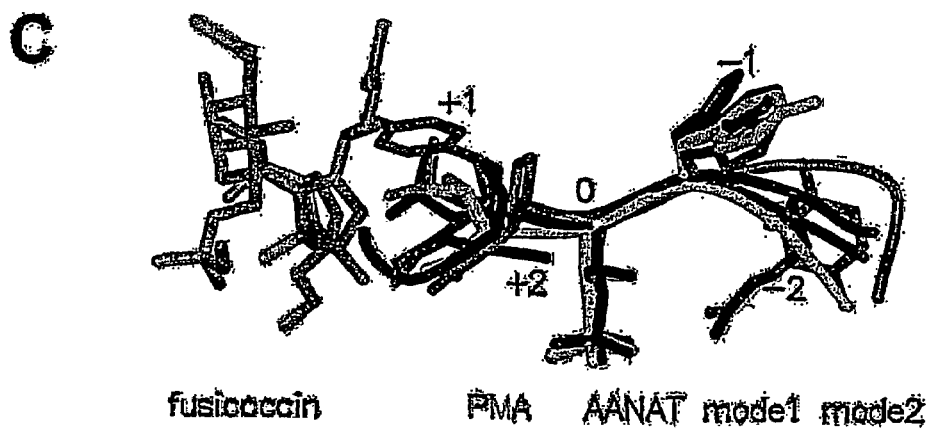

The structure of tobacco 14-3-3c was solved by molecular replacement using phases from human 14-3-3ζ (D. Liu et al. Nature 376, 191 (1995)), and shows 235 from a total of 260 residues. 14-3-3c forms the canonical dimer found in mammalian 14-3-3 proteins, with a root mean square deviation of the backbone Cα-atoms of 0.9 Å as compared to the human 14-3-3ζ (see table 3 and 4). Each monomer consists of nine antiparallel helices that arrange in form of an "U" to build a large central binding cavity (FIG. 1a). Structures of binary and ternary complexes of 14-3-3c with the phosphopeptide Gln-Ser-Tyr-pThr-Val (QSYpTV), (residues 952-956 of SEQ ID NO: 2, with a phosphothreonine at residue 955), conserved in plant H+-ATPFases, and with FC were determined using the unliganded 14-3-3c as a starting model. Data for the crystal structure analysis of the different complexes are summarized in Table 3, the coordinate file of the structure of 14-3-3 in conjunction with a fragment of PMA and fusicoccin is shown in table 4.

Table 4: Table of coordinates of atoms of the crystal structure of the ternary complex between Nicotiana tabacum 14-3-3 isoform c (SEQ ID NO: 1), Fusicoccin and a phosporylated pentapeptide from the C-terminus of PMA2 from NICOTIANA PLUMBAFINIFOLIA (residues 952-956 of SEQ ID NO: 2, with a phosphothreonine at residue 955) in PDB (protein data bank) formate. For explanation of PDB format see PDB-homepage www.resb.org/pdb. Table contains the atomic coordinates of non-hydrogen atoms of the said complex, as they were identified by x-ray crystallographical methods in the asymmetric unit of the crystals of claim XY solved at synctotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

TABLE 4

Table of coordinates of atoms of the crystal structure of the ternary complex between Nicotiana tabacum 14-3-3 isoform c (SEQ ID NO:1), Fusicoccin and a phosphorylated pentapeptide from the C-terminus of PMA2 from NICOTIANA PLUMBAGINIFOLIA (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| HEADER | | PROTEIN BINDING | 12-DEC-02 | 109F |
|---|---|---|---|---|
| TITLE | | STRUCTURAL VIEW OF A FUNGAL TOXIN ACTING ON A 14-3-3 | | |
| TITLE | 2 | REGULATORY COMPLEX | | |
| COMPND | | MOL_ID: 1; | | |
| COMPND | 2 | MOLECULE: 14-3-3-LIKE PROTEIN C; | | |
| COMPND | 3 | CHAIN: A; | | |
| COMPND | 4 | ENGINEERED: YES; | | |
| COMPND | 5 | OTHER_DETAILS: GENE BANK AAC49892; | | |
| COMPND | 6 | MOL_ID: 2; | | |
| COMPND | 7 | MOLECULE: PLASMA MEMBRANE H+ ATPASE; | | |
| COMPND | 8 | FRAGMENT: RESIDUES 436-440; | | |
| COMPND | 9 | CHAIN: P | | |
| SOURCE | | MOL_ID: 1; | | |
| SOURCE | 2 | ORGANISM_SCIENTIFIC: NICOTIANA TABACUM; | | |
| SOURCE | 3 | ORGANISM_COMMON: COMMON TOBACCO; | | |
| SOURCE | 4 | EXPRESSION_SYSTEM: ESCHERICHIA COLI; | | |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

```
SOURCE     5   MOL_ID: 2;
SOURCE     6   SYNTHETIC: YES;
SOURCE     7   ORGANISM_SCIENTIFIC: NICOTIANA PLUMBAGINIFOLIA;
SOURCE     8   ORGANISM_COMMON: LEADWORT-LEAVED TOBACCO;
KEYWDS         FUSICOCCIN, 14-3-3 FAMILY, ACTIVATING DRUG,
KEYWDS     2   PLANT PLASMA MEMBRANE (H+) ATPASE
EXPDTA         X-RAY DIFFRACTION
AUTHOR         M. WURTELE, C. JELICH-OTTMANN, A. WITTINGHOFER, C. OECKING
REVDAT     1   10-FEB-03 109F 0
JRNL           AUTH    M. WURTELE, C. JELICH-OTTMANN, A. WITTINGHOFER,
JRNL           AUTH 2  C. OECKING
JRNL           TITL    STRUCTURAL VIEW OF A FUNGAL TOXIN ACTING ON A
JRNL           TITL 2  14-3-3 REGULATORY COMPLEX
JRNL           REF     TO BE PUBLISHED
JRNL           REFN
REMARK     2
REMARK     2   RESOLUTION. 2.7 ANGSTROMS.
REMARK     3
REMARK     3   REFINEMENT.
REMARK     3   PROGRAM    : CNS 1.1
REMARK     3   AUTHORS    : BRUNGER, ADAMS, CLORE, DELANO, GROS,
REMARK     3                GROSSE-KUNSTLEVE, JIANG, KUSZEWSKI, NILGES,
REMARK     3                PANNU, READ, RICE, SIMONSON, WARREN
REMARK     3
REMARK     3   REFINEMENT TARGET: NULL
REMARK     3
REMARK     3   DATA USED IN REFINEMENT.
REMARK     3   RESOLUTION RANGE HIGH (ANGSTROMS)     : 2.7
REMARK     3   RESOLUTION RANGE LOW (ANGSTROMS)      : 19.21
REMARK     3   DATA CUTOFF (SIGMA(F))                : 0.0
REMARK     3   OUTLIER CUTOFF HIGH (RMS(ABS(F))      : 541374.11
REMARK     3   COMPLETENESS (WORKING + TEST) (%)     : 97.3
REMARK     3   NUMBER OF REFLECTIONS                 : 13179
REMARK     3
REMARK     3   FIT TO DATA USED IN REFINEMENT.
REMARK     3   CROSS-VALIDATION METHOD               : THROUGHOUT
REMARK     3   FREE R VALUE TEST SET SELECTION       : RANDOM
REMARK     3   R VALUE (WORKING SET)                 : 0.224
REMARK     3   FREE R VALUE                          : 0.263
REMARK     3   FREE R VALUE TEST SET SIZE (%)        : 5.0
REMARK     3   FREE R VALUE TEST SET COUNT           : 658
REMARK     3   ESTIMATED ERROR OF FREE R VALUE       : 0.010
REMARK     3
REMARK     3   FIT IN THE HIGHEST RESOLUTION BIN.
REMARK     3   TOTAL NUMBER OF BINS USED                           : 5
REMARK     3   BIN RESOLUTION RANGE HIGH                      (A)  : 2.7
REMARK     3   BIN RESOLUTION RANGE LOW                       (A)  : 2.87
REMARK     3   BIN COMPLETENESS        (WORKING + TEST) (%)        : 97.6
REMARK     3   REFLECTIONS IN BIN              (WORKING SET)       : 2407
REMARK     3   BIN R VALUE                     (WORKING SET)       : 0.305
REMARK     3   BIN FREE R VALUE                                    : 0.352
REMARK     3   BIN FREE R VALUE TEST SET SIZE                 (%)  : 4.9
REMARK     3   BIN FREE R VALUE TEST SET COUNT       : 106
REMARK     3   ESTIMATED ERROR OF BIN FREE R VALUE   : 0.034
REMARK     3
REMARK     3   NUMBER OF NON-HYDROGEN ATOMS USED IN REFINEMENT.
REMARK     3   PROTEIN ATOMS              : 1881
REMARK     3   NUCLEIC ACID ATOMS         : 0
REMARK     3   HETEROGEN ATOMS            : 59
REMARK     3   SOLVENT ATOMS              : 62
REMARK     3
REMARK     3   B VALUES.
REMARK     3   FROM WILSON PLOT (A2)      : 47.6
REMARK     3   MEAN B VALUE (OVERALL, A2) : 60.4
REMARK     3   OVERALL ANISOTROPIC B VALUE.
```

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

```
REMARK    3  B11 (A2): 11.15
REMARK    3  B22 (A2): 11.15
REMARK    3  B33 (A2): -22.30
REMARK    3  B12 (A2): 8.87
REMARK    3  B13 (A2): 0.00
REMARK    3  B23 (A2): 0.00
REMARK    3
REMARK    3  ESTIMATED COORDINATE ERROR.
REMARK    3  ESD FROM LUZZATI PLOT                          (A)  : 0.36
REMARK    3  ESD FROM SIGMAA                                (A)  : 0.39
REMARK    3  LOW RESOLUTION CUTOFF                          (A)  : 5.00
REMARK    3
REMARK    3  CROSS-VALIDATED ESTIMATED COORDINATE ERROR.
REMARK    3  ESD FROM C-V LUZZATI PLOT                      (A)  : 0.40
REMARK    3  ESD FROM C-V SIGMAA                            (A)  : 0.38
REMARK    3
REMARK    3  RMS DEVIATIONS FROM IDEAL VALUES.
REMARK    3  BOND LENGTHS                                   (A)      : 0.007
REMARK    3  BOND ANGLES                                    (DEGREES) : 1.2
REMARK    3  DIHEDRAL ANGLES                                (DEGREES) : 18.6
REMARK    3  IMPROPER ANGLES                                (DEGREES) : 0.82
REMARK    3
REMARK    3  ISOTROPIC THERMAL MODEL: NULL
REMARK    3
REMARK    3  ISOTROPIC THERMAL FACTOR RESTRAINTS. RMS SIGMA
REMARK    3   MAIN-CHAIN BOND                               (A2) : NULL; NULL
REMARK    3   MAIN-CHAIN ANGLE                              (A2) : NULL; NULL
REMARK    3   SIDE-CHAIN BOND                               (A2) : NULL; NULL
REMARK    3   SIDE-CHAIN ANGLE                              (A2) : NULL; NULL
REMARK    3
REMARK    3  BULK SOLVENT MODELING.
REMARK    3   METHOD USED   : FLAT MODEL
REMARK    3   KSOL          : 0.352667
REMARK    3   BSOL          : 49.7886
REMARK    3
REMARK    3  NCS MODEL: NONE
REMARK    3
REMARK    3  NCS RESTRAINTS. RMS SIGMA/WEIGHT
REMARK    3   GROUP 1 POSITIONAL            (A):  NULL; NULL
REMARK    3   GROUP 1 B-FACTOR              (A2): NULL; NULL
REMARK    3
REMARK    3  PARAMETER FILE 1    : NULL
REMARK    3  TOPOLOGY FILE 1     : NULL
REMARK    3
REMARK    3  OTHER REFINEMENT REMARKS: NULL
REMARK    4
REMARK    4  109F COMPLIES WITH FORMAT V. 2.3, 09-JULY-1998
REMARK  100
REMARK  100  THIS ENTRY HAS BEEN PROCESSED BY EBI ON 10-FEB-2003.
REMARK  100  THE EBI ID CODE IS EBI-11876.
REMARK  200
REMARK  200  EXPERIMENTAL DETAILS
REMARK  200   EXPERIMENT TYPE                       : X-RAY DIFFRACTION
REMARK  200   DATE OF DATA COLLECTION               : 15-DEC-2001
REMARK  200   TEMPERATURE (KELVIN)                  : 100
REMARK  200   PH                                    : 6.4
REMARK  200   NUMBER OF CRYSTALS USED               : 1
REMARK  200
REMARK  200   SYNCHROTRON (Y/N)                     : Y
REMARK  200   RADIATION SOURCE                      : ESRF BEAMLINE ID29
REMARK  200   BEAMLINE                              : ID29
REMARK  200   X-RAY GENERATOR MODEL                 : NULL
REMARK  200   MONOCHROMATIC OR LAUE (M/L)           : M
REMARK  200   WAVELENGTH OR RANGE (A)               : 0.979
REMARK  200   MONOCHROMATOR                         : NULL
```

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

```
REMARK   200  OPTICS                                   : NULL
REMARK   200
REMARK   200  DETECTOR TYPE *                          : NULL
REMARK   200  DETECTOR MANUFACTURER                    : NULL
REMARK   200  INTENSITY-INTEGRATION SOFTWARE           : XDS
REMARK   200  DATA SCALING SOFTWARE                    : XDS
REMARK   200
REMARK   200  NUMBER OF UNIQUE REFLECTIONS             : 13170
REMARK   200  RESOLUTION RANGE HIGH (A)                : 2.7
REMARK   200  RESOLUTION RANGE LOW (A)                 : 10
REMARK   200  REJECTION CRITERIA (SIGMA(I))            : 2
REMARK   200
REMARK   200  OVERALL.
REMARK   200  COMPLETENESS FOR RANGE (%)               : 96.8
REMARK   200  DATA REDUNDANCY                          : 4.3
REMARK   200  R MERGE (I)                              : 0.066
REMARK   200  R SYM (I)                                : NULL
REMARK   200  <I/SIGMA(I)> FOR THE DATA SET            : 14.0
REMARK   200
REMARK   200  IN THE HIGHEST RESOLUTION SHELL.
REMARK   200  HIGHEST RESOLUTION SHELL, RANGE HIGH (A): 2.7
REMARK   200  HIGHEST RESOLUTION SHELL, RANGE LOW (A): 2.8
REMARK   200  COMPLETENESS FOR SHELL (%)               : 97.2
REMARK   200  DATA REDUNDANCY IN SHELL                 : NULL
REMARK   200  R MERGE FOR SHELL (I)                    : 0.30
REMARK   200  R SYM FOR SHELL (I)                      : NULL
REMARK   200  <I/SIGMA(I)> FOR SHELL                   : 4.2
REMARK   200
REMARK   200  DIFFRACTION PROTOCOL: SINGLE WAVELENGTH
REMARK   200  METHOD USED TO DETERMINE THE STRUCTURE: MOLECULAR REPLACEMENT
REMARK   200  SOFTWARE USED: AMORE
REMARK   200  STARTING MODEL: PDB ENTRY 1A4O
REMARK   200
REMARK   200  REMARK: NULL
REMARK   280
REMARK   280  CRYSTAL
REMARK   280  SOLVENT CONTENT, VS (%): N/A
REMARK   280  MATTHEWS COEFFICIENT, VM (ANGSTROMS3/DA): NULL
REMARK   280
REMARK   280  CRYSTALLIZATION CONDITIONS: PEG400, CITRAT PH 4.7,
REMARK   280  0.2 MM AMMONIUM ACETATE
REMARK   290
REMARK   290  CRYSTALLOGRAPHIC SYMMETRY
REMARK   290  SYMMETRY OPERATORS FOR SPACE GROUP: P 65 2 2
REMARK   290
REMARK   290      SYMOP    SYMMETRY
REMARK   290      NNNMMM   OPERATOR
REMARK   290       1555    X, Y, Z
REMARK   290       2555    -Y, X - Y, 2/3 + Z
REMARK   290       3555    Y - X, -X, 1/3 + Z
REMARK   290       4555    -X, -Y, 1/2 + Z
REMARK   290       5555    Y, Y - X, 1/6 + Z
REMARK   290       6555    X - Y, X, 5/6 + Z
REMARK   290       7555    Y, X, 2/3 - Z
REMARK   290       8555    X - Y, -Y, -Z
REMARK   290       9555    -X, Y - X, 1/3 - Z
REMARK   290      10555    -Y, -X, 1/6 - Z
REMARK   290      11555    Y - X, Y, 1/2 - Z
REMARK   290      12555    X, X - Y, 5/6 - Z
REMARK   290
REMARK   290  WHERE NNN -> OPERATOR NUMBER
REMARK   290    MMM -> TRANSLATION VECTOR
REMARK   290
REMARK   290  CRYSTALLOGRAPHIC SYMMETRY TRANSFORMATIONS
REMARK   290  THE FOLLOWING TRANSFORMATIONS OPERATE ON THE ATOM/HETATM
```

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

```
REMARK   290 RECORDS IN THIS ENTRY TO PRODUCE CRYSTALLOGRAPHICALLY
REMARK   290 RELATED MOLECULES.
REMARK   290 SMTRY1    1   1.000000   0.000000   0.000000    0.00000
REMARK   290 SMTRY2    1   0.000000   1.000000   0.000000    0.00000
REMARK   290 SMTRY3    1   0.000000   0.000000   1.000000    0.00000
REMARK   290 SMTRY1    2  -0.500000  -0.866025   0.000000    0.00000
REMARK   290 SMTRY2    2   0.866025  -0.500000   0.000000    0.00000
REMARK   290 SMTRY3    2   0.000000   0.000000   1.000000   90.46667
REMARK   290 SMTRY1    3  -0.500000   0.866025   0.000000    0.00000
REMARK   290 SMTRY2    3  -0.866025  -0.500000   0.000000    0.00000
REMARK   290 SMTRY3    3   0.000000   0.000000   1.000000   45.23333
REMARK   290 SMTRY1    4  -1.000000   0.000000   0.000000    0.00000
REMARK   290 SMTRY2    4   0.000000  -1.000000   0.000000    0.00000
REMARK   290 SMTRY3    4   0.000000   0.000000   1.000000   67.85000
REMARK   290 SMTRY1    5   0.500000   0.866025   0.000000    0.00000
REMARK   290 SMTRY2    5  -0.866025   0.500000   0.000000    0.00000
REMARK   290 SMTRY3    5   0.000000   0.000000   1.000000   22.61667
REMARK   290 SMTRY1    6   0.500000  -0.866025   0.000000    0.00000
REMARK   290 SMTRY2    6   0.866025   0.500000   0.000000    0.00000
REMARK   290 SMTRY3    6   0.000000   0.000000   1.000000  113.08333
REMARK   290 SMTRY1    7  -0.500000   0.866025   0.000000    0.00000
REMARK   290 SMTRY2    7   0.866025   0.500000   0.000000    0.00000
REMARK   290 SMTRY3    7   0.000000   0.000000  -1.000000   90.46667
REMARK   290 SMTRY1    8   1.000000   0.000000   0.000000    0.00000
REMARK   290 SMTRY2    8   0.000000  -1.000000   0.000000    0.00000
REMARK   290 SMTRY3    8   0.000000   0.000000  -1.000000    0.00000
REMARK   290 SMTRY1    9  -0.500000  -0.866025   0.000000    0.00000
REMARK   290 SMTRY2    9  -0.866025   0.500000   0.000000    0.00000
REMARK   290 SMTRY3    9   0.000000   0.000000  -1.000000   45.23333
REMARK   290 SMTRY1   10   0.500000  -0.866025   0.000000    0.00000
REMARK   290 SMTRY2   10  -0.866025  -0.500000   0.000000    0.00000
REMARK   290 SMTRY3   10   0.000000   0.000000  -1.000000   22.61667
REMARK   290 SMTRY1   11  -1.000000   0.000000   0.000000    0.00000
REMARK   290 SMTRY2   11   0.000000   1.000000   0.000000    0.00000
REMARK   290 SMTRY3   11   0.000000   0.000000  -1.000000   67.85000
REMARK   290 SMTRY1   12   0.500000   0.866025   0.000000    0.00000
REMARK   290 SMTRY2   12   0.866025  -0.500000   0.000000    0.00000
REMARK   290 SMTRY3   12   0.000000   0.000000  -1.000000  113.08333
REMARK   290
REMARK   290 REMARK: NULL
REMARK   300
REMARK   300 BIOMOLECULE: 1
REMARK   300 THIS ENTRY CONTAINS THE CRYSTALLOGRAPHIC ASYMMETRIC UNIT
REMARK   300 WHICH CONSISTS OF 2 CHAIN(S). SEE REMARK 350 FOR
REMARK   300 INFORMATION ON GENERATING THE BIOLOGICAL MOLECULE(S)'.
REMARK   300
REMARK   300 QUATERNARY STRUCTURE FOR THIS ENTRY: TETRAMERIC
REMARK   350
REMARK   350 GENERATING THE BIOMOLECULE
REMARK   350 COORDINATES, FOR A COMPLETE MULTIMER REPRESENTING THE KNOWN
REMARK   350 BIOLOGICALLY SIGNIFICANT OLIGOMERIZATION STATE OF THE
REMARK   350 MOLECULE CAN BE GENERATED BY APPLYING BIOMT TRANSFORMATIONS
REMARK   350 GIVEN BELOW. BOTH NON-CRYSTALLOGRAPHIC AND
REMARK   350 CRYSTALLOGRAPHIC OPERATIONS ARE GIVEN.
REMARK   350
REMARK   350 BIOMOLECULE: 1
REMARK   350 APPLY THE FOLLOWING TO CHAINS: A, P
REMARK   350 BIOMT1    1   1.000000   0.000000   0.000000    0.00000
REMARK   350 BIOMT2    1   0.000000   1.000000   0.000000    0.00000
REMARK   350 BIOMT3    1   0.000000   0.000000   1.000000    0.00000
REMARK   350 BIOMT1    2  -1.000000   0.000000   0.000000  108.80000
REMARK   350 BIOMT2    2   0.000000   1.000000   0.000000    0.00000
REMARK   350 BIOMT3    2   0.000000   0.000000  -1.000000   67.85000
REMARK   375
REMARK   375 SPECIAL POSITION
```

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

```
REMARK   375 HOH Z 13 LIES ON A SPECIAL POSITION.
REMARK   465
REMARK   465 MISSING RESIDUES
REMARK   465 THE FOLLOWING RESIDUES WERE NOT LOCATED IN THE
REMARK   465 EXPERIMENT. (M = MODEL NUMBER; RES = RESIDUE NAME; C = CHAIN
REMARK   465 IDENTIFIER; SSSEQ = SEQUENCE NUMBER; I = INSERTION CODE.)
REMARK   465
REMARK   465   M RES C    SSSEQI
REMARK   465     MET A      1
REMARK   465     ALA A      2
REMARK   465     VAL A      3
REMARK   465     ALA A      4
REMARK   465     GLY A    216
REMARK   465     GLU A    217
REMARK   465     GLU A    218
REMARK   465     SER A    219
REMARK   465     MET A    241
REMARK   465     GLN A    242
REMARK   465     ASP A    243
REMARK   465     ASP A    244
REMARK   465     GLY A    245
REMARK   465     ALA A    246
REMARK   465     ASP A    247
REMARK   465     GLU A    248
REMARK   465     ILE A    249
REMARK   465     LYS A    250
REMARK   465     GLU A    251
REMARK   465     ASP A    252
REMARK   465     PRO A    253
REMARK   465     LYS A    254
REMARK   465     PRO A    255
REMARK   465     ASP A    256
REMARK   465     GLU A    257
REMARK   465     ALA A    258
REMARK   465     LYS A    259
REMARK   465     ASN A    260
REMARK   470
REMARK   470 MISSING ATOM
REMARK   470 THE FOLLOWING RESIDUES HAVE MISSING ATOMS (M = MODEL NUMBER;
REMARK   470 RES = RESIDUE NAME; C = CHAIN IDENTIFIER; SSEQ = SEQUENCE NUMBER;
REMARK   470 I = INSERTION CODE):
REMARK   470 M RES C SSEQ I    ATOMS
REMARK   470   ASP A 240   CA   C   O   CB   CG   OD1   OD2
REMARK   500
REMARK   500 GEOMETRY AND STEREOCHEMISTRY
REMARK   500 SUBTOPIC: COVALENT BOND ANGLES
REMARK   500
REMARK   500 THE STEREOCHEMICAL PARAMETERS OF THE FOLLOWING RESIDUES
REMARK   500 HAVE VALUES WHICH DEVIATE FROM. EXPECTED VALUES BY MORE
REMARK   500 THAN 6RMSD (M = MODEL NUMBER; RES = RESIDUE NAME; C = CHAIN
REMARK   500 IDENTIFIER; SSEQ = SEQUENCE NUMBER; I = INSERTION CODE).
REMARK   500
REMARK   500 STANDARD TABLE:
REMARK   500 FORMAT: (10X, I3, 1X, A3, 1X, A1, I4, A1, 3(1X, A4, 2X), 12X, F5.1)
REMARK   500
REMARK   500 EXPECTED VALUES: ENGH AND HUBER, 1991
REMARK   500
REMARK   500 M  RES  C    SSEQI ATM1   ATM2   ATM3
REMARK   500    ARG  A      23  N      CA     C       ANGL. DEV. = -9.0 DEGREES
REMARK   500    LEU  A      38  CA     CB     CG      ANGL. DEV. =  8.7 DEGREES
REMARK   500    THR  A     143  N      CA     C       ANGL. DEV. =  8.6 DEGREES
REMARK   500    GLU  A     168  N      CA     C       ANGL. DEV. =  9.5 DEGREES
REMARK   500    GLU  A     189  N      CA     C       ANGL. DEV. =  8.7 DEGREES
REMARK   500
REMARK   500 REMARK: NULL
```

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

```
REMARK   525
REMARK   525 SOLVENT
REMARK   525
REMARK   525 THE SOLVENT MOLECULES ARE GIVEN CHAIN IDENTIFIERS TO
REMARK   525 INDICATE THE PROTEIN CHAIN TO WHICH THEY ARE MOST CLOSELY
REMARK   525 ASSOCIATED WITH:
REMARK   525 PROTEIN CHAIN     SOLVENT CHAIN
REMARK   525 A                 Z
REMARK   525 P                 K
REMARK   525
REMARK   525 THE FOLLOWING SOLVENT MOLECULES LIE FARTHER THAN EXPECTED
REMARK   525 FROM THE PROTEIN OR NUCLEIC ACID MOLECULE AND MAY BE
REMARK   525 ASSOCIATED WITH A SYMMETRY RELATED MOLECULE (M = MODEL
REMARK   525 NUMBER; RES = RESIDUE NAME; C = CHAIN IDENTIFIER; SSEQ = SEQUENCE
REMARK   525 NUMBER; I = INSERTION CODE):
REMARK   525
REMARK   525 THESE MOLECULES CAN BE PLACED WITHIN 5.00 ANGSTROM OF THE
REMARK   525 OBSERVED OLIGOMER BY APPLYING THE SYMMETRY TRANSFORMATION
REMARK   525 INDICATED.
REMARK   525
                                        ORIGINAL
REMARK   525                           COORDINATES

REMARK   525  M RES  C  SSEQI    X       Y       Z     SYMMETRY  TRANS.  DIST.
REMARK   525  1 HOH  S  18    16.443  56.096  36.503     007      555    2.81
REMARK   525  1 HOH  S  21    23.251  53.904  40.248     007      555    2.83
REMARK   525  1 HOH  S  14    52.035  38.923  27.409     011      655    2.89
REMARK   525  1 HOH  S  7     21.217  52.108  39.440     007      555    2.82
REMARK   525  1 HOH  S  59    46.695  30.356  51.104     011      655    3.06
REMARK   525  1 HOH  S  26    37.575  38.780   8.192     010      665    2.76
REMARK   525  1 HOH  S  17    46.154  44.870  55.625     007      555    2.86
REMARK   800
REMARK   800 SITE
REMARK   800 SITE_IDENTIFIER: AC1
REMARK   800 SITE_DESCRIPTION: FSC BINDING SITE FOR CHAIN A
REMARK   900
REMARK   900 RELATED ENTRIES
REMARK   900 RELATED ID: 1O9C RELATED DB: PDB
REMARK   900 STRUCTURAL VIEW OF A FUNGAL TOXIN ACTING
REMARK   900 ON A 14-3-3 REGULATORY COMPLEX
REMARK   900 RELATED ENTRIES
REMARK   900 RELATED ID: 1O9E RELATED DB: PDB
REMARK   900 STRUCTURAL VIEW OF A FUNGAL TOXIN ACTING
REMARK   900 ON A 14-3-3 REGULATORY COMPLEX
REMARK   900 RELATED ID: 1O9D RELATED DB: PDB
REMARK   900 STRUCTURAL VIEW OF A FUNGAL TOXIN ACTING
REMARK   900 ON A 14-3-3 REGULATORY COMPLEX
DBREF  1O9F  A   1   260  SWS  P93343   143C__TOBAC     1     260
DBREF  1O9F  P   1     5  SWS  Q40409   Q40409        436     440
SEQRES    1 A  260  MET ALA VAL ALA PRO THR ALA ARG GLU GLU ASN VAL TYR
SEQRES    2 A  260  MET ALA LYS LEU ALA GLU GLN ALA GLU ARG TYR GLU GLU
SEQRES    3 A  260  MET VAL GLU PHE MET GLU LYS VAL SER ASN SER LEU GLY
SEQRES    4 A  260  SER GLU GLU LEU THR VAL GLU GLU ARG ASN LEU LEU SER
SEQRES    5 A  260  VAL ALA TYR LYS ASN VAL ILE GLY ALA ARG ARG ALA SER
SEQRES    6 A  260  TRP ARG ILE ILE SER SER ILE GLU GLN LYS GLU GLU SER
SEQRES    7 A  260  ARG GLY ASN GLU GLU HIS VAL ASN SER ILE ARG GLU TYR
SEQRES    8 A  260  ARG SER LYS ILE GLU ASN GLU LEU SER LYS ILE CYS ASP
SEQRES    9 A  260  GLY ILE LEU LYS LEU LEU ASP ALA LYS LEU ILE PRO SER
SEQRES   10 A  260  ALA ALA SER GLY ASP SER LYS VAL PHE TYR LEU LYS MET
SEQRES   11 A  260  LYS GLY ASP TYR HIS ARG TYR LEU ALA GLU PHE LYS THR
SEQRES   12 A  260  GLY ALA GLU ARG LYS GLU ALA ALA GLU SER THR LEU THR
SEQRES   13 A  260  ALA TYR LYS ALA ALA GLN ASP ILE ALA THR THR GLU LEU
SEQRES   14 A  260  ALA PRO THR HIS PRO ILE ARG LEU GLY LEU ALA LEU ASN
SEQRES   15 A  260  PHE SER VAL PHE TYR TYR GLU ILE LEU ASN SER PRO ASP
SEQRES   16 A  260  ARG ALA CYS ASN LEU ALA LYS GLN ALA PHE ASP GLU ALA
```

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

```
SEQRES      17    A     260   ILE ALA GLU LEU ASP THR LEU GLY GLU GLU SER TYR LYS
SEQRES      18    A     260   ASP SER THR LEU ILE MET GLN LEU LEU ARG ASP ASN LEU
SEQRES      19    A     260   THR LEU TRP THR SER ASP MET GLN ASP ASP GLY ALA ASP
SEQRES      20    A     260   GLU ILE LYS GLU ASP PRO LYS PRO ASP GLU ALA LYS ASN
SEQRES       1    P       5   GLN SER TYR TPO VAL
MODRES 1O9F TPO P   4    TPO PHOSPHOTHREONINE
HET     FSC   A1240       48
HET     TPO   P    4      11
HETNAM        TPO  PHOSPHOTHREONINE
HETSYN        TPO  PHOSPHONOTHREONINE
HETNAM        FSC  FUSICOCCIN
FORMUL    2   TPO     C4 H10 N1 O6 P1
FORMUL    3   FSC     C36 H58 O12
FORMUL    4   HOH    62 (H2 O1)
HELIX     1    1 THR  A      6  GLU  A    22   117
HELIX     2    2 ARG  A     23  LEU  A    38   116
HELIX     3    3 THR  A     44  SER  A    78   135
HELIX     4    4 ASN  A     81  LYS  A   113   133
HELIX     5    5 LEU  A    114  ALA  A   118    5 5
HELIX     6    6 SER  A    120  LYS  A   142   123
HELIX     7    7 GLY  A    144  LEU  A   169   126
HELIX     8    8 HIS  A    173  ILE  A   190   118
HELIX     9    9 SER  A    193  THR  A   214   122
HELIX    10   10 TYR  A    220  THR  A   238   119
LINK           C   TYR P   3        N   TPO P   4        1555  1555  1.33
LINK           N   VAL P   5        C   TPO P   4        1555  1555  1.33
SITE      1  AC1   13  ASN  A   49  PHE  A  126  LYS  A  129  MET  A  130
SITE      2  AC1   13  PRO  A  174  ILE  A  175  TYR  A  220  LYS  A  221
SITE      3  AC1   13  ASP  A  222  HOH  Z   54  HOH  Z   56  HOH  Z   57
SITE      4  AC1   13  HOH  Z   58
CRYST1  108.800  108.800  135.700  90.00  90.00 120.00 P 65 2 2     12
ORIGX1    1.000000  0.000000  0.000000     0.00000
ORIGX2    0.000000  1.000000  0.000000     0.00000
ORIGX3    0.000000  0.000000  1.000000     0.00000
SCALE1    0.009191  0.005306  0.000000     0.00000
SCALE2    0.000000  0.010613  0.000000     0.00000
SCALE3    0.000000  0.000000  0.007369     0.00000
ATOM      1   N    PRO  A    5     40.226  32.712  60.907  1.00  83.46  N
ATOM      2   CA   PRO  A    5     39.670  33.368  59.700  1.00  83.47  C
ATOM      3   C    PRO  A    5     39.281  32.334  58.651  1.00  82.83  C
ATOM      4   O    PRO  A    5     40.001  31.362  58.432  1.00  82.89  O
ATOM      5   CB   PRO  A    5     40.748  34.300  59.163  1.00  84.45  C
ATOM      6   CG   PRO  A    5     42.015  33.608  59.663  1.00  84.89  C
ATOM      7   CD   PRO  A    5     41.640  33.092  61.073  1.00  84.56  C
ATOM      8   N    THR  A    6     38.138  32.551  58.007  1.00  81.80  N
ATOM      9   CA   THR  A    6     37.639  31.644  56.979  1.00  80.32  C
ATOM     10   C    THR  A    6     38.607  31.514  55.810  1.00  79.48  C
ATOM     11   O    THR  A    6     39.457  32.375  55.600  1.00  80.01  O
ATOM     12   CB   THR  A    6     36.263  32.121  56.441  1.00  80.55  C
ATOM     13   OG1  THR  A    6     36.089  31.677  55.088  1.00  79.88  O
ATOM     14   CG2  THR  A    6     36.162  33.638  56.495  1.00  80.87  C
ATOM     15   N    ALA  A    7     38.478  30.428  55.055  1.00  78.82  N
ATOM     16   CA   ALA  A    7     39.333  30.201  53.895  1.00  78.71  C
ATOM     17   C    ALA  A    7     39.059  31.287  52.852  1.00  79.42  C
ATOM     18   O    ALA  A    7     39.991  31.913  52.341  1.00  80.21  O
ATOM     19   CB   ALA  A    7     39.064  28.818  53.302  1.00  76.74  C
ATOM     20   N    ARG  A    8     37.780  31.502  52.541  1.00  78.68  N
ATOM     21   CA   ARG  A    8     37.376  32.519  51.577  1.00  77.44  C
ATOM     22   C    ARG  A    8     37.986  33.859  51.963  1.00  77.35  C
ATOM     23   O    ARG  A    8     38.480  34.602  51.117  1.00  77.75  O
ATOM     24   CB   ARG  A    8     35.853  32.640  51.545  1.00  77.65  C
ATOM     25   CG   ARG  A    8     35.350  33.925  50.917  1.00  77.81  C
ATOM     26   CD   ARG  A    8     33.837  33.940  50.818  1.00  79.34  C
ATOM     27   NE   ARG  A    8     33.312  35.288  50.615  1.00  80.09  N
ATOM     28   CZ   ARG  A    8     32.019  35.579  50.488  1.00  80.93  C
```

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 29 | NH1 | ARG | A | 8 | 31.110 | 34.614 | 50.538 | 1.00 | 82.06 | N |
|---|---|---|---|---|---|---|---|---|---|---|---|
| ATOM | 30 | NH2 | ARG | A | 8 | 31.631 | 36.838 | 50.320 | 1.00 | 80.29 | N |
| ATOM | 31 | N | GLU | A | 9 | 37.952 | 34.166 | 53.250 | 1.00 | 76.33 | N |
| ATOM | 32 | CA | GLU | A | 9 | 38.517 | 35.412 | 53.729 | 1.00 | 76.44 | C |
| ATOM | 33 | C | GLU | A | 9 | 40.010 | 35.496 | 53.412 | 1.00 | 75.84 | C |
| ATOM | 34 | O | GLU | A | 9 | 40.531 | 36.569 | 53.118 | 1.00 | 75.72 | O |
| ATOM | 35 | CB | GLU | A | 9 | 38.303 | 35.523 | 55.229 | 1.00 | 77.10 | C |
| ATOM | 36 | CG | GLU | A | 9 | 38.767 | 36.823 | 55.820 | 1.00 | 78.65 | C |
| ATOM | 37 | CD | GLU | A | 9 | 38.380 | 36.941 | 57.275 | 1.00 | 80.63 | C |
| ATOM | 38 | OE1 | GLU | A | 9 | 38.700 | 37.984 | 57.885 | 1.00 | 81.12 | O |
| ATOM | 39 | OE2 | GLU | A | 9 | 37.754 | 35.987 | 57.800 | 1.00 | 81.40 | O |
| ATOM | 40 | N | GLU | A | 10 | 40.696 | 34.358 | 53.480 | 1.00 | 75.60 | N |
| ATOM | 41 | CA | GLU | A | 10 | 42.128 | 34.300 | 53.190 | 1.00 | 74.79 | C |
| ATOM | 42 | C | GLU | A | 10 | 42.432 | 34.526 | 51.706 | 1.00 | 72.16 | C |
| ATOM | 43 | O | GLU | A | 10 | 43.270 | 35.351 | 51.365 | 1.00 | 70.60 | O |
| ATOM | 44 | CB | GLU | A | 10 | 42.702 | 32.949 | 53.626 | 1.00 | 78.05 | C |
| ATOM | 45 | CG | GLU | A | 10 | 43.094 | 32.867 | 55.095 | 1.00 | 84.01 | C |
| ATOM | 46 | CD | GLU | A | 10 | 44.405 | 33.585 | 55.387 | 1.00 | 87.41 | C |
| ATOM | 47 | OE1 | GLU | A | 10 | 45.387 | 33.321 | 54.655 | 1.00 | 89.70 | O |
| ATOM | 48 | OE2 | GLU | A | 10 | 44.460 | 34.398 | 56.341 | 1.00 | 89.07 | O |
| ATOM | 49 | N | ASN | A | 11 | 41.756 | 33.793 | 50.827 | 1.00 | 69.85 | N |
| ATOM | 50 | CA | ASN | A | 11 | 41.985 | 33.947 | 49.398 | 1.00 | 69.43 | C |
| ATOM | 51 | C | ASN | A | 11 | 41.809 | 35.400 | 48.968 | 1.00 | 68.68 | C |
| ATOM | 52 | O | ASN | A | 11 | 42.575 | 35.920 | 48.145 | 1.00 | 68.01 | O |
| ATOM | 53 | CB | ASN | A | 11 | 41.019 | 33.071 | 48.597 | 1.00 | 72.18 | C |
| ATOM | 54 | CG | ASN | A | 11 | 41.293 | 31.587 | 48.763 | 1.00 | 73.84 | C |
| ATOM | 55 | OD1 | ASN | A | 11 | 42.418 | 31.117 | 48.570 | 1.00 | 73.72 | O |
| ATOM | 56 | ND2 | ASN | A | 11 | 40.255 | 30.838 | 49.107 | 1.00 | 75.45 | N |
| ATOM | 57 | N | VAL | A | 12 | 40.783 | 36.046 | 49.520 | 1.00 | 66.20 | N |
| ATOM | 58 | CA | VAL | A | 12 | 40.494 | 37.434 | 49.203 | 1.00 | 61.70 | C |
| ATOM | 59 | C | VAL | A | 12 | 41.671 | 38.288 | 49.611 | 1.00 | 59.78 | C |
| ATOM | 60 | O | VAL | A | 12 | 42.165 | 39.091 | 48.818 | 1.00 | 59.52 | O |
| ATOM | 61 | CB | VAL | A | 12 | 39.208 | 37.923 | 49.925 | 1.00 | 62.36 | C |
| ATOM | 62 | CG1 | VAL | A | 12 | 39.179 | 39.451 | 50.002 | 1.00 | 61.09 | C |
| ATOM | 63 | CG2 | VAL | A | 12 | 37.977 | 37.428 | 49.168 | 1.00 | 61.15 | C |
| ATOM | 64 | N | TYR | A | 13 | 42.129 | 38.106 | 50.845 | 1.00 | 58.08 | N |
| ATOM | 65 | CA | TYR | A | 13 | 43.258 | 38.882 | 51.336 | 1.00 | 58.04 | C |
| ATOM | 66 | C | TYR | A | 13 | 44.485 | 38.623 | 50.468 | 1.00 | 58.87 | C |
| ATOM | 67 | O | TYR | A | 13 | 45.253 | 39.535 | 50.152 | 1.00 | 58.12 | O |
| ATOM | 68 | CB | TYR | A | 13 | 43.584 | 38.527 | 52.785 | 1.00 | 54.60 | C |
| ATOM | 69 | CG | TYR | A | 13 | 44.546 | 39.515 | 53.390 | 1.00 | 52.71 | C |
| ATOM | 70 | CD1 | TYR | A | 13 | 44.157 | 40.831 | 53.619 | 1.00 | 49.74 | C |
| ATOM | 71 | CD2 | TYR | A | 13 | 45.867 | 39.157 | 53.670 | 1.00 | 53.55 | C |
| ATOM | 72 | CE1 | TYR | A | 13 | 45.057 | 41.772 | 54.105 | 1.00 | 50.68 | C |
| ATOM | 73 | CE2 | TYR | A | 13 | 46.781 | 40.093 | 54.161 | 1.00 | 51.61 | C |
| ATOM | 74 | CZ | TYR | A | 13 | 46.367 | 41.400 | 54.376 | 1.00 | 51.36 | C |
| ATOM | 75 | OH | TYR | A | 13 | 47.248 | 42.331 | 54.871 | 1.00 | 49.82 | O |
| ATOM | 76 | N | MET | A | 14 | 44.654 | 37.362 | 50.089 | 1.00 | 60.22 | N |
| ATOM | 77 | CA | MET | A | 14 | 45.762 | 36.934 | 49.252 | 1.00 | 60.22 | C |
| ATOM | 78 | C | MET | A | 14 | 45.670 | 37.639 | 47.885 | 1.00 | 59.66 | C |
| ATOM | 79 | O | MET | A | 14 | 46.655 | 38.188 | 47.391 | 1.00 | 59.05 | O |
| ATOM | 80 | CB | MET | A | 14 | 45.710 | 35.403 | 49.095 | 1.00 | 61.00 | C |
| ATOM | 81 | CG | MET | A | 14 | 47.063 | 34.706 | 49.175 | 1.00 | 65.70 | C |
| ATOM | 82 | SD | MET | A | 14 | 48.002 | 35.006 | 50.705 | 1.00 | 67.98 | S |
| ATOM | 83 | CE | MET | A | 14 | 47.672 | 33.458 | 51.583 | 1.00 | 69.59 | C |
| ATOM | 84 | N | ALA | A | 15 | 44.482 | 37.634 | 47.283 | 1.00 | 58.59 | N |
| ATOM | 85 | CA | ALA | A | 15 | 44.287 | 38.278 | 45.985 | 1.00 | 57.44 | C |
| ATOM | 86 | C | ALA | A | 15 | 44.653 | 39.767 | 46.035 | 1.00 | 57.05 | C |
| ATOM | 87 | O | ALA | A | 15 | 45.197 | 40.319 | 45.070 | 1.00 | 55.02 | O |
| ATOM | 88 | CB | ALA | A | 15 | 42.843 | 38.109 | 45.530 | 1.00 | 56.61 | C |
| ATOM | 89 | N | LYS | A | 16 | 44.347 | 40.415 | 47.157 | 1.00 | 56.39 | N |
| ATOM | 90 | CA | LYS | A | 16 | 44.655 | 41.832 | 47.319 | 1.00 | 56.90 | C |
| ATOM | 91 | C | LYS | A | 16 | 46.164 | 42.011 | 47.469 | 1.00 | 56.39 | C |
| ATOM | 92 | O | LYS | A | 16 | 46.715 | 43.078 | 47.175 | 1.00 | 57.54 | O |
| ATOM | 93 | CB | LYS | A | 16 | 43.890 | 42.401 | 48.519 | 1.00 | 56.77 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 94 | CG | LYS | A | 16 | 42.386 | 42.421 | 48.277 | 1.00 | 56.96 | C |
|------|----|----|-----|---|----|--------|--------|--------|------|-------|---|
| ATOM | 95 | CD | LYS | A | 16 | 41.568 | 42.333 | 49.561 | 1.00 | 58.11 | C |
| ATOM | 96 | CE | LYS | A | 16 | 41.505 | 43.652 | 50.317 | 1.00 | 56.80 | C |
| ATOM | 97 | NZ | LYS | A | 16 | 40.540 | 43.572 | 51.466 | 1.00 | 55.87 | N |
| ATOM | 98 | N | LEU | A | 17 | 46.833 | 40.958 | 47.924 | 1.00 | 53.96 | N |
| ATOM | 99 | CA | LEU | A | 17 | 48.284 | 40.992 | 48.044 | 1.00 | 51.79 | C |
| ATOM | 100 | C | LEU | A | 17 | 48.841 | 40.796 | 46.621 | 1.00 | 50.18 | C |
| ATOM | 101 | O | LEU | A | 17 | 49.691 | 41.562 | 46.162 | 1.00 | 49.61 | O |
| ATOM | 102 | CB | LEU | A | 17 | 48.772 | 39.873 | 48.967 | 1.00 | 50.54 | C |
| ATOM | 103 | CG | LEU | A | 17 | 48.602 | 40.138 | 50.459 | 1.00 | 49.73 | C |
| ATOM | 104 | CD1 | LEU | A | 17 | 49.074 | 38.912 | 51.244 | 1.00 | 50.39 | C |
| ATOM | 105 | CD2 | LEU | A | 17 | 49.388 | 41.385 | 50.851 | 1.00 | 47.44 | C |
| ATOM | 106 | N | ALA | A | 18 | 48.339 | 39.775 | 45.930 | 1.00 | 47.07 | N |
| ATOM | 107 | CA | ALA | A | 18 | 48.752 | 39.496 | 44.567 | 1.00 | 48.24 | C |
| ATOM | 108 | C | ALA | A | 18 | 48.638 | 40.774 | 43.728 | 1.00 | 49.99 | C |
| ATOM | 109 | O | ALA | A | 18 | 49.524 | 41.081 | 42.925 | 1.00 | 51.52 | O |
| ATOM | 110 | CB | ALA | A | 18 | 47.875 | 38.395 | 43.970 | 1.00 | 46.16 | C |
| ATOM | 111 | N | GLU | A | 19 | 47.544 | 41.511 | 43.916 | 1.00 | 50.49 | N |
| ATOM | 112 | CA | GLU | A | 19 | 47.315 | 42.756 | 43.196 | 1.00 | 50.11 | C |
| ATOM | 113 | C | GLU | A | 19 | 48.399 | 43.775 | 43.542 | 1.00 | 49.87 | C |
| ATOM | 114 | O | GLU | A | 19 | 48.992 | 44.387 | 42.656 | 1.00 | 48.16 | O |
| ATOM | 115 | CB | GLU | A | 19 | 45.926 | 43.316 | 43.535 | 1.00 | 52.48 | C |
| ATOM | 116 | CG | GLU | A | 19 | 45.702 | 44.767 | 43.100 | 1.00 | 54.36 | C |
| ATOM | 117 | CD | GLU | A | 19 | 44.297 | 45.267 | 43.391 | 1.00 | 58.24 | C |
| ATOM | 118 | OE1 | GLU | A | 19 | 43.760 | 45.000 | 44.493 | 1.00 | 60.33 | O |
| ATOM | 119 | OE2 | GLU | A | 19 | 43.722 | 45.943 | 42.513 | 1.00 | 61.91 | O |
| ATOM | 120 | N | GLN | A | 20 | 48.654 | 43.971 | 44.829 | 1.00 | 50.40 | N |
| ATOM | 121 | CA | GLN | A | 20 | 49.693 | 44.910 | 45.227 | 1.00 | 51.36 | C |
| ATOM | 122 | C | GLN | A | 20 | 51.040 | 44.504 | 44.623 | 1.00 | 49.83 | C |
| ATOM | 123 | O | GLN | A | 20 | 51.766 | 45.346 | 44.103 | 1.00 | 49.43 | O |
| ATOM | 124 | CB | GLN | A | 20 | 49.811 | 44.971 | 46.749 | 1.00 | 53.65 | C |
| ATOM | 125 | CG | GLN | A | 20 | 48.728 | 45.795 | 47.417 | 1.00 | 58.26 | C |
| ATOM | 126 | CD | GLN | A | 20 | 48.714 | 47.224 | 46.926 | 1.00 | 60.54 | C |
| ATOM | 127 | OE1 | GLN | A | 20 | 49.666 | 47.972 | 47.132 | 1.00 | 63.17 | O |
| ATOM | 128 | NE2 | GLN | A | 20 | 47.632 | 47.611 | 46.266 | 1.00 | 62.68 | N |
| ATOM | 129 | N | ALA | A | 21 | 51.363 | 43.216 | 44.692 | 1.00 | 46.83 | N |
| ATOM | 130 | CA | ALA | A | 21 | 52.618 | 42.712 | 44.150 | 1.00 | 46.91 | C |
| ATOM | 131 | C | ALA | A | 21 | 52.580 | 42.633 | 42.624 | 1.00 | 47.94 | C |
| ATOM | 132 | O | ALA | A | 21 | 53.596 | 42.345 | 41.982 | 1.00 | 46.89 | O |
| ATOM | 133 | CB | ALA | A | 21 | 52.923 | 41.339 | 44.734 | 1.00 | 46.39 | C |
| ATOM | 134 | N | GLU | A | 22 | 51.399 | 42.887 | 42.059 | 1.00 | 48.35 | N |
| ATOM | 135 | CA | GLU | A | 22 | 51.170 | 42.864 | 40.614 | 1.00 | 47.83 | C |
| ATOM | 136 | C | GLU | A | 22 | 51.400 | 41.511 | 39.942 | 1.00 | 47.52 | C |
| ATOM | 137 | O | GLU | A | 22 | 51.930 | 41.435 | 38.837 | 1.00 | 45.38 | O |
| ATOM | 138 | CB | GLU | A | 22 | 52.024 | 43.917 | 39.916 | 1.00 | 48.28 | C |
| ATOM | 139 | CG | GLU | A | 22 | 51.826 | 45.318 | 40.417 | 1.00 | 53.21 | C |
| ATOM | 140 | CD | GLU | A | 22 | 52.446 | 46.335 | 39.482 | 1.00 | 58.64 | C |
| ATOM | 141 | OE1 | GLU | A | 22 | 51.799 | 46.677 | 38.466 | 1.00 | 62.66 | O |
| ATOM | 142 | OE2 | GLU | A | 22 | 53.585 | 46.779 | 39.747 | 1.00 | 60.89 | O |
| ATOM | 143 | N | ARG | A | 23 | 51.005 | 40.441 | 40.612 | 1.00 | 48.79 | N |
| ATOM | 144 | CA | ARG | A | 23 | 51.140 | 39.107 | 40.038 | 1.00 | 49.98 | C |
| ATOM | 145 | C | ARG | A | 23 | 49.684 | 38.720 | 39.772 | 1.00 | 50.18 | C |
| ATOM | 146 | O | ARG | A | 23 | 49.042 | 38.051 | 40.577 | 1.00 | 50.14 | O |
| ATOM | 147 | CB | ARG | A | 23 | 51.797 | 38.166 | 41.048 | 1.00 | 48.81 | C |
| ATOM | 148 | CG | ARG | A | 23 | 52.694 | 38.897 | 42.036 | 1.00 | 50.41 | C |
| ATOM | 149 | CD | ARG | A | 23 | 54.049 | 38.251 | 42.154 | 1.00 | 50.35 | C |
| ATOM | 150 | NE | ARG | A | 23 | 53.941 | 36.810 | 42.347 | 1.00 | 49.57 | N |
| ATOM | 151 | CZ | ARG | A | 23 | 54.935 | 35.958 | 42.119 | 1.00 | 48.85 | C |
| ATOM | 152 | NH1 | ARG | A | 23 | 56.117 | 36.400 | 41.699 | 1.00 | 45.12 | N |
| ATOM | 153 | NH2 | ARG | A | 23 | 54.731 | 34.659 | 42.270 | 1.00 | 48.86 | N |
| ATOM | 154 | N | TYR | A | 24 | 49.169 | 39.170 | 38.635 | 1.00 | 50.02 | N |
| ATOM | 155 | CA | TYR | A | 24 | 47.781 | 38.943 | 38.292 | 1.00 | 51.01 | C |
| ATOM | 156 | C | TYR | A | 24 | 47.339 | 37.511 | 38.021 | 1.00 | 52.72 | C |
| ATOM | 157 | O | TYR | A | 24 | 46.196 | 37.159 | 38.324 | 1.00 | 53.56 | O |
| ATOM | 158 | CB | TYR | A | 24 | 47.407 | 39.867 | 37.137 | 1.00 | 49.73 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 159 | CG  | TYR | A | 24 | 47.659 | 41.323 | 37.482 | 1.00 | 50.93 | C |
|------|-----|-----|-----|---|----|--------|--------|--------|------|-------|---|
| ATOM | 160 | CD1 | TYR | A | 24 | 47.002 | 41.931 | 38.557 | 1.00 | 51.63 | C |
| ATOM | 161 | CD2 | TYR | A | 24 | 48.589 | 42.080 | 36.772 | 1.00 | 49.86 | C |
| ATOM | 162 | CE1 | TYR | A | 24 | 47.272 | 43.256 | 38.919 | 1.00 | 50.27 | C |
| ATOM | 163 | CE2 | TYR | A | 24 | 48.865 | 43.402 | 37.123 | 1.00 | 48.26 | C |
| ATOM | 164 | CZ  | TYR | A | 24 | 48.208 | 43.984 | 38.195 | 1.00 | 50.88 | C |
| ATOM | 165 | OH  | TYR | A | 24 | 48.497 | 45.288 | 38.550 | 1.00 | 50.63 | O |
| ATOM | 166 | N   | GLU | A | 25 | 48.212 | 36.677 | 37.466 | 1.00 | 52.97 | N |
| ATOM | 167 | CA  | GLU | A | 25 | 47.814 | 35.293 | 37.222 | 1.00 | 54.73 | C |
| ATOM | 168 | C   | GLU | A | 25 | 47.446 | 34.675 | 38.569 | 1.00 | 54.69 | C |
| ATOM | 169 | O   | GLU | A | 25 | 46.499 | 33.888 | 38.669 | 1.00 | 54.29 | O |
| ATOM | 170 | CB  | GLU | A | 25 | 48.945 | 34.466 | 36.594 | 1.00 | 56.60 | C |
| ATOM | 171 | CG  | GLU | A | 25 | 49.284 | 34.771 | 35.144 | 1.00 | 59.28 | C |
| ATOM | 172 | CD  | GLU | A | 25 | 50.027 | 36.087 | 34.979 | 1.00 | 64.08 | C |
| ATOM | 173 | OE1 | GLU | A | 25 | 50.552 | 36.625 | 35.990 | 1.00 | 63.86 | O |
| ATOM | 174 | OE2 | GLU | A | 25 | 50.094 | 36.578 | 33.829 | 1.00 | 65.51 | O |
| ATOM | 175 | N   | GLU | A | 26 | 48.204 | 35.035 | 39.601 | 1.00 | 54.10 | N |
| ATOM | 176 | CA  | GLU | A | 26 | 47.950 | 34.529 | 40.942 | 1.00 | 55.51 | C |
| ATOM | 177 | C   | GLU | A | 26 | 46.704 | 35.167 | 41.538 | 1.00 | 56.12 | C |
| ATOM | 178 | O   | GLU | A | 26 | 45.907 | 34.488 | 42.187 | 1.00 | 57.25 | O |
| ATOM | 179 | CB  | GLU | A | 26 | 49.158 | 34.775 | 41.844 | 1.00 | 55.06 | C |
| ATOM | 180 | CG  | GLU | A | 26 | 50.303 | 33.843 | 41.520 | 1.00 | 56.38 | C |
| ATOM | 181 | CD  | GLU | A | 26 | 51.523 | 34.077 | 42.376 | 1.00 | 58.17 | C |
| ATOM | 182 | OE1 | GLU | A | 26 | 52.418 | 33.212 | 42.362 | 1.00 | 60.78 | O |
| ATOM | 183 | OE2 | GLU | A | 26 | 51.598 | 35.119 | 43.055 | 1.00 | 59.47 | O |
| ATOM | 184 | N   | MET | A | 27 | 46.537 | 36.469 | 41.318 | 1.00 | 56.27 | N |
| ATOM | 185 | CA  | MET | A | 27 | 45.360 | 37.177 | 41.810 | 1.00 | 54.87 | C |
| ATOM | 186 | C   | MET | A | 27 | 44.135 | 36.501 | 41.179 | 1.00 | 54.03 | C |
| ATOM | 187 | O   | MET | A | 27 | 43.105 | 36.311 | 41.828 | 1.00 | 53.89 | O |
| ATOM | 188 | CB  | MET | A | 27 | 45.425 | 38.651 | 41.405 | 1.00 | 55.19 | C |
| ATOM | 189 | CG  | MET | A | 27 | 44.230 | 39.479 | 41.842 | 1.00 | 53.62 | C |
| ATOM | 190 | SD  | MET | A | 27 | 44.329 | 41.176 | 41.237 | 1.00 | 49.44 | S |
| ATOM | 191 | CE  | MET | A | 27 | 43.124 | 41.999 | 42.287 | 1.00 | 52.75 | C |
| ATOM | 192 | N   | VAL | A | 28 | 44.257 | 36.120 | 39.916 | 1.00 | 51.45 | N |
| ATOM | 193 | CA  | VAL | A | 28 | 43.155 | 35.452 | 39.262 | 1.00 | 52.74 | C |
| ATOM | 194 | C   | VAL | A | 28 | 42.850 | 34.145 | 39.978 | 1.00 | 54.86 | C |
| ATOM | 195 | O   | VAL | A | 28 | 41.705 | 33.890 | 40.341 | 1.00 | 54.91 | O |
| ATOM | 196 | CB  | VAL | A | 28 | 43.462 | 35.149 | 37.776 | 1.00 | 51.80 | C |
| ATOM | 197 | CG1 | VAL | A | 28 | 42.475 | 34.125 | 37.238 | 1.00 | 50.15 | C |
| ATOM | 198 | CG2 | VAL | A | 28 | 43.362 | 36.428 | 36.956 | 1.00 | 52.17 | C |
| ATOM | 199 | N   | GLU | A | 29 | 43.876 | 33.321 | 40.185 | 1.00 | 57.84 | N |
| ATOM | 200 | CA  | GLU | A | 29 | 43.711 | 32.021 | 40.842 | 1.00 | 58.93 | C |
| ATOM | 201 | C   | GLU | A | 29 | 43.023 | 32.085 | 42.202 | 1.00 | 58.72 | C |
| ATOM | 202 | O   | GLU | A | 29 | 42.190 | 31.231 | 42.524 | 1.00 | 57.11 | O |
| ATOM | 203 | CB  | GLU | A | 29 | 45.063 | 31.344 | 41.015 | 1.00 | 62.06 | C |
| ATOM | 204 | CG  | GLU | A | 29 | 45.680 | 30.820 | 39.742 | 1.00 | 67.09 | C |
| ATOM | 205 | CD  | GLU | A | 29 | 47.074 | 30.276 | 39.991 | 1.00 | 70.91 | C |
| ATOM | 206 | OE1 | GLU | A | 29 | 47.224 | 29.428 | 40.900 | 1.00 | 73.26 | O |
| ATOM | 207 | OE2 | GLU | A | 29 | 48.018 | 30.696 | 39.285 | 1.00 | 72.66 | O |
| ATOM | 208 | N   | PHE | A | 30 | 43.390 | 33.085 | 43.000 | 1.00 | 58.72 | N |
| ATOM | 209 | CA  | PHE | A | 30 | 42.806 | 33.267 | 44.320 | 1.00 | 59.78 | C |
| ATOM | 210 | C   | PHE | A | 30 | 41.327 | 33.617 | 44.227 | 1.00 | 61.27 | C |
| ATOM | 211 | O   | PHE | A | 30 | 40.501 | 33.012 | 44.911 | 1.00 | 62.08 | O |
| ATOM | 212 | CB  | PHE | A | 30 | 43.545 | 34.360 | 45.085 | 1.00 | 58.87 | C |
| ATOM | 213 | CG  | PHE | A | 30 | 44.907 | 33.948 | 45.553 | 1.00 | 60.26 | C |
| ATOM | 214 | CD1 | PHE | A | 30 | 45.072 | 32.794 | 46.319 | 1.00 | 59.92 | C |
| ATOM | 215 | CD2 | PHE | A | 30 | 46.027 | 34.719 | 45.251 | 1.00 | 60.35 | C |
| ATOM | 216 | CE1 | PHE | A | 30 | 46.333 | 32.413 | 46.782 | 1.00 | 58.92 | C |
| ATOM | 217 | CE2 | PHE | A | 30 | 47.292 | 34.350 | 45.706 | 1.00 | 61.30 | C |
| ATOM | 218 | CZ  | PHE | A | 30 | 47.446 | 33.191 | 46.475 | 1.00 | 60.95 | C |
| ATOM | 219 | N   | MET | A | 31 | 40.986 | 34.592 | 43.388 | 1.00 | 61.34 | N |
| ATOM | 220 | CA  | MET | A | 31 | 39.586 | 34.965 | 43.239 | 1.00 | 61.50 | C |
| ATOM | 221 | C   | MET | A | 31 | 38.830 | 33.836 | 42.560 | 1.00 | 61.52 | C |
| ATOM | 222 | O   | MET | A | 31 | 37.630 | 33.687 | 42.735 | 1.00 | 63.00 | O |
| ATOM | 223 | CB  | MET | A | 31 | 39.434 | 36.253 | 42.428 | 1.00 | 60.86 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 224 | CG  | MET | A | 31 | 39.886 | 37.504 | 43.162 | 1.00 | 60.57 | C |
|------|-----|-----|-----|---|----|--------|--------|--------|------|-------|---|
| ATOM | 225 | SD  | MET | A | 31 | 39.407 | 37.509 | 44.911 | 1.00 | 60.99 | S |
| ATOM | 226 | CE  | MET | A | 31 | 37.631 | 37.412 | 44.802 | 1.00 | 61.14 | C |
| ATOM | 227 | N   | GLU | A | 32 | 39.542 | 33.033 | 41.790 | 1.00 | 62.90 | N |
| ATOM | 228 | CA  | GLU | A | 32 | 38.924 | 31.916 | 41.102 | 1.00 | 64.46 | C |
| ATOM | 229 | C   | GLU | A | 32 | 38.532 | 30.860 | 42.137 | 1.00 | 65.23 | C |
| ATOM | 230 | O   | GLU | A | 32 | 37.571 | 30.113 | 41.946 | 1.00 | 64.77 | O |
| ATOM | 231 | CB  | GLU | A | 32 | 39.909 | 31.344 | 40.100 | 1.00 | 65.67 | C |
| ATOM | 232 | CG  | GLU | A | 32 | 39.289 | 30.470 | 39.063 | 1.00 | 70.24 | C |
| ATOM | 233 | CD  | GLU | A | 32 | 39.858 | 30.767 | 37.699 | 1.00 | 72.34 | C |
| ATOM | 234 | OE1 | GLU | A | 32 | 39.598 | 31.879 | 37.197 | 1.00 | 74.17 | O |
| ATOM | 235 | OE2 | GLU | A | 32 | 40.573 | 29.905 | 37.139 | 1.00 | 73.56 | O |
| ATOM | 236 | N   | LYS | A | 33 | 39.283 | 30.801 | 43.232 | 1.00 | 65.24 | N |
| ATOM | 237 | CA  | LYS | A | 33 | 38.985 | 29.859 | 44.298 | 1.00 | 66.83 | C |
| ATOM | 238 | C   | LYS | A | 33 | 37.759 | 30.361 | 45.041 | 1.00 | 68.31 | C |
| ATOM | 239 | O   | LYS | A | 33 | 36.808 | 29.615 | 45.246 | 1.00 | 68.71 | O |
| ATOM | 240 | CB  | LYS | A | 33 | 40.148 | 29.748 | 45.281 | 1.00 | 67.53 | C |
| ATOM | 241 | CG  | LYS | A | 33 | 41.327 | 28.963 | 44.776 | 1.00 | 70.68 | C |
| ATOM | 242 | CD  | LYS | A | 33 | 42.436 | 28.951 | 45.816 | 1.00 | 74.77 | C |
| ATOM | 243 | CE  | LYS | A | 33 | 43.724 | 28.339 | 45.265 | 1.00 | 76.47 | C |
| ATOM | 244 | NZ  | LYS | A | 33 | 44.862 | 28.492 | 46.223 | 1.00 | 76.91 | N |
| ATOM | 245 | N   | VAL | A | 34 | 37.790 | 31.629 | 45.446 | 1.00 | 69.92 | N |
| ATOM | 246 | CA  | VAL | A | 34 | 36.675 | 32.230 | 46.167 | 1.00 | 71.53 | C |
| ATOM | 247 | C   | VAL | A | 34 | 35.405 | 32.075 | 45.352 | 1.00 | 72.86 | C |
| ATOM | 248 | O   | VAL | A | 34 | 34.321 | 31.889 | 45.899 | 1.00 | 72.74 | O |
| ATOM | 249 | CB  | VAL | A | 34 | 36.888 | 33.736 | 46.415 | 1.00 | 70.92 | C |
| ATOM | 250 | CG1 | VAL | A | 34 | 35.692 | 34.311 | 47.176 | 1.00 | 71.18 | C |
| ATOM | 251 | CG2 | VAL | A | 34 | 38.162 | 33.958 | 47.195 | 1.00 | 71.60 | C |
| ATOM | 252 | N   | SER | A | 35 | 35.545 | 32.159 | 44.037 | 1.00 | 74.50 | N |
| ATOM | 253 | CA  | SER | A | 35 | 34.400 | 32.026 | 43.153 | 1.00 | 77.11 | C |
| ATOM | 254 | C   | SER | A | 35 | 33.811 | 30.633 | 43.310 | 1.00 | 77.93 | C |
| ATOM | 255 | O   | SER | A | 35 | 32.661 | 30.474 | 43.712 | 1.00 | 78.05 | O |
| ATOM | 256 | CB  | SER | A | 35 | 34.829 | 32.259 | 41.704 | 1.00 | 78.18 | C |
| ATOM | 257 | OG  | SER | A | 35 | 33.735 | 32.093 | 40.822 | 1.00 | 81.91 | O |
| ATOM | 258 | N   | ASN | A | 36 | 34.610 | 29.622 | 43.000 | 1.00 | 79.41 | N |
| ATOM | 259 | CA  | ASN | A | 36 | 34.164 | 28.247 | 43.120 | 1.00 | 80.88 | C |
| ATOM | 260 | C   | ASN | A | 36 | 33.888 | 27.874 | 44.583 | 1.00 | 82.11 | C |
| ATOM | 261 | O   | ASN | A | 36 | 33.330 | 26.815 | 44.867 | 1.00 | 81.28 | O |
| ATOM | 262 | CB  | ASN | A | 36 | 35.217 | 27.325 | 42.513 | 1.00 | 81.13 | C |
| ATOM | 263 | CG  | ASN | A | 36 | 35.416 | 27.574 | 41.029 | 1.00 | 81.44 | C |
| ATOM | 264 | OD1 | ASN | A | 36 | 34.504 | 27.372 | 40.227 | 1.00 | 81.09 | O |
| ATOM | 265 | ND2 | ASN | A | 36 | 36.610 | 28.022 | 40.657 | 1.00 | 82.48 | N |
| ATOM | 266 | N   | SER | A | 37 | 34.278 | 28.756 | 45.501 | 1.00 | 84.17 | N |
| ATOM | 267 | CA  | SER | A | 37 | 34.075 | 28.553 | 46.939 | 1.00 | 85.85 | C |
| ATOM | 268 | C   | SER | A | 37 | 32.583 | 28.467 | 47.228 | 1.00 | 87.16 | C |
| ATOM | 269 | O   | SER | A | 37 | 32.019 | 27.376 | 47.284 | 1.00 | 88.07 | O |
| ATOM | 270 | CB  | SER | A | 37 | 34.696 | 29.716 | 47.731 | 1.00 | 86.61 | C |
| ATOM | 271 | OG  | SER | A | 37 | 34.353 | 29.673 | 49.107 | 1.00 | 87.14 | O |
| ATOM | 272 | N   | LEU | A | 38 | 31.944 | 29.619 | 47.416 | 1.00 | 88.38 | N |
| ATOM | 273 | CA  | LEU | A | 38 | 30.510 | 29.638 | 47.673 | 1.00 | 89.67 | C |
| ATOM | 274 | C   | LEU | A | 38 | 29.746 | 29.147 | 46.444 | 1.00 | 90.34 | C |
| ATOM | 275 | O   | LEU | A | 38 | 30.241 | 29.215 | 45.315 | 1.00 | 90.00 | O |
| ATOM | 276 | CB  | LEU | A | 38 | 30.029 | 31.051 | 48.071 | 1.00 | 89.05 | C |
| ATOM | 277 | CG  | LEU | A | 38 | 30.531 | 32.368 | 47.442 | 1.00 | 88.68 | C |
| ATOM | 278 | CD1 | LEU | A | 38 | 31.896 | 32.714 | 48.011 | 1.00 | 87.60 | C |
| ATOM | 279 | CD2 | LEU | A | 38 | 30.562 | 32.277 | 45.920 | 1.00 | 87.45 | C |
| ATOM | 280 | N   | GLY | A | 39 | 28.546 | 28.628 | 46.675 | 1.00 | 90.97 | N |
| ATOM | 281 | CA  | GLY | A | 39 | 27.731 | 28.143 | 45.580 | 1.00 | 92.13 | C |
| ATOM | 282 | C   | GLY | A | 39 | 26.410 | 28.885 | 45.597 | 1.00 | 92.98 | C |
| ATOM | 283 | O   | GLY | A | 39 | 26.009 | 29.506 | 44.606 | 1.00 | 94.17 | O |
| ATOM | 284 | N   | SER | A | 40 | 25.737 | 28.833 | 46.741 | 1.00 | 92.11 | N |
| ATOM | 285 | CA  | SER | A | 40 | 24.454 | 29.501 | 46.897 | 1.00 | 91.48 | C |
| ATOM | 286 | C   | SER | A | 40 | 24.552 | 31.021 | 46.694 | 1.00 | 90.31 | C |
| ATOM | 287 | O   | SER | A | 40 | 23.868 | 31.578 | 45.832 | 1.00 | 89.94 | O |
| ATOM | 288 | CB  | SER | A | 40 | 23.855 | 29.170 | 48.278 | 1.00 | 92.30 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 289 | OG | SER | A | 40 | 24.818 | 29.277 | 49.318 | 1.00 | 91.50 | O |
|---|---|---|---|---|---|---|---|---|---|---|---|
| ATOM | 290 | N | GLU | A | 41 | 25.412 | 31.687 | 47.464 | 1.00 | 88.53 | N |
| ATOM | 291 | CA | GLU | A | 41 | 25.559 | 33.135 | 47.348 | 1.00 | 86.46 | C |
| ATOM | 292 | C | GLU | A | 41 | 26.521 | 33.551 | 46.228 | 1.00 | 84.47 | C |
| ATOM | 293 | O | GLU | A | 41 | 27.220 | 32.713 | 45.653 | 1.00 | 84.27 | O |
| ATOM | 294 | CB | GLU | A | 41 | 26.009 | 33.725 | 48.692 | 1.00 | 87.32 | C |
| ATOM | 295 | CG | GLU | A | 41 | 27.441 | 33.411 | 49.103 | 1.00 | 89.89 | C |
| ATOM | 296 | CD | GLU | A | 41 | 27.752 | 33.854 | 50.534 | 1.00 | 92.00 | C |
| ATOM | 297 | OE1 | GLU | A | 41 | 27.395 | 34.997 | 50.915 | 1.00 | 91.78 | O |
| ATOM | 298 | OE2 | GLU | A | 41 | 28.363 | 33.056 | 51.279 | 1.00 | 92.78 | O |
| ATOM | 299 | N | GLU | A | 42 | 26.532 | 34.845 | 45.906 | 1.00 | 81.42 | N |
| ATOM | 300 | CA | GLU | A | 42 | 27.406 | 35.372 | 44.860 | 1.00 | 78.06 | C |
| ATOM | 301 | C | GLU | A | 42 | 28.507 | 36.233 | 45.467 | 1.00 | 74.83 | C |
| ATOM | 302 | O | GLU | A | 42 | 28.397 | 36.667 | 46.616 | 1.00 | 74.21 | O |
| ATOM | 303 | CB | GLU | A | 42 | 26.607 | 36.201 | 43.844 | 1.00 | 79.86 | C |
| ATOM | 304 | CG | GLU | A | 42 | 25.840 | 37.390 | 44.426 | 1.00 | 81.45 | C |
| ATOM | 305 | CD | GLU | A | 42 | 25.325 | 38.338 | 43.346 | 1.00 | 83.16 | C |
| ATOM | 306 | OE1 | GLU | A | 42 | 24.449 | 39.177 | 43.648 | 1.00 | 83.81 | O |
| ATOM | 307 | OE2 | GLU | A | 42 | 25.804 | 38.254 | 42.193 | 1.00 | 84.28 | O |
| ATOM | 308 | N | LEU | A | 43 | 29.561 | 36.475 | 44.691 | 1.00 | 69.74 | N |
| ATOM | 309 | CA | LEU | A | 43 | 30.695 | 37.275 | 45.148 | 1.00 | 65.72 | C |
| ATOM | 310 | C | LEU | A | 43 | 30.240 | 38.661 | 45.570 | 1.00 | 62.66 | C |
| ATOM | 311 | O | LEU | A | 43 | 29.314 | 39.205 | 44.980 | 1.00 | 63.20 | O |
| ATOM | 312 | CB | LEU | A | 43 | 31.716 | 37.429 | 44.019 | 1.00 | 66.54 | C |
| ATOM | 313 | CG | LEU | A | 43 | 32.320 | 36.174 | 43.393 | 1.00 | 65.60 | C |
| ATOM | 314 | CD1 | LEU | A | 43 | 33.022 | 36.548 | 42.098 | 1.00 | 64.86 | C |
| ATOM | 315 | CD2 | LEU | A | 43 | 33.284 | 35.526 | 44.372 | 1.00 | 64.96 | C |
| ATOM | 316 | N | THR | A | 44 | 30.885 | 39.234 | 46.584 | 1.00 | 59.14 | N |
| ATOM | 317 | CA | THR | A | 44 | 30.543 | 40.589 | 47.028 | 1.00 | 56.64 | C |
| ATOM | 318 | C | THR | A | 44 | 30.941 | 41.587 | 45.937 | 1.00 | 55.07 | C |
| ATOM | 319 | O | THR | A | 44 | 31.531 | 41.214 | 44.925 | 1.00 | 54.64 | O |
| ATOM | 320 | CB | THR | A | 44 | 31.297 | 40.990 | 48.325 | 1.00 | 56.11 | C |
| ATOM | 321 | OG1 | THR | A | 44 | 32.706 | 40.780 | 48.159 | 1.00 | 54.97 | O |
| ATOM | 322 | CG2 | THR | A | 44 | 30.804 | 40.178 | 49.500 | 1.00 | 58.45 | C |
| ATOM | 323 | N | VAL | A | 45 | 30.618 | 42.855 | 46.131 | 1.00 | 53.51 | N |
| ATOM | 324 | CA | VAL | A | 45 | 30.997 | 43.853 | 45.143 | 1.00 | 54.94 | C |
| ATOM | 325 | C | VAL | A | 45 | 32.531 | 43.871 | 45.043 | 1.00 | 56.67 | C |
| ATOM | 326 | O | VAL | A | 45 | 33.101 | 43.905 | 43.947 | 1.00 | 55.98 | O |
| ATOM | 327 | CB | VAL | A | 45 | 30.496 | 45.255 | 45.546 | 1.00 | 52.81 | C |
| ATOM | 328 | CG1 | VAL | A | 45 | 30.977 | 46.289 | 44.552 | 1.00 | 48.87 | C |
| ATOM | 329 | CG2 | VAL | A | 45 | 28.994 | 45.253 | 45.601 | 1.00 | 53.79 | C |
| ATOM | 330 | N | GLU | A | 46 | 33.193 | 43.836 | 46.196 | 1.00 | 56.70 | N |
| ATOM | 331 | CA | GLU | A | 46 | 34.643 | 43.847 | 46.227 | 1.00 | 57.49 | C |
| ATOM | 332 | C | GLU | A | 46 | 35.221 | 42.611 | 45.538 | 1.00 | 57.85 | C |
| ATOM | 333 | O | GLU | A | 46 | 36.164 | 42.712 | 44.744 | 1.00 | 56.25 | O |
| ATOM | 334 | CB | GLU | A | 46 | 35.141 | 43.913 | 47.669 | 1.00 | 59.31 | C |
| ATOM | 335 | CG | GLU | A | 46 | 36.647 | 43.978 | 47.769 | 1.00 | 63.24 | C |
| ATOM | 336 | CD | GLU | A | 46 | 37.156 | 43.718 | 49.168 | 1.00 | 65.72 | C |
| ATOM | 337 | OE1 | GLU | A | 46 | 36.562 | 42.866 | 49.871 | 1.00 | 67.51 | O |
| ATOM | 338 | OE2 | GLU | A | 46 | 38.162 | 44.349 | 49.554 | 1.00 | 67.02 | O |
| ATOM | 339 | N | GLU | A | 47 | 34.653 | 41.445 | 45.834 | 1.00 | 58.10 | N |
| ATOM | 340 | CA | GLU | A | 47 | 35.131 | 40.201 | 45.238 | 1.00 | 59.52 | C |
| ATOM | 341 | C | GLU | A | 47 | 34.911 | 40.171 | 43.729 | 1.00 | 58.47 | C |
| ATOM | 342 | O | GLU | A | 47 | 35.825 | 39.858 | 42.969 | 1.00 | 56.55 | O |
| ATOM | 343 | CB | GLU | A | 47 | 34.454 | 39.009 | 45.918 | 1.00 | 60.71 | C |
| ATOM | 344 | CG | GLU | A | 47 | 34.847 | 38.899 | 47.380 | 1.00 | 64.78 | C |
| ATOM | 345 | CD | GLU | A | 47 | 34.096 | 37.819 | 48.128 | 1.00 | 68.00 | C |
| ATOM | 346 | OE1 | GLU | A | 47 | 34.401 | 37.616 | 49.327 | 1.00 | 68.69 | O |
| ATOM | 347 | OE2 | GLU | A | 47 | 33.206 | 37.178 | 47.522 | 1.00 | 70.70 | O |
| ATOM | 348 | N | ARG | A | 48 | 33.694 | 40.502 | 43.309 | 1.00 | 58.64 | N |
| ATOM | 349 | CA | ARG | A | 48 | 33.327 | 40.557 | 41.895 | 1.00 | 56.58 | C |
| ATOM | 350 | C | ARG | A | 48 | 34.303 | 41.491 | 41.162 | 1.00 | 55.13 | C |
| ATOM | 351 | O | ARG | A | 48 | 34.803 | 41.171 | 40.078 | 1.00 | 53.29 | O |
| ATOM | 352 | CB | ARG | A | 48 | 31.870 | 41.049 | 41.792 | 1.00 | 58.92 | C |
| ATOM | 353 | CG | ARG | A | 48 | 31.432 | 41.628 | 40.469 | 1.00 | 60.13 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 354 | CD  | ARG | A | 48 | 29.942 | 41.391 | 40.227 | 1.00 | 63.38 | C |
|------|-----|-----|-----|---|----|--------|--------|--------|------|-------|---|
| ATOM | 355 | NE  | ARG | A | 48 | 29.059 | 42.007 | 41.218 | 1.00 | 64.58 | N |
| ATOM | 356 | CZ  | ARG | A | 48 | 28.951 | 43.316 | 41.405 | 1.00 | 66.21 | C |
| ATOM | 357 | NH1 | ARG | A | 48 | 29.682 | 44.150 | 40.675 | 1.00 | 65.73 | N |
| ATOM | 358 | NH2 | ARG | A | 48 | 28.090 | 43.796 | 42.292 | 1.00 | 65.78 | N |
| ATOM | 359 | N   | ASN | A | 49 | 34.597 | 42.636 | 41.773 | 1.00 | 53.93 | N |
| ATOM | 360 | CA  | ASN | A | 49 | 35.524 | 43.600 | 41.180 | 1.00 | 54.03 | C |
| ATOM | 361 | C   | ASN | A | 49 | 36.974 | 43.101 | 41.111 | 1.00 | 52.88 | C |
| ATOM | 362 | O   | ASN | A | 49 | 37.659 | 43.320 | 40.105 | 1.00 | 52.48 | O |
| ATOM | 363 | CB  | ASN | A | 49 | 35.450 | 44.927 | 41.935 | 1.00 | 53.75 | C |
| ATOM | 364 | CG  | ASN | A | 49 | 34.229 | 45.740 | 41.551 | 1.00 | 55.15 | C |
| ATOM | 365 | OD1 | ASN | A | 49 | 33.338 | 45.256 | 40.837 | 1.00 | 52.84 | O |
| ATOM | 366 | ND2 | ASN | A | 49 | 34.179 | 46.984 | 42.017 | 1.00 | 56.08 | N |
| ATOM | 367 | N   | LEU | A | 50 | 37.439 | 42.443 | 42.176 | 1.00 | 50.97 | N |
| ATOM | 368 | CA  | LEU | A | 50 | 38.793 | 41.890 | 42.208 | 1.00 | 48.22 | C |
| ATOM | 369 | C   | LEU | A | 50 | 38.951 | 40.807 | 41.120 | 1.00 | 47.51 | C |
| ATOM | 370 | O   | LEU | A | 50 | 40.007 | 40.686 | 40.494 | 1.00 | 47.81 | O |
| ATOM | 371 | CB  | LEU | A | 50 | 39.101 | 41.279 | 43.583 | 1.00 | 45.17 | C |
| ATOM | 372 | CG  | LEU | A | 50 | 39.232 | 42.193 | 44.808 | 1.00 | 46.49 | C |
| ATOM | 373 | CD1 | LEU | A | 50 | 39.311 | 41.325 | 46.047 | 1.00 | 44.32 | C |
| ATOM | 374 | CD2 | LEU | A | 50 | 40.446 | 43.095 | 44.710 | 1.00 | 43.42 | C |
| ATOM | 375 | N   | LEU | A | 51 | 37.903 | 40.026 | 40.890 | 1.00 | 44.90 | N |
| ATOM | 376 | CA  | LEU | A | 51 | 37.974 | 38.977 | 39.890 | 1.00 | 44.50 | C |
| ATOM | 377 | C   | LEU | A | 51 | 38.152 | 39.523 | 38.477 | 1.00 | 44.41 | C |
| ATOM | 378 | O   | LEU | A | 51 | 38.931 | 38.979 | 37.700 | 1.00 | 43.87 | O |
| ATOM | 379 | CB  | LEU | A | 51 | 36.723 | 38.091 | 39.933 | 1.00 | 43.50 | C |
| ATOM | 380 | CG  | LEU | A | 51 | 36.734 | 37.017 | 38.836 | 1.00 | 45.49 | C |
| ATOM | 381 | CD1 | LEU | A | 51 | 37.933 | 36.089 | 39.048 | 1.00 | 43.73 | C |
| ATOM | 382 | CD2 | LEU | A | 51 | 35.430 | 36.233 | 38.843 | 1.00 | 43.22 | C |
| ATOM | 383 | N   | SER | A | 52 | 37.434 | 40.588 | 38.134 | 1.00 | 45.18 | N |
| ATOM | 384 | CA  | SER | A | 52 | 37.564 | 41.137 | 36.792 | 1.00 | 45.61 | C |
| ATOM | 385 | C   | SER | A | 52 | 38.802 | 42.015 | 36.647 | 1.00 | 45.11 | C |
| ATOM | 386 | O   | SER | A | 52 | 39.408 | 42.055 | 35.575 | 1.00 | 45.63 | O |
| ATOM | 387 | CB  | SER | A | 52 | 36.306 | 41.906 | 36.388 | 1.00 | 45.35 | C |
| ATOM | 388 | OG  | SER | A | 52 | 36.088 | 42.986 | 37.258 | 1.00 | 49.83 | O |
| ATOM | 389 | N   | VAL | A | 53 | 39.188 | 42.727 | 37.702 | 1.00 | 45.58 | N |
| ATOM | 390 | CA  | VAL | A | 53 | 40.399 | 43.540 | 37.604 | 1.00 | 46.44 | C |
| ATOM | 391 | C   | VAL | A | 53 | 41.572 | 42.582 | 37.374 | 1.00 | 46.58 | C |
| ATOM | 392 | O   | VAL | A | 53 | 42.481 | 42.872 | 36.597 | 1.00 | 46.92 | O |
| ATOM | 393 | CB  | VAL | A | 53 | 40.642 | 44.380 | 38.880 | 1.00 | 47.64 | C |
| ATOM | 394 | CG1 | VAL | A | 53 | 42.104 | 44.786 | 38.974 | 1.00 | 46.08 | C |
| ATOM | 395 | CG2 | VAL | A | 53 | 39.781 | 45.641 | 38.835 | 1.00 | 49.84 | C |
| ATOM | 396 | N   | ALA | A | 54 | 41.525 | 41.429 | 38.039 | 1.00 | 46.89 | N |
| ATOM | 397 | CA  | ALA | A | 54 | 42.550 | 40.404 | 37.900 | 1.00 | 47.07 | C |
| ATOM | 398 | C   | ALA | A | 54 | 42.590 | 39.895 | 36.453 | 1.09 | 47.63 | C |
| ATOM | 399 | O   | ALA | A | 54 | 43.638 | 39.916 | 35.805 | 1.00 | 48.87 | O |
| ATOM | 400 | CB  | ALA | A | 54 | 42.268 | 39.243 | 38.860 | 1.00 | 44.72 | C |
| ATOM | 401 | N   | TYR | A | 55 | 41.456 | 39.437 | 35.941 | 1.00 | 46.07 | N |
| ATOM | 402 | CA  | TYR | A | 55 | 41.436 | 38.942 | 34.574 | 1.00 | 47.07 | C |
| ATOM | 403 | C   | TYR | A | 55 | 41.803 | 40.039 | 33.601 | 1.00 | 48.89 | C |
| ATOM | 404 | O   | TYR | A | 55 | 42.574 | 39.821 | 32.661 | 1.00 | 50.46 | O |
| ATOM | 405 | CB  | TYR | A | 55 | 40.062 | 38.386 | 34.208 | 1.00 | 46.47 | C |
| ATOM | 406 | CG  | TYR | A | 55 | 39.997 | 36.886 | 34.338 | 1.00 | 46.61 | C |
| ATOM | 407 | CD1 | TYR | A | 55 | 39.539 | 36.289 | 35.505 | 1.00 | 46.86 | C |
| ATOM | 408 | CD2 | TYR | A | 55 | 40.434 | 36.061 | 33.299 | 1.00 | 45.60 | C |
| ATOM | 409 | CE1 | TYR | A | 55 | 39.514 | 34.903 | 35.641 | 1.00 | 47.50 | C |
| ATOM | 410 | CE2 | TYR | A | 55 | 40.416 | 34.685 | 33.421 | 1.00 | 46.49 | C |
| ATOM | 411 | CZ  | TYR | A | 55 | 39.954 | 34.108 | 34.600 | 1.00 | 48.55 | C |
| ATOM | 412 | OH  | TYR | A | 55 | 39.947 | 32.734 | 34.744 | 1.00 | 49.04 | O |
| ATOM | 413 | N   | LYS | A | 56 | 41.248 | 41.223 | 33.844 | 1.00 | 48.75 | N |
| ATOM | 414 | CA  | LYS | A | 56 | 41.486 | 42.379 | 33.004 | 1.00 | 47.35 | C |
| ATOM | 415 | C   | LYS | A | 56 | 42.976 | 42.621 | 32.815 | 1.00 | 46.96 | C |
| ATOM | 416 | O   | LYS | A | 56 | 43.418 | 42.926 | 31.707 | 1.00 | 46.99 | O |
| ATOM | 417 | CB  | LYS | A | 56 | 40.844 | 43.613 | 33.632 | 1.00 | 48.91 | C |
| ATOM | 418 | CG  | LYS | A | 56 | 40.613 | 44.771 | 32.664 | 1.00 | 52.53 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 419 | CD | LYS | A | 56 | 39.623 | 44.371 | 31.569 | 1.00 | 56.26 | C |
| --- | --- | --- | --- | --- | --- | --- | --- | --- | --- | --- | --- |
| ATOM | 420 | CE | LYS | A | 56 | 39.098 | 45.592 | 30.829 | 1.00 | 58.54 | C |
| ATOM | 421 | NZ | LYS | A | 56 | 40.202 | 46.390 | 30.224 | 1.00 | 59.97 | N |
| ATOM | 422 | N | ASN | A | 57 | 43.742 | 42.492 | 33.898 | 1.00 | 45.18 | N |
| ATOM | 423 | CA | ASN | A | 57 | 45.178 | 42.710 | 33.847 | 1.00 | 44.38 | C |
| ATOM | 424 | C | ASN | A | 57 | 45.911 | 41.557 | 33.199 | 1.00 | 45.90 | C |
| ATOM | 425 | O | ASN | A | 57 | 46.927 | 41.748 | 32.521 | 1.00 | 45.54 | O |
| ATOM | 426 | CB | ASN | A | 57 | 45.726 | 42.945 | 35.244 | 1.00 | 45.89 | C |
| ATOM | 427 | CG | ASN | A | 57 | 45.621 | 44.398 | 35.663 | 1.00 | 46.70 | C |
| ATOM | 428 | OD1 | ASN | A | 57 | 46.285 | 45.272 | 35.094 | 1.00 | 48.55 | O |
| ATOM | 429 | ND2 | ASN | A | 57 | 44.780 | 44.667 | 36.650 | 1.00 | 42.29 | N |
| ATOM | 430 | N | VAL | A | 58 | 45.403 | 40.350 | 33.400 | 1.00 | 45.13 | N |
| ATOM | 431 | CA | VAL | A | 58 | 46.036 | 39.207 | 32.784 | 1.00 | 44.18 | C |
| ATOM | 432 | C | VAL | A | 58 | 45.844 | 39.295 | 31.264 | 1.00 | 45.37 | C |
| ATOM | 433 | O | VAL | A | 58 | 46.810 | 39.163 | 30.504 | 1.00 | 47.13 | O |
| ATOM | 434 | CB | VAL | A | 58 | 45.457 | 37.891 | 33.326 | 1.00 | 43.04 | C |
| ATOM | 435 | CG1 | VAL | A | 58 | 46.075 | 36.703 | 32.593 | 1.00 | 40.75 | C |
| ATOM | 436 | CG2 | VAL | A | 58 | 45.751 | 37.786 | 34.807 | 1.00 | 43.18 | C |
| ATOM | 437 | N | ILE | A | 59 | 44.613 | 39.543 | 30.821 | 1.00 | 43.27 | N |
| ATOM | 438 | CA | ILE | A | 59 | 44.342 | 39.644 | 29.392 | 1.00 | 42.70 | C |
| ATOM | 439 | C | ILE | A | 59 | 44.978 | 40.912 | 28.815 | 1.00 | 44.04 | C |
| ATOM | 440 | O | ILE | A | 59 | 45.502 | 40.907 | 27.701 | 1.00 | 44.82 | O |
| ATOM | 441 | CB | ILE | A | 59 | 42.806 | 39.657 | 29.100 | 1.00 | 42.16 | C |
| ATOM | 442 | CG1 | ILE | A | 59 | 42.546 | 39.367 | 27.623 | 1.00 | 41.14 | C |
| ATOM | 443 | CG2 | ILE | A | 59 | 42.205 | 41.012 | 29.431 | 1.00 | 41.31 | C |
| ATOM | 444 | CD1 | ILE | A | 59 | 42.682 | 37.911 | 27.247 | 1.00 | 39.83 | C |
| ATOM | 445 | N | GLY | A | 60 | 44.945 | 41.995 | 29.585 | 1.00 | 45.52 | N |
| ATOM | 446 | CA | GLY | A | 60 | 45.508 | 43.254 | 29.126 | 1.00 | 46.64 | C |
| ATOM | 447 | C | GLY | A | 60 | 46.971 | 43.191 | 28.707 | 1.00 | 47.25 | C |
| ATOM | 448 | O | GLY | A | 60 | 47.385 | 43.864 | 27.761 | 1.00 | 47.79 | O |
| ATOM | 449 | N | ALA | A | 61 | 47.767 | 42.393 | 29.410 | 1.00 | 46.65 | N |
| ATOM | 450 | CA | ALA | A | 61 | 49.179 | 42.280 | 29.076 | 1.00 | 45.35 | C |
| ATOM | 451 | C | ALA | A | 61 | 49.331 | 41.630 | 27.703 | 1.00 | 45.94 | C |
| ATOM | 452 | O | ALA | A | 61 | 49.995 | 42.196 | 26.830 | 1.00 | 47.02 | O |
| ATOM | 453 | CB | ALA | A | 61 | 49.920 | 41.468 | 30.141 | 1.00 | 40.88 | C |
| ATOM | 454 | N | ARG | A | 62 | 48.724 | 40.455 | 27.505 | 1.00 | 43.65 | N |
| ATOM | 455 | CA | ARG | A | 62 | 48.822 | 39.784 | 26.211 | 1.00 | 40.82 | C |
| ATOM | 456 | C | ARG | A | 62 | 48.250 | 40.667 | 25.122 | 1.00 | 41.25 | C |
| ATOM | 457 | O | ARG | A | 62 | 48.711 | 40.629 | 23.981 | 1.00 | 41.35 | O |
| ATOM | 458 | CB | ARG | A | 62 | 48.072 | 38.451 | 26.202 | 1.00 | 39.80 | C |
| ATOM | 459 | CG | ARG | A | 62 | 48.771 | 37.317 | 26.935 | 1.00 | 37.47 | C |
| ATOM | 460 | CD | ARG | A | 62 | 48.875 | 37.618 | 28.407 | 1.00 | 36.91 | C |
| ATOM | 461 | NE | ARG | A | 62 | 49.607 | 36.578 | 29.116 | 1.00 | 37.38 | N |
| ATOM | 462 | CZ | ARG | A | 62 | 49.809 | 36.568 | 30.433 | 1.00 | 37.72 | C |
| ATOM | 463 | NH1 | ARG | A | 62 | 50.492 | 35.573 | 30.981 | 1.00 | 37.47 | N |
| ATOM | 464 | NH2 | ARG | A | 62 | 49.324 | 37.547 | 31.204 | 1.00 | 35.21 | N |
| ATOM | 465 | N | ARG | A | 63 | 47.238 | 41.462 | 25.460 | 1.00 | 42.98 | N |
| ATOM | 466 | CA | ARG | A | 63 | 46.634 | 42.347 | 24.464 | 1.00 | 42.67 | C |
| ATOM | 467 | C | ARG | A | 63 | 47.635 | 43.425 | 24.038 | 1.00 | 43.03 | C |
| ATOM | 468 | O | ARG | A | 63 | 47.768 | 43.734 | 22.847 | 1.00 | 41.94 | O |
| ATOM | 469 | CB | ARG | A | 63 | 45.343 | 42.952 | 25.014 | 1.00 | 40.79 | C |
| ATOM | 470 | CG | ARG | A | 63 | 44.108 | 42.361 | 24.325 | 1.00 | 44.85 | C |
| ATOM | 471 | CD | ARG | A | 63 | 42.910 | 42.198 | 25.244 | 1.00 | 41.94 | C |
| ATOM | 472 | NE | ARG | A | 63 | 42.469 | 43.461 | 25.823 | 1.00 | 44.39 | N |
| ATOM | 473 | CZ | ARG | A | 63 | 41.815 | 44.407 | 25.161 | 1.00 | 44.00 | C |
| ATOM | 474 | NH1 | ARG | A | 63 | 41.515 | 44.241 | 23.884 | 1.00 | 46.66 | N |
| ATOM | 475 | NH2 | ARG | A | 63 | 41.461 | 45.521 | 25.780 | 1.00 | 43.30 | N |
| ATOM | 476 | N | ALA | A | 64 | 48.364 | 43.968 | 25.008 | 1.00 | 41.73 | N |
| ATOM | 477 | CA | ALA | A | 64 | 49.365 | 44.975 | 24.710 | 1.00 | 42.12 | C |
| ATOM | 478 | C | ALA | A | 64 | 50.475 | 44.318 | 23.877 | 1.00 | 42.09 | C |
| ATOM | 479 | O | ALA | A | 64 | 50.884 | 44.851 | 22.843 | 1.00 | 41.51 | O |
| ATOM | 480 | CB | ALA | A | 64 | 49.924 | 45.555 | 26.001 | 1.00 | 41.53 | C |
| ATOM | 481 | N | SER | A | 65 | 50.952 | 43.158 | 24.319 | 1.00 | 41.07 | N |
| ATOM | 482 | CA | SER | A | 65 | 51.989 | 42.443 | 23.578 | 1.00 | 43.36 | C |
| ATOM | 483 | C | SER | A | 65 | 51.493 | 42.191 | 22.145 | 1.00 | 45.85 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 Å. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 484 | O   | SER | A | 65 | 52.222 | 42.410 | 21.172 | 1.00 | 48.20 | O |
|------|-----|-----|-----|---|----|--------|--------|--------|------|-------|---|
| ATOM | 485 | CB  | SER | A | 65 | 52.313 | 41.092 | 24.243 | 1.00 | 42.89 | C |
| ATOM | 486 | OG  | SER | A | 65 | 52.664 | 41.235 | 25.617 | 1.00 | 44.15 | O |
| ATOM | 487 | N   | TRP | A | 66 | 50.247 | 41.743 | 22.017 | 1.00 | 46.08 | N |
| ATOM | 488 | CA  | TRP | A | 66 | 49.681 | 41.454 | 20.706 | 1.00 | 46.46 | C |
| ATOM | 489 | C   | TRP | A | 66 | 49.698 | 42.675 | 19.783 | 1.00 | 48.34 | C |
| ATOM | 490 | O   | TRP | A | 66 | 50.048 | 42.557 | 18.606 | 1.00 | 48.57 | O |
| ATOM | 491 | CB  | TRP | A | 66 | 48.244 | 40.941 | 20.840 | 1.00 | 44.36 | C |
| ATOM | 492 | CG  | TRP | A | 66 | 47.690 | 40.393 | 19.559 | 1.00 | 39.82 | C |
| ATOM | 493 | CD1 | TRP | A | 66 | 47.753 | 39.100 | 19.125 | 1.00 | 39.79 | C |
| ATOM | 494 | CD2 | TRP | A | 66 | 47.041 | 41.133 | 18.521 | 1.00 | 38.84 | C |
| ATOM | 495 | NE1 | TRP | A | 66 | 47.182 | 38.984 | 17.876 | 1.00 | 37.56 | N |
| ATOM | 496 | CE2 | TRP | A | 66 | 46.739 | 40.218 | 17.479 | 1.00 | 39.22 | C |
| ATOM | 497 | CE3 | TRP | A | 66 | 46.686 | 42.481 | 18.366 | 1.00 | 37.32 | C |
| ATOM | 498 | CZ2 | TRP | A | 66 | 46.096 | 40.609 | 16.292 | 1.00 | 39.15 | C |
| ATOM | 499 | CZ3 | TRP | A | 66 | 46.047 | 42.875 | 17.190 | 1.00 | 38.22 | C |
| ATOM | 500 | CH2 | TRP | A | 66 | 45.758 | 41.936 | 16.164 | 1.00 | 40.34 | C |
| ATOM | 501 | N   | ARG | A | 67 | 49.321 | 43.840 | 20.305 | 1.00 | 48.75 | N |
| ATOM | 502 | CA  | ARG | A | 67 | 49.306 | 45.047 | 19.486 | 1.00 | 50.71 | C |
| ATOM | 503 | C   | ARG | A | 67 | 50.702 | 45.407 | 18.995 | 1.00 | 52.70 | C |
| ATOM | 504 | O   | ARG | A | 67 | 50.900 | 45.653 | 17.803 | 1.00 | 52.46 | O |
| ATOM | 505 | CB  | ARG | A | 67 | 48.669 | 46.206 | 20.261 | 1.00 | 50.96 | C |
| ATOM | 506 | CG  | ARG | A | 67 | 47.191 | 45.957 | 20.473 | 1.00 | 55.91 | C |
| ATOM | 507 | CD  | ARG | A | 67 | 46.463 | 46.972 | 21.333 | 1.00 | 61.32 | C |
| ATOM | 508 | NE  | ARG | A | 67 | 45.072 | 46.534 | 21.490 | 1.00 | 67.93 | N |
| ATOM | 509 | CZ  | ARG | A | 67 | 44.126 | 47.181 | 22.168 | 1.00 | 70.53 | C |
| ATOM | 510 | NH1 | ARG | A | 67 | 42.897 | 46.678 | 22.232 | 1.00 | 69.99 | N |
| ATOM | 511 | NH2 | ARG | A | 67 | 44.399 | 48.328 | 22.779 | 1.00 | 73.66 | N |
| ATOM | 512 | N   | ILE | A | 68 | 51.671 | 45.413 | 19.909 | 1.00 | 53.73 | N |
| ATOM | 513 | CA  | ILE | A | 68 | 53.055 | 45.727 | 19.561 | 1.00 | 54.50 | C |
| ATOM | 514 | C   | ILE | A | 68 | 53.501 | 44.825 | 18.423 | 1.00 | 53.98 | C |
| ATOM | 515 | O   | ILE | A | 68 | 53.905 | 45.290 | 17.359 | 1.00 | 54.18 | O |
| ATOM | 516 | CB  | ILE | A | 68 | 54.024 | 45.468 | 20.746 | 1.00 | 55.97 | C |
| ATOM | 517 | CG1 | ILE | A | 68 | 53.537 | 46.196 | 22.001 | 1.00 | 58.48 | C |
| ATOM | 518 | CG2 | ILE | A | 68 | 55.420 | 45.937 | 20.385 | 1.00 | 54.50 | C |
| ATOM | 519 | CD1 | ILE | A | 68 | 53.384 | 47.697 | 21.825 | 1.00 | 58.96 | C |
| ATOM | 520 | N   | ILE | A | 69 | 53.434 | 43.525 | 18.670 | 1.00 | 54.27 | N |
| ATOM | 521 | CA  | ILE | A | 69 | 53.835 | 42.541 | 17.683 | 1.00 | 55.54 | C |
| ATOM | 522 | C   | ILE | A | 69 | 53.098 | 42.758 | 16.365 | 1.00 | 57.32 | C |
| ATOM | 523 | O   | ILE | A | 69 | 53.713 | 42.875 | 15.307 | 1.00 | 57.53 | O |
| ATOM | 524 | CB  | ILE | A | 69 | 53.551 | 41.124 | 18.194 | 1.00 | 53.63 | C |
| ATOM | 525 | CG1 | ILE | A | 69 | 54.349 | 40.880 | 19.473 | 1.00 | 54.72 | C |
| ATOM | 526 | CG2 | ILE | A | 69 | 53.882 | 40.103 | 17.121 | 1.00 | 51.65 | C |
| ATOM | 527 | CD1 | ILE | A | 69 | 55.853 | 41.082 | 19.316 | 1.00 | 55.82 | C |
| ATOM | 528 | N   | SER | A | 70 | 51.777 | 42.819 | 16.436 | 1.00 | 57.62 | N |
| ATOM | 529 | CA  | SER | A | 70 | 50.969 | 43.017 | 15.245 | 1.00 | 57.49 | C |
| ATOM | 530 | C   | SER | A | 70 | 51.423 | 44.258 | 14.460 | 1.00 | 57.69 | C |
| ATOM | 531 | O   | SER | A | 70 | 51.559 | 44.214 | 13.235 | 1.00 | 56.89 | O |
| ATOM | 532 | CB  | SER | A | 70 | 49.496 | 43.140 | 15.648 | 1.00 | 56.04 | C |
| ATOM | 533 | OG  | SER | A | 70 | 48.658 | 43.190 | 14.514 | 1.00 | 55.69 | O |
| ATOM | 534 | N   | SER | A | 71 | 51.663 | 45.356 | 15.174 | 1.00 | 58.89 | N |
| ATOM | 535 | CA  | SER | A | 71 | 52.098 | 46.616 | 14.564 | 1.00 | 60.02 | C |
| ATOM | 536 | C   | SER | A | 71 | 53.435 | 46.471 | 13.841 | 1.00 | 61.49 | C |
| ATOM | 537 | O   | SER | A | 71 | 53.651 | 47.044 | 12.765 | 1.00 | 61.67 | O |
| ATOM | 538 | CB  | SER | A | 71 | 52.222 | 47.695 | 15.637 | 1.00 | 59.80 | C |
| ATOM | 539 | OG  | SER | A | 71 | 52.885 | 48.836 | 15.121 | 1.00 | 63.50 | O |
| ATOM | 540 | N   | ILE | A | 72 | 54.333 | 45.715 | 14.463 | 1.00 | 61.19 | N |
| ATOM | 541 | CA  | ILE | A | 72 | 55.648 | 45.454 | 13.916 | 1.00 | 61.14 | C |
| ATOM | 542 | C   | ILE | A | 72 | 55.473 | 44.623 | 12.650 | 1.00 | 64.83 | C |
| ATOM | 543 | O   | ILE | A | 72 | 56.002 | 44.962 | 11.594 | 1.00 | 66.72 | O |
| ATOM | 544 | CB  | ILE | A | 72 | 56.506 | 44.688 | 14.956 | 1.00 | 57.53 | C |
| ATOM | 545 | CG1 | ILE | A | 72 | 56.882 | 45.632 | 16.103 | 1.00 | 54.60 | C |
| ATOM | 546 | CG2 | ILE | A | 72 | 57.730 | 44.078 | 14.301 | 1.00 | 53.83 | C |
| ATOM | 547 | CD1 | ILE | A | 72 | 57.539 | 44.936 | 17.282 | 1.00 | 51.49 | C |
| ATOM | 548 | N   | GLU | A | 73 | 54.718 | 43.536 | 12.766 | 1.00 | 69.27 | N |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 549 | CA | GLU | A | 73 | 54.456 | 42.640 | 11.644 | 1.00 | 72.72 | C |
|---|---|---|---|---|---|---|---|---|---|---|---|
| ATOM | 550 | C | GLU | A | 73 | 53.956 | 43.422 | 10.437 | 1.00 | 74.01 | C |
| ATOM | 551 | O | GLU | A | 73 | 54.348 | 43.150 | 9.304 | 1.00 | 74.05 | O |
| ATOM | 552 | CB | GLU | A | 73 | 53.406 | 41.604 | 12.035 | 1.00 | 73.92 | C |
| ATOM | 553 | CG | GLU | A | 73 | 53.023 | 40.650 | 10.921 | 1.00 | 76.79 | C |
| ATOM | 554 | CD | GLU | A | 73 | 51.882 | 39.725 | 11.319 | 1.00 | 79.12 | C |
| ATOM | 555 | OE1 | GLU | A | 73 | 52.019 | 39.008 | 12.338 | 1.00 | 80.53 | O |
| ATOM | 556 | OE2 | GLU | A | 73 | 50.848 | 39.712 | 10.614 | 1.00 | 80.01 | O |
| ATOM | 557 | N | GLN | A | 74 | 53.078 | 44.387 | 10.682 | 1.00 | 74.31 | N |
| ATOM | 558 | CA | GLN | A | 74 | 52.544 | 45.198 | 9.602 | 1.00 | 76.16 | C |
| ATOM | 559 | C | GLN | A | 74 | 53.665 | 45.971 | 8.914 | 1.00 | 75.41 | C |
| ATOM | 560 | O | GLN | A | 74 | 53.822 | 45.907 | 7.693 | 1.00 | 74.85 | O |
| ATOM | 561 | CB | GLN | A | 74 | 51.508 | 46.183 | 10.134 | 1.00 | 78.74 | C |
| ATOM | 562 | CG | GLN | A | 74 | 51.160 | 47.260 | 9.130 | 1.00 | 83.91 | C |
| ATOM | 563 | CD | GLN | A | 74 | 50.368 | 48.389 | 9.744 | 1.00 | 87.77 | C |
| ATOM | 564 | OE1 | GLN | A | 74 | 49.173 | 48.249 | 10.033 | 1.00 | 88.08 | O |
| ATOM | 565 | NE2 | GLN | A | 74 | 51.036 | 49.523 | 9.963 | 1.00 | 89.51 | N |
| ATOM | 566 | N | LYS | A | 75 | 54.434 | 46.712 | 9.705 | 1.00 | 74.38 | N |
| ATOM | 567 | CA | LYS | A | 75 | 55.539 | 47.490 | 9.173 | 1.00 | 73.05 | C |
| ATOM | 568 | C | LYS | A | 75 | 56.503 | 46.628 | 8.366 | 1.00 | 73.99 | C |
| ATOM | 569 | O | LYS | A | 75 | 56.981 | 47.047 | 7.313 | 1.00 | 73.52 | O |
| ATOM | 570 | CB | LYS | A | 75 | 56.291 | 48.173 | 10.309 | 1.00 | 70.73 | C |
| ATOM | 571 | CG | LYS | A | 75 | 55.512 | 49.291 | 10.953 | 1.00 | 69.59 | C |
| ATOM | 572 | CD | LYS | A | 75 | 56.274 | 49.888 | 12.118 | 1.00 | 68.68 | C |
| ATOM | 573 | CE | LYS | A | 75 | 55.483 | 51.008 | 12.760 | 1.00 | 67.19 | C |
| ATOM | 574 | NZ | LYS | A | 75 | 56.143 | 51.523 | 13.990 | 1.00 | 68.33 | N |
| ATOM | 575 | N | GLU | A | 76 | 56.773 | 45.420 | 8.848 | 1.00 | 74.56 | N |
| ATOM | 576 | CA | GLU | A | 76 | 57.696 | 44.527 | 8.164 | 1.00 | 76.99 | C |
| ATOM | 577 | C | GLU | A | 76 | 57.177 | 43.922 | 6.871 | 1.00 | 79.54 | C |
| ATOM | 578 | O | GLU | A | 76 | 57.907 | 43.845 | 5.887 | 1.00 | 81.09 | O |
| ATOM | 579 | CB | GLU | A | 76 | 58.146 | 43.419 | 9.111 | 1.00 | 76.78 | C |
| ATOM | 580 | CG | GLU | A | 76 | 59.073 | 43.927 | 10.198 | 1.00 | 78.29 | C |
| ATOM | 581 | CD | GLU | A | 76 | 60.384 | 44.456 | 9.637 | 1.00 | 78.66 | C |
| ATOM | 582 | OE1 | GLU | A | 76 | 61.210 | 43.626 | 9.199 | 1.00 | 78.56 | O |
| ATOM | 583 | OE2 | GLU | A | 76 | 60.583 | 45.693 | 9.624 | 1.00 | 77.66 | O |
| ATOM | 584 | N | GLU | A | 77 | 55.924 | 43.486 | 6.856 | 1.00 | 82.69 | N |
| ATOM | 585 | CA | GLU | A | 77 | 55.372 | 42.895 | 5.643 | 1.00 | 85.13 | C |
| ATOM | 586 | C | GLU | A | 77 | 55.257 | 43.940 | 4.531 | 1.00 | 86.04 | C |
| ATOM | 587 | O | GLU | A | 77 | 55.382 | 43.606 | 3.348 | 1.00 | 86.80 | O |
| ATOM | 588 | CB | GLU | A | 77 | 54.004 | 42.273 | 5.923 | 1.00 | 86.36 | C |
| ATOM | 589 | CG | GLU | A | 77 | 52.942 | 43.280 | 6.317 | 1.00 | 88.31 | C |
| ATOM | 590 | CD | GLU | A | 77 | 51.668 | 42.619 | 6.804 | 1.00 | 89.10 | C |
| ATOM | 591 | OE1 | GLU | A | 77 | 50.741 | 43.362 | 7.205 | 1.00 | 88.75 | O |
| ATOM | 592 | OE2 | GLU | A | 77 | 51.598 | 41.366 | 6.786 | 1.00 | 87.83 | O |
| ATOM | 593 | N | SER | A | 78 | 55.027 | 45.199 | 4.904 | 1.00 | 85.49 | N |
| ATOM | 594 | CA | SER | A | 78 | 54.916 | 46.269 | 3.915 | 1.00 | 86.08 | C |
| ATOM | 595 | C | SER | A | 78 | 56.304 | 46.805 | 3.586 | 1.00 | 86.97 | C |
| ATOM | 596 | O | SER | A | 78 | 56.452 | 47.789 | 2.859 | 1.00 | 87.48 | O |
| ATOM | 597 | CB | SER | A | 78 | 54.039 | 47.410 | 4.437 | 1.00 | 86.25 | C |
| ATOM | 598 | OG | SER | A | 78 | 54.707 | 48.163 | 5.434 | 1.00 | 87.17 | O |
| ATOM | 599 | N | ARG | A | 79 | 57.320 | 46.155 | 4.141 | 1.00 | 87.66 | N |
| ATOM | 600 | CA | ARG | A | 79 | 58.706 | 46.536 | 3.906 | 1.00 | 87.71 | C |
| ATOM | 601 | C | ARG | A | 79 | 59.235 | 45.476 | 2.962 | 1.00 | 87.68 | C |
| ATOM | 602 | O | ARG | A | 79 | 60.338 | 45.583 | 2.435 | 1.00 | 88.01 | O |
| ATOM | 603 | CB | ARG | A | 79 | 59.503 | 46.484 | 5.208 | 1.00 | 88.16 | C |
| ATOM | 604 | CG | ARG | A | 79 | 60.843 | 47.173 | 5.153 | 1.00 | 89.13 | C |
| ATOM | 605 | CD | ARG | A | 79 | 60.705 | 48.601 | 5.625 | 1.00 | 90.58 | C |
| ATOM | 606 | NE | ARG | A | 79 | 60.108 | 48.644 | 6.958 | 1.00 | 92.61 | N |
| ATOM | 607 | CZ | ARG | A | 79 | 59.945 | 49.752 | 7.676 | 1.00 | 93.50 | C |
| ATOM | 608 | NH1 | ARG | A | 79 | 60.338 | 50.924 | 7.191 | 1.00 | 93.77 | N |
| ATOM | 609 | NH2 | ARG | A | 79 | 59.387 | 49.689 | 8.883 | 1.00 | 93.57 | N |
| ATOM | 610 | N | GLY | A | 80 | 58.428 | 44.439 | 2.769 | 1.00 | 87.78 | N |
| ATOM | 611 | CA | GLY | A | 80 | 58.814 | 43.351 | 1.898 | 1.00 | 88.38 | C |
| ATOM | 612 | C | GLY | A | 80 | 59.619 | 42.311 | 2.648 | 1.00 | 89.02 | C |
| ATOM | 613 | O | GLY | A | 80 | 59.684 | 41.154 | 2.240 | 1.00 | 89.02 | O |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 614 | N | ASN | A | 81 | 60.236 | 42.715 | 3.752 | 1.00 | 90.16 | N |
|---|---|---|---|---|---|---|---|---|---|---|---|
| ATOM | 615 | CA | ASN | A | 81 | 61.038 | 41.788 | 4.535 | 1.00 | 91.45 | C |
| ATOM | 616 | C | ASN | A | 81 | 60.167 | 40.637 | 5.018 | 1.00 | 91.45 | C |
| ATOM | 617 | O | ASN | A | 81 | 59.370 | 40.804 | 5.938 | 1.00 | 91.12 | O |
| ATOM | 618 | CB | ASN | A | 81 | 61.651 | 42.494 | 5.735 | 1.00 | 93.05 | C |
| ATOM | 619 | CG | ASN | A | 81 | 62.640 | 41.618 | 6.468 | 1.00 | 95.15 | C |
| ATOM | 620 | OD1 | ASN | A | 81 | 62.434 | 40.405 | 6.604 | 1.00 | 95.61 | O |
| ATOM | 621 | ND2 | ASN | A | 81 | 63.722 | 42.223 | 6.953 | 1.00 | 95.95 | N |
| ATOM | 622 | N | GLU | A | 82 | 60.343 | 39.465 | 4.412 | 1.00 | 91.99 | N |
| ATOM | 623 | CA | GLU | A | 82 | 59.545 | 38.293 | 4.757 | 1.00 | 92.50 | C |
| ATOM | 624 | C | GLU | A | 82 | 60.119 | 37.356 | 5.819 | 1.00 | 92.15 | C |
| ATOM | 625 | O | GLU | A | 82 | 59.363 | 36.705 | 6.539 | 1.00 | 92.37 | O |
| ATOM | 626 | CB | GLU | A | 82 | 59.240 | 37.488 | 3.491 | 1.00 | 94.09 | C |
| ATOM | 627 | CG | GLU | A | 82 | 58.475 | 38.259 | 2.422 | 1.00 | 96.82 | C |
| ATOM | 628 | CD | GLU | A | 82 | 57.176 | 38.863 | 2.943 | 1.00 | 99.40 | C |
| ATOM | 629 | OE1 | GLU | A | 82 | 56.375 | 38.127 | 3.565 | 1.00 | 101.32 | O |
| ATOM | 630 | OE2 | GLU | A | 82 | 56.951 | 40.075 | 2.725 | 1.00 | 100.89 | O |
| ATOM | 631 | N | GLU | A | 83 | 61.443 | 37.270 | 5.916 | 1.00 | 91.83 | N |
| ATOM | 632 | CA | GLU | A | 83 | 62.060 | 36.386 | 6.902 | 1.00 | 90.78 | C |
| ATOM | 633 | C | GLU | A | 83 | 61.666 | 36.798 | 8.313 | 1.00 | 88.31 | C |
| ATOM | 634 | O | GLU | A | 83 | 61.544 | 35.960 | 9.218 | 1.00 | 88.83 | O |
| ATOM | 635 | CB | GLU | A | 83 | 63.585 | 36.397 | 6.761 | 1.00 | 93.25 | C |
| ATOM | 636 | CG | GLU | A | 83 | 64.104 | 35.536 | 5.616 | 1.00 | 98.24 | C |
| ATOM | 637 | CD | GLU | A | 83 | 63.791 | 36.116 | 4.244 | 1.00 | 101.30 | C |
| ATOM | 638 | OE1 | GLU | A | 83 | 64.033 | 35.420 | 3.232 | 1.00 | 102.88 | O |
| ATOM | 639 | OE2 | GLU | A | 83 | 63.311 | 37.270 | 4.177 | 1.00 | 103.70 | O |
| ATOM | 640 | N | HIS | A | 84 | 61.465 | 38.096 | 8.493 | 1.00 | 83.32 | N |
| ATOM | 641 | CA | HIS | A | 84 | 61.070 | 38.620 | 9.782 | 1.00 | 79.12 | C |
| ATOM | 642 | C | HIS | A | 84 | 59.605 | 38.326 | 10.025 | 1.00 | 77.18 | C |
| ATOM | 643 | O | HIS | A | 84 | 59.239 | 37.803 | 11.077 | 1.00 | 76.52 | O |
| ATOM | 644 | CB | HIS | A | 84 | 61.323 | 40.127 | 9.837 | 1.00 | 77.97 | C |
| ATOM | 645 | CG | HIS | A | 84 | 62.742 | 40.481 | 10.157 | 1.00 | 76.86 | C |
| ATOM | 646 | ND1 | HIS | A | 84 | 63.209 | 41.778 | 10.146 | 1.00 | 76.03 | N |
| ATOM | 647 | CD2 | HIS | A | 84 | 63.794 | 39.705 | 10.513 | 1.00 | 74.94 | C |
| ATOM | 648 | CE1 | HIS | A | 84 | 64.487 | 41.785 | 10.481 | 1.00 | 75.06 | C |
| ATOM | 649 | NE2 | HIS | A | 84 | 64.866 | 40.540 | 10.709 | 1.00 | 74.76 | N |
| ATOM | 650 | N | VAL | A | 85 | 58.776 | 38.650 | 9.036 | 1.00 | 75.22 | N |
| ATOM | 651 | CA | VAL | A | 85 | 57.339 | 38.439 | 9.129 | 1.00 | 72.63 | C |
| ATOM | 652 | C | VAL | A | 85 | 56.990 | 37.028 | 9.615 | 1.00 | 71.46 | C |
| ATOM | 653 | O | VAL | A | 85 | 56.058 | 36.848 | 10.395 | 1.00 | 71.21 | O |
| ATOM | 654 | CB | VAL | A | 85 | 56.645 | 38.733 | 7.766 | 1.00 | 71.91 | C |
| ATOM | 655 | CG1 | VAL | A | 85 | 55.162 | 38.453 | 7.859 | 1.00 | 72.29 | C |
| ATOM | 656 | CG2 | VAL | A | 85 | 56.837 | 40.194 | 7.389 | 1.00 | 71.78 | C |
| ATOM | 657 | N | ASN | A | 86 | 57.740 | 36.025 | 9.187 | 1.00 | 70.56 | N |
| ATOM | 658 | CA | ASN | A | 86 | 57.439 | 34.670 | 9.635 | 1.00 | 71.50 | C |
| ATOM | 659 | C | ASN | A | 86 | 57.727 | 34.456 | 11.110 | 1.00 | 69.72 | C |
| ATOM | 660 | O | ASN | A | 86 | 57.108 | 33.612 | 11.757 | 1.00 | 69.52 | O |
| ATOM | 661 | CB | ASN | A | 86 | 58.207 | 33.652 | 8.802 | 1.00 | 73.96 | C |
| ATOM | 662 | CG | ASN | A | 86 | 57.583 | 33.446 | 7.447 | 1.00 | 77.38 | C |
| ATOM | 663 | OD1 | ASN | A | 86 | 56.442 | 32.982 | 7.343 | 1.00 | 78.78 | O |
| ATOM | 664 | ND2 | ASN | A | 86 | 58.313 | 33.804 | 6.396 | 1.00 | 78.44 | N |
| ATOM | 665 | N | SER | A | 87 | 58.676 | 35.219 | 11.635 | 1.00 | 67.97 | N |
| ATOM | 666 | CA | SER | A | 87 | 59.033 | 35.121 | 13.042 | 1.00 | 65.60 | C |
| ATOM | 667 | C | SER | A | 87 | 58.085 | 35.974 | 13.871 | 1.00 | 62.17 | C |
| ATOM | 668 | O | SER | A | 87 | 57.760 | 35.633 | 14.998 | 1.00 | 60.92 | O |
| ATOM | 669 | CB | SER | A | 87 | 60.476 | 35.582 | 13.257 | 1.00 | 66.50 | C |
| ATOM | 670 | OG | SER | A | 87 | 61.383 | 34.665 | 12.675 | 1.00 | 65.35 | O |
| ATOM | 671 | N | ILE | A | 88 | 57.652 | 37.091 | 13.306 | 1.00 | 61.11 | N |
| ATOM | 672 | CA | ILE | A | 88 | 56.727 | 37.975 | 13.993 | 1.00 | 60.92 | C |
| ATOM | 673 | C | ILE | A | 88 | 55.442 | 37.188 | 14.220 | 1.00 | 61.41 | C |
| ATOM | 674 | O | ILE | A | 88 | 54.938 | 37.121 | 15.342 | 1.00 | 61.26 | O |
| ATOM | 675 | CB | ILE | A | 88 | 56.379 | 39.230 | 13.138 | 1.00 | 61.93 | C |
| ATOM | 676 | CG1 | ILE | A | 88 | 57.654 | 39.874 | 12.579 | 1.00 | 60.46 | C |
| ATOM | 677 | CG2 | ILE | A | 88 | 55.610 | 40.238 | 13.978 | 1.00 | 60.02 | C |
| ATOM | 678 | CD1 | ILE | A | 88 | 58.605 | 40.324 | 13.621 | 1.00 | 62.02 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 679 | N | ARG | A | 89 | 54.923 | 36.584 | 13.147 | 1.00 | 62.06 | N |
|------|-----|-----|-----|---|----|--------|--------|--------|------|-------|---|
| ATOM | 680 | CA | ARG | A | 89 | 53.680 | 35.808 | 13.209 | 1.00 | 61.72 | C |
| ATOM | 681 | C | ARG | A | 89 | 53.808 | 34.554 | 14.061 | 1.00 | 60.43 | C |
| ATOM | 682 | O | ARG | A | 89 | 52.848 | 34.124 | 14.709 | 1.00 | 57.60 | O |
| ATOM | 683 | CB | ARG | A | 89 | 53.198 | 35.451 | 11.793 | 1.00 | 64.27 | C |
| ATOM | 684 | CG | ARG | A | 89 | 52.876 | 36.701 | 10.949 | 1.00 | 67.54 | C |
| ATOM | 685 | CD | ARG | A | 89 | 52.128 | 36.409 | 9.649 | 1.00 | 67.61 | C |
| ATOM | 686 | NE | ARG | A | 89 | 52.114 | 37.581 | 8.769 | 1.00 | 69.30 | N |
| ATOM | 687 | CZ | ARG | A | 89 | 51.509 | 37.632 | 7.582 | 1.00 | 68.85 | C |
| ATOM | 688 | NH1 | ARG | A | 89 | 50.855 | 36.569 | 7.127 | 1.00 | 70.10 | N |
| ATOM | 689 | NH2 | ARG | A | 89 | 51.577 | 38.733 | 6.839 | 1.00 | 64.94 | N |
| ATOM | 690 | N | GLU | A | 90 | 54.995 | 33.967 | 14.066 | 1.00 | 60.27 | N |
| ATOM | 691 | CA | GLU | A | 90 | 55.215 | 32.789 | 14.880 | 1.00 | 61.88 | C |
| ATOM | 692 | C | GLU | A | 90 | 55.079 | 33.225 | 16.339 | 1.00 | 60.81 | C |
| ATOM | 693 | O | GLU | A | 90 | 54.532 | 32.498 | 17.172 | 1.00 | 60.14 | O |
| ATOM | 694 | CB | GLU | A | 90 | 56.609 | 32.217 | 14.626 | 1.00 | 65.43 | C |
| ATOM | 695 | CG | GLU | A | 90 | 56.924 | 30.994 | 15.478 | 1.00 | 72.01 | C |
| ATOM | 696 | CD | GLU | A | 90 | 58.236 | 30.333 | 15.096 | 1.00 | 76.15 | C |
| ATOM | 697 | OE1 | GLU | A | 90 | 58.346 | 29.851 | 13.939 | 1.00 | 74.87 | O |
| ATOM | 698 | OE2 | GLU | A | 90 | 59.152 | 30.300 | 15.958 | 1.00 | 78.86 | O |
| ATOM | 699 | N | TYR | A | 91 | 55.572 | 34.424 | 16.635 | 1.00 | 59.33 | N |
| ATOM | 700 | CA | TYR | A | 91 | 55.496 | 34.962 | 17.988 | 1.00 | 59.06 | C |
| ATOM | 701 | C | TYR | A | 91 | 54.050 | 35.349 | 18.309 | 1.00 | 55.88 | C |
| ATOM | 702 | O | TYR | A | 91 | 53.552 | 35.065 | 19.390 | 1.00 | 52.77 | O |
| ATOM | 703 | CB | TYR | A | 91 | 56.398 | 36.189 | 18.135 | 1.00 | 61.20 | C |
| ATOM | 704 | CG | TYR | A | 91 | 56.893 | 36.370 | 19.544 | 1.00 | 64.15 | C |
| ATOM | 705 | CD1 | TYR | A | 91 | 57.827 | 35.496 | 20.076 | 1.00 | 66.84 | C |
| ATOM | 706 | CD2 | TYR | A | 91 | 56.414 | 37.392 | 20.356 | 1.00 | 65.89 | C |
| ATOM | 707 | CE1 | TYR | A | 91 | 58.274 | 35.627 | 21.376 | 1.00 | 67.94 | C |
| ATOM | 708 | CE2 | TYR | A | 91 | 56.859 | 37.531 | 21.668 | 1.00 | 66.71 | C |
| ATOM | 709 | CZ | TYR | A | 91 | 57.791 | 36.641 | 22.163 | 1.00 | 66.83 | C |
| ATOM | 710 | OH | TYR | A | 91 | 58.272 | 36.756 | 23.442 | 1.00 | 69.62 | O |
| ATOM | 711 | N | ARG | A | 92 | 53.384 | 36.000 | 17.361 | 1.00 | 55.04 | N |
| ATOM | 712 | CA | ARG | A | 92 | 51.996 | 36.395 | 17.548 | 1.00 | 55.40 | C |
| ATOM | 713 | C | ARG | A | 92 | 51.116 | 35.175 | 17.881 | 1.00 | 55.93 | C |
| ATOM | 714 | O | ARG | A | 92 | 50.284 | 35.243 | 18.793 | 1.00 | 55.28 | O |
| ATOM | 715 | CB | ARG | A | 92 | 51.475 | 37.104 | 16.296 | 1.00 | 52.86 | C |
| ATOM | 716 | CG | ARG | A | 92 | 50.079 | 37.656 | 16.463 | 1.00 | 53.09 | C |
| ATOM | 717 | CD | ARG | A | 92 | 49.842 | 38.826 | 15.543 | 1.00 | 52.72 | C |
| ATOM | 718 | NE | ARG | A | 92 | 49.914 | 38.451 | 14.133 | 1.00 | 56.87 | N |
| ATOM | 719 | CZ | ARG | A | 92 | 48.941 | 37.840 | 13.453 | 1.00 | 56.85 | C |
| ATOM | 720 | NH1 | ARG | A | 92 | 47.794 | 37.519 | 14.045 | 1.00 | 57.03 | N |
| ATOM | 721 | NH2 | ARG | A | 92 | 49.113 | 37.565 | 12.166 | 1.00 | 55.41 | N |
| ATOM | 722 | N | SER | A | 93 | 51.307 | 34.069 | 17.151 | 1.00 | 55.38 | N |
| ATOM | 723 | CA | SER | A | 93 | 50.542 | 32.846 | 17.399 | 1.00 | 54.14 | C |
| ATOM | 724 | C | SER | A | 93 | 50.614 | 32.550 | 18.869 | 1.00 | 53.63 | C |
| ATOM | 725 | O | SER | A | 93 | 49.591 | 32.368 | 19.521 | 1.00 | 53.80 | O |
| ATOM | 726 | CB | SER | A | 93 | 51.123 | 31.643 | 16.651 | 1.00 | 55.41 | C |
| ATOM | 727 | OG | SER | A | 93 | 50.765 | 31.631 | 15.279 | 1.00 | 57.03 | O |
| ATOM | 728 | N | LYS | A | 94 | 51.840 | 32.509 | 19.388 | 1.00 | 54.61 | N |
| ATOM | 729 | CA | LYS | A | 94 | 52.067 | 32.228 | 20.802 | 1.00 | 54.31 | C |
| ATOM | 730 | C | LYS | A | 94 | 51.259 | 33.187 | 21.694 | 1.00 | 53.47 | C |
| ATOM | 731 | O | LYS | A | 94 | 50.600 | 32.749 | 22.637 | 1.00 | 53.27 | O |
| ATOM | 732 | CB | LYS | A | 94 | 53.573 | 32.294 | 21.117 | 1.00 | 54.33 | C |
| ATOM | 733 | CG | LYS | A | 94 | 53.963 | 31.877 | 22.558 | 1.00 | 59.30 | C |
| ATOM | 734 | CD | LYS | A | 94 | 55.390 | 31.250 | 22.667 | 1.00 | 62.72 | C |
| ATOM | 735 | CE | LYS | A | 94 | 56.521 | 32.118 | 22.048 | 1.00 | 64.82 | C |
| ATOM | 736 | NZ | LYS | A | 94 | 57.912 | 31.552 | 22.219 | 1.00 | 63.26 | N |
| ATOM | 737 | N | ILE | A | 95 | 51.281 | 34.483 | 21.384 | 1.00 | 52.81 | N |
| ATOM | 738 | CA | ILE | A | 95 | 50.528 | 35.450 | 22.185 | 1.00 | 52.38 | C |
| ATOM | 739 | C | ILE | A | 95 | 49.038 | 35.140 | 22.083 | 1.00 | 51.75 | C |
| ATOM | 740 | O | ILE | A | 95 | 48.305 | 35.221 | 23.072 | 1.00 | 50.93 | O |
| ATOM | 741 | CB | ILE | A | 95 | 50.711 | 36.920 | 21.704 | 1.00 | 52.10 | C |
| ATOM | 742 | CG1 | ILE | A | 95 | 52.195 | 37.272 | 21.520 | 1.00 | 50.18 | C |
| ATOM | 743 | CG2 | ILE | A | 95 | 50.062 | 37.862 | 22.718 | 1.00 | 49.50 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 744 | CD1 | ILE | A | 95 | 53.018 | 37.222 | 22.783 | 1.00 | 51.57 | C |
|---|---|---|---|---|---|---|---|---|---|---|---|
| ATOM | 745 | N | GLU | A | 96 | 48.599 | 34.786 | 20.879 | 1.00 | 50.81 | N |
| ATOM | 746 | CA | GLU | A | 96 | 47.196 | 34.482 | 20.636 | 1.00 | 52.42 | C |
| ATOM | 747 | C | GLU | A | 96 | 46.687 | 33.230 | 21.345 | 1.00 | 53.54 | C |
| ATOM | 748 | O | GLU | A | 96 | 45.528 | 33.171 | 21.763 | 1.00 | 54.41 | O |
| ATOM | 749 | CB | GLU | A | 96 | 46.935 | 34.377 | 19.135 | 1.00 | 51.10 | C |
| ATOM | 750 | CG | GLU | A | 96 | 47.218 | 35.669 | 18.406 | 1.00 | 50.96 | C |
| ATOM | 751 | CD | GLU | A | 96 | 46.929 | 35.566 | 16.938 | 1.00 | 51.66 | C |
| ATOM | 752 | OE1 | GLU | A | 96 | 46.879 | 34.423 | 16.433 | 1.00 | 52.21 | O |
| ATOM | 753 | OE2 | GLU | A | 96 | 46.763 | 36.621 | 16.288 | 1.00 | 50.73 | O |
| ATOM | 754 | N | ASN | A | 97 | 47.542 | 32.226 | 21.483 | 1.00 | 53.94 | N |
| ATOM | 755 | CA | ASN | A | 97 | 47.134 | 31.015 | 22.169 | 1.00 | 53.27 | C |
| ATOM | 756 | C | ASN | A | 97 | 46.847 | 31.365 | 23.618 | 1.00 | 51.69 | C |
| ATOM | 757 | O | ASN | A | 97 | 45.870 | 30.883 | 24.198 | 1.00 | 50.26 | O |
| ATOM | 758 | CB | ASN | A | 97 | 48.235 | 29.964 | 22.069 | 1.00 | 58.04 | C |
| ATOM | 759 | CG | ASN | A | 97 | 48.279 | 29.308 | 20.697 | 1.00 | 64.26 | C |
| ATOM | 760 | OD1 | ASN | A | 97 | 48.082 | 29.964 | 19.663 | 1.00 | 67.77 | O |
| ATOM | 761 | ND2 | ASN | A | 97 | 48.539 | 28.008 | 20.678 | 1.00 | 67.12 | N |
| ATOM | 762 | N | GLU | A | 98 | 47.692 | 32.213 | 24.200 | 1.00 | 50.67 | N |
| ATOM | 763 | CA | GLU | A | 98 | 47.503 | 32.634 | 25.585 | 1.00 | 50.17 | C |
| ATOM | 764 | C | GLU | A | 98 | 46.205 | 33.425 | 25.737 | 1.00 | 49.37 | C |
| ATOM | 765 | O | GLU | A | 98 | 45.466 | 33.249 | 26.709 | 1.00 | 47.16 | O |
| ATOM | 766 | CB | GLU | A | 98 | 48.680 | 33.481 | 26.049 | 1.00 | 51.36 | C |
| ATOM | 767 | CG | GLU | A | 98 | 49.731 | 32.686 | 26.773 | 1.00 | 54.32 | C |
| ATOM | 768 | CD | GLU | A | 98 | 50.890 | 33.536 | 27.228 | 1.00 | 55.21 | C |
| ATOM | 769 | OE1 | GLU | A | 98 | 50.660 | 34.608 | 27.825 | 1.00 | 55.83 | O |
| ATOM | 770 | OE2 | GLU | A | 98 | 52.039 | 33.123 | 26.993 | 1.00 | 58.12 | O |
| ATOM | 771 | N | LEU | A | 99 | 45.934 | 34.300 | 24.772 | 1.00 | 47.96 | N |
| ATOM | 772 | CA | LEU | A | 99 | 44.711 | 35.082 | 24.808 | 1.00 | 48.25 | C |
| ATOM | 773 | C | LEU | A | 99 | 43.539 | 34.111 | 24.791 | 1.00 | 48.41 | C |
| ATOM | 774 | O | LEU | A | 99 | 42.600 | 34.261 | 25.570 | 1.00 | 48.05 | O |
| ATOM | 775 | CB | LEU | A | 99 | 44.645 | 36.045 | 23.613 | 1.00 | 45.79 | C |
| ATOM | 776 | CG | LEU | A | 99 | 45.590 | 37.253 | 23.723 | 1.00 | 45.22 | C |
| ATOM | 777 | CD1 | LEU | A | 99 | 45.728 | 37.949 | 22.372 | 1.00 | 41.64 | C |
| ATOM | 778 | CD2 | LEU | A | 99 | 45.068 | 38.218 | 24.795 | 1.00 | 43.58 | C |
| ATOM | 779 | N | SER | A | 100 | 43.607 | 33.104 | 23.921 | 1.00 | 49.67 | N |
| ATOM | 780 | CA | SER | A | 100 | 42.543 | 32.095 | 23.830 | 1.00 | 51.61 | C |
| ATOM | 781 | C | SER | A | 100 | 42.321 | 31.393 | 25.169 | 1.00 | 52.11 | C |
| ATOM | 782 | O | SER | A | 100 | 41.195 | 31.298 | 25.641 | 1.00 | 53.34 | O |
| ATOM | 783 | CB | SER | A | 100 | 42.871 | 31.048 | 22.759 | 1.00 | 49.42 | C |
| ATOM | 784 | OG | SER | A | 100 | 42.740 | 31.596 | 21.459 | 1.00 | 51.87 | O |
| ATOM | 785 | N | LYS | A | 101 | 43.396 | 30.910 | 25.782 | 1.00 | 52.79 | N |
| ATOM | 786 | CA | LYS | A | 101 | 43.284 | 30.231 | 27.059 | 1.00 | 53.85 | C |
| ATOM | 787 | C | LYS | A | 101 | 42.712 | 31.155 | 26.121 | 1.00 | 54.42 | C |
| ATOM | 788 | O | LYS | A | 101 | 41.778 | 30.781 | 28.833 | 1.00 | 55.45 | O |
| ATOM | 789 | CB | LYS | A | 101 | 44.649 | 29.703 | 27.505 | 1.00 | 56.03 | C |
| ATOM | 790 | CG | LYS | A | 101 | 45.250 | 28.683 | 26.539 | 1.00 | 60.89 | C |
| ATOM | 791 | CD | LYS | A | 101 | 46.558 | 28.086 | 27.067 | 1.00 | 65.04 | C |
| ATOM | 792 | CE | LYS | A | 101 | 47.244 | 27.212 | 26.012 | 1.00 | 66.55 | C |
| ATOM | 793 | NZ | LYS | A | 101 | 46.394 | 26.053 | 25.607 | 1.00 | 68.49 | N |
| ATOM | 794 | N | ILE | A | 102 | 43.267 | 32.360 | 28.229 | 1.00 | 53.82 | N |
| ATOM | 795 | CA | ILE | A | 102 | 42.793 | 33.329 | 29.214 | 1.00 | 52.64 | C |
| ATOM | 796 | C | ILE | A | 102 | 41.298 | 33.553 | 29.048 | 1.00 | 52.85 | C |
| ATOM | 797 | O | ILE | A | 102 | 40.537 | 33.418 | 30.007 | 1.00 | 53.38 | O |
| ATOM | 798 | CB | ILE | A | 102 | 43.525 | 34.689 | 29.071 | 1.00 | 53.53 | C |
| ATOM | 799 | CG1 | ILE | A | 102 | 45.005 | 34.523 | 29.425 | 1.00 | 51.68 | C |
| ATOM | 800 | CG2 | ILE | A | 102 | 42.903 | 35.730 | 30.002 | 1.00 | 51.72 | C |
| ATOM | 801 | CD1 | ILE | A | 102 | 45.833 | 35.731 | 29.092 | 1.00 | 50.92 | C |
| ATOM | 802 | N | CYS | A | 103 | 40.878 | 33.888 | 27.832 | 1.00 | 52.15 | N |
| ATOM | 803 | CA | CYS | A | 103 | 39.465 | 34.128 | 27.555 | 1.00 | 52.94 | C |
| ATOM | 804 | C | CYS | A | 103 | 38.595 | 32.924 | 27.907 | 1.00 | 54.22 | C |
| ATOM | 805 | O | CYS | A | 103 | 37.481 | 33.064 | 28.412 | 1.00 | 54.38 | O |
| ATOM | 806 | CB | CYS | A | 103 | 39.260 | 34.479 | 26.077 | 1.00 | 52.10 | C |
| ATOM | 807 | SG | CYS | A | 103 | 39.788 | 36.144 | 25.593 | 1.00 | 48.22 | S |
| ATOM | 808 | N | ASP | A | 104 | 39.119 | 31.738 | 27.640 | 1.00 | 55.75 | N |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 809 | CA  | ASP | A | 104 | 38.402 | 30.501 | 27.903 | 1.00 | 57.51 | C |
|------|-----|-----|-----|---|-----|--------|--------|--------|------|-------|---|
| ATOM | 810 | C   | ASP | A | 104 | 38.160 | 30.249 | 29.395 | 1.00 | 55.98 | C |
| ATOM | 811 | O   | ASP | A | 104 | 37.082 | 29.816 | 29.794 | 1.00 | 56.40 | O |
| ATOM | 812 | CB  | ASP | A | 104 | 39.178 | 29.327 | 27.293 | 1.00 | 61.16 | C |
| ATOM | 813 | CG  | ASP | A | 104 | 38.428 | 28.017 | 27.396 | 1.00 | 66.28 | C |
| ATOM | 814 | OD1 | ASP | A | 104 | 37.379 | 27.880 | 26.720 | 1.00 | 67.03 | O |
| ATOM | 815 | OD2 | ASP | A | 104 | 38.883 | 27.128 | 28.159 | 1.00 | 68.42 | O |
| ATOM | 816 | N   | GLY | A | 105 | 39.162 | 30.517 | 30.220 | 1.00 | 54.55 | N |
| ATOM | 817 | CA  | GLY | A | 105 | 39.006 | 30.284 | 31.643 | 1.00 | 53.50 | C |
| ATOM | 818 | C   | GLY | A | 105 | 37.947 | 31.149 | 32.304 | 1.00 | 54.23 | C |
| ATOM | 819 | O   | GLY | A | 105 | 37.179 | 30.669 | 33.138 | 1.00 | 55.07 | O |
| ATOM | 820 | N   | ILE | A | 106 | 37.908 | 32.427 | 31.938 | 1.00 | 52.62 | N |
| ATOM | 821 | CA  | ILE | A | 106 | 36.945 | 33.349 | 32.514 | 1.00 | 50.09 | C |
| ATOM | 822 | C   | ILE | A | 106 | 35.553 | 33.172 | 31.909 | 1.00 | 50.61 | C |
| ATOM | 823 | O   | ILE | A | 106 | 34.548 | 33.420 | 32.582 | 1.00 | 49.27 | O |
| ATOM | 824 | CB  | ILE | A | 106 | 37.396 | 34.819 | 32.333 | 1.00 | 46.60 | C |
| ATOM | 825 | CG1 | ILE | A | 106 | 36.362 | 35.764 | 32.949 | 1.00 | 45.02 | C |
| ATOM | 826 | CG2 | ILE | A | 106 | 37.614 | 35.116 | 30.865 | 1.00 | 47.13 | C |
| ATOM | 827 | CD1 | ILE | A | 106 | 36.096 | 35.507 | 34.442 | 1.00 | 41.02 | C |
| ATOM | 828 | N   | LEU | A | 107 | 35.487 | 32.744 | 30.650 | 1.00 | 50.32 | N |
| ATOM | 829 | CA  | LEU | A | 107 | 34.193 | 32.552 | 30.012 | 1.00 | 51.20 | C |
| ATOM | 830 | C   | LEU | A | 107 | 33.496 | 31.332 | 30.612 | 1.00 | 54.43 | C |
| ATOM | 831 | O   | LEU | A | 107 | 32.275 | 31.346 | 30.851 | 1.00 | 55.89 | O |
| ATOM | 832 | CB  | LEU | A | 107 | 34.352 | 32.412 | 28.497 | 1.00 | 47.68 | C |
| ATOM | 833 | CG  | LEU | A | 107 | 34.565 | 33.767 | 27.801 | 1.00 | 48.19 | C |
| ATOM | 834 | CD1 | LEU | A | 107 | 34.779 | 33.590 | 26.305 | 1.00 | 43.25 | C |
| ATOM | 835 | CD2 | LEU | A | 107 | 33.356 | 34.660 | 28.062 | 1.00 | 45.17 | C |
| ATOM | 836 | N   | LYS | A | 108 | 34.273 | 30.285 | 30.878 | 1.00 | 54.70 | N |
| ATOM | 837 | CA  | LYS | A | 108 | 33.732 | 29.078 | 31.483 | 1.00 | 54.49 | C |
| ATOM | 838 | C   | LYS | A | 108 | 33.298 | 29.379 | 32.907 | 1.00 | 52.41 | C |
| ATOM | 839 | O   | LYS | A | 108 | 32.257 | 28.913 | 33.359 | 1.00 | 53.22 | O |
| ATOM | 840 | CB  | LYS | A | 108 | 34.773 | 27.959 | 31.476 | 1.00 | 58.35 | C |
| ATOM | 841 | CG  | LYS | A | 108 | 34.879 | 27.254 | 30.128 | 1.00 | 63.84 | C |
| ATOM | 842 | CD  | LYS | A | 108 | 35.921 | 26.141 | 30.149 | 1.00 | 69.12 | C |
| ATOM | 843 | CE  | LYS | A | 108 | 35.772 | 25.213 | 28.944 | 1.00 | 70.26 | C |
| ATOM | 844 | NZ  | LYS | A | 108 | 35.748 | 25.966 | 27.658 | 1.00 | 73.12 | N |
| ATOM | 845 | N   | LEU | A | 109 | 34.091 | 30.167 | 33.615 | 1.00 | 50.22 | N |
| ATOM | 846 | CA  | LEU | A | 109 | 33.738 | 30.518 | 34.984 | 1.00 | 50.30 | C |
| ATOM | 847 | C   | LEU | A | 109 | 32.459 | 31.359 | 34.998 | 1.00 | 51.02 | C |
| ATOM | 848 | O   | LEU | A | 109 | 31.678 | 31.296 | 35.950 | 1.00 | 50.88 | O |
| ATOM | 849 | CB  | LEU | A | 109 | 34.867 | 31.305 | 35.656 | 1.00 | 48.38 | C |
| ATOM | 850 | CG  | LEU | A | 109 | 34.601 | 31.534 | 37.142 | 1.00 | 48.80 | C |
| ATOM | 851 | CD1 | LEU | A | 109 | 34.554 | 30.181 | 37.840 | 1.00 | 47.03 | C |
| ATOM | 852 | CD2 | LEU | A | 109 | 35.673 | 32.417 | 37.750 | 1.00 | 48.16 | C |
| ATOM | 853 | N   | LEU | A | 110 | 32.254 | 32.147 | 33.943 | 1.00 | 51.41 | N |
| ATOM | 854 | CA  | LEU | A | 110 | 31.069 | 32.996 | 33.837 | 1.00 | 52.67 | C |
| ATOM | 855 | C   | LEU | A | 110 | 29.787 | 32.172 | 33.688 | 1.00 | 54.53 | C |
| ATOM | 856 | O   | LEU | A | 110 | 28.775 | 32.461 | 34.333 | 1.00 | 53.21 | O |
| ATOM | 857 | CB  | LEU | A | 110 | 31.200 | 33.963 | 32.647 | 1.00 | 50.75 | C |
| ATOM | 858 | CG  | LEU | A | 110 | 32.136 | 35.175 | 32.781 | 1.00 | 49.15 | C |
| ATOM | 859 | CD1 | LEU | A | 110 | 32.247 | 35.895 | 31.440 | 1.00 | 45.61 | C |
| ATOM | 860 | CD2 | LEU | A | 110 | 31.616 | 36.112 | 33.843 | 1.00 | 47.06 | C |
| ATOM | 861 | N   | ASP | A | 111 | 29.842 | 31.140 | 32.847 | 1.00 | 57.01 | N |
| ATOM | 862 | CA  | ASP | A | 111 | 28.688 | 30.280 | 32.604 | 1.00 | 58.58 | C |
| ATOM | 863 | C   | ASP | A | 111 | 28.403 | 29.296 | 33.727 | 1.00 | 59.61 | C |
| ATOM | 864 | O   | ASP | A | 111 | 27.244 | 29.058 | 34.072 | 1.00 | 60.23 | O |
| ATOM | 865 | CB  | ASP | A | 111 | 28.865 | 29.502 | 31.298 | 1.00 | 59.60 | C |
| ATOM | 866 | CG  | ASP | A | 111 | 28.437 | 30.302 | 30.084 | 1.00 | 63.44 | C |
| ATOM | 867 | OD1 | ASP | A | 111 | 27.882 | 31.407 | 30.268 | 1.00 | 63.25 | O |
| ATOM | 868 | OD2 | ASP | A | 111 | 28.645 | 29.827 | 28.943 | 1.00 | 67.04 | O |
| ATOM | 869 | N   | ALA | A | 112 | 29.459 | 28.742 | 34.307 | 1.00 | 59.67 | N |
| ATOM | 870 | CA  | ALA | A | 112 | 29.318 | 27.754 | 35.362 | 1.00 | 60.53 | C |
| ATOM | 871 | C   | ALA | A | 112 | 28.949 | 28.293 | 36.734 | 1.00 | 61.74 | C |
| ATOM | 872 | O   | ALA | A | 112 | 28.144 | 27.694 | 37.448 | 1.00 | 61.23 | O |
| ATOM | 873 | CB  | ALA | A | 112 | 30.599 | 26.947 | 35.469 | 1.00 | 61.02 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 874 | N | LYS | A | 113 | 29.531 | 29.420 | 37.113 | 1.00 | 62.67 | N |
|---|---|---|---|---|---|---|---|---|---|---|---|
| ATOM | 875 | CA | LYS | A | 113 | 29.262 | 29.964 | 38.437 | 1.00 | 64.13 | C |
| ATOM | 876 | C | LYS | A | 113 | 28.781 | 31.407 | 38.483 | 1.00 | 62.82 | C |
| ATOM | 877 | O | LYS | A | 113 | 27.717 | 31.703 | 39.030 | 1.00 | 62.93 | O |
| ATOM | 878 | CB | LYS | A | 113 | 30.521 | 29.833 | 39.304 | 1.00 | 65.56 | C |
| ATOM | 879 | CG | LYS | A | 113 | 30.802 | 28.432 | 39.811 | 1.00 | 69.57 | C |
| ATOM | 880 | CD | LYS | A | 113 | 30.421 | 28.335 | 41.281 | 1.00 | 73.61 | C |
| ATOM | 881 | CE | LYS | A | 113 | 30.686 | 26.949 | 41.856 | 1.00 | 76.08 | C |
| ATOM | 882 | NZ | LYS | A | 113 | 30.440 | 26.918 | 43.335 | 1.00 | 75.96 | N |
| ATOM | 883 | N | LEU | A | 114 | 29.573 | 32.298 | 37.902 | 1.00 | 60.38 | N |
| ATOM | 884 | CA | LEU | A | 114 | 29.276 | 33.713 | 37.925 | 1.00 | 58.01 | C |
| ATOM | 885 | C | LEU | A | 114 | 27.865 | 34.140 | 37.541 | 1.00 | 57.53 | C |
| ATOM | 886 | O | LEU | A | 114 | 27.152 | 34.716 | 38.362 | 1.00 | 56.38 | O |
| ATOM | 887 | CB | LEU | A | 114 | 30.319 | 34.449 | 37.090 | 1.00 | 56.40 | C |
| ATOM | 888 | CG | LEU | A | 114 | 31.719 | 34.234 | 37.683 | 1.00 | 55.99 | C |
| ATOM | 889 | CD1 | LEU | A | 114 | 32.749 | 35.062 | 36.928 | 1.00 | 52.73 | C |
| ATOM | 890 | CD2 | LEU | A | 114 | 31.698 | 34.612 | 39.169 | 1.00 | 52.55 | C |
| ATOM | 891 | N | ILE | A | 115 | 27.452 | 33.860 | 36.312 | 1.00 | 56.45 | N |
| ATOM | 892 | CA | ILE | A | 115 | 26.121 | 34.255 | 35.875 | 1.00 | 56.06 | C |
| ATOM | 893 | C | ILE | A | 115 | 24.980 | 33.565 | 36.636 | 1.00 | 57.35 | C |
| ATOM | 894 | O | ILE | A | 115 | 24.015 | 34.217 | 37.046 | 1.00 | 57.49 | O |
| ATOM | 895 | CB | ILE | A | 115 | 25.966 | 34.030 | 34.359 | 1.00 | 54.97 | C |
| ATOM | 896 | CG1 | ILE | A | 115 | 26.886 | 35.003 | 33.614 | 1.00 | 53.47 | C |
| ATOM | 897 | CG2 | ILE | A | 115 | 24.525 | 34.232 | 33.934 | 1.00 | 53.09 | C |
| ATOM | 898 | CD1 | ILE | A | 115 | 27.029 | 34.721 | 32.129 | 1.00 | 51.06 | C |
| ATOM | 899 | N | PRO | A | 116 | 25.071 | 32.243 | 36.842 | 1.00 | 58.03 | N |
| ATOM | 900 | CA | PRO | A | 116 | 23.978 | 31.595 | 37.569 | 1.00 | 57.35 | C |
| ATOM | 901 | C | PRO | A | 116 | 23.713 | 32.173 | 38.956 | 1.00 | 56.71 | C |
| ATOM | 902 | O | PRO | A | 116 | 22.607 | 32.060 | 39.471 | 1.00 | 58.23 | O |
| ATOM | 903 | CB | PRO | A | 116 | 24.425 | 30.135 | 37.630 | 1.00 | 56.40 | C |
| ATOM | 904 | CG | PRO | A | 116 | 25.156 | 29.962 | 36.338 | 1.00 | 57.06 | C |
| ATOM | 905 | CD | PRO | A | 116 | 25.991 | 31.236 | 36.275 | 1.00 | 59.09 | C |
| ATOM | 906 | N | SER | A | 117 | 24.709 | 32.810 | 39.553 | 1.00 | 56.39 | N |
| ATOM | 907 | CA | SER | A | 117 | 24.547 | 33.354 | 40.899 | 1.00 | 56.08 | C |
| ATOM | 908 | C | SER | A | 117 | 24.146 | 34.822 | 40.979 | 1.00 | 56.70 | C |
| ATOM | 909 | O | SER | A | 117 | 23.934 | 35.337 | 42.077 | 1.00 | 56.03 | O |
| ATOM | 910 | CB | SER | A | 117 | 25.845 | 33.189 | 41.681 | 1.00 | 58.12 | C |
| ATOM | 911 | OG | SER | A | 117 | 26.842 | 34.077 | 41.174 | 1.00 | 58.98 | O |
| ATOM | 912 | N | ALA | A | 118 | 24.052 | 35.507 | 39.846 | 1.00 | 58.05 | N |
| ATOM | 913 | CA | ALA | A | 118 | 23.692 | 36.919 | 39.880 | 1.00 | 60.22 | C |
| ATOM | 914 | C | ALA | A | 118 | 22.266 | 37.126 | 40.382 | 1.00 | 61.29 | C |
| ATOM | 915 | O | ALA | A | 118 | 21.296 | 36.841 | 39.678 | 1.00 | 62.05 | O |
| ATOM | 916 | CB | ALA | A | 118 | 23.858 | 37.540 | 38.494 | 1.00 | 60.02 | C |
| ATOM | 917 | N | ALA | A | 119 | 22.132 | 37.618 | 41.605 | 1.00 | 62.06 | N |
| ATOM | 918 | CA | ALA | A | 119 | 20.806 | 37.841 | 42.172 | 1.00 | 63.33 | C |
| ATOM | 919 | C | ALA | A | 119 | 20.324 | 39.301 | 42.101 | 1.00 | 64.22 | C |
| ATOM | 920 | O | ALA | A | 119 | 19.519 | 39.715 | 42.941 | 1.00 | 65.34 | O |
| ATOM | 921 | CB | ALA | A | 119 | 20.795 | 37.353 | 43.637 | 1.00 | 61.80 | C |
| ATOM | 922 | N | SER | A | 120 | 20.788 | 40.074 | 41.117 | 1.00 | 63.50 | N |
| ATOM | 923 | CA | SER | A | 120 | 20.366 | 41.474 | 41.009 | 1.00 | 63.47 | C |
| ATOM | 924 | C | SER | A | 120 | 20.750 | 42.113 | 39.678 | 1.00 | 63.16 | C |
| ATOM | 925 | O | SER | A | 120 | 21.530 | 41.541 | 38.921 | 1.00 | 62.78 | O |
| ATOM | 926 | CB | SER | A | 120 | 20.967 | 42.295 | 42.151 | 1.00 | 62.98 | C |
| ATOM | 927 | OG | SER | A | 120 | 22.371 | 42.406 | 42.001 | 1.00 | 64.77 | O |
| ATOM | 928 | N | GLY | A | 121 | 20.196 | 43.290 | 39.386 | 1.00 | 61.97 | N |
| ATOM | 929 | CA | GLY | A | 121 | 20.527 | 43.953 | 38.137 | 1.00 | 61.04 | C |
| ATOM | 930 | C | GLY | A | 121 | 22.012 | 44.267 | 38.089 | 1.00 | 60.71 | C |
| ATOM | 931 | O | GLY | A | 121 | 22.666 | 44.106 | 37.059 | 1.00 | 59.63 | O |
| ATOM | 932 | N | ASP | A | 122 | 22.541 | 44.708 | 39.224 | 1.00 | 60.57 | N |
| ATOM | 933 | CA | ASP | A | 122 | 23.948 | 45.055 | 39.334 | 1.00 | 60.61 | C |
| ATOM | 934 | C | ASP | A | 122 | 24.884 | 43.954 | 38.851 | 1.00 | 61.49 | C |
| ATOM | 935 | O | ASP | A | 122 | 25.685 | 44.178 | 37.933 | 1.00 | 62.64 | O |
| ATOM | 936 | CB | ASP | A | 122 | 24.296 | 45.412 | 40.778 | 1.00 | 61.13 | C |
| ATOM | 937 | CG | ASP | A | 122 | 23.570 | 46.652 | 41.265 | 1.00 | 62.34 | C |
| ATOM | 938 | OD1 | ASP | A | 122 | 23.759 | 47.741 | 40.680 | 1.00 | 62.03 | O |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 939 | OD2 | ASP | A | 122 | 22.805 | 46.537 | 42.240 | 1.00 | 66.21 | O |
|------|-----|-----|-----|---|-----|--------|--------|--------|------|-------|---|
| ATOM | 940 | N   | SER | A | 123 | 24.791 | 42.767 | 39.451 | 1.00 | 60.28 | N |
| ATOM | 941 | CA  | SER | A | 123 | 25.679 | 41.675 | 39.054 | 1.00 | 58.43 | C |
| ATOM | 942 | C   | SER | A | 123 | 25.349 | 41.051 | 37.702 | 1.00 | 56.77 | C |
| ATOM | 943 | O   | SER | A | 123 | 26.249 | 40.617 | 36.994 | 1.00 | 58.45 | O |
| ATOM | 944 | CB  | SER | A | 123 | 25.754 | 40.594 | 40.148 | 1.00 | 57.48 | C |
| ATOM | 945 | OG  | SER | A | 123 | 24.493 | 40.024 | 40.439 | 1.00 | 57.65 | O |
| ATOM | 946 | N   | LYS | A | 124 | 24.079 | 41.021 | 37.323 | 1.00 | 55.84 | N |
| ATOM | 947 | CA  | LYS | A | 124 | 23.710 | 40.442 | 36.037 | 1.00 | 54.65 | C |
| ATOM | 948 | C   | LYS | A | 124 | 24.285 | 41.232 | 34.861 | 1.00 | 54.09 | C |
| ATOM | 949 | O   | LYS | A | 124 | 24.752 | 40.646 | 33.881 | 1.00 | 53.84 | O |
| ATOM | 950 | CB  | LYS | A | 124 | 22.196 | 40.355 | 35.906 | 1.00 | 56.40 | C |
| ATOM | 951 | CG  | LYS | A | 124 | 21.573 | 39.332 | 36.825 | 1.00 | 60.82 | C |
| ATOM | 952 | CD  | LYS | A | 124 | 20.070 | 39.268 | 36.621 | 1.00 | 64.39 | C |
| ATOM | 953 | CE  | LYS | A | 124 | 19.449 | 38.122 | 37.399 | 1.00 | 64.26 | C |
| ATOM | 954 | NZ  | LYS | A | 124 | 17.990 | 38.025 | 37.110 | 1.00 | 69.01 | N |
| ATOM | 955 | N   | VAL | A | 125 | 24.246 | 42.558 | 34.939 | 1.00 | 52.34 | N |
| ATOM | 956 | CA  | VAL | A | 125 | 24.802 | 43.357 | 33.852 | 1.00 | 51.45 | C |
| ATOM | 957 | C   | VAL | A | 125 | 26.322 | 43.202 | 33.884 | 1.00 | 50.78 | C |
| ATOM | 958 | O   | VAL | A | 125 | 26.975 | 43.116 | 32.838 | 1.00 | 50.30 | O |
| ATOM | 959 | CB  | VAL | A | 125 | 24.454 | 44.863 | 33.990 | 1.00 | 51.59 | C |
| ATOM | 960 | CG1 | VAL | A | 125 | 25.102 | 45.647 | 32.859 | 1.00 | 50.32 | C |
| ATOM | 961 | CG2 | VAL | A | 125 | 22.947 | 45.063 | 33.961 | 1.00 | 50.56 | C |
| ATOM | 962 | N   | PHE | A | 126 | 26.870 | 43.152 | 35.100 | 1.00 | 50.31 | N |
| ATOM | 963 | CA  | PHE | A | 126 | 28.306 | 43.012 | 35.319 | 1.00 | 47.63 | C |
| ATOM | 964 | C   | PHE | A | 126 | 28.853 | 41.749 | 34.676 | 1.00 | 48.21 | C |
| ATOM | 965 | O   | PHE | A | 126 | 29.800 | 41.806 | 33.883 | 1.00 | 48.27 | O |
| ATOM | 966 | CB  | PHE | A | 126 | 28.601 | 43.002 | 36.818 | 1.00 | 46.97 | C |
| ATOM | 967 | CG  | PHE | A | 126 | 30.072 | 43.031 | 37.164 | 1.00 | 47.54 | C |
| ATOM | 968 | CD1 | PHE | A | 126 | 30.884 | 41.917 | 36.944 | 1.00 | 46.87 | C |
| ATOM | 969 | CD2 | PHE | A | 126 | 30.640 | 44.168 | 37.739 | 1.00 | 47.80 | C |
| ATOM | 970 | CE1 | PHE | A | 126 | 32.235 | 41.931 | 37.293 | 1.00 | 45.81 | C |
| ATOM | 971 | CE2 | PHE | A | 126 | 32.000 | 44.192 | 38.093 | 1.00 | 49.41 | C |
| ATOM | 972 | CZ  | PHE | A | 126 | 32.795 | 43.069 | 37.869 | 1.00 | 46.13 | C |
| ATOM | 973 | N   | TYR | A | 127 | 28.260 | 40.608 | 34.998 | 1.00 | 48.22 | N |
| ATOM | 974 | CA  | TYR | A | 127 | 28.749 | 39.361 | 34.427 | 1.00 | 49.72 | C |
| ATOM | 975 | C   | TYR | A | 127 | 28.460 | 39.246 | 32.943 | 1.00 | 49.04 | C |
| ATOM | 976 | O   | TYR | A | 127 | 29.275 | 38.712 | 32.193 | 1.00 | 50.48 | O |
| ATOM | 977 | CB  | TYR | A | 127 | 28.186 | 38.150 | 35.185 | 1.00 | 48.78 | C |
| ATOM | 978 | CG  | TYR | A | 127 | 28.696 | 38.057 | 36.608 | 1.00 | 49.75 | C |
| ATOM | 979 | CD1 | TYR | A | 127 | 30.063 | 38.169 | 36.885 | 1.00 | 49.68 | C |
| ATOM | 980 | CD2 | TYR | A | 127 | 27.815 | 37.904 | 37.688 | 1.00 | 49.44 | C |
| ATOM | 981 | CE1 | TYR | A | 127 | 30.546 | 38.141 | 38.203 | 1.00 | 48.84 | C |
| ATOM | 982 | CE2 | TYR | A | 127 | 28.291 | 37.873 | 39.010 | 1.00 | 48.74 | C |
| ATOM | 983 | CZ  | TYR | A | 127 | 29.655 | 37.996 | 39.255 | 1.00 | 48.38 | C |
| ATOM | 984 | OH  | TYR | A | 127 | 30.131 | 38.007 | 40.545 | 1.00 | 49.62 | O |
| ATOM | 985 | N   | LEU | A | 128 | 27.318 | 39.756 | 32.503 | 1.00 | 49.23 | N |
| ATOM | 986 | CA  | LEU | A | 128 | 26.987 | 39.674 | 31.082 | 1.00 | 49.04 | C |
| ATOM | 987 | C   | LEU | A | 128 | 27.926 | 40.542 | 30.266 | 1.00 | 47.32 | C |
| ATOM | 988 | O   | LEU | A | 128 | 28.215 | 40.237 | 29.108 | 1.00 | 46.05 | O |
| ATOM | 989 | CB  | LEU | A | 128 | 25.535 | 40.089 | 30.838 | 1.00 | 49.14 | C |
| ATOM | 990 | CG  | LEU | A | 128 | 24.493 | 39.057 | 31.291 | 1.00 | 52.09 | C |
| ATOM | 991 | CD1 | LEU | A | 128 | 23.098 | 39.674 | 31.181 | 1.00 | 50.53 | C |
| ATOM | 992 | CD2 | LEU | A | 128 | 24.606 | 37.776 | 30.440 | 1.00 | 48.78 | C |
| ATOM | 993 | N   | LYS | A | 129 | 28.402 | 41.624 | 30.874 | 1.00 | 46.41 | N |
| ATOM | 994 | CA  | LYS | A | 129 | 29.336 | 42.511 | 30.192 | 1.00 | 46.87 | C |
| ATOM | 995 | C   | LYS | A | 129 | 30.672 | 41.790 | 30.014 | 1.00 | 45.82 | C |
| ATOM | 996 | O   | LYS | A | 129 | 31.246 | 41.811 | 28.927 | 1.00 | 45.02 | O |
| ATOM | 997 | CB  | LYS | A | 129 | 29.545 | 43.802 | 30.989 | 1.00 | 47.76 | C |
| ATOM | 998 | CG  | LYS | A | 129 | 30.670 | 44.680 | 30.455 | 1.00 | 46.11 | C |
| ATOM | 999 | CD  | LYS | A | 129 | 30.769 | 45.975 | 31.227 | 1.00 | 46.48 | C |
| ATOM | 1000 | CE | LYS | A | 129 | 31.937 | 46.814 | 30.755 | 1.00 | 45.86 | C |
| ATOM | 1001 | NZ | LYS | A | 129 | 33.221 | 46.220 | 31.177 | 1.00 | 46.36 | N |
| ATOM | 1002 | N  | MET | A | 130 | 31.159 | 41.163 | 31.086 | 1.00 | 45.46 | N |
| ATOM | 1003 | CA | MET | A | 130 | 32.412 | 40.416 | 31.035 | 1.00 | 46.20 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 1004 | C   | MET | A | 130 | 32.337 | 39.404 | 29.905 | 1.00 | 47.42 | C |
|------|------|-----|-----|---|-----|--------|--------|--------|------|-------|---|
| ATOM | 1005 | O   | MET | A | 130 | 33.292 | 39.232 | 29.139 | 1.00 | 48.37 | O |
| ATOM | 1006 | CB  | MET | A | 130 | 32.666 | 39.661 | 32.345 | 1.00 | 46.76 | C |
| ATOM | 1007 | CG  | MET | A | 130 | 33.318 | 40.482 | 33.439 | 1.00 | 51.56 | C |
| ATOM | 1008 | SD  | MET | A | 130 | 33.736 | 39.505 | 34.910 | 1.00 | 54.34 | S |
| ATOM | 1009 | CE  | MET | A | 130 | 35.421 | 39.089 | 34.548 | 1.00 | 55.18 | C |
| ATOM | 1010 | N   | LYS | A | 131 | 31.193 | 38.735 | 29.805 | 1.00 | 47.72 | N |
| ATOM | 1011 | CA  | LYS | A | 131 | 30.996 | 37.733 | 28.776 | 1.00 | 48.17 | C |
| ATOM | 1012 | C   | LYS | A | 131 | 31.259 | 38.340 | 27.416 | 1.00 | 47.45 | C |
| ATOM | 1013 | O   | LYS | A | 131 | 31.980 | 37.772 | 26.605 | 1.00 | 49.76 | O |
| ATOM | 1014 | CB  | LYS | A | 131 | 29.571 | 37.178 | 28.826 | 1.00 | 49.33 | C |
| ATOM | 1015 | CG  | LYS | A | 131 | 29.355 | 36.046 | 27.840 | 1.00 | 52.47 | C |
| ATOM | 1016 | CD  | LYS | A | 131 | 28.034 | 35.325 | 28.078 | 1.00 | 55.51 | C |
| ATOM | 1017 | CE  | LYS | A | 131 | 27.952 | 34.038 | 27.253 | 1.00 | 56.41 | C |
| ATOM | 1018 | NZ  | LYS | A | 131 | 26.758 | 33.217 | 27.614 | 1.00 | 57.35 | N |
| ATOM | 1019 | N   | GLY | A | 132 | 30.681 | 39.508 | 27.173 | 1.00 | 46.87 | N |
| ATOM | 1020 | CA  | GLY | A | 132 | 30.865 | 40.161 | 25.894 | 1.00 | 47.25 | C |
| ATOM | 1021 | C   | GLY | A | 132 | 32.296 | 40.617 | 25.699 | 1.00 | 47.32 | C |
| ATOM | 1022 | O   | GLY | A | 132 | 32.876 | 40.465 | 24.617 | 1.00 | 43.80 | O |
| ATOM | 1023 | N   | ASP | A | 133 | 32.862 | 41.186 | 26.758 | 1.00 | 48.10 | N |
| ATOM | 1024 | CA  | ASP | A | 133 | 34.229 | 41.673 | 26.718 | 1.00 | 47.97 | C |
| ATOM | 1025 | C   | ASP | A | 133 | 35.222 | 40.627 | 26.221 | 1.00 | 47.55 | C |
| ATOM | 1026 | O   | ASP | A | 133 | 36.020 | 40.902 | 25.311 | 1.00 | 45.64 | O |
| ATOM | 1027 | CB  | ASP | A | 133 | 34.660 | 42.165 | 28.103 | 1.00 | 48.23 | C |
| ATOM | 1028 | CG  | ASP | A | 133 | 33.957 | 43.446 | 28.510 | 1.00 | 47.17 | C |
| ATOM | 1029 | OD1 | ASP | A | 133 | 33.431 | 44.127 | 27.609 | 1.00 | 47.48 | O |
| ATOM | 1030 | OD2 | ASP | A | 133 | 33.947 | 43.776 | 29.718 | 1.00 | 44.63 | O |
| ATOM | 1031 | N   | TYR | A | 134 | 35.157 | 39.426 | 26.793 | 1.00 | 46.42 | N |
| ATOM | 1032 | CA  | TYR | A | 134 | 36.103 | 38.385 | 26.412 | 1.00 | 46.92 | C |
| ATOM | 1033 | C   | TYR | A | 134 | 35.870 | 37.754 | 25.060 | 1.00 | 47.63 | C |
| ATOM | 1034 | O   | TYR | A | 134 | 36.815 | 37.265 | 24.435 | 1.00 | 49.40 | O |
| ATOM | 1035 | CB  | TYR | A | 134 | 36.231 | 37.339 | 27.532 | 1.00 | 45.13 | C |
| ATOM | 1036 | CG  | TYR | A | 134 | 36.975 | 37.931 | 28.700 | 1.00 | 40.91 | C |
| ATOM | 1037 | CD1 | TYR | A | 134 | 36.304 | 38.670 | 29.680 | 1.00 | 42.07 | C |
| ATOM | 1038 | CD2 | TYR | A | 134 | 38.365 | 37.917 | 28.729 | 1.00 | 42.08 | C |
| ATOM | 1039 | CE1 | TYR | A | 134 | 37.005 | 39.400 | 30.658 | 1.00 | 40.91 | C |
| ATOM | 1040 | CE2 | TYR | A | 134 | 39.080 | 38.639 | 29.701 | 1.00 | 44.82 | C |
| ATOM | 1041 | CZ  | TYR | A | 134 | 38.394 | 39.383 | 30.658 | 1.00 | 42.38 | C |
| ATOM | 1042 | OH  | TYR | A | 134 | 39.103 | 40.123 | 31.580 | 1.00 | 41.13 | O |
| ATOM | 1043 | N   | HIS | A | 135 | 34.630 | 37.765 | 24.588 | 1.00 | 46.93 | N |
| ATOM | 1044 | CA  | HIS | A | 135 | 34.379 | 37.243 | 23.253 | 1.00 | 46.82 | C |
| ATOM | 1045 | C   | HIS | A | 135 | 34.897 | 38.331 | 22.311 | 1.00 | 45.91 | C |
| ATOM | 1046 | O   | HIS | A | 135 | 35.288 | 38.061 | 21.172 | 1.00 | 46.56 | O |
| ATOM | 1047 | CB  | HIS | A | 135 | 32.886 | 36.993 | 23.032 | 1.00 | 48.46 | C |
| ATOM | 1048 | CG  | HIS | A | 135 | 32.410 | 35.682 | 23.582 | 1.00 | 50.27 | C |
| ATOM | 1049 | ND1 | HIS | A | 135 | 32.730 | 34.473 | 23.002 | 1.00 | 50.67 | N |
| ATOM | 1050 | CD2 | HIS | A | 135 | 31.670 | 35.389 | 24.678 | 1.00 | 49.34 | C |
| ATOM | 1051 | CE1 | HIS | A | 135 | 32.210 | 33.491 | 23.718 | 1.00 | 50.13 | C |
| ATOM | 1052 | NE2 | HIS | A | 135 | 31.563 | 34.020 | 24.741 | 1.00 | 50.59 | N |
| ATOM | 1053 | N   | ARG | A | 136 | 34.917 | 39.567 | 22.806 | 1.00 | 45.21 | N |
| ATOM | 1054 | CA  | ARG | A | 136 | 35.410 | 40.692 | 22.020 | 1.00 | 44.44 | C |
| ATOM | 1055 | C   | ARG | A | 136 | 36.929 | 40.603 | 21.906 | 1.00 | 45.26 | C |
| ATOM | 1056 | O   | ARG | A | 136 | 37.486 | 40.815 | 20.831 | 1.00 | 44.78 | O |
| ATOM | 1057 | CB  | ARG | A | 136 | 35.010 | 42.030 | 22.654 | 1.00 | 42.32 | C |
| ATOM | 1058 | CG  | ARG | A | 136 | 35.520 | 43.250 | 21.883 | 1.00 | 42.31 | C |
| ATOM | 1059 | CD  | ARG | A | 136 | 34.760 | 44.522 | 22.233 | 1.00 | 43.48 | C |
| ATOM | 1060 | NE  | ARG | A | 136 | 34.802 | 44.831 | 23.665 | 1.00 | 47.24 | N |
| ATOM | 1061 | CZ  | ARG | A | 136 | 35.803 | 45.458 | 24.282 | 1.00 | 47.12 | C |
| ATOM | 1062 | NH1 | ARG | A | 136 | 36.870 | 45.866 | 23.598 | 1.00 | 43.98 | N |
| ATOM | 1063 | NH2 | ARG | A | 136 | 35.742 | 45.665 | 25.593 | 1.00 | 45.87 | N |
| ATOM | 1064 | N   | TYR | A | 137 | 37.601 | 40.280 | 23.008 | 1.00 | 44.60 | N |
| ATOM | 1065 | CA  | TYR | A | 137 | 39.048 | 40.168 | 22.966 | 1.00 | 44.64 | C |
| ATOM | 1066 | C   | TYR | A | 137 | 39.441 | 39.102 | 21.946 | 1.00 | 46.50 | C |
| ATOM | 1067 | O   | TYR | A | 137 | 40.475 | 39.217 | 21.273 | 1.00 | 45.97 | O |
| ATOM | 1068 | CB  | TYR | A | 137 | 39.607 | 39.840 | 24.361 | 1.00 | 42.45 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 1069 | CG  | TYR | A | 137 | 39.260 | 40.893 | 25.391 | 1.00 | 40.97 | C |
| ATOM | 1070 | CD1 | TYR | A | 137 | 39.188 | 42.243 | 25.028 | 1.00 | 39.84 | C |
| ATOM | 1071 | CD2 | TYR | A | 137 | 38.940 | 40.544 | 26.703 | 1.00 | 38.81 | C |
| ATOM | 1072 | CE1 | TYR | A | 137 | 38.800 | 43.215 | 25.933 | 1.00 | 38.39 | C |
| ATOM | 1073 | CE2 | TYR | A | 137 | 38.545 | 41.511 | 27.625 | 1.00 | 38.20 | C |
| ATOM | 1074 | CZ  | TYR | A | 137 | 38.473 | 42.847 | 27.230 | 1.00 | 40.65 | C |
| ATOM | 1075 | OH  | TYR | A | 137 | 38.039 | 43.817 | 28.110 | 1.00 | 41.74 | O |
| ATOM | 1076 | N   | LEU | A | 138 | 38.606 | 38.070 | 21.826 | 1.00 | 47.89 | N |
| ATOM | 1077 | CA  | LEU | A | 138 | 38.857 | 37.005 | 20.862 | 1.00 | 47.44 | C |
| ATOM | 1078 | C   | LEU | A | 138 | 38.726 | 37.582 | 19.463 | 1.00 | 48.10 | C |
| ATOM | 1079 | O   | LEU | A | 138 | 39.619 | 37.423 | 18.624 | 1.00 | 47.68 | O |
| ATOM | 1080 | CB  | LEU | A | 138 | 37.851 | 35.869 | 21.042 | 1.00 | 47.15 | C |
| ATOM | 1081 | CG  | LEU | A | 138 | 38.130 | 34.949 | 22.229 | 1.00 | 49.60 | C |
| ATOM | 1082 | CD1 | LEU | A | 138 | 36.977 | 33.992 | 22.428 | 1.00 | 48.84 | C |
| ATOM | 1083 | CD2 | LEU | A | 138 | 39.426 | 34.183 | 21.980 | 1.00 | 49.57 | C |
| ATOM | 1084 | N   | ALA | A | 139 | 37.611 | 38.272 | 19.234 | 1.00 | 47.35 | N |
| ATOM | 1085 | CA  | ALA | A | 139 | 37.313 | 38.879 | 17.941 | 1.00 | 48.86 | C |
| ATOM | 1086 | C   | ALA | A | 139 | 38.393 | 39.826 | 17.427 | 1.00 | 49.42 | C |
| ATOM | 1087 | O   | ALA | A | 139 | 38.528 | 40.022 | 16.220 | 1.00 | 52.43 | O |
| ATOM | 1088 | CB  | ALA | A | 139 | 35.970 | 39.614 | 18.014 | 1.00 | 46.92 | C |
| ATOM | 1089 | N   | GLU | A | 140 | 39.161 | 40.412 | 18.336 | 1.00 | 50.11 | N |
| ATOM | 1090 | CA  | GLU | A | 140 | 40.205 | 41.345 | 17.950 | 1.00 | 50.61 | C |
| ATOM | 1091 | C   | GLU | A | 140 | 41.296 | 40.708 | 17.118 | 1.00 | 51.52 | C |
| ATOM | 1092 | O   | GLU | A | 140 | 41.831 | 41.344 | 16.215 | 1.00 | 52.65 | O |
| ATOM | 1093 | CB  | GLU | A | 140 | 40.842 | 41.988 | 19.180 | 1.00 | 50.62 | C |
| ATOM | 1094 | CG  | GLU | A | 140 | 39.904 | 42.848 | 19.985 | 1.00 | 51.12 | C |
| ATOM | 1095 | CD  | GLU | A | 140 | 40.597 | 43.508 | 21.158 | 1.00 | 52.52 | C |
| ATOM | 1096 | OE1 | GLU | A | 140 | 41.347 | 42.804 | 21.884 | 1.00 | 49.06 | O |
| ATOM | 1097 | OE2 | GLU | A | 140 | 40.382 | 44.730 | 21.349 | 1.00 | 53.85 | O |
| ATOM | 1098 | N   | PHE | A | 141 | 41.642 | 39.460 | 17.416 | 1.00 | 52.90 | N |
| ATOM | 1099 | CA  | PHE | A | 141 | 42.696 | 38.804 | 16.656 | 1.00 | 51.80 | C |
| ATOM | 1100 | C   | PHE | A | 141 | 42.206 | 37.708 | 15.727 | 1.00 | 52.24 | C |
| ATOM | 1101 | O   | PHE | A | 141 | 42.918 | 37.310 | 14.816 | 1.00 | 53.37 | O |
| ATOM | 1102 | CB  | PHE | A | 141 | 43.786 | 38.247 | 17.591 | 1.00 | 49.92 | C |
| ATOM | 1103 | CG  | PHE | A | 141 | 43.313 | 37.165 | 18.520 | 1.00 | 46.68 | C |
| ATOM | 1104 | CD1 | PHE | A | 141 | 42.688 | 37.484 | 19.721 | 1.00 | 46.65 | C |
| ATOM | 1105 | CD2 | PHE | A | 141 | 43.511 | 35.822 | 18.202 | 1.00 | 44.79 | C |
| ATOM | 1106 | CE1 | PHE | A | 141 | 42.268 | 36.474 | 20.601 | 1.00 | 45.69 | C |
| ATOM | 1107 | CE2 | PHE | A | 141 | 43.096 | 34.806 | 19.068 | 1.00 | 43.96 | C |
| ATOM | 1108 | CZ  | PHE | A | 141 | 42.474 | 35.135 | 20.272 | 1.00 | 45.35 | C |
| ATOM | 1109 | N   | LYS | A | 142 | 40.999 | 37.210 | 15.944 | 1.00 | 54.62 | N |
| ATOM | 1110 | CA  | LYS | A | 142 | 40.495 | 36.163 | 15.067 | 1.00 | 57.32 | C |
| ATOM | 1111 | C   | LYS | A | 142 | 40.114 | 36.752 | 13.718 | 1.00 | 59.77 | C |
| ATOM | 1112 | O   | LYS | A | 142 | 39.906 | 37.963 | 13.591 | 1.00 | 60.48 | O |
| ATOM | 1113 | CB  | LYS | A | 142 | 39.329 | 35.425 | 15.736 | 1.00 | 56.13 | C |
| ATOM | 1114 | CG  | LYS | A | 142 | 39.853 | 34.381 | 16.718 | 1.00 | 57.05 | C |
| ATOM | 1115 | CD  | LYS | A | 142 | 38.784 | 33.779 | 17.586 | 1.00 | 58.36 | C |
| ATOM | 1116 | CE  | LYS | A | 142 | 39.261 | 32.446 | 18.151 | 1.00 | 60.09 | C |
| ATOM | 1117 | NZ  | LYS | A | 142 | 40.601 | 32.544 | 18.796 | 1.00 | 62.58 | N |
| ATOM | 1118 | N   | THR | A | 143 | 40.020 | 35.902 | 12.704 | 1.00 | 63.19 | N |
| ATOM | 1119 | CA  | THR | A | 143 | 39.730 | 36.410 | 11.376 | 1.00 | 66.65 | C |
| ATOM | 1120 | C   | THR | A | 143 | 38.640 | 35.749 | 10.530 | 1.00 | 68.51 | C |
| ATOM | 1121 | O   | THR | A | 143 | 37.702 | 36.416 | 10.076 | 1.00 | 67.83 | O |
| ATOM | 1122 | CB  | THR | A | 143 | 41.034 | 36.435 | 10.546 | 1.00 | 66.59 | C |
| ATOM | 1123 | OG1 | THR | A | 143 | 40.742 | 36.883 | 9.217  | 1.00 | 68.52 | O |
| ATOM | 1124 | CG2 | THR | A | 143 | 41.685 | 35.038 | 10.512 | 1.00 | 64.14 | C |
| ATOM | 1125 | N   | GLY | A | 144 | 38.770 | 34.449 | 10.300 | 1.00 | 70.04 | N |
| ATOM | 1126 | CA  | GLY | A | 144 | 37.801 | 33.770 | 9.460  | 1.00 | 71.64 | C |
| ATOM | 1127 | C   | GLY | A | 144 | 36.407 | 33.599 | 10.031 | 1.00 | 71.34 | C |
| ATOM | 1128 | O   | GLY | A | 144 | 35.671 | 34.563 | 10.270 | 1.00 | 70.85 | O |
| ATOM | 1129 | N   | ALA | A | 145 | 36.042 | 32.340 | 10.226 | 1.00 | 70.50 | N |
| ATOM | 1130 | CA  | ALA | A | 145 | 34.749 | 31.994 | 10.770 | 1.00 | 68.73 | C |
| ATOM | 1131 | C   | ALA | A | 145 | 34.844 | 32.141 | 12.280 | 1.00 | 67.83 | C |
| ATOM | 1132 | O   | ALA | A | 145 | 33.832 | 32.271 | 12.972 | 1.00 | 68.15 | O |
| ATOM | 1133 | CB  | ALA | A | 145 | 34.404 | 30.568 | 10.399 | 1.00 | 67.16 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 1134 | N   | GLU | A | 146 | 36.071 | 32.116 | 12.788 | 1.00 | 66.41 | N |
|------|------|-----|-----|---|-----|--------|--------|--------|------|-------|---|
| ATOM | 1135 | CA  | GLU | A | 146 | 36.280 | 32.246 | 14.221 | 1.00 | 65.98 | C |
| ATOM | 1136 | C   | GLU | A | 146 | 35.868 | 33.646 | 14.646 | 1.00 | 63.45 | C |
| ATOM | 1137 | O   | GLU | A | 146 | 35.193 | 33.821 | 15.662 | 1.00 | 61.03 | O |
| ATOM | 1138 | CB  | GLU | A | 146 | 37.743 | 31.976 | 14.564 | 1.00 | 68.25 | C |
| ATOM | 1139 | CG  | GLU | A | 146 | 38.211 | 30.625 | 14.058 | 1.00 | 74.10 | C |
| ATOM | 1140 | CD  | GLU | A | 146 | 39.569 | 30.228 | 14.593 | 1.00 | 77.11 | C |
| ATOM | 1141 | OE1 | GLU | A | 146 | 39.708 | 30.141 | 15.833 | 1.00 | 79.21 | O |
| ATOM | 1142 | OE2 | GLU | A | 146 | 40.488 | 29.997 | 13.773 | 1.00 | 79.26 | O |
| ATOM | 1143 | N   | ARG | A | 147 | 36.257 | 34.634 | 13.843 | 1.00 | 61.73 | N |
| ATOM | 1144 | CA  | ARG | A | 147 | 35.920 | 36.021 | 14.114 | 1.00 | 59.38 | C |
| ATOM | 1145 | C   | ARG | A | 147 | 34.414 | 36.195 | 14.108 | 1.00 | 59.58 | C |
| ATOM | 1146 | O   | ARG | A | 147 | 33.851 | 36.792 | 15.023 | 1.00 | 59.18 | O |
| ATOM | 1147 | CB  | ARG | A | 147 | 36.524 | 36.936 | 13.062 | 1.00 | 57.96 | C |
| ATOM | 1148 | CG  | ARG | A | 147 | 36.199 | 38.405 | 13.274 | 1.00 | 56.11 | C |
| ATOM | 1149 | CD  | ARG | A | 147 | 36.860 | 39.232 | 12.204 | 1.00 | 57.32 | C |
| ATOM | 1150 | NE  | ARG | A | 147 | 37.320 | 40.510 | 12.730 | 1.00 | 58.40 | N |
| ATOM | 1151 | CZ  | ARG | A | 147 | 36.532 | 41.552 | 12.953 | 1.00 | 56.76 | C |
| ATOM | 1152 | NH1 | ARG | A | 147 | 37.053 | 42.671 | 13.438 | 1.00 | 55.11 | N |
| ATOM | 1153 | NH2 | ARG | A | 147 | 35.233 | 41.478 | 12.673 | 1.00 | 57.72 | N |
| ATOM | 1154 | N   | LYS | A | 148 | 33.764 | 35.671 | 13.074 | 1.00 | 60.37 | N |
| ATOM | 1155 | CA  | LYS | A | 148 | 32.317 | 35.783 | 12.967 | 1.00 | 61.79 | C |
| ATOM | 1156 | C   | LYS | A | 148 | 31.600 | 35.269 | 14.211 | 1.00 | 62.13 | C |
| ATOM | 1157 | O   | LYS | A | 148 | 30.674 | 35.918 | 14.700 | 1.00 | 63.15 | O |
| ATOM | 1158 | CB  | LYS | A | 148 | 31.789 | 35.028 | 11.743 | 1.00 | 63.19 | C |
| ATOM | 1159 | CG  | LYS | A | 148 | 30.283 | 35.212 | 11.531 | 1.00 | 64.98 | C |
| ATOM | 1160 | CD  | LYS | A | 148 | 29.696 | 34.153 | 10.606 | 1.00 | 68.69 | C |
| ATOM | 1161 | CE  | LYS | A | 148 | 28.167 | 34.250 | 10.533 | 1.00 | 69.63 | C |
| ATOM | 1162 | NZ  | LYS | A | 148 | 27.537 | 33.030 | 9.924  | 1.00 | 69.87 | N |
| ATOM | 1163 | N   | GLU | A | 149 | 32.009 | 34.116 | 14.735 | 1.00 | 61.95 | N |
| ATOM | 1164 | CA  | GLU | A | 149 | 31.324 | 33.609 | 15.914 | 1.00 | 63.82 | C |
| ATOM | 1165 | C   | GLU | A | 149 | 31.689 | 34.350 | 17.201 | 1.00 | 62.14 | C |
| ATOM | 1166 | O   | GLU | A | 149 | 30.867 | 34.443 | 18.113 | 1.00 | 61.91 | O |
| ATOM | 1167 | CB  | GLU | A | 149 | 31.532 | 32.097 | 16.076 | 1.00 | 67.62 | C |
| ATOM | 1168 | CG  | GLU | A | 149 | 32.919 | 31.643 | 16.448 | 1.00 | 74.22 | C |
| ATOM | 1169 | CD  | GLU | A | 149 | 32.935 | 30.180 | 16.900 | 1.00 | 78.50 | C |
| ATOM | 1170 | OE1 | GLU | A | 149 | 32.408 | 29.888 | 18.002 | 1.00 | 79.17 | O |
| ATOM | 1171 | OE2 | GLU | A | 149 | 33.466 | 29.322 | 16.153 | 1.00 | 80.05 | O |
| ATOM | 1172 | N   | ALA | A | 150 | 32.906 | 34.884 | 17.275 | 1.00 | 59.18 | N |
| ATOM | 1173 | CA  | ALA | A | 150 | 33.314 | 35.639 | 18.452 | 1.00 | 56.73 | C |
| ATOM | 1174 | C   | ALA | A | 150 | 32.482 | 36.916 | 18.434 | 1.00 | 56.80 | C |
| ATOM | 1175 | O   | ALA | A | 150 | 32.019 | 37.399 | 19.466 | 1.00 | 56.54 | O |
| ATOM | 1176 | CB  | ALA | A | 150 | 34.792 | 35.977 | 18.380 | 1.00 | 56.23 | C |
| ATOM | 1177 | N   | ALA | A | 151 | 32.288 | 37.455 | 17.237 | 1.00 | 56.21 | N |
| ATOM | 1178 | CA  | ALA | A | 151 | 31.505 | 38.663 | 17.067 | 1.00 | 56.43 | C |
| ATOM | 1179 | C   | ALA | A | 151 | 30.046 | 38.394 | 17.459 | 1.00 | 56.92 | C |
| ATOM | 1180 | O   | ALA | A | 151 | 29.455 | 39.147 | 18.241 | 1.00 | 55.95 | O |
| ATOM | 1181 | CB  | ALA | A | 151 | 31.598 | 39.136 | 15.622 | 1.00 | 55.17 | C |
| ATOM | 1182 | N   | GLU | A | 152 | 29.467 | 37.323 | 16.920 | 1.00 | 57.23 | N |
| ATOM | 1183 | CA  | GLU | A | 152 | 28.083 | 36.980 | 17.238 | 1.00 | 57.40 | C |
| ATOM | 1184 | C   | GLU | A | 152 | 27.909 | 36.831 | 18.744 | 1.00 | 55.91 | C |
| ATOM | 1185 | O   | GLU | A | 152 | 26.956 | 37.373 | 19.315 | 1.00 | 55.80 | O |
| ATOM | 1186 | CB  | GLU | A | 152 | 27.672 | 35.681 | 16.546 | 1.00 | 59.64 | C |
| ATOM | 1187 | CG  | GLU | A | 152 | 27.395 | 35.818 | 15.058 | 1.00 | 66.37 | C |
| ATOM | 1188 | CD  | GLU | A | 152 | 27.118 | 34.472 | 14.384 | 1.00 | 71.49 | C |
| ATOM | 1189 | OE1 | GLU | A | 152 | 26.200 | 33.747 | 14.838 | 1.00 | 75.32 | O |
| ATOM | 1190 | OE2 | GLU | A | 152 | 27.817 | 34.137 | 13.397 | 1.00 | 72.78 | O |
| ATOM | 1191 | N   | SER | A | 153 | 28.827 | 36.099 | 19.383 | 1.00 | 53.80 | N |
| ATOM | 1192 | CA  | SER | A | 153 | 28.782 | 35.888 | 20.836 | 1.00 | 51.80 | C |
| ATOM | 1193 | C   | SER | A | 153 | 28.857 | 37.217 | 21.592 | 1.00 | 51.43 | C |
| ATOM | 1194 | O   | SER | A | 153 | 28.126 | 37.424 | 22.565 | 1.00 | 51.19 | O |
| ATOM | 1195 | CB  | SER | A | 153 | 29.934 | 34.985 | 21.297 | 1.00 | 51.54 | C |
| ATOM | 1196 | OG  | SER | A | 153 | 29.751 | 33.638 | 20.902 | 1.00 | 47.95 | O |
| ATOM | 1197 | N   | THR | A | 154 | 29.742 | 38.110 | 21.146 | 1.00 | 50.45 | N |
| ATOM | 1198 | CA  | THR | A | 154 | 29.895 | 39.424 | 21.772 | 1.00 | 49.80 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 1199 | C   | THR | A | 154 | 28.573 | 40.175 | 21.738 | 1.00 | 49.82 | C |
|------|------|-----|-----|---|-----|--------|--------|--------|------|-------|---|
| ATOM | 1200 | O   | THR | A | 154 | 28.083 | 40.648 | 22.766 | 1.00 | 49.88 | O |
| ATOM | 1201 | CB  | THR | A | 154 | 30.948 | 40.287 | 21.042 | 1.00 | 49.23 | C |
| ATOM | 1202 | OG1 | THR | A | 154 | 32.240 | 39.684 | 21.182 | 1.00 | 49.13 | O |
| ATOM | 1203 | CG2 | THR | A | 154 | 30.979 | 41.696 | 21.619 | 1.00 | 45.57 | C |
| ATOM | 1204 | N   | LEU | A | 155 | 28.001 | 40.269 | 20.542 | 1.00 | 49.60 | N |
| ATOM | 1205 | CA  | LEU | A | 155 | 26.739 | 40.958 | 20.333 | 1.00 | 48.80 | C |
| ATOM | 1206 | C   | LEU | A | 155 | 25.610 | 40.406 | 21.201 | 1.00 | 49.00 | C |
| ATOM | 1207 | O   | LEU | A | 155 | 24.819 | 41.167 | 21.770 | 1.00 | 48.28 | O |
| ATOM | 1208 | CB  | LEU | A | 155 | 26.346 | 40.867 | 18.864 | 1.00 | 49.41 | C |
| ATOM | 1209 | CG  | LEU | A | 155 | 25.136 | 41.717 | 18.478 | 1.00 | 52.13 | C |
| ATOM | 1210 | CD1 | LEU | A | 155 | 25.356 | 43.175 | 18.935 | 1.00 | 51.66 | C |
| ATOM | 1211 | CD2 | LEU | A | 155 | 24.922 | 41.639 | 16.968 | 1.00 | 51.84 | C |
| ATOM | 1212 | N   | THR | A | 156 | 25.530 | 39.087 | 21.302 | 1.00 | 47.91 | N |
| ATOM | 1213 | CA  | THR | A | 156 | 24.491 | 38.469 | 22.110 | 1.00 | 49.54 | C |
| ATOM | 1214 | C   | THR | A | 156 | 24.634 | 38.839 | 23.582 | 1.00 | 51.15 | C |
| ATOM | 1215 | O   | THR | A | 156 | 23.659 | 39.225 | 24.237 | 1.00 | 50.50 | O |
| ATOM | 1216 | CB  | THR | A | 156 | 24.550 | 36.950 | 22.000 | 1.00 | 50.89 | C |
| ATOM | 1217 | OG1 | THR | A | 156 | 24.285 | 36.568 | 20.649 | 1.00 | 53.51 | O |
| ATOM | 1218 | CG2 | THR | A | 156 | 23.528 | 36.305 | 22.924 | 1.00 | 49.31 | C |
| ATOM | 1219 | N   | ALA | A | 157 | 25.853 | 38.709 | 24.099 | 1.00 | 51.11 | N |
| ATOM | 1220 | CA  | ALA | A | 157 | 26.120 | 39.024 | 25.492 | 1.00 | 51.48 | C |
| ATOM | 1221 | C   | ALA | A | 157 | 25.830 | 40.494 | 25.792 | 1.00 | 52.54 | C |
| ATOM | 1222 | O   | ALA | A | 157 | 25.160 | 40.804 | 26.778 | 1.00 | 52.61 | O |
| ATOM | 1223 | CB  | ALA | A | 157 | 27.571 | 38.688 | 25.836 | 1.00 | 50.32 | C |
| ATOM | 1224 | N   | TYR | A | 158 | 26.325 | 41.399 | 24.948 | 1.00 | 52.20 | N |
| ATOM | 1225 | CA  | TYR | A | 158 | 26.095 | 42.822 | 25.177 | 1.00 | 53.87 | C |
| ATOM | 1226 | C   | TYR | A | 158 | 24.621 | 43.209 | 25.112 | 1.00 | 55.82 | C |
| ATOM | 1227 | O   | TYR | A | 158 | 24.160 | 44.026 | 25.915 | 1.00 | 56.22 | O |
| ATOM | 1228 | CB  | TYR | A | 158 | 26.889 | 43.682 | 24.188 | 1.00 | 52.37 | C |
| ATOM | 1229 | CG  | TYR | A | 158 | 28.373 | 43.799 | 24.497 | 1.00 | 51.38 | C |
| ATOM | 1230 | CD1 | TYR | A | 158 | 28.872 | 43.539 | 25.778 | 1.00 | 48.84 | C |
| ATOM | 1231 | CD2 | TYR | A | 158 | 29.275 | 44.217 | 23.515 | 1.00 | 49.37 | C |
| ATOM | 1232 | CE1 | TYR | A | 158 | 30.234 | 43.695 | 26.073 | 1.00 | 47.34 | C |
| ATOM | 1233 | CE2 | TYR | A | 158 | 30.632 | 44.377 | 23.801 | 1.00 | 48.09 | C |
| ATOM | 1234 | CZ  | TYR | A | 158 | 31.105 | 44.118 | 25.080 | 1.00 | 47.44 | C |
| ATOM | 1235 | OH  | TYR | A | 158 | 32.439 | 44.316 | 25.357 | 1.00 | 44.37 | O |
| ATOM | 1236 | N   | LYS | A | 159 | 23.883 | 42.641 | 24.159 | 1.00 | 56.85 | N |
| ATOM | 1237 | CA  | LYS | A | 159 | 22.462 | 42.947 | 24.046 | 1.00 | 58.57 | C |
| ATOM | 1238 | C   | LYS | A | 159 | 21.713 | 42.459 | 25.288 | 1.00 | 58.54 | C |
| ATOM | 1239 | O   | LYS | A | 159 | 20.848 | 43.162 | 25.823 | 1.00 | 58.21 | O |
| ATOM | 1240 | CB  | LYS | A | 159 | 21.867 | 42.307 | 22.794 | 1.00 | 60.80 | C |
| ATOM | 1241 | CG  | LYS | A | 159 | 22.222 | 43.030 | 21.506 | 1.00 | 65.02 | C |
| ATOM | 1242 | CD  | LYS | A | 159 | 21.536 | 42.379 | 20.314 | 1.00 | 68.85 | C |
| ATOM | 1243 | CE  | LYS | A | 159 | 21.920 | 43.040 | 18.980 | 1.00 | 72.78 | C |
| ATOM | 1244 | NZ  | LYS | A | 159 | 21.473 | 44.466 | 18.835 | 1.00 | 74.42 | N |
| ATOM | 1245 | N   | ALA | A | 160 | 22.051 | 41.258 | 25.748 | 1.00 | 57.18 | N |
| ATOM | 1246 | CA  | ALA | A | 160 | 21.423 | 40.701 | 26.941 | 1.00 | 56.34 | C |
| ATOM | 1247 | C   | ALA | A | 160 | 21.748 | 41.591 | 28.135 | 1.00 | 56.94 | C |
| ATOM | 1248 | O   | ALA | A | 160 | 20.906 | 41.811 | 29.002 | 1.00 | 57.36 | O |
| ATOM | 1249 | CB  | ALA | A | 160 | 21.930 | 39.286 | 27.194 | 1.00 | 55.65 | C |
| ATOM | 1250 | N   | ALA | A | 161 | 22.977 | 42.101 | 28.171 | 1.00 | 57.61 | N |
| ATOM | 1251 | CA  | ALA | A | 161 | 23.415 | 42.973 | 29.254 | 1.00 | 58.24 | C |
| ATOM | 1252 | C   | ALA | A | 161 | 22.662 | 44.302 | 29.185 | 1.00 | 58.83 | C |
| ATOM | 1253 | O   | ALA | A | 161 | 22.216 | 44.842 | 30.198 | 1.00 | 59.58 | O |
| ATOM | 1254 | CB  | ALA | A | 161 | 24.919 | 43.216 | 29.151 | 1.00 | 56.55 | C |
| ATOM | 1255 | N   | GLN | A | 162 | 22.515 | 44.822 | 27.976 | 1.00 | 58.80 | N |
| ATOM | 1256 | CA  | GLN | A | 162 | 21.829 | 46.082 | 27.784 | 1.00 | 59.46 | C |
| ATOM | 1257 | C   | GLN | A | 162 | 20.361 | 46.069 | 28.204 | 1.00 | 59.88 | C |
| ATOM | 1258 | O   | GLN | A | 162 | 19.874 | 47.035 | 28.790 | 1.00 | 59.72 | O |
| ATOM | 1259 | CB  | GLN | A | 162 | 21.933 | 46.493 | 26.333 | 1.00 | 59.28 | C |
| ATOM | 1260 | CG  | GLN | A | 162 | 21.372 | 47.849 | 26.074 | 1.00 | 59.05 | C |
| ATOM | 1261 | CD  | GLN | A | 162 | 21.632 | 48.274 | 24.665 | 1.00 | 60.50 | C |
| ATOM | 1262 | OE1 | GLN | A | 162 | 21.293 | 47.556 | 23.719 | 1.00 | 58.70 | O |
| ATOM | 1263 | NE2 | GLN | A | 162 | 22.245 | 49.445 | 24.505 | 1.00 | 62.00 | N |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 1264 | N | ASP | A | 163 | 19.651 | 44.987 | 27.896 | 1.00 | 60.72 | N |
|---|---|---|---|---|---|---|---|---|---|---|---|
| ATOM | 1265 | CA | ASP | A | 163 | 18.238 | 44.880 | 28.263 | 1.00 | 61.62 | C |
| ATOM | 1266 | C | ASP | A | 163 | 18.025 | 45.078 | 29.753 | 1.00 | 60.97 | C |
| ATOM | 1267 | O | ASP | A | 163 | 17.102 | 45.779 | 30.172 | 1.00 | 60.95 | O |
| ATOM | 1268 | CB | ASP | A | 163 | 17.686 | 43.519 | 27.864 | 1.00 | 63.70 | C |
| ATOM | 1269 | CG | ASP | A | 163 | 17.664 | 43.331 | 26.375 | 1.00 | 66.86 | C |
| ATOM | 1270 | OD1 | ASP | A | 163 | 17.222 | 42.252 | 25.921 | 1.00 | 70.48 | O |
| ATOM | 1271 | OD2 | ASP | A | 163 | 18.093 | 44.268 | 25.661 | 1.00 | 67.46 | O |
| ATOM | 1272 | N | ILE | A | 164 | 18.885 | 44.448 | 30.547 | 1.00 | 59.40 | N |
| ATOM | 1273 | CA | ILE | A | 164 | 18.801 | 44.552 | 31.989 | 1.00 | 58.43 | C |
| ATOM | 1274 | C | ILE | A | 164 | 19.249 | 45.921 | 32.476 | 1.00 | 59.41 | C |
| ATOM | 1275 | O | ILE | A | 164 | 18.578 | 46.537 | 33.298 | 1.00 | 61.31 | O |
| ATOM | 1276 | CB | ILE | A | 164 | 19.649 | 43.462 | 32.667 | 1.00 | 57.59 | C |
| ATOM | 1277 | CG1 | ILE | A | 164 | 19.085 | 42.089 | 32.296 | 1.00 | 55.07 | C |
| ATOM | 1278 | CG2 | ILE | A | 164 | 19.661 | 43.668 | 34.189 | 1.00 | 54.37 | C |
| ATOM | 1279 | CD1 | ILE | A | 164 | 19.878 | 40.933 | 32.850 | 1.00 | 57.98 | C |
| ATOM | 1280 | N | ALA | A | 165 | 20.375 | 46.405 | 31.963 | 1.00 | 59.39 | N |
| ATOM | 1281 | CA | ALA | A | 165 | 20.889 | 47.702 | 32.378 | 1.00 | 61.08 | C |
| ATOM | 1282 | C | ALA | A | 165 | 19.920 | 48.848 | 32.059 | 1.00 | 62.03 | C |
| ATOM | 1283 | O | ALA | A | 165 | 19.706 | 49.740 | 32.881 | 1.00 | 61.22 | O |
| ATOM | 1284 | CB | ALA | A | 165 | 22.246 | 47.957 | 31.720 | 1.00 | 61.18 | C |
| ATOM | 1285 | N | THR | A | 166 | 19.334 | 48.815 | 30.865 | 1.00 | 63.38 | N |
| ATOM | 1286 | CA | THR | A | 166 | 18.403 | 49.849 | 30.425 | 1.00 | 65.41 | C |
| ATOM | 1287 | C | THR | A | 166 | 17.178 | 49.975 | 31.322 | 1.00 | 65.91 | C |
| ATOM | 1288 | O | THR | A | 166 | 16.676 | 51.078 | 31.566 | 1.00 | 66.18 | O |
| ATOM | 1289 | CB | THR | A | 166 | 17.917 | 49.571 | 28.994 | 1.00 | 66.71 | C |
| ATOM | 1290 | OG1 | THR | A | 166 | 19.021 | 49.675 | 28.089 | 1.00 | 68.31 | O |
| ATOM | 1291 | CG2 | THR | A | 166 | 16.844 | 50.572 | 28.590 | 1.00 | 69.15 | C |
| ATOM | 1292 | N | THR | A | 167 | 16.695 | 48.841 | 31.814 | 1.00 | 65.08 | N |
| ATOM | 1293 | CA | THR | A | 167 | 15.517 | 48.845 | 32.667 | 1.00 | 64.51 | C |
| ATOM | 1294 | C | THR | A | 167 | 15.808 | 48.895 | 34.172 | 1.00 | 63.92 | C |
| ATOM | 1295 | O | THR | A | 167 | 15.204 | 49.691 | 34.896 | 1.00 | 64.44 | O |
| ATOM | 1296 | CB | THR | A | 167 | 14.640 | 47.605 | 32.387 | 1.00 | 64.60 | C |
| ATOM | 1297 | OG1 | THR | A | 167 | 15.300 | 46.433 | 32.871 | 1.00 | 64.68 | O |
| ATOM | 1298 | CG2 | THR | A | 167 | 14.409 | 47.441 | 30.893 | 1.00 | 64.45 | C |
| ATOM | 1299 | N | GLU | A | 168 | 16.749 | 48.072 | 34.634 | 1.00 | 61.13 | N |
| ATOM | 1300 | CA | GLU | A | 168 | 17.051 | 47.982 | 36.058 | 1.00 | 58.60 | C |
| ATOM | 1301 | C | GLU | A | 168 | 18.084 | 48.906 | 36.695 | 1.00 | 57.57 | C |
| ATOM | 1302 | O | GLU | A | 168 | 18.109 | 49.038 | 37.917 | 1.00 | 58.93 | O |
| ATOM | 1303 | CB | GLU | A | 168 | 17.409 | 46.536 | 36.398 | 1.00 | 59.19 | C |
| ATOM | 1304 | CG | GLU | A | 168 | 16.479 | 45.522 | 35.761 | 1.00 | 60.66 | C |
| ATOM | 1305 | CD | GLU | A | 168 | 16.733 | 44.108 | 36.243 | 1.00 | 64.10 | C |
| ATOM | 1306 | OE1 | GLU | A | 168 | 16.250 | 43.164 | 35.575 | 1.00 | 65.96 | O |
| ATOM | 1307 | OE2 | GLU | A | 168 | 17.403 | 43.938 | 37.288 | 1.00 | 63.85 | O |
| ATOM | 1308 | N | LEU | A | 169 | 18.935 | 49.547 | 35.907 | 1.00 | 55.35 | N |
| ATOM | 1309 | CA | LEU | A | 169 | 19.944 | 50.419 | 36.501 | 1.00 | 53.66 | C |
| ATOM | 1310 | C | LEU | A | 169 | 19.860 | 51.848 | 35.987 | 1.00 | 53.79 | C |
| ATOM | 1311 | O | LEU | A | 169 | 19.390 | 52.098 | 34.876 | 1.00 | 53.36 | O |
| ATOM | 1312 | CB | LEU | A | 169 | 21.347 | 49.868 | 36.220 | 1.00 | 54.54 | C |
| ATOM | 1313 | CG | LEU | A | 169 | 21.625 | 48.406 | 36.583 | 1.00 | 54.00 | C |
| ATOM | 1314 | CD1 | LEU | A | 169 | 22.921 | 47.968 | 35.913 | 1.00 | 55.93 | C |
| ATOM | 1315 | CD2 | LEU | A | 169 | 21.702 | 48.242 | 38.095 | 1.00 | 51.36 | C |
| ATOM | 1316 | N | ALA | A | 170 | 20.328 | 52.782 | 36.807 | 1.00 | 53.70 | N |
| ATOM | 1317 | CA | ALA | A | 170 | 20.328 | 54.193 | 36.455 | 1.00 | 53.70 | C |
| ATOM | 1318 | C | ALA | A | 170 | 21.305 | 54.481 | 35.313 | 1.00 | 55.30 | C |
| ATOM | 1319 | O | ALA | A | 170 | 22.266 | 53.746 | 35.099 | 1.00 | 56.55 | O |
| ATOM | 1320 | CB | ALA | A | 170 | 20.704 | 55.016 | 37.670 | 1.00 | 52.49 | C |
| ATOM | 1321 | N | PRO | A | 171 | 21.053 | 55.549 | 34.547 | 1.00 | 56.41 | N |
| ATOM | 1322 | CA | PRO | A | 171 | 21.924 | 55.931 | 33.430 | 1.00 | 55.19 | C |
| ATOM | 1323 | C | PRO | A | 171 | 23.277 | 56.381 | 33.965 | 1.00 | 54.47 | C |
| ATOM | 1324 | O | PRO | A | 171 | 24.261 | 56.443 | 33.229 | 1.00 | 54.37 | O |
| ATOM | 1325 | CB | PRO | A | 171 | 21.163 | 57.088 | 32.779 | 1.00 | 55.50 | C |
| ATOM | 1326 | CG | PRO | A | 171 | 19.737 | 56.726 | 33.029 | 1.00 | 56.97 | C |
| ATOM | 1327 | CD | PRO | A | 171 | 19.771 | 56.274 | 34.478 | 1.00 | 57.41 | C |
| ATOM | 1328 | N | THR | A | 172 | 23.311 | 56.707 | 35.254 | 1.00 | 54.23 | N |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 1329 | CA  | THR | A | 172 | 24.547 | 57.158 | 35.902 | 1.00 | 53.98 | C |
|------|------|-----|-----|---|-----|--------|--------|--------|------|-------|---|
| ATOM | 1330 | C   | THR | A | 172 | 25.327 | 55.983 | 36.508 | 1.00 | 52.70 | C |
| ATOM | 1331 | O   | THR | A | 172 | 26.465 | 56.137 | 36.958 | 1.00 | 51.65 | O |
| ATOM | 1332 | CB  | THR | A | 172 | 24.250 | 58.186 | 37.027 | 1.00 | 52.71 | C |
| ATOM | 1333 | OG1 | THR | A | 172 | 23.321 | 57.619 | 37.961 | 1.00 | 52.94 | O |
| ATOM | 1334 | CG2 | THR | A | 172 | 23.677 | 59.468 | 36.446 | 1.00 | 50.93 | C |
| ATOM | 1335 | N   | HIS | A | 173 | 24.710 | 54.810 | 36.519 | 1.00 | 50.77 | N |
| ATOM | 1336 | CA  | HIS | A | 173 | 25.363 | 53.636 | 37.072 | 1.00 | 52.99 | C |
| ATOM | 1337 | C   | HIS | A | 173 | 26.639 | 53.311 | 36.268 | 1.00 | 53.54 | C |
| ATOM | 1338 | O   | HIS | A | 173 | 26.612 | 53.245 | 35.037 | 1.00 | 52.99 | O |
| ATOM | 1339 | CB  | HIS | A | 173 | 24.391 | 52.451 | 37.031 | 1.00 | 53.35 | C |
| ATOM | 1340 | CG  | HIS | A | 173 | 24.759 | 51.344 | 37.961 | 1.00 | 53.01 | C |
| ATOM | 1341 | ND1 | HIS | A | 173 | 26.053 | 50.891 | 38.100 | 1.00 | 53.00 | N |
| ATOM | 1342 | CD2 | HIS | A | 173 | 24.005 | 50.604 | 38.806 | 1.00 | 54.42 | C |
| ATOM | 1343 | CE1 | HIS | A | 173 | 26.079 | 49.920 | 38.996 | 1.00 | 54.75 | C |
| ATOM | 1344 | NE2 | HIS | A | 173 | 24.850 | 49.725 | 39.440 | 1.00 | 53.27 | N |
| ATOM | 1345 | N   | PRO | A | 174 | 27.773 | 53.113 | 36.957 | 1.00 | 53.56 | N |
| ATOM | 1346 | CA  | PRO | A | 174 | 29.037 | 52.800 | 36.278 | 1.00 | 52.89 | C |
| ATOM | 1347 | C   | PRO | A | 174 | 29.048 | 51.479 | 35.479 | 1.00 | 52.84 | C |
| ATOM | 1348 | O   | PRO | A | 174 | 29.675 | 51.405 | 34.412 | 1.00 | 51.22 | O |
| ATOM | 1349 | CB  | PRO | A | 174 | 30.053 | 52.821 | 37.422 | 1.00 | 53.37 | C |
| ATOM | 1350 | CG  | PRO | A | 174 | 29.235 | 52.381 | 38.608 | 1.00 | 53.13 | C |
| ATOM | 1351 | CD  | PRO | A | 174 | 27.971 | 53.191 | 38.415 | 1.00 | 54.39 | C |
| ATOM | 1352 | N   | ILE | A | 175 | 28.375 | 50.438 | 35.982 | 1.00 | 51.82 | N |
| ATOM | 1353 | CA  | ILE | A | 175 | 28.338 | 49.178 | 35.242 | 1.00 | 50.45 | C |
| ATOM | 1354 | C   | ILE | A | 175 | 27.642 | 49.458 | 33.914 | 1.00 | 51.29 | C |
| ATOM | 1355 | O   | ILE | A | 175 | 28.159 | 49.124 | 32.851 | 1.00 | 52.96 | O |
| ATOM | 1356 | CB  | ILE | A | 175 | 27.539 | 48.048 | 35.965 | 1.00 | 49.35 | C |
| ATOM | 1357 | CG1 | ILE | A | 175 | 28.380 | 47.347 | 37.037 | 1.00 | 48.50 | C |
| ATOM | 1358 | CG2 | ILE | A | 175 | 27.156 | 46.979 | 34.953 | 1.00 | 47.76 | C |
| ATOM | 1359 | CD1 | ILE | A | 175 | 28.708 | 48.173 | 38.230 | 1.00 | 51.01 | C |
| ATOM | 1360 | N   | ARG | A | 176 | 26.465 | 50.074 | 33.984 | 1.00 | 51.70 | N |
| ATOM | 1361 | CA  | ARG | A | 176 | 25.693 | 50.399 | 32.791 | 1.00 | 52.18 | C |
| ATOM | 1362 | C   | ARG | A | 176 | 26.455 | 51.355 | 31.883 | 1.00 | 51.70 | C |
| ATOM | 1363 | O   | ARG | A | 176 | 26.408 | 51.241 | 30.664 | 1.00 | 53.15 | O |
| ATOM | 1364 | CB  | ARG | A | 176 | 24.363 | 51.041 | 33.180 | 1.00 | 52.57 | C |
| ATOM | 1365 | CG  | ARG | A | 176 | 23.481 | 51.399 | 32.001 | 1.00 | 52.35 | C |
| ATOM | 1366 | CD  | ARG | A | 176 | 22.220 | 52.090 | 32.470 | 1.00 | 56.32 | C |
| ATOM | 1367 | NE  | ARG | A | 176 | 21.291 | 52.356 | 31.373 | 1.00 | 58.90 | N |
| ATOM | 1368 | CZ  | ARG | A | 176 | 20.162 | 53.052 | 31.497 | 1.00 | 58.75 | C |
| ATOM | 1369 | NH1 | ARG | A | 176 | 19.815 | 53.562 | 32.672 | 1.00 | 58.33 | N |
| ATOM | 1370 | NH2 | ARG | A | 176 | 19.374 | 53.229 | 30.446 | 1.00 | 58.26 | N |
| ATOM | 1371 | N   | LEU | A | 177 | 27.155 | 52.301 | 32.490 | 1.00 | 51.14 | N |
| ATOM | 1372 | CA  | LEU | A | 177 | 27.918 | 53.284 | 31.745 | 1.00 | 50.95 | C |
| ATOM | 1373 | C   | LEU | A | 177 | 29.096 | 52.598 | 31.052 | 1.00 | 52.12 | C |
| ATOM | 1374 | O   | LEU | A | 177 | 29.446 | 52.944 | 29.920 | 1.00 | 53.33 | O |
| ATOM | 1375 | CB  | LEU | A | 177 | 28.401 | 54.375 | 32.704 | 1.00 | 50.59 | C |
| ATOM | 1376 | CG  | LEU | A | 177 | 28.424 | 55.844 | 32.261 | 1.00 | 52.26 | C |
| ATOM | 1377 | CD1 | LEU | A | 177 | 27.164 | 56.209 | 31.474 | 1.00 | 45.75 | C |
| ATOM | 1378 | CD2 | LEU | A | 177 | 28.558 | 56.722 | 33.525 | 1.00 | 50.82 | C |
| ATOM | 1379 | N   | GLY | A | 178 | 29.697 | 51.623 | 31.733 | 1.00 | 50.70 | N |
| ATOM | 1380 | CA  | GLY | A | 178 | 30.813 | 50.898 | 31.158 | 1.00 | 48.72 | C |
| ATOM | 1381 | C   | GLY | A | 178 | 30.340 | 49.972 | 30.052 | 1.00 | 48.59 | C |
| ATOM | 1382 | O   | GLY | A | 178 | 31.050 | 49.742 | 29.063 | 1.00 | 48.74 | O |
| ATOM | 1383 | N   | LEU | A | 179 | 29.134 | 49.438 | 30.216 | 1.00 | 46.59 | N |
| ATOM | 1384 | CA  | LEU | A | 179 | 28.565 | 48.542 | 29.223 | 1.00 | 45.94 | C |
| ATOM | 1385 | C   | LEU | A | 179 | 28.354 | 49.311 | 27.938 | 1.00 | 46.33 | C |
| ATOM | 1386 | O   | LEU | A | 179 | 28.555 | 48.787 | 26.853 | 1.00 | 47.37 | O |
| ATOM | 1387 | CB  | LEU | A | 179 | 27.224 | 47.986 | 29.695 | 1.00 | 45.55 | C |
| ATOM | 1388 | CG  | LEU | A | 179 | 26.427 | 47.243 | 28.622 | 1.00 | 43.49 | C |
| ATOM | 1389 | CD1 | LEU | A | 179 | 27.215 | 46.043 | 28.147 | 1.00 | 43.10 | C |
| ATOM | 1390 | CD2 | LEU | A | 179 | 25.091 | 46.807 | 29.177 | 1.00 | 44.09 | C |
| ATOM | 1391 | N   | ALA | A | 180 | 27.937 | 50.561 | 28.063 | 1.00 | 46.76 | N |
| ATOM | 1392 | CA  | ALA | A | 180 | 27.704 | 51.378 | 26.887 | 1.00 | 47.56 | C |
| ATOM | 1393 | C   | ALA | A | 180 | 29.045 | 51.670 | 26.219 | 1.00 | 47.71 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 1394 | O   | ALA | A | 180 | 29.185 | 51.544 | 24.998 | 1.00 | 48.80 | O |
|------|------|-----|-----|---|-----|--------|--------|--------|------|-------|---|
| ATOM | 1395 | CB  | ALA | A | 180 | 27.012 | 52.673 | 27.285 | 1.00 | 49.44 | C |
| ATOM | 1396 | N   | LEU | A | 181 | 30.029 | 52.053 | 27.026 | 1.00 | 46.51 | N |
| ATOM | 1397 | CA  | LEU | A | 181 | 31.360 | 52.355 | 26.524 | 1.00 | 45.67 | C |
| ATOM | 1398 | C   | LEU | A | 181 | 31.900 | 51.199 | 25.671 | 1.00 | 47.30 | C |
| ATOM | 1399 | O   | LEU | A | 181 | 32.311 | 51.391 | 24.518 | 1.00 | 45.48 | O |
| ATOM | 1400 | CB  | LEU | A | 181 | 32.317 | 52.606 | 27.688 | 1.00 | 42.78 | C |
| ATOM | 1401 | CG  | LEU | A | 181 | 33.767 | 52.903 | 27.289 | 1.00 | 42.31 | C |
| ATOM | 1402 | CD1 | LEU | A | 181 | 33.809 | 54.202 | 26.505 | 1.00 | 43.41 | C |
| ATOM | 1403 | CD2 | LEU | A | 181 | 34.651 | 53.009 | 28.516 | 1.00 | 39.61 | C |
| ATOM | 1404 | N   | ASN | A | 182 | 31.887 | 49.999 | 26.246 | 1.00 | 46.65 | N |
| ATOM | 1405 | CA  | ASN | A | 182 | 32.396 | 48.826 | 25.559 | 1.00 | 46.08 | C |
| ATOM | 1406 | C   | ASN | A | 182 | 31.582 | 48.398 | 24.361 | 1.00 | 47.49 | C |
| ATOM | 1407 | O   | ASN | A | 182 | 32.143 | 48.082 | 23.301 | 1.00 | 45.74 | O |
| ATOM | 1408 | CB  | ASN | A | 182 | 32.524 | 47.674 | 26.542 | 1.00 | 44.07 | C |
| ATOM | 1409 | CG  | ASN | A | 182 | 33.691 | 47.864 | 27.476 | 1.00 | 44.24 | C |
| ATOM | 1410 | OD1 | ASN | A | 182 | 34.247 | 48.960 | 27.558 | 1.00 | 40.51 | O |
| ATOM | 1411 | ND2 | ASN | A | 182 | 34.069 | 46.807 | 28.194 | 1.00 | 44.08 | N |
| ATOM | 1412 | N   | PHE | A | 183 | 30.264 | 48.387 | 24.537 | 1.00 | 48.16 | N |
| ATOM | 1413 | CA  | PHE | A | 183 | 29.343 | 47.994 | 23.481 | 1.00 | 48.58 | C |
| ATOM | 1414 | C   | PHE | A | 183 | 29.530 | 48.910 | 22.269 | 1.00 | 49.13 | C |
| ATOM | 1415 | O   | PHE | A | 183 | 29.492 | 48.448 | 21.126 | 1.00 | 48.98 | O |
| ATOM | 1416 | CB  | PHE | A | 183 | 27.895 | 48.073 | 23.997 | 1.00 | 48.42 | C |
| ATOM | 1417 | CG  | PHE | A | 183 | 26.888 | 47.319 | 23.156 | 1.00 | 47.93 | C |
| ATOM | 1418 | CD1 | PHE | A | 183 | 27.268 | 46.660 | 21.990 | 1.00 | 48.96 | C |
| ATOM | 1419 | CD2 | PHE | A | 183 | 25.550 | 47.275 | 23.535 | 1.00 | 49.73 | C |
| ATOM | 1420 | CE1 | PHE | A | 183 | 26.330 | 45.972 | 21.216 | 1.00 | 48.17 | C |
| ATOM | 1421 | CE2 | PHE | A | 183 | 24.605 | 46.588 | 22.765 | 1.00 | 49.37 | C |
| ATOM | 1422 | CZ  | PHE | A | 183 | 25.000 | 45.936 | 21.606 | 1.00 | 47.68 | C |
| ATOM | 1423 | N   | SER | A | 184 | 29.741 | 50.203 | 22.513 | 1.00 | 48.73 | N |
| ATOM | 1424 | CA  | SER | A | 184 | 29.919 | 51.135 | 21.405 | 1.00 | 49.37 | C |
| ATOM | 1425 | C   | SER | A | 184 | 31.296 | 50.966 | 20.788 | 1.00 | 49.35 | C |
| ATOM | 1426 | O   | SER | A | 184 | 31.494 | 51.249 | 19.608 | 1.00 | 52.16 | O |
| ATOM | 1427 | CB  | SER | A | 184 | 29.731 | 52.588 | 21.859 | 1.00 | 47.70 | C |
| ATOM | 1428 | OG  | SER | A | 184 | 30.841 | 53.031 | 22.604 | 1.00 | 47.66 | O |
| ATOM | 1429 | N   | VAL | A | 185 | 32.258 | 50.516 | 21.579 | 1.00 | 48.39 | N |
| ATOM | 1430 | CA  | VAL | A | 185 | 33.585 | 50.305 | 21.035 | 1.00 | 48.52 | C |
| ATOM | 1431 | C   | VAL | A | 185 | 33.510 | 49.068 | 20.146 | 1.00 | 49.64 | C |
| ATOM | 1432 | O   | VAL | A | 185 | 34.186 | 48.974 | 19.121 | 1.00 | 50.40 | O |
| ATOM | 1433 | CB  | VAL | A | 185 | 34.620 | 50.115 | 22.157 | 1.00 | 47.62 | C |
| ATOM | 1434 | CG1 | VAL | A | 185 | 35.874 | 49.432 | 21.620 | 1.00 | 44.18 | C |
| ATOM | 1435 | CG2 | VAL | A | 185 | 34.977 | 51.469 | 22.732 | 1.00 | 46.52 | C |
| ATOM | 1436 | N   | PHE | A | 186 | 32.663 | 48.126 | 20.540 | 1.00 | 50.09 | N |
| ATOM | 1437 | CA  | PHE | A | 186 | 32.471 | 46.905 | 19.779 | 1.00 | 49.73 | C |
| ATOM | 1438 | C   | PHE | A | 186 | 31.956 | 47.241 | 18.385 | 1.00 | 51.03 | C |
| ATOM | 1439 | O   | PHE | A | 186 | 32.414 | 46.671 | 17.396 | 1.00 | 52.60 | O |
| ATOM | 1440 | CB  | PHE | A | 186 | 31.468 | 46.005 | 20.484 | 1.00 | 48.19 | C |
| ATOM | 1441 | CG  | PHE | A | 186 | 31.067 | 44.810 | 19.684 | 1.00 | 48.27 | C |
| ATOM | 1442 | CD1 | PHE | A | 186 | 32.024 | 43.911 | 19.231 | 1.00 | 49.95 | C |
| ATOM | 1443 | CD2 | PHE | A | 186 | 29.730 | 44.568 | 19.403 | 1.00 | 48.26 | C |
| ATOM | 1444 | CE1 | PHE | A | 186 | 31.656 | 42.786 | 18.511 | 1.00 | 49.29 | C |
| ATOM | 1445 | CE2 | PHE | A | 186 | 29.349 | 43.446 | 18.686 | 1.00 | 48.00 | C |
| ATOM | 1446 | CZ  | PHE | A | 186 | 30.312 | 42.554 | 18.240 | 1.00 | 50.13 | C |
| ATOM | 1447 | N   | TYR | A | 187 | 30.999 | 48.157 | 18.305 | 1.00 | 51.09 | N |
| ATOM | 1448 | CA  | TYR | A | 187 | 30.457 | 48.557 | 17.013 | 1.00 | 53.10 | C |
| ATOM | 1449 | C   | TYR | A | 187 | 31.509 | 49.232 | 16.155 | 1.00 | 52.89 | C |
| ATOM | 1450 | O   | TYR | A | 187 | 31.634 | 48.937 | 14.970 | 1.00 | 52.60 | O |
| ATOM | 1451 | CB  | TYR | A | 187 | 29.281 | 49.522 | 17.179 | 1.00 | 53.08 | C |
| ATOM | 1452 | CG  | TYR | A | 187 | 27.989 | 48.837 | 17.519 | 1.00 | 53.86 | C |
| ATOM | 1453 | CD1 | TYR | A | 187 | 27.485 | 47.829 | 16.704 | 1.00 | 52.58 | C |
| ATOM | 1454 | CD2 | TYR | A | 187 | 27.275 | 49.182 | 18.670 | 1.00 | 54.35 | C |
| ATOM | 1455 | CE1 | TYR | A | 187 | 26.306 | 47.174 | 17.021 | 1.00 | 54.09 | C |
| ATOM | 1456 | CE2 | TYR | A | 187 | 26.093 | 48.532 | 19.001 | 1.00 | 53.43 | C |
| ATOM | 1457 | CZ  | TYR | A | 187 | 25.615 | 47.529 | 18.173 | 1.00 | 54.40 | C |
| ATOM | 1458 | OH  | TYR | A | 187 | 24.451 | 46.871 | 18.499 | 1.00 | 56.53 | O |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 1459 | N | TYR | A | 188 | 32.265 | 50.132 | 16.769 | 1.00 | 53.58 | N |
|---|---|---|---|---|---|---|---|---|---|---|---|
| ATOM | 1460 | CA | TYR | A | 188 | 33.291 | 50.886 | 16.067 | 1.00 | 55.91 | C |
| ATOM | 1461 | C | TYR | A | 188 | 34.534 | 50.119 | 15.649 | 1.00 | 57.26 | C |
| ATOM | 1462 | O | TYR | A | 188 | 35.078 | 50.369 | 14.574 | 1.00 | 58.14 | O |
| ATOM | 1463 | CB | TYR | A | 188 | 33.750 | 52.071 | 16.913 | 1.00 | 56.05 | C |
| ATOM | 1464 | CG | TYR | A | 188 | 34.605 | 53.038 | 16.134 | 1.00 | 56.12 | C |
| ATOM | 1465 | CD1 | TYR | A | 188 | 34.020 | 54.048 | 15.375 | 1.00 | 56.84 | C |
| ATOM | 1466 | CD2 | TYR | A | 188 | 35.997 | 52.920 | 16.117 | 1.00 | 54.97 | C |
| ATOM | 1467 | CE1 | TYR | A | 188 | 34.793 | 54.919 | 14.616 | 1.00 | 57.80 | C |
| ATOM | 1468 | CE2 | TYR | A | 188 | 36.783 | 53.790 | 15.358 | 1.00 | 55.80 | C |
| ATOM | 1469 | CZ | TYR | A | 188 | 36.171 | 54.789 | 14.611 | 1.00 | 57.40 | C |
| ATOM | 1470 | OH | TYR | A | 188 | 36.920 | 55.678 | 13.871 | 1.00 | 60.71 | O |
| ATOM | 1471 | N | GLU | A | 189 | 34.997 | 49.199 | 16.488 | 1.00 | 58.59 | N |
| ATOM | 1472 | CA | GLU | A | 189 | 36.216 | 48.473 | 16.166 | 1.00 | 61.10 | C |
| ATOM | 1473 | C | GLU | A | 189 | 36.135 | 47.055 | 15.641 | 1.00 | 60.50 | C |
| ATOM | 1474 | O | GLU | A | 189 | 37.071 | 46.596 | 14.995 | 1.00 | 59.91 | O |
| ATOM | 1475 | CB | GLU | A | 189 | 37.169 | 48.533 | 17.359 | 1.00 | 63.29 | C |
| ATOM | 1476 | CG | GLU | A | 189 | 37.849 | 49.878 | 17.423 | 1.00 | 70.60 | C |
| ATOM | 1477 | CD | GLU | A | 189 | 38.641 | 50.100 | 18.683 | 1.00 | 75.54 | C |
| ATOM | 1478 | OE1 | GLU | A | 189 | 39.168 | 51.224 | 18.817 | 1.00 | 77.89 | O |
| ATOM | 1479 | OE2 | GLU | A | 189 | 38.738 | 49.173 | 19.530 | 1.00 | 78.34 | O |
| ATOM | 1480 | N | ILE | A | 190 | 35.044 | 46.351 | 15.913 | 1.00 | 59.97 | N |
| ATOM | 1481 | CA | ILE | A | 190 | 34.920 | 44.990 | 15.412 | 1.00 | 60.05 | C |
| ATOM | 1482 | C | ILE | A | 190 | 33.913 | 44.952 | 14.269 | 1.00 | 60.63 | C |
| ATOM | 1483 | O | ILE | A | 190 | 34.105 | 44.252 | 13.278 | 1.00 | 63.00 | O |
| ATOM | 1484 | CB | ILE | A | 190 | 34.489 | 44.006 | 16.532 | 1.00 | 59.23 | C |
| ATOM | 1485 | CG1 | ILE | A | 190 | 35.695 | 43.631 | 17.404 | 1.00 | 58.50 | C |
| ATOM | 1486 | CG2 | ILE | A | 190 | 33.920 | 42.737 | 15.914 | 1.00 | 56.18 | C |
| ATOM | 1487 | CD1 | ILE | A | 190 | 36.468 | 44.794 | 17.968 | 1.00 | 58.25 | C |
| ATOM | 1488 | N | LEU | A | 191 | 32.844 | 45.721 | 14.407 | 1.00 | 59.81 | N |
| ATOM | 1489 | CA | LEU | A | 191 | 31.821 | 45.769 | 13.387 | 1.00 | 60.09 | C |
| ATOM | 1490 | C | LEU | A | 191 | 32.046 | 46.941 | 12.445 | 1.00 | 61.49 | C |
| ATOM | 1491 | O | LEU | A | 191 | 31.269 | 47.157 | 11.513 | 1.00 | 62.12 | O |
| ATOM | 1492 | CB | LEU | A | 191 | 30.444 | 45.868 | 14.042 | 1.00 | 60.23 | C |
| ATOM | 1493 | CG | LEU | A | 191 | 29.772 | 44.537 | 14.401 | 1.00 | 59.91 | C |
| ATOM | 1494 | CD1 | LEU | A | 191 | 30.785 | 43.539 | 14.964 | 1.00 | 56.95 | C |
| ATOM | 1495 | CD2 | LEU | A | 191 | 28.639 | 44.819 | 15.380 | 1.00 | 57.94 | C |
| ATOM | 1496 | N | ASN | A | 192 | 33.107 | 47.701 | 12.686 | 1.00 | 62.23 | N |
| ATOM | 1497 | CA | ASN | A | 192 | 33.430 | 48.841 | 11.830 | 1.00 | 64.84 | C |
| ATOM | 1498 | C | ASN | A | 192 | 32.194 | 49.668 | 11.458 | 1.00 | 66.06 | C |
| ATOM | 1499 | O | ASN | A | 192 | 32.028 | 50.075 | 10.304 | 1.00 | 67.04 | O |
| ATOM | 1500 | CB | ASN | A | 192 | 34.132 | 48.347 | 10.553 | 1.00 | 65.30 | C |
| ATOM | 1501 | CG | ASN | A | 192 | 35.470 | 47.673 | 10.845 | 1.00 | 67.44 | C |
| ATOM | 1502 | OD1 | ASN | A | 192 | 36.399 | 48.307 | 11.356 | 1.00 | 66.12 | O |
| ATOM | 1503 | ND2 | ASN | A | 192 | 35.569 | 46.378 | 10.530 | 1.00 | 67.89 | N |
| ATOM | 1504 | N | SER | A | 193 | 31.334 | 49.914 | 12.444 | 1.00 | 67.40 | N |
| ATOM | 1505 | CA | SER | A | 193 | 30.108 | 50.687 | 12.243 | 1.00 | 68.11 | C |
| ATOM | 1506 | C | SER | A | 193 | 30.115 | 51.917 | 13.143 | 1.00 | 68.01 | C |
| ATOM | 1507 | O | SER | A | 193 | 29.401 | 51.960 | 14.143 | 1.00 | 67.76 | O |
| ATOM | 1508 | CB | SER | A | 193 | 28.878 | 49.834 | 12.578 | 1.00 | 69.57 | C |
| ATOM | 1509 | OG | SER | A | 193 | 28.954 | 48.552 | 11.970 | 1.00 | 71.14 | O |
| ATOM | 1510 | N | PRO | A | 194 | 30.922 | 52.935 | 12.797 | 1.00 | 69.02 | N |
| ATOM | 1511 | CA | PRO | A | 194 | 31.029 | 54.179 | 13.574 | 1.00 | 69.06 | C |
| ATOM | 1512 | C | PRO | A | 194 | 29.693 | 54.880 | 13.809 | 1.00 | 68.92 | C |
| ATOM | 1513 | O | PRO | A | 194 | 29.542 | 55.666 | 14.746 | 1.00 | 68.75 | O |
| ATOM | 1514 | CB | PRO | A | 194 | 32.000 | 55.023 | 12.748 | 1.00 | 68.88 | C |
| ATOM | 1515 | CG | PRO | A | 194 | 31.806 | 54.507 | 11.351 | 1.00 | 69.37 | C |
| ATOM | 1516 | CD | PRO | A | 194 | 31.719 | 53.021 | 11.561 | 1.00 | 69.17 | C |
| ATOM | 1517 | N | ASP | A | 195 | 28.723 | 54.586 | 12.955 | 1.00 | 69.83 | N |
| ATOM | 1518 | CA | ASP | A | 195 | 27.403 | 55.171 | 13.085 | 1.00 | 70.76 | C |
| ATOM | 1519 | C | ASP | A | 195 | 26.709 | 54.612 | 14.326 | 1.00 | 69.43 | C |
| ATOM | 1520 | O | ASP | A | 195 | 26.320 | 55.368 | 15.214 | 1.00 | 68.11 | O |
| ATOM | 1521 | CB | ASP | A | 195 | 26.580 | 54.882 | 11.825 | 1.00 | 74.93 | C |
| ATOM | 1522 | CG | ASP | A | 195 | 26.429 | 56.109 | 10.926 | 1.00 | 78.71 | C |
| ATOM | 1523 | OD1 | ASP | A | 195 | 27.454 | 56.770 | 10.625 | 1.00 | 78.09 | O |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 1524 | OD2 | ASP | A | 195 | 25.279 | 56.408 | 10.519 | 1.00 | 81.81 | O |
|---|---|---|---|---|---|---|---|---|---|---|---|
| ATOM | 1525 | N | ARG | A | 196 | 26.564 | 53.290 | 14.384 | 1.00 | 68.99 | N |
| ATOM | 1526 | CA | ARG | A | 196 | 25.930 | 52.634 | 15.524 | 1.00 | 68.37 | C |
| ATOM | 1527 | C | ARG | A | 196 | 26.711 | 52.894 | 16.812 | 1.00 | 66.22 | C |
| ATOM | 1528 | O | ARG | A | 196 | 26.127 | 53.029 | 17.883 | 1.00 | 65.73 | O |
| ATOM | 1529 | CB | ARG | A | 196 | 25.815 | 51.131 | 15.260 | 1.00 | 71.38 | C |
| ATOM | 1530 | CG | ARG | A | 196 | 24.775 | 50.804 | 14.204 | 1.00 | 77.57 | C |
| ATOM | 1531 | CD | ARG | A | 196 | 25.148 | 49.595 | 13.339 | 1.00 | 84.72 | C |
| ATOM | 1532 | NE | ARG | A | 196 | 24.993 | 48.300 | 14.008 | 1.00 | 89.48 | N |
| ATOM | 1533 | CZ | ARG | A | 196 | 25.081 | 47.124 | 13.383 | 1.00 | 91.49 | C |
| ATOM | 1534 | NH1 | ARG | A | 196 | 25.320 | 47.086 | 12.077 | 1.00 | 92.47 | N |
| ATOM | 1535 | NH2 | ARG | A | 196 | 24.929 | 45.985 | 14.054 | 1.00 | 91.87 | N |
| ATOM | 1536 | N | ALA | A | 197 | 28.032 | 52.985 | 16.702 | 1.00 | 64.67 | N |
| ATOM | 1537 | CA | ALA | A | 197 | 28.882 | 53.239 | 17.863 | 1.00 | 62.70 | C |
| ATOM | 1538 | C | ALA | A | 197 | 28.645 | 54.633 | 18.460 | 1.00 | 62.09 | C |
| ATOM | 1539 | O | ALA | A | 197 | 28.405 | 54.769 | 19.664 | 1.00 | 60.00 | O |
| ATOM | 1540 | CB | ALA | A | 197 | 30.345 | 53.081 | 17.477 | 1.00 | 60.93 | C |
| ATOM | 1541 | N | CYS | A | 198 | 28.714 | 55.661 | 17.617 | 1.00 | 61.45 | N |
| ATOM | 1542 | CA | CYS | A | 198 | 28.509 | 57.033 | 18.075 | 1.00 | 62.35 | C |
| ATOM | 1543 | C | CYS | A | 198 | 27.120 | 57.265 | 18.669 | 1.00 | 61.92 | C |
| ATOM | 1544 | O | CYS | A | 198 | 26.971 | 57.987 | 19.659 | 1.00 | 60.88 | O |
| ATOM | 1545 | CB | CYS | A | 198 | 28.754 | 58.020 | 16.931 | 1.00 | 61.65 | C |
| ATOM | 1546 | SG | CYS | A | 198 | 30.484 | 58.136 | 16.417 | 1.00 | 65.04 | S |
| ATOM | 1547 | N | ASN | A | 199 | 26.103 | 56.661 | 18.063 | 1.00 | 62.14 | N |
| ATOM | 1548 | CA | ASN | A | 199 | 24.741 | 56.809 | 18.558 | 1.00 | 62.16 | C |
| ATOM | 1549 | C | ASN | A | 199 | 24.689 | 56.320 | 19.996 | 1.00 | 61.90 | C |
| ATOM | 1550 | O | ASN | A | 199 | 24.284 | 57.057 | 20.904 | 1.00 | 62.23 | O |
| ATOM | 1551 | CB | ASN | A | 199 | 23.765 | 55.984 | 17.715 | 1.00 | 64.61 | C |
| ATOM | 1552 | CG | ASN | A | 199 | 23.681 | 56.464 | 16.268 | 1.00 | 67.61 | C |
| ATOM | 1553 | OD1 | ASN | A | 199 | 23.013 | 55.840 | 15.433 | 1.00 | 69.07 | O |
| ATOM | 1554 | ND2 | ASN | A | 199 | 24.352 | 57.575 | 15.967 | 1.00 | 68.08 | N |
| ATOM | 1555 | N | LEU | A | 200 | 25.120 | 55.075 | 20.190 | 1.00 | 59.88 | N |
| ATOM | 1556 | CA | LEU | A | 200 | 25.124 | 54.447 | 21.500 | 1.00 | 58.61 | C |
| ATOM | 1557 | C | LEU | A | 200 | 25.925 | 55.265 | 22.502 | 1.00 | 57.71 | C |
| ATOM | 1558 | O | LEU | A | 200 | 25.416 | 55.643 | 23.556 | 1.00 | 57.35 | O |
| ATOM | 1559 | CB | LEU | A | 200 | 25.697 | 53.031 | 21.395 | 1.00 | 60.15 | C |
| ATOM | 1560 | CG | LEU | A | 200 | 25.331 | 52.035 | 22.505 | 1.00 | 62.00 | C |
| ATOM | 1561 | CD1 | LEU | A | 200 | 25.833 | 50.653 | 22.131 | 1.00 | 62.34 | C |
| ATOM | 1562 | CD2 | LEU | A | 200 | 25.924 | 52.469 | 23.836 | 1.00 | 64.51 | C |
| ATOM | 1563 | N | ALA | A | 201 | 27.179 | 55.541 | 22.173 | 1.00 | 58.03 | N |
| ATOM | 1564 | CA | ALA | A | 201 | 28.033 | 56.319 | 23.066 | 1.00 | 58.70 | C |
| ATOM | 1565 | C | ALA | A | 201 | 27.353 | 57.636 | 23.432 | 1.00 | 59.62 | C |
| ATOM | 1566 | O | ALA | A | 201 | 27.203 | 57.959 | 24.608 | 1.00 | 59.14 | O |
| ATOM | 1567 | CB | ALA | A | 201 | 29.377 | 56.589 | 22.400 | 1.00 | 56.37 | C |
| ATOM | 1568 | N | LYS | A | 202 | 26.935 | 58.386 | 22.414 | 1.00 | 61.46 | N |
| ATOM | 1569 | CA | LYS | A | 202 | 26.270 | 59.669 | 22.616 | 1.00 | 62.55 | C |
| ATOM | 1570 | C | LYS | A | 202 | 25.016 | 59.513 | 23.465 | 1.00 | 62.71 | C |
| ATOM | 1571 | O | LYS | A | 202 | 24.793 | 60.272 | 24.405 | 1.00 | 62.33 | O |
| ATOM | 1572 | CB | LYS | A | 202 | 25.883 | 60.289 | 21.268 | 1.00 | 64.57 | C |
| ATOM | 1573 | CG | LYS | A | 202 | 25.306 | 61.702 | 21.359 | 1.00 | 64.85 | C |
| ATOM | 1574 | CD | LYS | A | 202 | 26.392 | 62.742 | 21.657 | 1.00 | 68.77 | C |
| ATOM | 1575 | CE | LYS | A | 202 | 25.797 | 64.109 | 22.026 | 1.00 | 69.31 | C |
| ATOM | 1576 | NZ | LYS | A | 202 | 24.774 | 64.566 | 21.040 | 1.00 | 69.06 | N |
| ATOM | 1577 | N | GLN | A | 203 | 24.197 | 58.524 | 23.139 | 1.00 | 62.61 | N |
| ATOM | 1578 | CA | GLN | A | 203 | 22.967 | 58.317 | 23.883 | 1.00 | 63.52 | C |
| ATOM | 1579 | C | GLN | A | 203 | 23.169 | 58.011 | 25.367 | 1.00 | 62.84 | C |
| ATOM | 1580 | O | GLN | A | 203 | 22.439 | 58.528 | 26.213 | 1.00 | 62.57 | O |
| ATOM | 1581 | CB | GLN | A | 203 | 22.151 | 57.194 | 23.253 | 1.00 | 66.39 | C |
| ATOM | 1582 | CG | GLN | A | 203 | 20.846 | 56.947 | 23.986 | 1.00 | 71.88 | C |
| ATOM | 1583 | CD | GLN | A | 203 | 20.142 | 55.696 | 23.509 | 1.00 | 75.72 | C |
| ATOM | 1584 | OE1 | GLN | A | 203 | 19.720 | 55.612 | 22.355 | 1.00 | 78.00 | O |
| ATOM | 1585 | NE2 | GLN | A | 203 | 20.019 | 54.707 | 24.397 | 1.00 | 77.27 | N |
| ATOM | 1586 | N | ALA | A | 204 | 24.147 | 57.165 | 25.680 | 1.00 | 60.82 | N |
| ATOM | 1587 | CA | ALA | A | 204 | 24.413 | 56.792 | 27.062 | 1.00 | 59.05 | C |
| ATOM | 1588 | C | ALA | A | 204 | 24.972 | 57.973 | 27.829 | 1.00 | 58.57 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 1589 | O | ALA | A | 204 | 24.642 | 58.189 | 28.996 | 1.00 | 58.90 | O |
|---|---|---|---|---|---|---|---|---|---|---|---|
| ATOM | 1590 | CB | ALA | A | 204 | 25.393 | 55.628 | 27.114 | 1.00 | 58.41 | C |
| ATOM | 1591 | N | PHE | A | 205 | 25.829 | 58.735 | 27.166 | 1.00 | 58.87 | N |
| ATOM | 1592 | CA | PHE | A | 205 | 26.447 | 59.899 | 27.779 | 1.00 | 59.71 | C |
| ATOM | 1593 | C | PHE | A | 205 | 25.387 | 60.952 | 28.071 | 1.00 | 60.84 | C |
| ATOM | 1594 | O | PHE | A | 205 | 25.357 | 61.551 | 29.146 | 1.00 | 59.96 | O |
| ATOM | 1595 | CB | PHE | A | 205 | 27.490 | 60.491 | 26.838 | 1.00 | 58.39 | C |
| ATOM | 1596 | CG | PHE | A | 205 | 28.293 | 61.594 | 27.454 | 1.00 | 59.16 | C |
| ATOM | 1597 | CD1 | PHE | A | 205 | 29.436 | 61.305 | 28.197 | 1.00 | 58.47 | C |
| ATOM | 1598 | CD2 | PHE | A | 205 | 27.897 | 62.921 | 27.313 | 1.00 | 57.71 | C |
| ATOM | 1599 | CE1 | PHE | A | 205 | 30.175 | 62.322 | 28.788 | 1.00 | 58.36 | C |
| ATOM | 1600 | CE2 | PHE | A | 205 | 28.628 | 63.945 | 27.903 | 1.00 | 57.36 | C |
| ATOM | 1601 | CZ | PHE | A | 205 | 29.771 | 63.643 | 28.642 | 1.00 | 58.25 | C |
| ATOM | 1602 | N | ASP | A | 206 | 24.517 | 61.175 | 27.095 | 1.00 | 62.36 | N |
| ATOM | 1603 | CA | ASP | A | 206 | 23.462 | 62.155 | 27.246 | 1.00 | 63.84 | C |
| ATOM | 1604 | C | ASP | A | 206 | 22.503 | 61.795 | 28.371 | 1.00 | 63.83 | C |
| ATOM | 1605 | O | ASP | A | 206 | 22.159 | 62.652 | 29.188 | 1.00 | 63.21 | O |
| ATOM | 1606 | CB | ASP | A | 206 | 22.694 | 62.318 | 25.934 | 1.00 | 66.07 | C |
| ATOM | 1607 | CG | ASP | A | 206 | 23.530 | 62.982 | 24.846 | 1.00 | 68.89 | C |
| ATOM | 1608 | OD1 | ASP | A | 206 | 24.478 | 63.736 | 25.186 | 1.00 | 68.58 | O |
| ATOM | 1609 | OD2 | ASP | A | 206 | 23.226 | 62.758 | 23.651 | 1.00 | 69.88 | O |
| ATOM | 1610 | N | GLU | A | 207 | 22.071 | 60.538 | 28.422 | 1.00 | 62.72 | N |
| ATOM | 1611 | CA | GLU | A | 207 | 21.152 | 60.115 | 29.473 | 1.00 | 62.89 | C |
| ATOM | 1612 | C | GLU | A | 207 | 21.790 | 60.297 | 30.840 | 1.00 | 61.24 | C |
| ATOM | 1613 | O | GLU | A | 207 | 21.109 | 60.603 | 31.815 | 1.00 | 61.70 | O |
| ATOM | 1614 | CB | GLU | A | 207 | 20.743 | 58.658 | 29.284 | 1.00 | 64.10 | C |
| ATOM | 1615 | CG | GLU | A | 207 | 20.168 | 58.372 | 27.923 | 1.00 | 70.28 | C |
| ATOM | 1616 | CD | GLU | A | 207 | 19.763 | 56.926 | 27.760 | 1.00 | 74.81 | C |
| ATOM | 1617 | OE1 | GLU | A | 207 | 18.690 | 56.553 | 28.281 | 1.00 | 78.58 | O |
| ATOM | 1618 | OE2 | GLU | A | 207 | 20.521 | 56.160 | 27.122 | 1.00 | 77.87 | O |
| ATOM | 1619 | N | ALA | A | 208 | 23.101 | 60.117 | 30.913 | 1.00 | 59.85 | N |
| ATOM | 1620 | CA | ALA | A | 208 | 23.793 | 60.277 | 32.177 | 1.00 | 60.03 | C |
| ATOM | 1621 | C | ALA | A | 208 | 23.749 | 61.748 | 32.585 | 1.00 | 60.73 | C |
| ATOM | 1622 | O | ALA | A | 208 | 23.392 | 62.085 | 33.716 | 1.00 | 61.03 | O |
| ATOM | 1623 | CB | ALA | A | 208 | 25.228 | 59.810 | 32.045 | 1.00 | 59.44 | C |
| ATOM | 1624 | N | ILE | A | 209 | 24.122 | 62.620 | 31.656 | 1.00 | 61.19 | N |
| ATOM | 1625 | CA | ILE | A | 209 | 24.121 | 64.051 | 31.900 | 1.00 | 62.29 | C |
| ATOM | 1626 | C | ILE | A | 209 | 22.716 | 64.509 | 32.286 | 1.00 | 63.96 | C |
| ATOM | 1627 | O | ILE | A | 209 | 22.554 | 65.347 | 33.172 | 1.00 | 65.89 | O |
| ATOM | 1628 | CB | ILE | A | 209 | 24.587 | 64.828 | 30.643 | 1.00 | 61.96 | C |
| ATOM | 1629 | CG1 | ILE | A | 209 | 26.075 | 64.583 | 30.399 | 1.00 | 63.44 | C |
| ATOM | 1630 | CG2 | ILE | A | 209 | 24.351 | 66.306 | 30.817 | 1.00 | 61.53 | C |
| ATOM | 1631 | CD1 | ILE | A | 209 | 26.969 | 65.032 | 31.550 | 1.00 | 63.71 | C |
| ATOM | 1632 | N | ALA | A | 210 | 21.705 | 63.953 | 31.623 | 1.00 | 64.05 | N |
| ATOM | 1633 | CA | ALA | A | 210 | 20.313 | 64.306 | 31.897 | 1.00 | 64.43 | C |
| ATOM | 1634 | C | ALA | A | 210 | 19.957 | 63.987 | 33.340 | 1.00 | 64.60 | C |
| ATOM | 1635 | O | ALA | A | 210 | 19.579 | 64.870 | 34.108 | 1.00 | 65.48 | O |
| ATOM | 1636 | CB | ALA | A | 210 | 19.379 | 63.547 | 30.956 | 1.00 | 64.35 | C |
| ATOM | 1637 | N | GLU | A | 211 | 20.066 | 62.712 | 33.690 | 1.00 | 64.60 | N |
| ATOM | 1638 | CA | GLU | A | 211 | 19.784 | 62.252 | 35.037 | 1.00 | 64.25 | C |
| ATOM | 1639 | C | GLU | A | 211 | 20.576 | 63.108 | 36.022 | 1.00 | 63.72 | C |
| ATOM | 1640 | O | GLU | A | 211 | 20.044 | 63.607 | 37.007 | 1.00 | 63.34 | O |
| ATOM | 1641 | CB | GLU | A | 211 | 20.193 | 60.784 | 35.161 | 1.00 | 64.86 | C |
| ATOM | 1642 | CG | GLU | A | 211 | 20.247 | 60.254 | 36.577 | 1.00 | 67.95 | C |
| ATOM | 1643 | CD | GLU | A | 211 | 19.235 | 59.157 | 36.827 | 1.00 | 70.61 | C |
| ATOM | 1644 | OE1 | GLU | A | 211 | 19.410 | 58.428 | 37.834 | 1.00 | 70.65 | O |
| ATOM | 1645 | OE2 | GLU | A | 211 | 18.270 | 59.032 | 36.026 | 1.00 | 70.97 | O |
| ATOM | 1646 | N | LEU | A | 212 | 21.855 | 63.288 | 35.733 | 1.00 | 64.02 | N |
| ATOM | 1647 | CA | LEU | A | 212 | 22.729 | 64.071 | 36.590 | 1.00 | 65.24 | C |
| ATOM | 1648 | C | LEU | A | 212 | 22.195 | 65.492 | 36.785 | 1.00 | 66.80 | C |
| ATOM | 1649 | O | LEU | A | 212 | 22.232 | 66.039 | 37.894 | 1.00 | 66.15 | O |
| ATOM | 1650 | CB | LEU | A | 212 | 24.130 | 64.105 | 35.970 | 1.00 | 63.36 | C |
| ATOM | 1651 | CG | LEU | A | 212 | 25.325 | 63.738 | 36.855 | 1.00 | 62.20 | C |
| ATOM | 1652 | CD1 | LEU | A | 212 | 24.949 | 62.632 | 37.829 | 1.00 | 60.65 | C |
| ATOM | 1653 | CD2 | LEU | A | 212 | 26.484 | 63.303 | 35.965 | 1.00 | 60.28 | C |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 1654 | N   | ASP | A | 213 | 21.688 | 66.068 | 35.696 | 1.00 | 68.14 | N |
|------|------|-----|-----|---|-----|--------|--------|--------|------|-------|---|
| ATOM | 1655 | CA  | ASP | A | 213 | 21.150 | 67.424 | 35.679 | 1.00 | 68.61 | C |
| ATOM | 1656 | C   | ASP | A | 213 | 19.903 | 67.588 | 36.542 | 1.00 | 69.04 | C |
| ATOM | 1657 | O   | ASP | A | 213 | 19.830 | 68.501 | 37.366 | 1.00 | 68.33 | O |
| ATOM | 1658 | CB  | ASP | A | 213 | 20.828 | 67.832 | 34.239 | 1.00 | 70.43 | C |
| ATOM | 1659 | CG  | ASP | A | 213 | 20.439 | 69.298 | 34.118 | 1.00 | 72.23 | C |
| ATOM | 1660 | OD1 | ASP | A | 213 | 19.993 | 69.700 | 33.020 | 1.00 | 71.92 | O |
| ATOM | 1661 | OD2 | ASP | A | 213 | 20.586 | 70.045 | 35.114 | 1.00 | 71.72 | O |
| ATOM | 1662 | N   | THR | A | 214 | 18.918 | 66.716 | 36.345 | 1.00 | 69.30 | N |
| ATOM | 1663 | CA  | THR | A | 214 | 17.692 | 66.786 | 37.125 | 1.00 | 70.44 | C |
| ATOM | 1664 | C   | THR | A | 214 | 17.900 | 66.203 | 38.523 | 1.00 | 72.84 | C |
| ATOM | 1665 | O   | THR | A | 214 | 18.566 | 66.809 | 39.362 | 1.00 | 73.49 | O |
| ATOM | 1666 | CB  | THR | A | 214 | 16.526 | 66.051 | 36.418 | 1.00 | 68.23 | C |
| ATOM | 1667 | OG1 | THR | A | 214 | 16.910 | 64.709 | 36.110 | 1.00 | 66.45 | O |
| ATOM | 1668 | CG2 | THR | A | 214 | 16.150 | 66.765 | 35.134 | 1.00 | 68.10 | C |
| ATOM | 1669 | N   | LEU | A | 215 | 17.345 | 65.022 | 38.767 | 1.00 | 76.79 | N |
| ATOM | 1670 | CA  | LEU | A | 215 | 17.459 | 64.368 | 40.071 | 1.00 | 80.18 | C |
| ATOM | 1671 | C   | LEU | A | 215 | 18.894 | 64.053 | 40.502 | 1.00 | 81.17 | C |
| ATOM | 1672 | O   | LEU | A | 215 | 19.411 | 64.759 | 41.400 | 1.00 | 81.68 | O |
| ATOM | 1673 | CB  | LEU | A | 215 | 16.611 | 63.084 | 40.088 | 1.00 | 81.18 | C |
| ATOM | 1674 | CG  | LEU | A | 215 | 16.890 | 61.914 | 39.133 | 1.00 | 82.54 | C |
| ATOM | 1675 | CD1 | LEU | A | 215 | 15.789 | 60.873 | 39.312 | 1.00 | 83.62 | C |
| ATOM | 1676 | CD2 | LEU | A | 215 | 16.919 | 62.374 | 37.684 | 1.00 | 83.59 | C |
| ATOM | 1677 | OXT | LEU | A | 215 | 19.491 | 63.111 | 39.939 | 1.00 | 83.13 | O |
| ATOM | 1678 | N   | TYR | A | 220 | 29.737 | 60.468 | 41.081 | 1.00 | 93.52 | N |
| ATOM | 1679 | CA  | TYR | A | 220 | 30.590 | 59.269 | 41.367 | 1.00 | 93.74 | C |
| ATOM | 1680 | C   | TYR | A | 220 | 31.885 | 59.313 | 40.544 | 1.00 | 92.02 | C |
| ATOM | 1681 | O   | TYR | A | 220 | 31.835 | 59.290 | 39.315 | 1.00 | 91.47 | O |
| ATOM | 1682 | CB  | TYR | A | 220 | 29.822 | 57.979 | 41.032 | 1.00 | 95.36 | C |
| ATOM | 1683 | CG  | TYR | A | 220 | 28.620 | 57.699 | 41.912 | 1.00 | 97.21 | C |
| ATOM | 1684 | CD1 | TYR | A | 220 | 27.685 | 58.697 | 42.193 | 1.00 | 98.44 | C |
| ATOM | 1685 | CD2 | TYR | A | 220 | 28.402 | 56.424 | 42.448 | 1.00 | 98.40 | C |
| ATOM | 1686 | CE1 | TYR | A | 220 | 26.561 | 58.436 | 42.988 | 1.00 | 98.81 | C |
| ATOM | 1687 | CE2 | TYR | A | 220 | 27.279 | 56.152 | 43.244 | 1.00 | 98.19 | C |
| ATOM | 1688 | CZ  | TYR | A | 220 | 26.365 | 57.164 | 43.510 | 1.00 | 98.38 | C |
| ATOM | 1689 | OH  | TYR | A | 220 | 25.262 | 56.918 | 44.299 | 1.00 | 98.09 | O |
| ATOM | 1690 | N   | LYS | A | 221 | 33.036 | 59.383 | 41.220 | 1.00 | 90.45 | N |
| ATOM | 1691 | CA  | LYS | A | 221 | 34.337 | 59.415 | 40.535 | 1.00 | 88.30 | C |
| ATOM | 1692 | C   | LYS | A | 221 | 34.369 | 58.191 | 39.632 | 1.00 | 85.58 | C |
| ATOM | 1693 | O   | LYS | A | 221 | 35.003 | 58.166 | 38.573 | 1.00 | 83.95 | O |
| ATOM | 1694 | CB  | LYS | A | 221 | 35.485 | 59.348 | 41.554 | 1.00 | 88.67 | C |
| ATOM | 1695 | CG  | LYS | A | 221 | 36.874 | 59.297 | 40.927 | 1.00 | 90.28 | C |
| ATOM | 1696 | CD  | LYS | A | 221 | 37.972 | 59.511 | 41.957 | 1.00 | 91.41 | C |
| ATOM | 1697 | CE  | LYS | A | 221 | 37.901 | 60.918 | 42.543 | 1.00 | 93.06 | C |
| ATOM | 1698 | NZ  | LYS | A | 221 | 39.016 | 61.212 | 43.492 | 1.00 | 93.88 | N |
| ATOM | 1699 | N   | ASP | A | 222 | 33.641 | 57.186 | 40.091 | 1.00 | 82.91 | N |
| ATOM | 1700 | CA  | ASP | A | 222 | 33.474 | 55.910 | 39.428 | 1.00 | 79.23 | C |
| ATOM | 1701 | C   | ASP | A | 222 | 32.915 | 56.126 | 38.018 | 1.00 | 77.84 | C |
| ATOM | 1702 | O   | ASP | A | 222 | 33.537 | 55.756 | 37.018 | 1.00 | 77.75 | O |
| ATOM | 1703 | CB  | ASP | A | 222 | 32.501 | 55.088 | 40.275 | 1.00 | 77.65 | C |
| ATOM | 1704 | CG  | ASP | A | 222 | 32.514 | 53.641 | 39.931 | 1.00 | 76.33 | C |
| ATOM | 1705 | OD1 | ASP | A | 222 | 33.457 | 53.217 | 39.239 | 1.00 | 78.01 | O |
| ATOM | 1706 | OD2 | ASP | A | 222 | 31.590 | 52.927 | 40.367 | 1.00 | 75.26 | O |
| ATOM | 1707 | N   | SER | A | 223 | 31.738 | 56.749 | 37.960 | 1.00 | 75.46 | N |
| ATOM | 1708 | CA  | SER | A | 223 | 31.036 | 57.023 | 36.710 | 1.00 | 71.51 | C |
| ATOM | 1709 | C   | SER | A | 223 | 31.594 | 58.209 | 35.929 | 1.00 | 69.38 | C |
| ATOM | 1710 | O   | SER | A | 223 | 31.513 | 58.244 | 34.702 | 1.00 | 69.84 | O |
| ATOM | 1711 | CB  | SER | A | 223 | 29.557 | 57.272 | 37.005 | 1.00 | 71.33 | C |
| ATOM | 1712 | OG  | SER | A | 223 | 29.025 | 56.237 | 37.813 | 1.00 | 70.30 | O |
| ATOM | 1713 | N   | THR | A | 224 | 32.151 | 59.184 | 36.636 | 1.00 | 66.50 | N |
| ATOM | 1714 | CA  | THR | A | 224 | 32.706 | 60.364 | 35.986 | 1.00 | 63.52 | C |
| ATOM | 1715 | C   | THR | A | 224 | 33.841 | 59.999 | 35.040 | 1.00 | 61.54 | C |
| ATOM | 1716 | O   | THR | A | 224 | 33.957 | 60.572 | 33.957 | 1.00 | 61.25 | O |
| ATOM | 1717 | CB  | THR | A | 224 | 33.233 | 61.385 | 37.014 | 1.00 | 63.07 | C |
| ATOM | 1718 | OG1 | THR | A | 224 | 32.192 | 61.714 | 37.942 | 1.00 | 65.13 | O |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 1719 | CG2 | THR | A | 224 | 33.687 | 62.653 | 36.312 | 1.00 | 60.87 | C |
|---|---|---|---|---|---|---|---|---|---|---|---|
| ATOM | 1720 | N | LEU | A | 225 | 34.682 | 59.052 | 35.450 | 1.00 | 59.77 | N |
| ATOM | 1721 | CA | LEU | A | 225 | 35.798 | 58.627 | 34.612 | 1.00 | 58.33 | C |
| ATOM | 1722 | C | LEU | A | 225 | 35.280 | 57.911 | 33.371 | 1.00 | 57.53 | C |
| ATOM | 1723 | O | LEU | A | 225 | 35.733 | 58.180 | 32.253 | 1.00 | 56.53 | O |
| ATOM | 1724 | CB | LEU | A | 225 | 36.747 | 57.704 | 35.388 | 1.00 | 58.68 | C |
| ATOM | 1725 | CG | LEU | A | 225 | 37.898 | 57.066 | 34.594 | 1.00 | 59.24 | C |
| ATOM | 1726 | CD1 | LEU | A | 225 | 39.042 | 56.718 | 35.526 | 1.00 | 60.41 | C |
| ATOM | 1727 | CD2 | LEU | A | 225 | 37.410 | 55.815 | 33.889 | 1.00 | 60.70 | C |
| ATOM | 1728 | N | ILE | A | 226 | 34.327 | 57.005 | 33.565 | 1.00 | 55.09 | N |
| ATOM | 1729 | CA | ILE | A | 226 | 33.772 | 56.271 | 32.441 | 1.00 | 54.10 | C |
| ATOM | 1730 | C | ILE | A | 226 | 33.138 | 57.216 | 31.432 | 1.00 | 55.54 | C |
| ATOM | 1731 | O | ILE | A | 226 | 33.222 | 56.985 | 30.219 | 1.00 | 55.77 | O |
| ATOM | 1732 | CB | ILE | A | 226 | 32.725 | 55.243 | 32.900 | 1.00 | 52.60 | C |
| ATOM | 1733 | CG1 | ILE | A | 226 | 33.402 | 54.164 | 33.751 | 1.00 | 50.18 | C |
| ATOM | 1734 | CG2 | ILE | A | 226 | 32.034 | 54.629 | 31.688 | 1.00 | 52.08 | C |
| ATOM | 1735 | CD1 | ILE | A | 226 | 32.476 | 53.038 | 34.174 | 1.00 | 48.17 | C |
| ATOM | 1736 | N | MET | A | 227 | 32.507 | 58.280 | 31.927 | 1.00 | 56.05 | N |
| ATOM | 1737 | CA | MET | A | 227 | 31.865 | 59.246 | 31.039 | 1.00 | 56.46 | C |
| ATOM | 1738 | C | MET | A | 227 | 32.915 | 60.019 | 30.281 | 1.00 | 55.48 | C |
| ATOM | 1739 | O | MET | A | 227 | 32.719 | 60.378 | 29.123 | 1.00 | 53.76 | O |
| ATOM | 1740 | CB | MET | A | 227 | 30.975 | 60.220 | 31.815 | 1.00 | 56.93 | C |
| ATOM | 1741 | CG | MET | A | 227 | 29.681 | 59.607 | 32.278 | 1.00 | 59.89 | C |
| ATOM | 1742 | SD | MET | A | 227 | 28.443 | 60.843 | 32.670 | 1.00 | 65.56 | S |
| ATOM | 1743 | CE | MET | A | 227 | 28.806 | 61.129 | 34.407 | 1.00 | 67.09 | C |
| ATOM | 1744 | N | GLN | A | 228 | 34.040 | 60.271 | 30.934 | 1.00 | 56.73 | N |
| ATOM | 1745 | CA | GLN | A | 228 | 35.101 | 61.000 | 30.275 | 1.00 | 60.35 | C |
| ATOM | 1746 | C | GLN | A | 228 | 35.637 | 60.148 | 29.123 | 1.00 | 60.59 | C |
| ATOM | 1747 | O | GLN | A | 228 | 36.061 | 60.674 | 28.096 | 1.00 | 60.28 | O |
| ATOM | 1748 | CB | GLN | A | 228 | 36.218 | 61.345 | 31.265 | 1.00 | 63.44 | C |
| ATOM | 1749 | CG | GLN | A | 228 | 37.212 | 62.344 | 30.697 | 1.00 | 69.56 | C |
| ATOM | 1750 | CD | GLN | A | 228 | 36.514 | 63.510 | 30.000 | 1.00 | 74.11 | C |
| ATOM | 1751 | OE1 | GLN | A | 228 | 35.734 | 64.248 | 30.621 | 1.00 | 76.89 | O |
| ATOM | 1752 | NE2 | GLN | A | 228 | 36.783 | 63.676 | 28.700 | 1.00 | 73.62 | N |
| ATOM | 1753 | N | LEU | A | 229 | 35.604 | 58.828 | 29.299 | 1.00 | 60.51 | N |
| ATOM | 1754 | CA | LEU | A | 229 | 36.064 | 57.908 | 28.267 | 1.00 | 59.60 | C |
| ATOM | 1755 | C | LEU | A | 229 | 35.057 | 57.919 | 27.112 | 1.00 | 60.30 | C |
| ATOM | 1756 | O | LEU | A | 229 | 35.436 | 57.955 | 25.941 | 1.00 | 60.53 | O |
| ATOM | 1757 | CB | LEU | A | 229 | 36.201 | 56.495 | 28.844 | 1.00 | 56.49 | C |
| ATOM | 1758 | CG | LEU | A | 229 | 37.205 | 56.386 | 29.989 | 1.00 | 55.14 | C |
| ATOM | 1759 | CD1 | LEU | A | 229 | 37.145 | 55.007 | 30.609 | 1.00 | 53.32 | C |
| ATOM | 1760 | CD2 | LEU | A | 229 | 38.592 | 56.686 | 29.471 | 1.00 | 53.34 | C |
| ATOM | 1761 | N | LEU | A | 230 | 33.772 | 57.889 | 27.441 | 1.00 | 60.56 | N |
| ATOM | 1762 | CA | LEU | A | 230 | 32.749 | 57.923 | 26.410 | 1.00 | 61.81 | C |
| ATOM | 1763 | C | LEU | A | 230 | 32.921 | 59.171 | 25.553 | 1.00 | 63.41 | C |
| ATOM | 1764 | O | LEU | A | 230 | 32.756 | 59.125 | 24.337 | 1.00 | 62.64 | O |
| ATOM | 1765 | CB | LEU | A | 230 | 31.356 | 57.922 | 27.038 | 1.00 | 60.49 | C |
| ATOM | 1766 | CG | LEU | A | 230 | 30.779 | 56.545 | 27.348 | 1.00 | 59.45 | C |
| ATOM | 1767 | CD1 | LEU | A | 230 | 29.494 | 56.699 | 28.126 | 1.00 | 58.55 | C |
| ATOM | 1768 | CD2 | LEU | A | 230 | 30.538 | 55.792 | 26.049 | 1.00 | 57.74 | C |
| ATOM | 1769 | N | ARG | A | 231 | 33.257 | 60.288 | 26.189 | 1.00 | 65.56 | N |
| ATOM | 1770 | CA | ARG | A | 231 | 33.433 | 61.534 | 25.459 | 1.00 | 67.45 | C |
| ATOM | 1771 | C | ARG | A | 231 | 34.702 | 61.511 | 24.620 | 1.00 | 66.03 | C |
| ATOM | 1772 | O | ARG | A | 231 | 34.677 | 61.898 | 23.452 | 1.00 | 66.11 | O |
| ATOM | 1773 | CB | ARG | A | 231 | 33.462 | 62.725 | 26.422 | 1.00 | 71.93 | C |
| ATOM | 1774 | CG | ARG | A | 231 | 33.671 | 64.067 | 25.728 | 1.00 | 78.61 | C |
| ATOM | 1775 | CD | ARG | A | 231 | 32.590 | 65.070 | 26.114 | 1.00 | 85.77 | C |
| ATOM | 1776 | NE | ARG | A | 231 | 32.562 | 65.337 | 27.555 | 1.00 | 92.30 | N |
| ATOM | 1777 | CZ | ARG | A | 231 | 33.508 | 65.996 | 28.224 | 1.00 | 94.07 | C |
| ATOM | 1778 | NH1 | ARG | A | 231 | 34.571 | 66.470 | 27.583 | 1.00 | 94.86 | N |
| ATOM | 1779 | NH2 | ARG | A | 231 | 33.393 | 66.174 | 29.539 | 1.00 | 93.94 | N |
| ATOM | 1780 | N | ASP | A | 232 | 35.807 | 61.060 | 25.209 | 1.00 | 64.10 | N |
| ATOM | 1781 | CA | ASP | A | 232 | 37.064 | 60.991 | 24.479 | 1.00 | 63.58 | C |
| ATOM | 1782 | C | ASP | A | 232 | 36.896 | 60.127 | 23.242 | 1.00 | 63.86 | C |
| ATOM | 1783 | O | ASP | A | 232 | 37.494 | 60.405 | 22.205 | 1.00 | 64.99 | O |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 1784 | CB  | ASP | A | 232 | 38.184 | 60.401 | 25.335 | 1.00 | 65.20 | C |
|------|------|-----|-----|---|-----|--------|--------|--------|------|-------|---|
| ATOM | 1785 | CG  | ASP | A | 232 | 38.450 | 61.203 | 26.593 | 1.00 | 67.00 | C |
| ATOM | 1786 | OD1 | ASP | A | 232 | 38.246 | 62.438 | 26.568 | 1.00 | 67.48 | O |
| ATOM | 1787 | OD2 | ASP | A | 232 | 38.878 | 60.595 | 27.603 | 1.00 | 66.48 | O |
| ATOM | 1788 | N   | ASN | A | 233 | 36.093 | 59.071 | 23.345 | 1.00 | 63.19 | N |
| ATOM | 1789 | CA  | ASN | A | 233 | 35.871 | 58.202 | 22.193 | 1.00 | 63.35 | C |
| ATOM | 1790 | C   | ASN | A | 233 | 34.998 | 58.900 | 21.162 | 1.00 | 63.97 | C |
| ATOM | 1791 | O   | ASN | A | 233 | 35.248 | 58.803 | 19.968 | 1.00 | 63.90 | O |
| ATOM | 1792 | CB  | ASN | A | 233 | 35.219 | 56.876 | 22.606 | 1.00 | 61.17 | C |
| ATOM | 1793 | CG  | ASN | A | 233 | 36.218 | 55.883 | 23.153 | 1.00 | 59.63 | C |
| ATOM | 1794 | OD1 | ASN | A | 233 | 37.424 | 56.105 | 23.086 | 1.00 | 59.94 | O |
| ATOM | 1795 | ND2 | ASN | A | 233 | 35.723 | 54.776 | 23.692 | 1.00 | 59.23 | N |
| ATOM | 1796 | N   | LEU | A | 234 | 33.973 | 59.605 | 21.625 | 1.00 | 65.92 | N |
| ATOM | 1797 | CA  | LEU | A | 234 | 33.084 | 60.316 | 20.718 | 1.00 | 67.08 | C |
| ATOM | 1798 | C   | LEU | A | 234 | 33.860 | 61.324 | 19.887 | 1.00 | 67.56 | C |
| ATOM | 1799 | O   | LEU | A | 234 | 33.736 | 61.340 | 18.662 | 1.00 | 67.14 | O |
| ATOM | 1800 | CB  | LEU | A | 234 | 31.972 | 61.022 | 21.496 | 1.00 | 67.20 | C |
| ATOM | 1801 | CG  | LEU | A | 234 | 30.816 | 60.115 | 21.926 | 1.00 | 69.47 | C |
| ATOM | 1802 | CD1 | LEU | A | 234 | 29.864 | 60.874 | 22.840 | 1.00 | 69.67 | C |
| ATOM | 1803 | CD2 | LEU | A | 234 | 30.080 | 59.610 | 20.689 | 1.00 | 69.71 | C |
| ATOM | 1804 | N   | THR | A | 235 | 34.667 | 62.156 | 20.543 | 1.00 | 69.04 | N |
| ATOM | 1805 | CA  | THR | A | 235 | 35.449 | 63.159 | 19.819 | 1.00 | 70.89 | C |
| ATOM | 1806 | C   | THR | A | 235 | 36.461 | 62.452 | 18.925 | 1.00 | 71.33 | C |
| ATOM | 1807 | O   | THR | A | 235 | 36.645 | 62.815 | 17.767 | 1.00 | 72.45 | O |
| ATOM | 1808 | CB  | THR | A | 235 | 36.203 | 64.125 | 20.780 | 1.00 | 70.27 | C |
| ATOM | 1809 | OG1 | THR | A | 235 | 37.387 | 63.496 | 21.277 | 1.00 | 71.53 | O |
| ATOM | 1810 | CG2 | THR | A | 235 | 35.318 | 64.506 | 21.957 | 1.00 | 70.56 | C |
| ATOM | 1811 | N   | LEU | A | 236 | 37.095 | 61.425 | 19.477 | 1.00 | 72.94 | N |
| ATOM | 1812 | CA  | LEU | A | 236 | 38.092 | 60.635 | 18.768 | 1.00 | 74.18 | C |
| ATOM | 1813 | C   | LEU | A | 236 | 37.531 | 60.049 | 17.467 | 1.00 | 74.71 | C |
| ATOM | 1814 | O   | LEU | A | 236 | 38.164 | 60.149 | 16.410 | 1.00 | 75.14 | O |
| ATOM | 1815 | CB  | LEU | A | 236 | 38.579 | 59.511 | 19.685 | 1.00 | 75.05 | C |
| ATOM | 1816 | CG  | LEU | A | 236 | 39.741 | 58.622 | 19.248 | 1.00 | 76.86 | C |
| ATOM | 1817 | CD1 | LEU | A | 236 | 40.981 | 59.472 | 19.025 | 1.00 | 76.69 | C |
| ATOM | 1818 | CD2 | LEU | A | 236 | 39.997 | 57.565 | 20.328 | 1.00 | 77.66 | C |
| ATOM | 1819 | N   | TRP | A | 237 | 36.343 | 59.449 | 17.550 | 1.00 | 73.91 | N |
| ATOM | 1820 | CA  | TRP | A | 237 | 35.699 | 58.841 | 16.388 | 1.00 | 73.69 | C |
| ATOM | 1821 | C   | TRP | A | 237 | 35.191 | 59.863 | 15.388 | 1.00 | 76.47 | C |
| ATOM | 1822 | O   | TRP | A | 237 | 34.839 | 59.507 | 14.258 | 1.00 | 76.66 | O |
| ATOM | 1823 | CB  | TRP | A | 237 | 34.529 | 57.948 | 16.811 | 1.00 | 69.64 | C |
| ATOM | 1824 | CG  | TRP | A | 237 | 34.917 | 56.806 | 17.696 | 1.00 | 65.49 | C |
| ATOM | 1825 | CD1 | TRP | A | 237 | 36.144 | 56.214 | 17.786 | 1.00 | 63.96 | C |
| ATOM | 1826 | CD2 | TRP | A | 237 | 34.063 | 56.097 | 18.597 | 1.00 | 63.06 | C |
| ATOM | 1827 | NE1 | TRP | A | 237 | 36.107 | 55.178 | 18.687 | 1.00 | 62.19 | N |
| ATOM | 1828 | CE2 | TRP | A | 237 | 34.839 | 55.082 | 19.197 | 1.00 | 62.32 | C |
| ATOM | 1829 | CE3 | TRP | A | 237 | 32.715 | 56.214 | 18.951 | 1.00 | 61.23 | C |
| ATOM | 1830 | CZ2 | TRP | A | 237 | 34.312 | 54.195 | 20.134 | 1.00 | 60.66 | C |
| ATOM | 1831 | CZ3 | TRP | A | 237 | 32.194 | 55.332 | 19.878 | 1.00 | 60.87 | C |
| ATOM | 1832 | CH2 | TRP | A | 237 | 32.992 | 54.332 | 20.458 | 1.00 | 60.55 | C |
| ATOM | 1833 | N   | THR | A | 238 | 35.134 | 61.126 | 15.801 | 1.00 | 79.20 | N |
| ATOM | 1834 | CA  | THR | A | 238 | 34.679 | 62.182 | 14.906 | 1.00 | 82.28 | C |
| ATOM | 1835 | C   | THR | A | 238 | 35.891 | 62.706 | 14.134 | 1.00 | 83.39 | C |
| ATOM | 1836 | O   | THR | A | 238 | 36.112 | 63.909 | 14.011 | 1.00 | 83.05 | O |
| ATOM | 1837 | CB  | THR | A | 238 | 33.998 | 63.326 | 15.685 | 1.00 | 83.16 | C |
| ATOM | 1838 | OG1 | THR | A | 238 | 32.963 | 62.784 | 16.515 | 1.00 | 82.23 | O |
| ATOM | 1839 | CG2 | THR | A | 238 | 33.366 | 64.323 | 14.718 | 1.00 | 83.84 | C |
| ATOM | 1840 | N   | SER | A | 239 | 36.674 | 61.756 | 13.628 | 1.00 | 85.98 | N |
| ATOM | 1841 | CA  | SER | A | 239 | 37.880 | 62.014 | 12.845 | 1.00 | 86.48 | C |
| ATOM | 1842 | C   | SER | A | 239 | 38.184 | 60.728 | 12.053 | 1.00 | 87.25 | C |
| ATOM | 1843 | O   | SER | A | 239 | 37.552 | 60.518 | 10.992 | 1.00 | 86.96 | O |
| ATOM | 1844 | CB  | SER | A | 239 | 39.061 | 62.339 | 13.775 | 1.00 | 86.51 | C |
| ATOM | 1845 | OG  | SER | A | 239 | 38.733 | 63.356 | 14.707 | 1.00 | 84.84 | O |
| ATOM | 1846 | N   | ASP | A | 240 | 39.027 | 59.926 | 12.522 | 1.00 | 86.95 | N |
| TER  | 1847 |     | ASP | A | 240 |        |        |        |      |       |   |
| ATOM | 1848 | N   | GLN | P | 1   | 42.908 | 51.915 | 18.407 | 1.00 | 84.64 | N |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| ATOM | 1849 | CA | GLN | P | 1 | 41.974 | 51.422 | 19.456 | 1.00 | 84.49 | C |
|---|---|---|---|---|---|---|---|---|---|---|---|
| ATOM | 1850 | C | GLN | P | 1 | 41.256 | 52.550 | 20.180 | 1.00 | 83.15 | C |
| ATOM | 1851 | O | GLN | P | 1 | 41.616 | 53.723 | 20.056 | 1.00 | 82.70 | O |
| ATOM | 1852 | CB | GLN | P | 1 | 42.717 | 50.550 | 20.474 | 1.00 | 86.06 | C |
| ATOM | 1853 | CG | GLN | P | 1 | 42.745 | 49.068 | 20.116 | 1.00 | 90.24 | C |
| ATOM | 1854 | CD | GLN | P | 1 | 43.373 | 48.788 | 18.754 | 1.00 | 92.35 | C |
| ATOM | 1855 | OE1 | GLN | P | 1 | 42.844 | 49.194 | 17.714 | 1.00 | 93.53 | O |
| ATOM | 1856 | NE2 | GLN | P | 1 | 44.508 | 48.090 | 18.757 | 1.00 | 93.16 | N |
| ATOM | 1857 | N | SER | P | 2 | 40.230 | 52.172 | 20.937 | 1.00 | 81.51 | N |
| ATOM | 1858 | CA | SER | P | 2 | 39.425 | 53.123 | 21.688 | 1.00 | 77.98 | C |
| ATOM | 1859 | C | SER | P | 2 | 39.425 | 52.754 | 23.165 | 1.00 | 76.04 | C |
| ATOM | 1860 | O | SER | P | 2 | 39.822 | 51.649 | 23.545 | 1.00 | 75.27 | O |
| ATOM | 1861 | CB | SER | P | 2 | 37.985 | 53.134 | 21.158 | 1.00 | 78.00 | C |
| ATOM | 1862 | OG | SER | P | 2 | 37.939 | 53.474 | 19.779 | 1.00 | 77.42 | O |
| ATOM | 1863 | N | TYR | P | 3 | 38.966 | 53.693 | 23.985 | 1.00 | 73.68 | N |
| ATOM | 1864 | CA | TYR | P | 3 | 38.901 | 53.518 | 25.427 | 1.00 | 69.73 | C |
| ATOM | 1865 | C | TYR | P | 3 | 37.765 | 52.599 | 25.866 | 1.00 | 66.45 | C |
| ATOM | 1866 | O | TYR | P | 3 | 36.616 | 52.752 | 25.430 | 1.00 | 63.97 | O |
| ATOM | 1867 | CB | TYR | P | 3 | 38.733 | 54.882 | 26.107 | 1.00 | 72.59 | C |
| ATOM | 1868 | CG | TYR | P | 3 | 39.847 | 55.859 | 25.809 | 1.00 | 75.37 | C |
| ATOM | 1869 | CD1 | TYR | P | 3 | 41.126 | 55.678 | 26.345 | 1.00 | 75.71 | C |
| ATOM | 1870 | CD2 | TYR | P | 3 | 39.633 | 56.950 | 24.966 | 1.00 | 76.77 | C |
| ATOM | 1871 | CE1 | TYR | P | 3 | 42.162 | 56.555 | 26.048 | 1.00 | 77.35 | C |
| ATOM | 1872 | CE2 | TYR | P | 3 | 40.663 | 57.836 | 24.658 | 1.00 | 78.32 | C |
| ATOM | 1873 | CZ | TYR | P | 3 | 41.924 | 57.632 | 25.202 | 1.00 | 78.62 | C |
| ATOM | 1874 | OH | TYR | P | 3 | 42.944 | 58.501 | 24.887 | 1.00 | 79.70 | O |
| HETATM | 1875 | N | TPO | P | 4 | 38.105 | 51.645 | 26.733 | 1.00 | 63.36 | N |
| HETATM | 1876 | CA | TPO | P | 4 | 37.141 | 50.699 | 27.302 | 1.00 | 60.94 | C |
| HETATM | 1877 | CB | TPO | P | 4 | 37.244 | 49.313 | 26.667 | 1.00 | 57.26 | C |
| HETATM | 1878 | CG2 | TPO | P | 4 | 37.144 | 49.400 | 25.136 | 1.00 | 56.15 | C |
| HETATM | 1879 | OG1 | TPO | P | 4 | 38.497 | 48.759 | 27.064 | 1.00 | 52.32 | O |
| HETATM | 1880 | P | TPO | P | 4 | 38.922 | 47.276 | 26.625 | 1.00 | 49.68 | P |
| HETATM | 1881 | O1P | TPO | P | 4 | 39.005 | 47.301 | 25.039 | 1.00 | 50.06 | O |
| HETATM | 1882 | O2P | TPO | P | 4 | 37.813 | 46.256 | 27.162 | 1.00 | 46.58 | O |
| HETATM | 1883 | O3P | TPO | P | 4 | 40.380 | 47.062 | 27.290 | 1.00 | 49.41 | O |
| HETATM | 1884 | C | TPO | P | 4 | 37.411 | 50.568 | 28.798 | 1.00 | 61.70 | C |
| HETATM | 1885 | O | TPO | P | 4 | 38.436 | 51.035 | 29.282 | 1.00 | 62.63 | O |
| ATOM | 1886 | N | VAL | P | 5 | 36.504 | 49.935 | 29.533 | 1.00 | 63.13 | N |
| ATOM | 1887 | CA | VAL | P | 5 | 36.695 | 49.769 | 30.970 | 1.00 | 63.78 | C |
| ATOM | 1888 | C | VAL | P | 5 | 36.288 | 48.363 | 31.393 | 1.00 | 65.21 | C |
| ATOM | 1889 | O | VAL | P | 5 | 35.676 | 47.660 | 30.552 | 1.00 | 65.53 | O |
| ATOM | 1890 | CB | VAL | P | 5 | 35.866 | 50.814 | 31.770 | 1.00 | 62.99 | C |
| ATOM | 1891 | CG1 | VAL | P | 5 | 34.375 | 50.626 | 31.500 | 1.00 | 62.42 | C |
| ATOM | 1892 | CG2 | VAL | P | 5 | 36.167 | 50.695 | 33.248 | 1.00 | 61.55 | C |
| ATOM | 1893 | OXT | VAL | P | 5 | 36.582 | 47.986 | 32.552 | 1.00 | 65.06 | O |
| TER | 1894 | | VAL | P | 5 | | | | | | |
| HETATM | 1895 | C1 | FSC | A | 1240 | 35.814 | 49.417 | 38.212 | 1.00 | 59.59 | C |
| HETATM | 1896 | C4 | FSC | A | 1240 | 36.597 | 50.380 | 37.645 | 1.00 | 60.88 | C |
| HETATM | 1897 | C11 | FSC | A | 1240 | 36.301 | 51.883 | 37.679 | 1.00 | 61.29 | C |
| HETATM | 1898 | C18 | FSC | A | 1240 | 35.844 | 52.372 | 36.303 | 1.00 | 60.60 | C |
| HETATM | 1899 | C17 | FSC | A | 1240 | 37.538 | 52.663 | 38.103 | 1.00 | 61.14 | C |
| HETATM | 1900 | O24 | FSC | A | 1240 | 37.210 | 54.056 | 38.157 | 1.00 | 63.73 | O |
| HETATM | 1901 | C31 | FSC | A | 1240 | 37.905 | 54.867 | 38.991 | 1.00 | 65.62 | C |
| HETATM | 1902 | O37 | FSC | A | 1240 | 38.772 | 54.412 | 39.723 | 1.00 | 66.63 | O |
| HETATM | 1903 | C36 | FSC | A | 1240 | 37.609 | 56.347 | 39.017 | 1.00 | 65.45 | C |
| HETATM | 1904 | C10 | FSC | A | 1240 | 37.791 | 49.739 | 36.945 | 1.00 | 59.09 | C |
| HETATM | 1905 | C6 | FSC | A | 1240 | 37.671 | 48.227 | 37.189 | 1.00 | 58.48 | C |
| HETATM | 1906 | O13 | FSC | A | 1240 | 38.042 | 47.466 | 36.034 | 1.00 | 59.94 | O |
| HETATM | 1907 | C2 | FSC | A | 1240 | 36.197 | 48.056 | 37.641 | 1.00 | 58.60 | C |
| HETATM | 1908 | C7 | FSC | A | 1240 | 36.091 | 46.945 | 38.704 | 1.00 | 56.65 | C |
| HETATM | 1909 | C5 | FSC | A | 1240 | 35.384 | 47.550 | 36.446 | 1.00 | 56.78 | C |
| HETATM | 1910 | C12 | FSC | A | 1240 | 34.230 | 47.960 | 35.848 | 1.00 | 55.73 | C |
| HETATM | 1911 | C20 | FSC | A | 1240 | 33.802 | 47.173 | 34.627 | 1.00 | 54.79 | C |
| HETATM | 1912 | C27 | FSC | A | 1240 | 33.252 | 45.794 | 35.006 | 1.00 | 53.12 | C |
| HETATM | 1913 | O32 | FSC | A | 1240 | 33.210 | 44.971 | 33.846 | 1.00 | 52.44 | O |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| HETATM | 1914 | C38 | FSC | A | 1240 | 32.441 | 43.789 | 34.059 | 1.00 | 52.67 | C |
|---|---|---|---|---|---|---|---|---|---|---|---|
| HETATM | 1915 | C26 | FSC | A | 1240 | 32.728 | 48.015 | 33.906 | 1.00 | 54.44 | C |
| HETATM | 1916 | C25 | FSC | A | 1240 | 32.177 | 49.009 | 34.950 | 1.00 | 55.37 | C |
| HETATM | 1917 | C19 | FSC | A | 1240 | 33.215 | 49.088 | 36.087 | 1.00 | 56.69 | C |
| HETATM | 1918 | C15 | FSC | A | 1240 | 32.533 | 49.136 | 37.530 | 1.00 | 57.81 | C |
| HETATM | 1919 | C23 | FSC | A | 1240 | 32.320 | 47.757 | 38.190 | 1.00 | 56.17 | C |
| HETATM | 1920 | C9 | FSC | A | 1240 | 33.277 | 50.097 | 38.531 | 1.00 | 58.55 | C |
| HETATM | 1921 | O16 | FSC | A | 1240 | 32.389 | 50.377 | 39.608 | 1.00 | 58.57 | O |
| HETATM | 1922 | C3 | FSC | A | 1240 | 34.625 | 49.583 | 39.175 | 1.00 | 60.87 | C |
| HETATM | 1923 | O8 | FSC | A | 1240 | 35.014 | 50.539 | 40.180 | 1.00 | 64.62 | O |
| HETATM | 1924 | C14 | FSC | A | 1240 | 35.105 | 50.066 | 41.549 | 1.00 | 66.62 | C |
| HETATM | 1925 | O22 | FSC | A | 1240 | 36.367 | 49.347 | 41.762 | 1.00 | 67.71 | O |
| HETATM | 1926 | C30 | FSC | A | 1240 | 37.579 | 50.172 | 41.635 | 1.00 | 70.48 | C |
| HETATM | 1927 | C33 | FSC | A | 1240 | 37.515 | 51.531 | 42.430 | 1.00 | 70.89 | C |
| HETATM | 1928 | O39 | FSC | A | 1240 | 38.621 | 52.345 | 42.021 | 1.00 | 70.71 | O |
| HETATM | 1929 | C28 | FSC | A | 1240 | 36.168 | 52.233 | 42.095 | 1.00 | 70.83 | C |
| HETATM | 1930 | O34 | FSC | A | 1240 | 35.945 | 53.596 | 42.582 | 1.00 | 74.43 | O |
| HETATM | 1931 | C40 | FSC | A | 1240 | 36.570 | 54.150 | 43.661 | 1.00 | 77.54 | C |
| HETATM | 1932 | O43 | FSC | A | 1240 | 37.723 | 54.559 | 43.570 | 1.00 | 80.70 | O |
| HETATM | 1933 | C42 | FSC | A | 1240 | 35.824 | 54.305 | 44.964 | 1.00 | 78.36 | C |
| HETATM | 1934 | C21 | FSC | A | 1240 | 35.006 | 51.293 | 42.492 | 1.00 | 67.68 | C |
| HETATM | 1935 | O29 | FSC | A | 1240 | 33.762 | 51.954 | 42.275 | 1.00 | 67.46 | O |
| HETATM | 1936 | C35 | FSC | A | 1240 | 38.802 | 49.362 | 42.076 | 1.00 | 71.75 | C |
| HETATM | 1937 | O41 | FSC | A | 1240 | 38.477 | 48.559 | 43.239 | 1.00 | 74.59 | O |
| HETATM | 1938 | C44 | FSC | A | 1240 | 39.211 | 47.326 | 43.506 | 1.00 | 73.70 | C |
| HETATM | 1939 | C47 | FSC | A | 1240 | 39.205 | 46.415 | 42.268 | 1.00 | 72.37 | C |
| HETATM | 1940 | C46 | FSC | A | 1240 | 38.548 | 46.571 | 44.665 | 1.00 | 72.52 | C |
| HETATM | 1941 | C45 | FSC | A | 1240 | 40.660 | 47.652 | 43.880 | 1.00 | 74.22 | C |
| HETATM | 1942 | C48 | FSC | A | 1240 | 40.962 | 48.588 | 44.810 | 1.00 | 74.88 | C |
| HETATM | 1943 | O | HOH | K | 1 | 43.511 | 54.215 | 23.733 | 1.00 | 58.47 | O |
| HETATM | 1944 | O | HOH | K | 2 | 36.480 | 45.516 | 33.282 | 1.00 | 63.00 | O |
| HETATM | 1945 | O | HOH | Z | 1 | 40.049 | 39.017 | 53.672 | 1.00 | 48.51 | O |
| HETATM | 1946 | O | HOH | Z | 2 | 45.663 | 45.503 | 46.746 | 1.00 | 48.47 | O |
| HETATM | 1947 | O | HOH | Z | 3 | 40.359 | 42.288 | 53.964 | 1.00 | 59.48 | O |
| HETATM | 1948 | O | HOH | Z | 4 | 51.439 | 48.250 | 43.138 | 1.00 | 61.11 | O |
| HETATM | 1949 | O | HOH | Z | 5 | 35.057 | 47.088 | 50.219 | 1.00 | 48.58 | O |
| HETATM | 1950 | O | HOH | Z | 6 | 56.765 | 38.923 | 40.441 | 1.00 | 39.99 | O |
| HETATM | 1951 | O | HOH | Z | 7 | 47.594 | 48.044 | 28.196 | 1.00 | 52.47 | O |
| HETATM | 1952 | O | HOH | Z | 8 | 51.302 | 35.878 | 38.674 | 1.00 | 41.20 | O |
| HETATM | 1953 | O | HOH | Z | 9 | 50.930 | 39.525 | 36.263 | 1.00 | 51.93 | O |
| HETATM | 1954 | O | HOH | Z | 10 | 51.134 | 49.168 | 19.891 | 1.00 | 66.11 | O |
| HETATM | 1955 | O | HOH | Z | 11 | 46.607 | 30.036 | 44.507 | 1.00 | 66.63 | O |
| HETATM | 1956 | O | HOH | Z | 12 | 28.696 | 36.942 | 49.509 | 1.00 | 54.08 | O |
| HETATM | 1957 | O | HOH | Z | 13 | 23.882 | 41.369 | 45.214 | 1.00 | 75.38 | O |
| HETATM | 1958 | O | HOH | Z | 14 | 33.905 | 41.800 | 50.307 | 1.00 | 68.26 | O |
| HETATM | 1959 | O | HOH | Z | 15 | 37.713 | 41.885 | 52.009 | 1.00 | 42.98 | O |
| HETATM | 1960 | O | HOH | Z | 16 | 34.518 | 44.428 | 51.027 | 1.00 | 49.10 | O |
| HETATM | 1961 | O | HOH | Z | 17 | 30.494 | 46.526 | 40.692 | 1.00 | 46.79 | O |
| HETATM | 1962 | O | HOH | Z | 18 | 44.783 | 41.316 | 21.090 | 1.00 | 56.22 | O |
| HETATM | 1963 | O | HOH | Z | 19 | 42.450 | 44.453 | 29.124 | 1.00 | 55.50 | O |
| HETATM | 1964 | O | HOH | Z | 20 | 46.122 | 46.402 | 31.941 | 1.00 | 57.97 | O |
| HETATM | 1965 | O | HOH | Z | 21 | 45.660 | 46.449 | 27.100 | 1.00 | 57.78 | O |
| HETATM | 1966 | O | HOH | Z | 22 | 52.549 | 44.117 | 27.899 | 1.00 | 47.75 | O |
| HETATM | 1967 | O | HOH | Z | 23 | 49.147 | 32.380 | 30.590 | 1.00 | 52.57 | O |
| HETATM | 1968 | O | HOH | Z | 24 | 50.519 | 47.346 | 22.841 | 1.00 | 59.77 | O |
| HETATM | 1969 | O | HOH | Z | 25 | 43.928 | 44.340 | 20.238 | 1.00 | 53.49 | O |
| HETATM | 1970 | O | HOH | Z | 26 | 62.105 | 30.356 | 16.746 | 1.00 | 58.88 | O |
| HETATM | 1971 | O | HOH | Z | 27 | 52.562 | 30.599 | 13.304 | 1.00 | 57.25 | O |
| HETATM | 1972 | O | HOH | Z | 28 | 58.120 | 31.795 | 18.947 | 1.00 | 53.98 | O |
| HETATM | 1973 | O | HOH | Z | 29 | 44.760 | 30.924 | 19.395 | 1.00 | 50.40 | O |
| HETATM | 1974 | O | HOH | Z | 30 | 38.698 | 30.383 | 24.193 | 1.00 | 55.20 | O |
| HETATM | 1975 | O | HOH | Z | 31 | 30.427 | 32.694 | 29.058 | 1.00 | 62.01 | O |
| HETATM | 1976 | O | HOH | Z | 32 | 21.047 | 35.169 | 37.135 | 1.00 | 64.63 | O |
| HETATM | 1977 | O | HOH | Z | 33 | 22.406 | 49.889 | 41.663 | 1.00 | 47.69 | O |
| HETATM | 1978 | O | HOH | Z | 34 | 28.502 | 39.332 | 42.299 | 1.00 | 58.99 | O |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

| HETATM | 1979 | O | HOH | Z | 35 | 24.874 | 35.546 | 26.470 | 1.00 | 50.51 | O |
|---|---|---|---|---|---|---|---|---|---|---|---|
| HETATM | 1980 | O | HOH | Z | 36 | 36.230 | 43.707 | 31.591 | 1.00 | 65.83 | O |
| HETATM | 1981 | O | HOH | Z | 37 | 37.492 | 41.658 | 33.346 | 1.00 | 45.94 | O |
| HETATM | 1982 | O | HOH | Z | 38 | 33.915 | 33.497 | 20.724 | 1.00 | 52.79 | O |
| HETATM | 1983 | O | HOH | Z | 39 | 30.783 | 31.924 | 26.471 | 1.00 | 52.82 | O |
| HETATM | 1984 | O | HOH | Z | 40 | 42.487 | 40.421 | 22.362 | 1.00 | 36.39 | O |
| HETATM | 1985 | O | HOH | Z | 41 | 37.857 | 45.976 | 20.755 | 1.00 | 44.81 | O |
| HETATM | 1986 | O | HOH | Z | 42 | 45.060 | 36.074 | 14.073 | 1.00 | 80.89 | O |
| HETATM | 1987 | O | HOH | Z | 43 | 40.956 | 33.413 | 13.300 | 1.00 | 51.69 | O |
| HETATM | 1988 | O | HOH | Z | 44 | 39.603 | 42.293 | 14.425 | 1.00 | 81.78 | O |
| HETATM | 1989 | O | HOH | Z | 45 | 31.653 | 31.923 | 19.858 | 1.00 | 47.27 | O |
| HETATM | 1990 | O | HOH | Z | 46 | 23.956 | 50.060 | 27.409 | 1.00 | 53.47 | O |
| HETATM | 1991 | O | HOH | Z | 47 | 34.427 | 50.754 | 9.084 | 1.00 | 49.74 | O |
| HETATM | 1992 | O | HOH | Z | 48 | 27.621 | 52.504 | 10.679 | 1.00 | 75.46 | O |
| HETATM | 1993 | O | HOH | Z | 49 | 22.857 | 45.260 | 15.577 | 1.00 | 67.48 | O |
| HETATM | 1994 | O | HOH | Z | 50 | 15.782 | 62.406 | 34.842 | 1.00 | 70.12 | O |
| HETATM | 1995 | O | HOH | Z | 51 | 32.501 | 64.473 | 32.075 | 1.00 | 60.39 | O |
| HETATM | 1996 | O | HOH | Z | 52 | 31.816 | 58.850 | 12.575 | 1.00 | 51.95 | O |
| HETATM | 1997 | O | HOH | Z | 53 | 35.569 | 61.278 | 9.828 | 1.00 | 56.86 | O |
| HETATM | 1998 | O | HOH | Z | 54 | 37.499 | 45.033 | 35.704 | 1.00 | 50.86 | O |
| HETATM | 1999 | O | HOH | Z | 55 | 41.346 | 48.435 | 36.316 | 1.00 | 53.27 | O |
| HETATM | 2000 | O | HOH | Z | 56 | 38.934 | 48.805 | 33.793 | 1.00 | 57.46 | O |
| HETATM | 2001 | O | HOH | Z | 57 | 35.857 | 47.981 | 44.108 | 1.00 | 71.51 | O |
| HETATM | 2002 | O | HOH | Z | 58 | 31.661 | 48.821 | 41.645 | 1.00 | 63.44 | O |
| HETATM | 2003 | O | HOH | Z | 59 | 40.202 | 48.685 | 23.123 | 1.00 | 56.76 | O |
| HETATM | 2004 | O | HOH | Z | 60 | 42.410 | 48.682 | 25.431 | 1.00 | 42.29 | O |
| CONECT | 1865 | 1875 | | | | | | | | | |
| CONECT | 1886 | 1884 | | | | | | | | | |
| CONECT | 1895 | 1896 | 1907 | 1922 | | | | | | | |
| CONECT | 1896 | 1895 | 1897 | 1904 | | | | | | | |
| CONECT | 1897 | 1896 | 1898 | 1899 | | | | | | | |
| CONECT | 1898 | 1897 | | | | | | | | | |
| CONECT | 1899 | 1897 | 1900 | | | | | | | | |
| CONECT | 1900 | 1899 | 1901 | | | | | | | | |
| CONECT | 1901 | 1900 | 1902 | 1903 | | | | | | | |
| CONECT | 1902 | 1901 | | | | | | | | | |
| CONECT | 1903 | 1901 | | | | | | | | | |
| CONECT | 1904 | 1896 | 1905 | | | | | | | | |
| CONECT | 1905 | 1904 | 1906 | 1907 | | | | | | | |
| CONECT | 1906 | 1905 | | | | | | | | | |
| CONECT | 1907 | 1895 | 1905 | 1908 | 1909 | | | | | | |
| CONECT | 1908 | 1907 | | | | | | | | | |
| CONECT | 1909 | 1907 | 1910 | | | | | | | | |
| CONECT | 1910 | 1909 | 1911 | 1917 | | | | | | | |
| CONECT | 1911 | 1910 | 1912 | 1915 | | | | | | | |
| CONECT | 1912 | 1911 | 1913 | | | | | | | | |
| CONECT | 1913 | 1912 | 1914 | | | | | | | | |
| CONECT | 1914 | 1913 | | | | | | | | | |
| CONECT | 1915 | 1911 | 1916 | | | | | | | | |
| CONECT | 1916 | 1915 | 1917 | | | | | | | | |
| CONECT | 1917 | 1910 | 1916 | 1918 | | | | | | | |
| CONECT | 1918 | 1917 | 1919 | 1920 | | | | | | | |
| CONECT | 1919 | 1918 | | | | | | | | | |
| CONECT | 1920 | 1918 | 1921 | 1922 | | | | | | | |
| CONECT | 1921 | 1920 | | | | | | | | | |
| CONECT | 1922 | 1895 | 1920 | 1923 | | | | | | | |
| CONECT | 1923 | 1922 | 1924 | | | | | | | | |
| CONECT | 1924 | 1923 | 1925 | 1934 | | | | | | | |
| CONECT | 1925 | 1924 | 1926 | | | | | | | | |
| CONECT | 1926 | 1925 | 1927 | 1936 | | | | | | | |
| CONECT | 1927 | 1926 | 1928 | 1929 | | | | | | | |
| CONECT | 1928 | 1927 | | | | | | | | | |
| CONECT | 1929 | 1927 | 1930 | 1934 | | | | | | | |
| CONECT | 1930 | 1929 | 1931 | | | | | | | | |
| CONECT | 1931 | 1930 | 1932 | 1933 | | | | | | | |

TABLE 4-continued

Table of coordinates of atoms of the crystal structure of the ternary complex between *Nicotiana tabacum* 14-3-3 isoform c (SEQ ID NO:1), Fusicoccin and a phosphorylated pentapeptide from the C-terminus of PMA2 from *NICOTIANA PLUMBAGINIFOLIA* (residues 952-956 of SEQ ID NO:2 with a phosphothreonine at residue 955) in PDB (protein data bank) formate. For explanation of PDB format see PDB-homepage www.rcsb.org/pdb. Table contains the atomic coordinates of non-hydrogen atoms of the said complex, as they were identified by x-ray crystallographical methods in the asymmetric unit of the crystals of claim XY solved at syncrotron radiation to a resolution of 2.7 A. Identified solvent molecules are also included. Numeration of protein chains is "A" for Protein and "B" for the Phospho-Peptide. Fusicoccin is tagged with code "A1240" (residue 1240 of chain A). Crystals were grown as explained and processed as explained in the example. Crystallographic Data was processed using XDS. Structure was solved using AMORE and refined using CNS. R-factors and other crystalographic data are included in the header of the PDB file.

```
CONECT 1932 1931
CONECT 1933 1931
CONECT 1934 1924 1929 1935
CONECT 1935 1934
CONECT 1936 1926 1937
CONECT 1937 1936 1938
CONECT 1938 1937 1939 1940 1941
CONECT 1939 1938
CONECT 1940 1938
CONECT 1941 1938 1942
CONECT 1942 1941
CONECT 1875 1865 1876
CONECT 1876 1875 1877 1884
CONECT 1877 1876 1878 1879
CONECT 1878 1877
CONECT 1879 1877 1880
CONECT 1880 1879 1881 1882 1883
CONECT 1881 1880
CONECT 1882 1880
CONECT 1883 1880
CONECT 1884 1886 1876 1885
CONECT 1885 1884
MASTER    355   0   2  10   0   0   4   6 2002   2  61  21
END
```

The phosphopeptide occupies the central binding groove of 14-3-3c in an extended conformation. The phosphate moiety of the phosphothreonine forms electrostatic interactions with a positively charged patch formed by residues Lys56, Arg63, and Arg136 and a H-bond to Tyr137 (FIG. 1b). This indicates that high-affinity binding of 14-3-3 to PMA is dependent on phosphorylation. Indeed, binding could not be detected by applying a non-phosphorylated 16mer PMA peptide (T. Fugisang et al. *J. Biol. Chem.* 274, 36774 (1999)) as well as a non-phosphorylated version of the peptide used in this study (not shown). Additionally, there are a number of H-bonds (cut-off limit 3.4 Å) between the peptide, mostly from the main-chain, and conserved protein side-chains. The peptide's C-terminal barboxylate is mostly contacted by basic residues and the side chains of the Val and Tyr residue flanking the phosphothreonine form van der Waals contacts to the protein (FIG. 1b). The structure confirms the notion that the C-terminal YTV-motif is highly conserved in plant P-type H$^+$-ATPases.

A superimposition (FIG. 1c) shows that the PMA2 phosphopeptide is in a similar conformation and orientation compared with two library derived peptides (K. Rittinger et al. Mol. *Cell,* 4, 153 (1999); M. B. Yaffe et al. *Cell* 91, 961 (1997)) or the phosphorylated serotonin N-acetyltransferase bound to 14-3-3ζ (T. Obsil, R. Ghirlando, D. C. Klein, S. Ganguly, F. Dyda, *Cell* 105, 257 (2001)). In these complexes the interactions of the phosphate with two arginines, a lysine and one tyrosine are well conserved, as are some of the interactions of the main chain such as the double hydrogen bond between an Asn from 14-3-3 and the main chain CO and NH of the −1 peptide residue. The orientation of the main chain and interactions of the side chains are deviating in the −2 and beyond the +1 positions. The PMA2 binding peptide QSYpTV-COOH is different from the optimal consensus binding motifs, RSXpS/TXP and RXXXpS/TXP, that are recognized by all mammalian 14-3-3 isoforms (T. Obsil, R. Ghirlando, D. C. Klein, S. Ganguly, F. Dyda, *Cell* 105, 257 (2001); C. Petosa et al. *J. Biol. Chem.* 273, 16305 (1998); M. B. Yaffe, *FEBS Lett.* 513, 53 (2002); G. Tzivion, J. Avruch, *J. Biol. Chem.* 277,3061 (2002); P. C. Sehnke, J. M. DeLille, R. J. Ferl, Plant Cell 14, 339 (2002)). The most significant difference is the absence of residues beyond the +1 position (FIG. 1c), which would sterically interfere with FC binding (see below).

The structure of the ternary 14-3-3-FC-phosphopeptide complex shows that the toxin is accommodated into the large binding groove of 14-3-3 right next to the C-terminus of the peptide (FIG. 2a). Comparison of the peptide conformation in the binary and ternary complexes indicates the C-terminal Val to adopt a different rotameric conformation to accommodate the toxin (FIG. 2b). Whereas the glycosidic part of the phytotoxin is solvent exposed and forms two hydrogen bonds to Asn49 and Asp222 as well as some hydrophobic interactions, the diterpene part is buried and makes extensive hydrophobic contacts to 14-3-3c, with two additional H-bonds to Asp 222 and Lys 129 (FIG. 2c).

The peptide and FC contact each other very closely and together fill the central cavity of 14-3-3 (FIG. 2c). The interaction involves the peptide's C-terminal Val of the peptide and the five- and eight-membered carbocycles of FC. These contacts bury an extra exposed solvent accessible surface of ca. 50 Å$^2$ when compared to the corresponding binary complexes. FC has been reported to require PMA for binding to 14-3-3. However, the structural model of the ternary complex and thermodynamic considerations (see below) argue for an albeit weak binding site for FC on 14-3-3 in the absence of the H$^+$-ATPase. By soaking FC into the crystal we were indeed able to determine the structure of the binary 14-3-3·fusicoccin complex. The toxin occupies the same site as found in the ternary complex and there are only minor rearrangements of its conformation between the binary and ternary complex (FIG. 2b). Notably, comparison with the structure of FC in solution determined by NMR (A. Ballio et al. *Phytochemistry* 30, 137 (1991); A. Ballio et al. *Experimentia,* 24, 631 (1968)) shows a similar conformation for unbound FC also.

EXAMPLE 3

Isothermal Titration Calorimetry

In order to obtain more quantitative data with respect to the phosphorylated pentapeptide used in the structural analysis, thermodynamic constants were determined by means of isothermal titration calorimetry (ITC, 16).

Binding of ligands to 14-3-3c was measured with a MCS isothermal titration calorimeter (MicroCal Inc., Northampton). Ligands (fusicoccin 0.4 mM; phosphopbeptides 0.5 mM) were titrated in 8 to 20 µl steps by injection into solutions containing 14-3-3c (0.05 mM) alone or 14-3-3c saturated with one of the ligands in 25 mM HEPES buffer pH 6.5, 10 mM MgCl$_2$, 5 mM CaCl$_2$, 5 mM DTE at 35° C. Binding isotherms were fitted using a single binding site model and used to calculate the binding enthalpy ($\Delta$H) and association constant ($K_a$) of the binding reaction. Dissociation constants ($K_D$=1/$K_a$), Gibbs free energy changes ($\Delta$G=$-$RTln$K_a$) and entropy changes (T$\Delta$S=$\Delta$H$-\Delta$G) were calculated from $\Delta$H and $K_a$. For the binding of peptide to a FC/14-3-3c complex, we also used non-saturating conditions of FC and observed two binding events which were fitted independently to $K_1$ and $K_4$. All measurements were repeated at least three times.

For the interaction between 14-3-3, FC and the peptide, four coupled equilibria can be defined (FIG. 3a). For the interaction between peptide and protein, a $K_D$ of 2.5 µM was obtained. This binding affinity is weaker than values previously reported for larger fragments of the H$^+$-ATPase. The affinity of a phosphorylated 16mer was found to be 88 nM (T. Fuglsang et al. *J. Biol. Chem.* 274, 36774 (1999)) measured under different conditions using surface plasmon resonance. Titration of FC to a saturated binary 14-3-3/peptide complex results in a $K_D$ of 0.7 µM. The affinity of FC to 14-3-3 was determined to be in the order of 50 µM. The low affinity and the insolubility of FC in aqueous solutions made direct determination somewhat unreliable. However, from the affinity of the peptide to the 14-3-3·fusicoccin complex ($K_4$) and since $K_1 \times K_2 = K_3 \times K_4$, we get a more reliable value of 66 µM. Considering the complete binding cycle, we can conclude that fusicoccin increases the binding affinity of the peptide 93 fold, and that its own affinity is increased correspondingly by the peptide. Since it has been shown that the binding site of PMA on 14-3-3 involves other features than just the C-terminal end (C. Jelich-Ottmann, E. W. Weiler, C. Oecking, *J. Biol. Chem.* 276, 39852 (2001)), the phosphopeptide affinities measured by ITC may not quantitatively reflect the fusicoccin effect. However, since increases in affinity by FC have been described for any N-terminally extended fragment of the PMA C-terminus (5-7), we are confident that the affinities measured here faithfully reproduce and give a molecular explanation for the physiological effect of FC on the proton ATPase.

In order to probe for the nature of the stabilizing effect of FC, ITC data were analyzed for other thermodynamic parameters of the binding cycle. The negative enthalpy ($\Delta$H) of peptide binding to the unliganded 14-3-3 is increased from $-$10 to $-$11.8 kcal/mole for the 14-3-3·FC complex. The full increase in binding affinity is additionally due to relieving the unfavourable entropy change of peptide binding to 14-3-3, as $-$TAS decreases from 1.7 to 0.4 kcal/mole. Similarly, the tighter binding of FC to 14-3-3 is due to both a more favourable enthalpy and entropy change in the presence of the peptide. We can only speculate as to the nature of the observed effect that leads to the stabilization of PMA binding to 14-3-3. However, since the tight juxtaposition of the two ligands in the binding site buries ca. 50 Å$^2$ surface, and does not involve major conformational changes, we would propose that the observed effects are due to the additional interactions between FC and the peptide's C-terminal valine and the release of ordered water molecules from the 14-3-3-binding cavity.

PMA binding to-14-3-3 is unique in that the penultimate C-terminal residue is the phosphorylated threonine (YpTV-COOH). The structure shows that FC binding would clash with binding of the 14-3-3 consensus motifs that involve residues C-terminal to the +1 position. Indeed, FC binding to 14-3-3c preloaded with the C-terminally extended phosphopeptide Gln-Ser-Tyr-pThr-Val-Pro, which more resembles a consensus 14-3-3 binding peptide was severely impaired (FIG. 3b, upper panel). Furthermore, binding of FC actually requires the interactions with the C-terminal Val, as deletion of the latter again results in a significant lower binding affinity (FIG. 3b, lower panel). Taken together; this explains why there is no effect of FC on any other known 14-3-3-ligand interaction. To date, all plant proteins characterized as interacting directly with 14-3-3 homologs contain the consensus binding motifs with the notable exception of the plasma membrane H$^+$-ATPase. In addition, the weak binding of FC to unliganded 14-3-3 prevents interference with 14-3-3 protein interactions other than the proton pump.

Example 4

Site Directed Mutagenesis of 14-3-3 and Loss of FC Binding

The three-dimensional structure of the ternary complex of 14-3-3 strongly suggested the presence of a ligand binding pocket in 14-3-3 and a number of crucial aminoacids mediating FC-14-3-3 interaction. Moreover, the three-dimensional structure showed that particularly 14-3-3 residues Glu19, Leu54, Val53, Phe126, Met130, Pro174, Ile175, Gly178, Lys221, Leu225 und Ile226 are engaged in hydrophobic interactions with fusicoccin and are, thus important for FC binding. In addition, 14-3-3 residues Asp49 and Asp222 establish hydrogen bonds to the FC molecule (FIG. 2c).

In order to study the functional relevance of selected amino acids within the above-described binding pocket, residues the following point mutants were analysed in respect FC binding: (a) N49Q, (b) D222E, (c) F126E and (d) I175E in the homologous sequence of human 14-3-3z. The mutant proteins were expressed, purified and FC binding were tested in an in vitro assay in the presence of the 66 C-terminal residues of a PMA-GST fusion construct.

For the detection of FC binding a far-western-blot (FIG. 4) was performed. In this in vitro assay, the PMA-GST fusion construct, containing the 66 C-terminal residues of PMA, was immobilised on a nitrocellulose membrane via electroblotting of SDS-PAGE-separated proteins. The interacting protein, a his-tagged 14-3-3 construct was allowed to react with the GST-fusion protein in an overlay-solution. The interaction of these two proteins was mediated by fusicoccin. In the case of wild type 14-3-3, interaction was only observed in the presence of fusicoccin. The actual binding of the his-tagged 14-3-3 protein was visualized after washing the membrane by immunodetecton with an anti-His-antibody, which was employed as primary antibody. A typical results of a pull-down experiment is shown in FIG. 4 and demonstrates that the mutations N49Q and D222E have a strong reduction of fusicoccin mediated PMA binding, whereas F126E and I175E result in a complete inhibition of binding.

Alternatively, a second in-vitro method was used to screen for fusicoccin binding. In this pull-down assay (FIG. 5), the GST-PMA fusion protein is immobilized on GSH-sepharose-beads and the his-tagged 14-3-3 protein will bind in the presence of fusioccin to the GST-fusion protein and can subsequently be found in the sepharose-fraction after washing and centrifugation of the beads. The detection again takes place via SDS-PAGE and Western-Blotting with subsequent immunodetection. A typical results of a pull-down experiment is shown in FIG. 5 and demonstrates that the mutations N49Q and D222E have a strong reduction of fusicoccin mediated PMA binding, whereas F126E and I175E result in a complete inhibition of binding (compare signal intensities in panel C).

The invention claimed is:

1. A crystal of a ternary complex composed of the protein 14-3-3, a ligand thereof and a fragment of Plasma Membrane ATPase (PMA), wherein the crystal has a space group of P6$_5$22 with unit cell parameters of a=109.0 Å, b=109.0 Å and c=135.8 Å wherein:
   (a) the protein 14-3-3 consists of the amino acid sequence of SEQ ID NO: 1;
   (b) the ligand is Fusicoccin; and
   (c) the PMA fragment is a C-terminal peptide of up to 15 amino acid residues of the amino acid sequence of SEQ ID NO: 2 and which minimally possesses amino acids 952-956 of said C-terminal SEQ ID NO: 2.

2. The crystal of claim 1, wherein said ternary complex of the crystal is represented by the structure coordinates of table 4 or by structural coordinates which differ by a root mean square deviation from the C-alpha carbons of table 4 by less than 1.5 Å.

3. The crystal of claim 1, wherein the 14-3-3 protein contains up to 10 additional N-terminal or C-terminal amino acid residues.

4. The crystal of claim 1, further comprising at least one compound selected from the group consisting of HEPES, NaCI, PEG 100, PEG 200, PIEG 400, PEG 600, PEG 800, PEG 1000, PEG 2000, PEG 3000 PEG, 4000 PEG, 5000 PEG, 6000, PEG 7000, PEG 8000, Isopropanol, Citrate buffer, Tris buffer, Cacodylate Buffer, MES-Buffer, Dithiothreitol, Octylglycopyranoside, and Umnylacelate.

5. The crystal of claim 1, wherein
   (a) the 14-3-3 protein consists of the amino acid sequence of SEQ NO: 1;
   (b) the PMA fragment is a C-terminal fragment of SEQ ID NO:2 consisting of the residues QSYpTV (residues 952-956 of SEQ ID NO: 2);
   (c) the ligand is Fusicoccin; and
   (d) optionally, one or more components are contained, which arc selected from the group consisting of PEG 400, sodium citrate, ammonium acetate, H2O, DTE salts containing magnesium, calcium, sodium, chlorine, bromine, iodine, rubidium, phosphorus, sulfur, potassium, manganese, boron, molybdenum, selenium, silicon cobalt, vanadium, and nickel.

6. The crystal of claim 5, wherein the crystal has one 14-3-3 molecule per asymmetric unit, and which is further characterized by the three-dimensional coordinates of Table 4.

7. A method for detecting ligand binding to the complex of the protein 14-3-3 and PMA, comprising soaking the crystal of claim 1 in a solution of candidate compounds to be screened and detecting binding of the compound to the 14-3-3 protein or the 14-3-3 ligand binding site.

8. The method of claim 7, wherein ligand binding is detected by isothermal titration calorimetry, filter-binding methods using radiolabeled compounds, ELISAs, Surface Plasmon Resonance or fluorescence spectroscopy.

9. The method of claim 7, wherein liQand binding is detected by subjecting the crystal of claim 12 to X-ray diffraction and determining the three-dimensional coordinates of the new ternary complex comprising the 14-3-3 protein PMA and the candidate ligand.

10. A method for the production of a ligand with increased or decreased affinity to the ligand binding site, comprising the steps of the method of claim 7 and further comprising the steps of:

(a) selecting a ligand with the desired properties; and
(b) synthesizing the ligand in an amount allowing its commercial use in plant breeding.

11. A method for identifying candidate ligands to the complex of a 14-3-3 protein and PMA comprising the steps of:
(a) subjecting the crystal from claim 1 to X-ray diffraction and determining the three-dimensional coordinates of the ternary complex;
(b) employing the three-dimensional structure coordinates as determined in step (a) to model said ternary complex in silico;
(c) replacing the Fusicoccin ligand of the ternary complex as determined in step (b) with structure coordinates for other candidate ligand(s);
(d) selecting those candidate ligands from step (c) which fit into the ligand binding site of the 14-3-3 protein; (e) contacting the potential ligands identified in step (d) in an in vitro or in vivo assay with the 14-3-3 protein to determine which candidate ligands bind to protein 14-3-3 thereby identifying new candidate ligands.

12. The method of claim 11 further comprising-the step of modifying said candidate ligand) to alter, add or eliminate a portion thereof suspected of interacting with a binding site of the binding cavity, thereby increasing or decreasing the affinity of the ligand to the binding site or binding cavity.

* * * * *